US012139542B2

(12) United States Patent
Layne et al.

(10) Patent No.: US 12,139,542 B2
(45) Date of Patent: Nov. 12, 2024

(54) INHIBITORS OF AORTIC CARBOXYPEPTIDASE-LIKE PROTEIN (ACLP)

(71) Applicant: TRUSTEES OF BOSTON UNIVERSITY, Boston, MA (US)

(72) Inventors: Matthew D. Layne, Dedham, MA (US); Kathleen E. Tumelty, Brookline, MA (US); Robert Lafyatis, Arlington, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/313,257

(22) PCT Filed: May 27, 2015

(86) PCT No.: PCT/US2015/032658
§ 371 (c)(1),
(2) Date: Nov. 22, 2016

(87) PCT Pub. No.: WO2015/183943
PCT Pub. Date: Dec. 3, 2015

(65) Prior Publication Data
US 2017/0190778 A1    Jul. 6, 2017

Related U.S. Application Data

(60) Provisional application No. 62/051,503, filed on Sep. 17, 2014, provisional application No. 62/003,288, filed on May 27, 2014.

(51) Int. Cl.
*C07K 16/28*    (2006.01)
*A61K 38/16*    (2006.01)

(52) U.S. Cl.
CPC .......... *C07K 16/2863* (2013.01); *A61K 38/16* (2013.01)

(58) Field of Classification Search
CPC ............................ C07K 16/2863; A61K 38/16
See application file for complete search history.

(56) References Cited

U.S. PATENT DOCUMENTS

| 7,094,878 B2 | 8/2006 | Lee et al. | |
| 2002/0137679 A1 | 9/2002 | Lawler | |
| 2006/0286597 A1* | 12/2006 | Lee ........................ | C07K 14/47 435/6.16 |
| 2008/0311573 A1 | 12/2008 | Lillie et al. | |
| 2014/0045714 A1 | 2/2014 | Gerszten et al. | |

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000, 10:398-400) (Year: 2000).*
Vajdos et al. (J Mol Biol. Jul. 5, 2002;320(2):415-28 ) (Year: 2002).*
Brown et al. (J Immunol. May 1996; 156(9):3285-91 (Year: 1996).*
Guido et al.(Curr Med Chem. 2008; 15(1):37-46) (Year: 2008).*
Clark et al.(J. Med. Chem., 2014, 57 (12), pp. 5023-5038) (Year: 2014).*
Caestecker (Cytokine & Growth Factor Reviews 15 (2004) 1-11) (Year: 2004).*
Schissel et al., Abstract: "Aortic Carboxypeptidase—Like Protein, a Discoidin Domain Protein, Regulates Lung Fibroblast Lamellipodia Formation and Collagen Contraction", Am J. Respir. Crit. Care Med. 179:A3485 (2009).
Schissel et al., "Aortic Carboxypeptidase-Like Protein Is Expressed in Fibrotic Human Lung and its Absence Protects against Bleomycin-Induced Lung Fibrosis", Am J Pathol, 174(3):818-28 (2009).
Tumelty et al., "Aortic Carboxypeptidase-like Protein (ACLP) Enhances Lung Myofibroblast Differentiation through Transforming Growth Factor β Receptor-dependent and -independent Pathways", JBC, 289:2526-36 (2013).
Tumelty et al., "Adipocyte Enhancer Binding Protein 1 and Aortic Carboxypeptidase-Like Protein", Handbook of Proteolytic Enzymes Rawlings, Barrett, Woessner (Eds) 1348-1353 (2012).
Abe et al., "An assay for transforming growth factor-beta using cells transfected with a plasminogen activator inhibitor-1 promoter-luciferase construct", Anal Biochem, 216(2) 216:276-284 (1994).
Danzer et al., "Gastroschisis in mic lacking aortic carboxypeptidase-like protein is associated with a defect in hueromuscular development of the eviscerated intestine", Pediatr Res, 68(1), 23-28 (2010).
Gagnon et al., "Aortic carboxypeptidase-like protein is regulated by transforming growth factor beta in 3T3-L1 preadipocytes", Exp Cell Res, 308(2), 265-272 (2005).
Horan et al., "Partial Inhibition of Integrin αvβ6 Prevents Pulmonary Fibrosis without Exacerbating Inflammation", Am J Respir Crit Care Med, 177(1) 56-65 (2008).
Ith et al., "Aortic carboxypeptidase-like protein is expressed in collagen-rich tissues during mouse embryonic development", Gene Expr Patterns, 5(4), 533-537 (2005).
Layne et al., "Aortic carboxypeptidase-like protein, a novel protein with discoidin and carboxypeptidase-like domains, is up-regulated durig vascular smooth muscle cell differentiation", J Biol Chem, 273(25) 15654-15660 (1998).
Layne et al., "Characterization of the mouse aortic carboxypeptidase-like protein promoter reveals activity in differentiated and dedifferentiated vascular smooth muscle cells", Circ Res, 90(6), 728-736 (2002).

(Continued)

*Primary Examiner* — Brian Gangle
*Assistant Examiner* — Andrea K McCollum
(74) *Attorney, Agent, or Firm* — Nixon Peabody LLP; Ronald I. Eisenstein; Ravinderjit S. Braich

(57) ABSTRACT

The present invention generally relates to the field of treatment of fibroproliferative diseases and disorders and cancer. Embodiments of the present invention generally relate to compostions, methods and kits comprising an inhibitor of a portion of the N-terminal pro-fibrotic domain (PFD) of Aortic Carboxypeptidase-Like Protein (ACLP), and in some embodiments, in combination with an inhibitor of the discoidin (DS) domain of ACLP, for use in methods for the treatment of fibroproliferative diseases and cancer, and inhibition of ACLP-mediated activation of a member of the TGFβ receptor superfamily.

9 Claims, 20 Drawing Sheets
Specification includes a Sequence Listing.

(56) References Cited

OTHER PUBLICATIONS

Layne et al., "Impaired abdominal wall development and deficient wound healing in mice lacking aortic carboxypeptidase-like protein", Mol Cell Biol, 21(15), 5256-5261 (2001).
Macias-Silva et al., "MADR2 is a Substrate of the TGFBeta Receptor and Its Phosphorylation Is Required for Nuclean Accumulation and Signaling", Cell, 87(7) 1215-1224 (1996).
Murphy et al., "Transforming Growth Factor-Beta Complexes with Thrombospondin", Mol Biol Cell, 3(2) 181-188, (1992).
Zhang et al., "Recptor-associated Man homologues synergize as effectors of the TGF-beta response", Nature 383 (6596), 186-172 (1996).

* cited by examiner

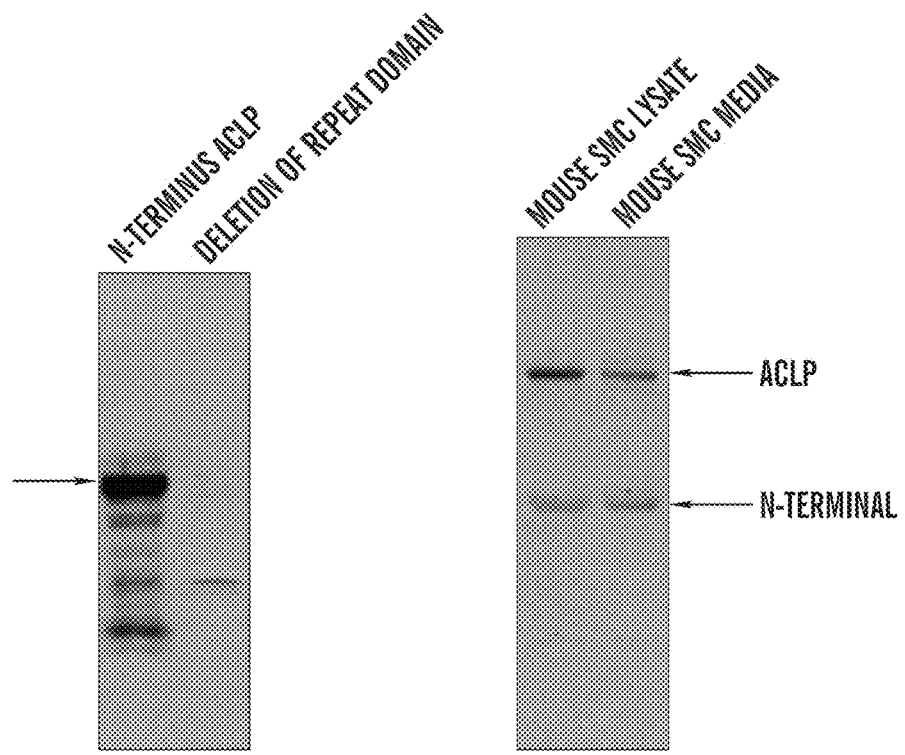
FIG. 9A  FIG. 9B
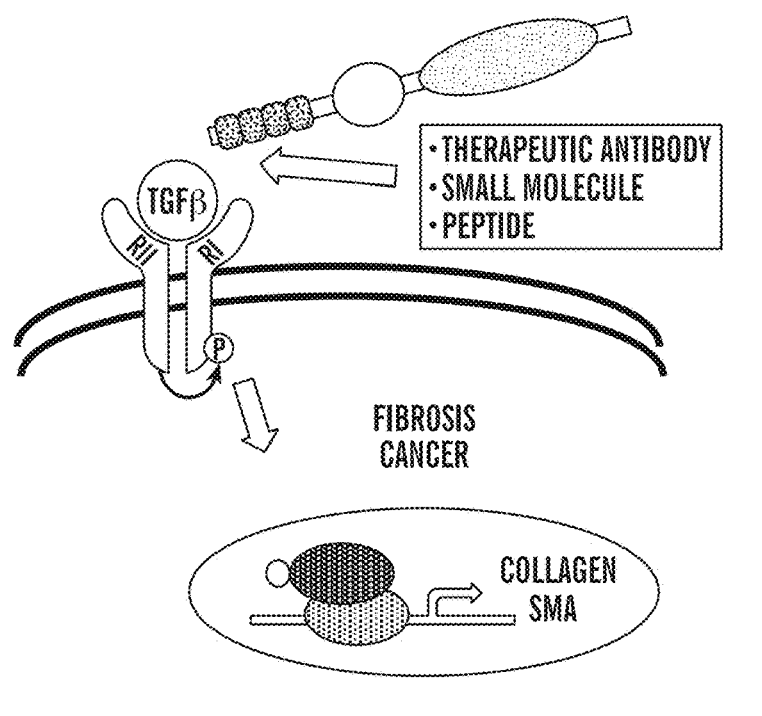
FIG. 10

```
hum-ACLP  NP_001120.3| adipocyte enhancer-binding protein 1 precursor [Homo sapiens]
mus-ACLP  NP_033766.2| adipocyte enhancer-binding protein 1 isoform 2 precursor [Mus musculus]
cyn-ACLP  XP_005549751.1| adipocyte enhancer-binding protein 1 isoform X3 [Macaca fascicularis]
rat-ACLP  NP_001094440.1 | adipocyte enhancer-binding protein 1 precursor [Rattus norvegicus]

hum-ACLP    MAAVRGAPLLSCLLALLALCPGGRPQTVLTDDEIEEFLEGFLSELEPE--PREDDVEAPP
mus-ACLP    MAPVRTASLLCGLLALLTLCPEGNPQTVLTDDEIEEFLEGFLSELETQSPPREDDVEVQP
cyn-ACLP    MAAVRGAPLLGCLLALLALCPGGRPQTVLTDDEIEEFLEGFLSELGPE--PREDDMEAPP
rat-ACLP    MAAVRTASLLCGLLALLALCPEGSPQTVLTDDEIQEFLEGFLSEFETQSPPREDDVEAQP
              *  *:* * *******:*****;  .: ***:*. * hum-ACLP    PPEPTPRVRKAQAGGKPGKRPGTAAEVPPEKTKDKGKKGKKDKGPKVPKESLEGSPRPPK
mus-ACLP    LPEPTQRPRKSKAGGKQR-----ADVEVPPEKNKDKEKKGKKDKGPKATKP-LEGSTRPTK
cyn-ACLP    PPEPTPRVRKAQAGGKPGARPGAAAEVPPEKTKDKGKKGKKDKGPKVPKESLEGSPKPPK
rat-ACLP    LPEPTQRARKSKAGGKPR-----ADAEAPPEKNKDKEKKGKKDKGPKAAKH-LEGSTRPTK
            **** * ;:.** *       *. *.*.******** *  ****.;*.* hum-ACLP    KGKEKPPKATKKPKEKPPKATKKPKEKPPKATKKPKEKPPKATKKPPSGKRPPILAPSET
mus-ACLP    KPKEKPPKATKKPKEKPPKATKKPKEKPPKATKKPKEKPPKATKRPSAGKKFSTVAPLET
cyn-ACLP    KGKEKPPKATKKPKEKPPKATKKPKEKPPKATKKPKEKPPKATKKPPSGKRPPTLAPSET
rat-ACLP    KPKEKPPKATKKPKEKPPKATKKPKEKPPKATKKPKEKPPKATKRPSAGKRFSTVAPLET
            * ******************************************:.*:.  , , ** hum-ACLP    LEWPLPPPPSPGPEELPQEGGAPLSNNWQNPGEETHVEAREHQPEPEEETEQPTLDYNDQ
mus-ACLP    LDRLLPSPSNPSAQELPQKRDTPFPNAWQGQGEETQVEAKQPRPEPEEETEMPTLDYNDQ
cyn-ACLP    LEWPLPPPPSPGPEELPQEGGGPLPNNWQNPGEETRVEAREHQPEPEEETELPTLDYNDQ
rat-ACLP    PERSLTSPSNPGTRELPEERGRTSLNTWQGQGEETQVEARQHRPEPEEETEMPTLDYNDQ
            ; *..*.*..*** ;;  . .  * . .*;; ;*****.***** hum-ACLP    IEREDYEDFEYIRRQKQPRPPPSRRRRPERVWPEPPEEKAPAPAPE--ERIEPPVKPLLP
mus-ACLP    IEKEDYEDFEYIRRQKQPRPTPSRRR----LWPERPEEKTEEPEER-----KEVEPPLKP
cyn-ACLP    IEREDYEDFEYIRRQKQPRPPPSRRRRPERVWPEPPEEKAPAPAPAPEERIEPPVKPLLP
rat-ACLP    IEREDYEDFEYIRRQKQPRPTPSRKR----IWPEPPEEKTQEPEER-----KEVDPPLKP
            **;*****************.***;*     ;*** ****. *       ;    ** *
```

FIG. 12A

```
hum-ACLP  PLPPDYGDGYVIPNYDDMDYYFGPPPPQKPDAERQTDEEKEELKKPKKEDSSPKE-ETDK
mus-ACLP  LLPPDYGDSYVIPNYDDLYYFPHPPPQKPDVGQEVDEEKEEMKKPKKEGSSPKEDTEDK
cyn-ACLP  LLPPDYGDGYVIPNYDDMDYYFGPPPPQKPDAERQTDEEKEELKKPKKEDGRPKE-ETDK
rat-ACLP  LLPPDYGDGYLIPNYDDLYYFPHPPPQKPDVGQEVDEEKEELKKPKKEGSSPKEDTEDK
          *******.*:****.  **, :;,*:*.. *   ** hum-ACLP  WAVEKGKDHKE-PRKGEELEEEWTPTEKVKCPPIGMESHRIEDNQIRASSMLRHGLGAQR
mus-ACLP  WTVEKNKDHKG-PRKGEELEEEWAPVEKIKCPPIGMESHRIEDNQIRASSMLRHGLGAQR
cyn-ACLP  WAVEKGKDHKE-PRKGEEVEEEWTPTEKVKCPPIGMESHRIEDNQIRASSMLRHGLGAQR
rat-ACLP  WAAEKNKDHKAGPRKGEELEEEWGPVEKIKCPPIGMESHRIEDNQIRASSMLRHGLGAQR
          *:,.  **,** *..********************* hum-ACLP  GRLNMQTGATEDDYYDGAWCAEDDARTQWIEVDTRRTTRFTGVITQGRDSSIHDDFVTTF
mus-ACLP  GRLNMQAGANEDDYYDGAWCAEDESQTQWIEVDTRRTTRFTGVITQGRDSSIHDDFVTTF
cyn-ACLP  GRLNMQAGATEDDYYDGAWCAEDDARTQWIEVDTRRTTRFTGVITQGRDSSIHDDFVTTF
rat-ACLP  GRLNMQAGANEDDYYDGAWCAEDESQTQWIEVDTRRTTRFTGVITQGRDSSIHDDFVTTF
          ****:,**********;:;********************************* hum-ACLP  FVGFSNDSQTWVMYTNGYEEMTFHGNVDKDTPVLSELPEPVVARFIRIYPLTWNGSLCMR
mus-ACLP  FVGFSNDSQTWVMYTNGYEEMTFYGNVDKDTPVLSELPEPVVARFIRIYPLTWNGSLCMR
cyn-ACLP  FVGFSNDSQTWVMYTNGYEEMTFHGNVDKDTPVLSELPEPVVARFIRIYPLTWNGSLCMR
rat-ACLP  FVGFSNDSQTWVMYTNGYEEMTFHGNVDKDTPVLSELPEPVVARFIRIYPLTWNGSLCMR
          ********************:*********************************** hum-ACLP  LEVLGCSVAPVYSYYAQNEVVATDDLDFRHHSYKDMRQLMKVVNEECPTITRTYSLGKSS
mus-ACLP  LEVLGCPVTPVYSYYAQNEVVTTDSLDFRHHSYKDMRQLMKAVNEECPTITRTYSLGKSS
cyn-ACLP  LEVLGCPVAPVYSYYAQNEVVATDDLDFRHHSYKDMRQLMKVVNEECPTITRTYSLGKSS
rat-ACLP  LEVLGCPVTPVYSYYAQNEVVTTDSLDFRHHSYKDMRQLMKVVNEECPTITRTYSLGKSS
          ******.*:*********.***.**.****************:*****************
```

FIG. 12A (cont.)

```
hum-ACLP  RGLKIYAMEISDNPGEHELGEPEFRYTAGIHGNEVLGRELLLLLMQYLCREYRDGNPRVR
mus-ACLP  RGLKIYAMEISDNPGDHELGEPEFRYTAGIHGNEVLGRELLLLLMQYLCQEYRDGNPRVR
cyn-ACLP  RGLKIYAMEISDNPGEHELGEPEFRYTAGIHGNEVLGRELLLLLMQYLCREYRDGNPRVR
rat-ACLP  RGLKIYAMEISDNPGEHELGEPEFRYTAGMHGNEVLGRELLLLLMQYLCHEYRDGNPRVR
          ************.**********,*****************,****** hum-ACLP  SLVQDTRIHLVPSLNPDGYEVAAQMGSEFGNWALGLWTEEGFDIFEDFPDLNSVLWGAEE
mus-ACLP  NLVQDTRIHLVPSLNPDGYEVAAQMGSEFGNWALGLWTEEGFDIFEDFPDLNSVLWAAEE
cyn-ACLP  SLVQDTRIHLVPSLNPDGYEVAAQMGSEFGNWALGLWTEEGFDIFEDFPDLNSVLWGAEE
rat-ACLP  NLVQDTRIHLVPSLNPDGYEVAAQMGSEFGNWALGLWTEEGFDIFEDFPDLNSVLWAAEE
          .*********************************************************.* hum-ACLP  RKWVPYRVPNNNLPIPERYLSPDATVSTEVRAIIAWMEKNPFVLGANLNGGERLVSYPYD
mus-ACLP  KKWVPYRVPNNNLPIPERYLSPDATVSTEVRAIISWMEKNPFVLGANLNGGERLVSYPYD
cyn-ACLP  RKWVPYRVPNNNLPIPERYLSPDATVSTEVRAIIAWMEKNPFVLGANLNGGERLVSYPYD
rat-ACLP  KKWVPYRVPNNNLPIPERYLSPDATVSTEVRAIISWMEKNPFVLGANLNGGERLVSYPYD
          ;******************************.************************ hum-ACLP  MARTPTQEQLLAAAMAAARGEDEDEVSEAQETPDHAIFRWLAISFASAHLTLTEPYRGGC
mus-ACLP  MARTPSQEQLLAEALAAARGEDDDGVSEAQETPDHAIFRWLAISFASAHLTMTEPYRGGC
cyn-ACLP  MTRTPTQEQLLAAAMAAARGEDEDEVSEAQETPDHAIFRWLAISFASAHLTLTEPYRGGC
rat-ACLP  MARTPSQEQLLAAALAAARGEDEDEVSEAQETPDHAIFRWLAISFASAHLTMTEPYRGGC
          *.*,**** *,*******,* **********************.****** hum-ACLP  QAQDYTGGMGIVNGAKWNPRTGTINDFSYLHTNCLELSFYLGCDKFPHESELPREWENNK
mus-ACLP  QAQDYTSGMGIVNGAKWNPRSGTFNDFSYLHTNCLELSVYLGCDKFPHESELPREWENNK
cyn-ACLP  QAQDYTGGMGIVNGAKWNPRSGTINDFSYLHTNCLELSFYLGCDKFPHESELPREWENNK
rat-ACLP  QAQDYTSGMGIVNGAKWNPRSGTFNDFSYLHTNCLELSIYLGCDKFPHESELPREWENNK
          ******.********** ***.**.************.********************
```

*FIG. 12A (cont.)*

```
hum-ACLP  EALLTFMEQVHRGIKGVVTDEQGIPIANATISVSGINHGVKTASGGDYWRILNPGEYRVT
mus-ACLP  EALLTFMEQVHRGIKGVVTDEQGIPIANATISVSGINHGVKTASGGDYWRILNPGEYRVT
cyn-ACLP  EALLTFMEQVHRGIKGVVTDEQGIPIANATISVSGINHGVKTASGGDYWRILNPGEYRVT
rat-ACLP  EALLTFMEQVHRGIKGVVTDEQGIPIANATISVSGINHGVKTASGGDYWRILNPGEYRVT
          ************************************************************ hum-ACLP  AHAEGYTPSAKTCNVDYDIGATQCNFILARSNWKRIREIMAMNGNRPIPHIDPSRPMTPQ
mus-ACLP  AHAEGYTSSAKICNVDYDIGATQCNFILARSNWKRIREILAMNGNRPILRVDPSRPMTPQ
cyn-ACLP  AHAEGYTPSAKTCNVDYDIGATQCNFILARSNWKRIREIMAMNGNRPIPHIDPSRPMTPQ
rat-ACLP  AHAEGYTSSAKICNVDYDIGATQCNFILARSNWKRIREILAMNGNRPILRVDPSRPMTPQ
          *****.* **************************:*** ::******* hum-ACLP  QRRLQQRRLQHRLRLRAQMRLRRLNATTTLGPHTVPPTLPPAPATTLSTTIEPWGLIPPT
mus-ACLP  QRRMQQRRLQYRLRMREQMRLRRLNSTAGPATSPTP-ALMPPPSPTPAITLRPWEVLPTT
cyn-ACLP  QRRLQQRRLQHRLRLRAQMRLRRLNATTTLGPHTVPSTLPPAPATTLSTTIEPWGLVPPT
rat-ACLP  QRRLQQRRLRYRLRMREQMRLRRLNSTTGPATSPTP-ALTLPPSPTPGSTSRLWEILPTT
          *:*:.*:*:******:.  .. ..* :*  .*:,.*  . *  . * :;*.* hum-ACLP  TAGWEESETETYTEVVTEFGTEVEPEFGTKVEPEFETQLEPEFETQLEPEFE---------
mus-ACLP  TAGWEESETETYTEVVTEFETEYG-------------------------------TDLEVE
cyn-ACLP  TAGWEESETETYTEVVTEFGTEVEPEFGTKVEPEFETQLETEFETQLEPEFETQLEPEFE
rat-ACLP  AAGWEESETETYTEVVTEFETEYG-------------------------------PDLEVE
          .**************** hum-ACLP  --EEEEEEKEEEIATGQAFPFTTVETYTVNFGDF  (SEQ ID NO: 1)
mus-ACLP  EIEEEEEEEEEEMDTGLTFPLTTVETYTVNFGDF  (SEQ ID NO: 49)
cyn-ACLP  EEEEEEEEEEEEIATGQAFPFTTVETYTVNFGDF  (SEQ ID NO: 50)
rat-ACLP  ELEEEEEEEE-MDTGLTFPVTTVETYTVNFGDF   (SEQ ID NO: 51)
          ******.** : ** .**.*************
```

*FIG. 12A (cont.)*

```
                    20                    40                      60        70
MAAVRGAPLLSCLLALLALCPGGRPQTVLTDDEIEEFLEGFLSELEPEPREDDVEAPPPPEPTPRVRKAQ
          90                   110                    130          140
GGKPGKRPGTAAEVPPEKTKDKGKKGKKDKGPKVPKESLEGSPRPPKKGKEKPPKATKKPKEKPPKATKK
          160                  180                    200          210
PKEKPPKATKKPKEKPPKATKKPSGKRPPILAPSETLEWPLPPPPSPGPEELPQEGGAPLSNNWQNPGE
          230                  250                    270          280
ETHVEAREHQPEPEEETEQPTLDYNDQIEREDYEDFEYIRRQKQPRPPPSRRRRPERVWPEPPEEKAPAP
          300                  320                    340          350
APEERIEPPVKPLLPPLPPDYGDGYVIPNYDDMDYYFGPPPPQKPDAERQTDEEKEELKKPKKEDSSPKE
          370                  390                    410          420
ETDKWAVEKGKDHKEPRKGEELEEEWTPTEKVKCPPIGMESHRIEDNQIRASSMLRHGLGAQRGRLNMQT
          440                  460                    480          490
GATEDDYYDGAWCAEDDARTQWIEVDTRRTTRFTGVITQGRDSSIHDDFVTTFFVGFSNDSQTWVMYTNG
          510                  530                    550          560
YEEMTFHGNVDKDTPVLSELPEPVVARFIRIYPLTWNGSLCMRLEVLGCSVAPVYSYYAQNEVVATDDLD
          580                  600                    620          630
FRHHSYKDMRQLMKVVNEECPTITRTYSLGKSSRGLKIYAMEISDNPGEHELGEPEFRYTAGIHGNEVLG
          650                  670                    690          700
RELLLLLMQYLCREYRDGNPRVRSLVQDTRIHLVPSLNPDGYEVAAQMGSEFGNWALGLWTEEGFDIFED
          720                  740                    760          770
FPDLNSVLWGAEERKWVPYRVPNNNLPIPERYLSPDATVSTEVRAIIAWMEKNPFVLGANLNGGERLVSY
          790                  800                    810          820
PYDMARTPTQEQLLAAAMAAARGEDEDEVSEAQETPDHAIFRWLAISFASAHLTLTEPYRGGCQAQDYTG
          840                  860                    880          890
GMGIVNGAKWNPRTGTINDFSYLHTNCLELSFYLGCDKFPHESELPREWENNKEALLTFMEQVHRGIKGV
          910                  930                    950          960
VTDEQGIPIANATISVSGINHGVKTASGGDYWRILNPGEYRVTAHAEGYTPSAKTCNVDYDIGATQCNFI
          970                  990                    1100         1110
LARSNWKRIREIMAMNGNRPIPHIDPSRPMTPQQRRLQQRRLQHRLRLRAQMRLRRINATTTLGPHTVPP
          1130                 1150                   1170         1180
TLPPAPATTLSTTIEPWGLIPPTTAGWEESETETYTEVVTEFGTEVEPEFGTKVEPEFETQLEPEFETQL
          1200         1217
EPEFEEEEEEEKEEEIATGQAFPFTTVETYTVNFGDF (SEQ ID NO: 1)
```

*FIG. 12B*

```
                         Loop1                                    Loop2
DDR1  CRYALGMQDRTIPDSDISASS------SWSDSTAARHSRLESSDG-----------DGAWCP
DDR2  CRYPLGMSGGQIPDEDITASS------QWSESTAAKYGRLDSEEG-----------DGAWCP
ACLP  CP-PIGMESHRIEDNQIRASS------MLRHGLGAQRGRLNMQTGATEDDYYDGAWCA
FV    CSTPIGMENGKIENKQITASSFKKSWWGDYWEPFRARLNAQGR--------VNAWQA
                  Loop3                                  Loop4
DDR1  AGSVFPKE-EEYLQVDLQRLHLVALVGTQGRHAGGLGKEFSRSYRLRYSRDGRRWM (SEQ ID NO:52)
DDR2  EIPVEPDDLKEFLQIDLHTLHFITLVGTQGRHAGGHGIEFAPMYKINYSRDGTRWI (SEQ ID NO:53)
ACLP  ED----DARTQWIEVDTRRTRFTGVITQGRDSSIH-DDFVTTFFVGFSNDSQTWV (SEQ ID NO:54)
FV    KAN----NNKQWLEIDLLKIKKITAIITQG-CKSLSSEMYVKSYTIHYSEQGVEWK (SEQ ID NO:55)
```

*FIG. 13B*

INHIBITORS OF AORTIC CARBOXYPEPTIDASE-LIKE PROTEIN (ACLP)

CROSS REFERENCE TO RELATED APPLICATIONS

This application is a 371 National Phase Entry of International Application PCT/US2015/032658 filed on May 27, 2015 which claims benefit under 35 U.S.C. § 119(e) of U.S. Provisional Patent Application Ser. No. 62/003,288 filed on May 27, 2014 and U.S. Provisional Patent Application Ser. No. 62/051,503 filed on Sep. 17, 2014, the contents of which are incorporated herein in their entirety by reference.

GOVERNMENT SUPPORT

This invention was made with Government Support under Grant number HL078869 awarded by the National Institutes of Health (NIH). The U.S. Government has certain rights to the invention.

FIELD OF THE INVENTION

The present invention relates generally to the fields of treatment of fibroproliferative diseases and disorders and cancer therapy and cancer prevention. More particularly, the present invention generally relates to an inhibitor of at least a portion of the N-terminal pro-fibrotic domain (PFD) of the Aortic carboxypeptidase-like protein (ACLP), and in some embodiments, in combination with an inhibitor of the discoidin (DS) domain of ACLP.

SEQUENCE LISTING

The sequence listing of the present application has been submitted electronically via EFS-Web as an ASCII formatted sequence listing with a file name "701586-081803-PCT_SL" creation date of Nov. 17, 2016 and a size of 69,791. The sequence listing submitted via EFS-Web is part of the specification and is herein incorporated by reference in its entirety.

BACKGROUND OF THE INVENTION

Systemic sclerosis (SSc) is a heterogeneous and variably progressive disease with no effective therapies. Significantly, the morbidity and mortality associated with SSc is caused by fibrotic changes in the skin and internal organs including the lung. Although soluble factors such as transforming growth factor β (TGFβ) are generally accepted to contribute to the pathogenesis of SSc, the absence of effective SSc therapies reflects our incomplete understanding of the molecules and pathways that mediate the fibrosis and how these molecules can be targeted for intervention. Because SSc is a complex disease involving numerous cell types and their interaction with the extracellular environment, combined therapies that modulate multiple pathways are likely required to interrupt disease progression. One such cell is the myofibroblast that accumulates and persists, and is central to the decline in tissue function. These cells not only secrete excessive amounts of extracellular matrix (ECM) molecules including collagens, but they also express the contractile actin isoform, α-smooth muscle actin (SMA), leading to tissue stiffening and amplifying fibrosis.

Solid tumors are complex structures composed of carcinoma cells embedded in a collagen-rich extracellular matrix generated in part by smooth muscle actin (SMA) positive cancer-associated fibroblasts (CAF). The transformed epithelial cells are genetically unstable leading to the development of resistance to chemotherapies. The tumor microenvironment further fosters resistance to cancer treatments. A recent study examining numerous combinations of stromal cells, cancer cells, and current chemotherapies determined that stroma-mediated drug resistance is likely mediated through secreted proteins derived from the stromal cells or CAF. However, stroma directed adjuvant therapies are currently lacking. In the case of stromal/mesenchymal transitions in cancer, a very small set of genes including collagens has been identified.

Integrated in this gene set is aortic carboxypeptidase-like protein (ACLP protein, gene name ACLP or AEBP1), and it was previously discovered that ACLP is robustly expressed in the breast cancer stroma, and promotes epithelial cell changes consistent with epithelial-to-mesenchymal transition. ACLP expression correlates with relapse free survival in patients with Her2+ breast tumors. However the function of proteins such as ACLP within the reactive stroma are essentially unknown.

SUMMARY OF THE INVENTION

Aortic carboxypeptidase-like protein (ACLP) is a secreted protein which is important for wound repair and fibroproliferative diseases. In particular, inhibitors of the ACLP protein can be used to inhibit fibroproliferation in diseases including cardiovascular, cancer, and fibrosis (including solid organ and scleroderma), and other fibroproliferative diseases, e.g., of the lung, heart, kidney and vasculature.

Importantly, the inventors have surprisingly discovered that a specific portion of the Aortic carboxypeptidase-like protein (ACLP) protein is the active component and have used structural predictions to demonstrate that inhibition of a specific portion of this protein can be targeted for treatment of fibroproliferative diseases and disorders, fibrosis and scleroderma, as well as cancers with a fibrotic core. ACLP is comprised of 3 main domains: a N-terminal pro-fibrotic domain (PFD), a discoidin (DS) domain and a carboxypeptidase domain.

More specifically, the inventors have surprisingly discovered that the N-terminal pro-fibrotic domain (PFD) of ACLP is important in mediating transforming growth factor (TGF) signaling. The PFD domain comprises a series of thrombospondin-like (referred to herein as "Tsp") motifs, and the inventors have discovered that inhibition (e.g., by removing) of one or more of these Tsp motifs can inhibit TGF signaling. Accordingly, the inventors have discovered the ability to specifically inhibit ACLP function with inhibitors, such as, for example peptides or blocking antibodies generated against the N-terminal pro-fibrotic domain (PFD). Such inhibitors are advantageous as they can block the PFD domain of the ACLP protein binding to, and activating TGFβRII, and therefore specifically inhibit ACLP-mediated TGFβ signaling. In addition, the present invention also encompasses blocking peptides or small molecules that bind to the PFD domain to inhibit ACLP induced stimulation of fibrotic changes.

Previously, the inventors have discovered that the ACLP protein is upregulated in the human fibrotic lung and its absence in vivo protects against fibrosis. It is known that ACLP expression correlates with the severity of human scleroderma and tracks with response to other therapies. Expression profiling in numerous cancers have identified ACLP (gene name AEBP1) as part of a core signature of stromal activation. Herein, the inventors have discovered that elevated ACLP expression occurs with decreased survival in breast cancer patients.

The inventors have previously established that ACLP activates pro-fibrotic pathways in part through the TGFβ receptor (e.g., TGFβRII). However, in contrast to the previous reports which did not know which region of the ACLP protein was functional for contributing to fibrosis, or mediating ACLP-induced TGFβRII signaling, herein, the inventors have surprisingly discovered herein that the activity of ACLP (e.g., ACLP-mediated TGFβ signaling) is dependent on a pro-fibrotic domain (herein referred to the "PFD"). Importantly, the PFD domain comprises four thrombospondin-like (Tsp) motifs which, although are predicted to form a tertiary structure similar to that of thrombospondin, has a very different and unique amino acid sequence. Importantly, one Tsp-Tsp2 has a unique 11-amino acid sequence repeated 4 times, and is highly conserved across different mammalian species. However, while some proteins with thrombospondin motifs are often selected as targets for cancer therapies, because the thrombospondin-like (Tsp) motifs at the N-terminal of ACLP have a unique amino acid sequence as compared to thrombospondin or other proteins comprising thrombospondin motifs, inhibitors of the Tsp motifs in the N-terminal PFD of ACLP will be specific to blocking and/or inhibiting ACLP function but not other proteins comprising a thrombospondin motif. Accordingly, an inhibitor of one or more Tsp motifs in the PFD of ACLP are useful in methods as disclosed herein to decrease or prevent fibrosis, and/or treat fibrotic diseases, for example, but not limited to, fibroproliferative disease, scleroderma, and cancer.

Another advantage of the present invention over other cancer therapies and other thrombospondin inhibitors is that as ACLP does not target the beneficial effect of TGFβ and since ACLP is activated at sites of injury, fibrosis, or cancer, inhibiting ACLP, in particular the pro-fibrotic domain of ACLP will be specific at sites of injury, fibrosis, and/or cancer, and therefore have minimal non-specific side effects or impact on normal tissues.

Accordingly, the present invention relates to an inhibitor, such as, for example, a neutralizing antibody (also referred to as a blocking antibody), small molecule, RNAi agent, peptide or antibodies, which can inhibit the activity of ACLP, or block the expression of ACLP, or inhibit or reduce the pro-fibrotic domain (PFD) function. In particular, the present invention relates to ACLP inhibitors which prevent the interaction of the PFD domain of the ACLP protein with the members of the TGF beta Receptor superfamily, including type I and type II serine/threonine kinases, for example, but not limited to, TGFβ receptor II (TGFβRII), TGFβ R1/ALK-5, TGFβ R3, BMP receptor (e.g., BMP RII), MIS RII, thereby preventing TGFβ signaling. In some embodiments, the present invention relates to ACLP inhibitors which prevent the interaction of the PFD domain of the ACLP protein with the members of the TGF Receptor super family, including but not limited to, Activin RIA/ALK-2, GFR alpha-1/GDNF R alpha-1, Activin RIB/ALK-4, GFR alpha-2/GDNF R alpha-2, Activin RIIA, GFR alpha-3/GDNF R alpha-3, Activin RIIA/B, GFR alpha-4/GDNF R alpha-4, Activin RIIB, MIS RII, ALK-1, NCAM-1/CD56, ALK-7, Ret, BMPR-IA/ALK-3, RGM-A, BMPR-IB/ALK-6, RGM-B, BMPR-II, RGM-C/Hemojuvelin, CD109, TGF-beta RI (TGFRβII)/ALK-5, Cripto, TGF-beta RII (TGFRβI), Endoglin/CD105, TGF-beta RIII (TGFRβIII) and Erbin.

As disclosed herein, the inventors have discovered that the PFD domain of mammalian ACLP protein comprises four (4) Tsp motifs (referred to herein as Tsp1, Tsp2, Tsp3 and Tsp4), where at least one, or at least 2 or at least 3 or at least all four of these Tsp motifs function to allow the ACLP protein to bind to, and activate TGFβRII signaling. Tsp2, which is the second of the Tsp motifs in the N-terminal PFD comprises a unique 11-amino acid sequence which is repeated 4 times (e.g., 4×11-amino acid sequence), which is highly conserved among mammalian species, e.g., human, mouse, monkey (*Macaca fascicularis*) and rat.

In some embodiments, an inhibitor of the PFD domain of mammalian ACLP is an inhibitor that specifically binds to Tsp2, and/or inhibits Tsp2 from interacting with another protein, e.g., a TGFβRII, a co-factor of ACLP or another portion of the ACLP protein (e.g., interaction of Tsp2 with the discoidin domain).

Accordingly, in some embodiments, the ACLP inhibitor is a blocking or neutralizing antibody, or a fragment thereof, which specifically binds to one or more Tsp motifs of the PFD domain, in particular, specifically binds to at least one Tsp motif in the PFD domain, thereby preventing the interaction of the PFD domain of the ACLP protein with the TGFβ receptor II (TGFβRII).

In some embodiments, an ACLP inhibitor encompassed for use in the methods and compositions as disclosed herein is a decoy ligand (or competitive peptide), e.g., a decoy of ACLP protein, comprising for example, a non-functional mimetic peptide or peptide fragment of the PFD of the ACLP protein which binds to TGFβRII but does not induce TGFβ signaling, thereby acting as a competitive inhibitor and preventing the interaction of the PFD domain of the ACLP protein with the TGFβ receptor II (TGFβRII). In some embodiments, such a decoy ligand which is a non-functional mimetic or fragment of the PFD of the ACLP protein comprises one or more ectopic mutations rendering the PFD to be unable to activate TGFβRII signaling.

Accordingly, in some embodiments, the ACLP inhibitor is a competing peptide, e.g., peptide with homology to one or more of the Tsp motifs of human ACLP, where the competing peptide can bind to the TGFβ receptor II (TGFβRII), or a member of the TGF receptor superfamily and thereby competitively inhibiting the PFD of the ACLP protein from binding. In some embodiments, a competing peptide has homology to, e.g., at least 80% homology to the amino acid sequence of Tsp2 of human ACLP. In some embodiments, a competing peptide (also known as a competitive peptide) has at least about 80%, or at least about 85%, or at least about 90%, or at least about 95%, or at least about 96%, or at least about 97%, or at least about 98% or at least about 99%, or at least about 100% homology to the amino acid sequence of one, or more than one, of the Tsp motifs of ACLP protein, e.g., human ACLP protein. In some embodiments, a competing peptide (also known as a competitive peptide) has at least about 80% and comprises one or more ectopic mutations rendering the Tsp domain of the PFD non-functional and unable to activate TGFβRII signaling.

In alternative embodiments, a ACLP inhibitor can be a competing peptide, e.g., a peptide with homology to part of the discoidin domain of ACLP, that has, for example, at least about or at least about 85%, or at least about 90%, or at least about 95%, or at least about 96%, or at least about 97%, or at least about 98% or at least about 99%, or at least about 100% homology to a portion of the discoidin domain of human ACLP. It is surprising that an inhibitor of the discoidin domain, or a competitive inhibitor of discoidin, is useful in the methods as disclosed herein, as although the discoidin domain interacts with collagen and contributes to fibrosis by mechanical signaling, in normal in vitro assays, the discoidin domain is non-functional and appears to be not involved and dispensable for TGFβ signaling. Accordingly, inhibitors of the discoidin domain are not expected to be useful in inhibiting ACLP-mediated TGFβ signaling. However, the inventors have surprisingly discovered that in the presence of collagen, the discoidin domain appears to potentiate TGFβ signaling, and therefore, an inhibitor of discoidin in combination with an inhibitor of the PFD domain of the human ACLP protein is encompassed for use in the compositions, methods and kits as disclosed herein.

In some embodiments, more than one competitive peptide inhibitor can be used together. For example, a competing peptide that has homology to one or more Tsp motifs of human ACLP can be used with a competing peptide with homology to the discoidin domain of human ACLP protein. For example, but not limited to, a competitive peptide with homology to Tsp2 of human ALCP protein can be used with a competitive inhibitor of the discoidin domain of human ACLP protein.

In alternative embodiments, an ACLP inhibitor encompassed for use in the methods and compositions as disclosed herein is a decoy receptor, e.g., a decoy TGFβRII receptor, comprising for example, a non-functional mimetic or fragment of TGFβRII which binds to the PFD of the ACLP protein, thereby preventing or inhibiting the interaction of the PFD domain of the ACLP protein with the TGFβ receptor II (TGFβRII). In some embodiments, such a decoy TGFβRII receptor has at least 80% homology to a region of TGFβRII, or a fragment thereof, which is the binding site for one or more Tsp 11-amino acid repeats of ACLP, or binds at least one Tsp motif (e.g., Tsp2) of ACLP protein. In some embodiments, such a decoy TGFβRII receptor is conjugated or fused to a molecule to increase it stability, and in some embodiments, a decoy TGFβRII receptor is fused to Fc.

One aspect of the present invention relates to compositions and methods of treating cancer and/or fibrosis or other fibroproliferative diseases, in particular, scleroderma with at least one ACLP inhibitor, where the ACLP inhibitor decreases or inhibits the function of the PFD domain or the discoidin domain of mammalian ACLP protein, e.g., human ACLP protein. In some embodiments, the method comprises administering to a subject an inhibitor of at least one Tsp motif in the PFD domain, alone, or in combination with an inhibitor of the discoidin domain of mammalian ACLP, e.g., human ACLP protein.

Furthermore, the inventors also demonstrate herein that ACLP is expressed and secreted from Cancer-Associated Fibroblast (CAF) cells in mammalian breast tumors, and elevated ACLP expression correlates with poor cancer prognosis and increases the chance of relapse in a subject with breast cancer (e.g., subjects with Her 2+ breast cancer). Moreover, the inventors also demonstrate herein that ACLP protein is detected in the fibrotic core of a solid tumor and contributes to altering epithelial cell phenotype in the tumor. Accordingly, another aspect of the present invention relates to methods and compositions for the treatment of cancer, e.g., breast cancer and other epithelial cancers, and method to reduce cancer progression by administering inhibitors of PFD of mammalian ACLP, and/or in combination with inhibitors of discoidin, according to the methods and compositions as disclosed herein.

One aspect of the present invention relates to a method for treating a fibroproliferative disease or disorder, or a cancer in a subject comprising administering to the subject a therapeutically effective amount of a pharmaceutical composition comprising at least one ACLP inhibitor (ACLPi), wherein the ACLP inhibitor inhibits the activity of the pro-fibrotic domain (PFD) of the ACLP polypeptide.

Another aspect of the present invention relates to a composition comprising at least one ACLP inhibitor (ACLPi), where the ACLPi inhibitor inhibits the activity of the pro-fibrotic domain (PFD) of the ACLP polypeptide (e.g., is an inhibitor of the PFD (e.g., a PFDi)), and at least a second ACLP inhibitor, wherein the second ACLP inhibitor inhibits the function of the discoidin (DS) domain of the ACLP polypeptide. In such embodiments, a second ACLP inhibitor is a discoidin inhibitor (DSi). In some embodiments, the composition comprises a pharmaceutically acceptable carrier. In some embodiments, the composition comprises an admixture of a pharmaceutically acceptable amount of a PFDi and a pharmaceutically acceptable amount a DCi.

Another aspect of the present invention relates to a kit comprising at least one ACLP inhibitor (ACLPi), where the ACLPi inhibitor inhibits the activity of the pro-fibrotic domain (PFD) of the ACLP polypeptide (e.g., is an inhibitor of the PFD (e.g., a PFDi)), and at least a second ACLP inhibitor, wherein the second ACLP inhibitor inhibits the function of the discoidin (DS) domain of the ACLP polypeptide, and a container comprising the PFDi and DCi.

In some embodiments, an ACLP inhibitor (ACLPi) is an inhibitor of the PFD (e.g., a PFDi) and in some embodiments, a PFDi is an antibody which binds to a region of the PFD of ACLP polypeptide from amino acids 25-381 of SEQ ID NO: 1. In some embodiments, an ACLP inhibitor binds to at least one Tsp repeat located in amino acid residues 25-381 of SEQ ID NO: 1. In some embodiments, an ACLP inhibitor is an antibody that specifically binds to an epitope on SEQ ID NO: 1 from amino acid residues 121-163, or an antibody or inhibitor which binds to at least 5 consecutive or non-consecutive amino acids in the Tsp2 motif, which comprises KEKPPKATKKPKEKPPKATKKPKEKPPKATKKPKEKPPKATKKP (SEQ ID NO: 4). In some embodiments, an ACLP inhibitor binds to at least part of the amino acid sequence KEKPPKATKKP (SEQ ID NO: 3), which is a 11-amino acid unique repeat in Tsp2 motif of the PFD.

In alternative embodiments, an ACLP inhibitor is a peptide or peptide analogue that inhibits the binding of the PFD of ACLP polypeptide to a member of the TGFβ receptor superfamily, e.g., TGFβ R II or BMP RI. In some embodiments, the peptide comprises at a portion of amino acids 25-381 of SEQ ID NO: 1, and in some embodiments, the ACLPi can comprise at least 5 consecutive amino acid of KEKPPKATKKPKEKPPKATKKPKEKPPKATKKPKEKPPKATKKP (SEQ ID NO: 4). In some embodiments, where the ACLP inhibitor is a peptide or polypeptide, the peptide is fused to another protein, e.g., for increased stability, and in some embodiments, the peptide or polypeptide ACLPi (e.g., a ACLPi comprising at least 5 consecutive amino acid of KEKPPKATKKPKEKPPKATKKPKEKPPKATKKPKEKPPKATKKP (SEQ ID NO: 4)) can be fused to Fc or fragment of SEQ ID NO: 48.

In all aspects herein, the method for treating a fibroproliferative disease or disorder, or a cancer using an ACLPi which inhibits the activity of the pro-fibrotic domain (PFD) of the ACLP polypeptide can further comprise administering a second ACLP inhibitor, wherein the second ACLP inhibitor inhibits the function of the discoidin (DS) domain of the ACLP polypeptide. In such embodiments, a second ACLP inhibitor is a discoidin inhibitor (DSi), and in some embodiments, a DSi is an antibody which specifically binds to at least a region of amino acids 384-539 of SEQ ID NO: 1. In some embodiments, a DSi is an antibody which specifically binds to at least one loop region within amino acids 384-539 of SEQ ID NO: 1, wherein the loop regions are selected from amino acids; MLRHGLG (SEQ ID NO: 12), QTGATED-DYYDGA (SEQ ID NO: 13), DARTQ (SEQ ID NO: 14) or RDSSIHDD (SEQ ID NO: 15).

In all aspects of the present invention, a ACLPi (e.g. a PFDi) or a DSi which is an antibody or antibody fragment is selected from, a monoclonal antibody, a humanized antibody, a human antibody, a single-chain antibody, an antigen binding fragment selected from the group consisting of F(ab')2 fragment of a Fab fragment.

In some embodiments, a second ACLP inhibitor, such as a DCi is a peptide comprising at least 5 amino acids of residues 384-539 of SEQ ID NO: 1, and is, for example, a peptide which comprises at least 5 amino consecutive from at least one of; MLRHGLG (SEQ ID NO: 12), QTGATED-DYYDGA (SEQ ID NO: 13), DARTQ (SEQ ID NO: 14) or RDSSIHDD (SEQ ID NO: 15). In some embodiments, a DCi is a peptide is selected from the group consisting of, MLRHGLG (SEQ ID NO: 12); MLRHGLGA (SEQ ID NO: 16); MLRHGLGAQ (SEQ ID NO: 17); SMLRHGLG (SEQ ID NO: 18); SMLRHGLG (SEQ ID NO: 19); SMLRHGLGA (SEQ ID NO: 20); SMLRHGLGAQ (SEQ ID NO: 21); SSMLRHGLGA (SEQ ID NO: 22); SSMLRHGLGAQ (SEQ ID NO: 23); QTGATED-DYYDGA (SEQ ID NO: 13); QTGATEDDYYDGAW (SEQ ID NO: 24); QTGATEDDYYDGAWC (SEQ ID NO: 25); MQTGATEDDYYDGA (SEQ ID NO: 26); NMQT-GATEDDYYDGA (SEQ ID NO: 27); MQTGATEDDYYD-GAW (SEQ ID NO: 28); MQTGATEDDYYDGAWC (SEQ ID NO: 29); NMQTGATEDDYYDGAW (SEQ ID NO: 30); NMQTGATEDDYYDGAWC (SEQ ID NO: 31); DARTQ (SEQ ID NO: 14); DARTQW (SEQ ID NO: 32); DARTQWI (SEQ ID NO: 33); DDARTQ (SEQ ID NO: 34); EDDARTQ (SEQ ID NO: 35); DDARTQW (SEQ ID NO: 36); DDART-QWI (SEQ ID NO: 37); EDDARTQW (SEQ ID NO: 38); EDDARTQWI (SEQ ID NO: 39); RDSSIHDD (SEQ ID NO: 15); RDSSIHDDF (SEQ ID NO: 40); RDSSIHDDFV (SEQ ID NO: 41); GRDSSIHDD (SEQ ID NO: 42); QGRDSSIHDD (SEQ ID NO: 43); GRDSSIHDDF (SEQ ID NO: 44); GRDSSIHDDFV (SEQ ID NO: 45); QGRDSSIHDDF (SEQ ID NO: 46); or QGRDSSIHDDFV (SEQ ID NO: 47). In some embodiments where a DCi which is a peptide or polypeptide, the peptide or polypeptide is fused to another protein, e.g., for increased stability, and in some embodiments, the peptide or polypeptide DCi is fused to Fc or fragment of SEQ ID NO: 48.

In some embodiments, a peptide or polypeptide inhibitor of ACLP (e.g., PFDi or DCi) comprises one or more ectopic mutations from the sequence from which it is derived.

In all aspects as disclosed herein, a fibroproliferative disease or disorder is selected from a fibroproliferative disorder of the lung, heart, liver, kidney or vasculature. In some embodiments, a fibroproliferative disorder of the kidney is selected from the group consisting of: membranoproliferative glomerulonephritis, diffuse proliferative glomerulonephritis, diabetic nephrology or lupus nephritis. In some embodiments, a fibroproliferative disorder is further characterized by extracellular matrix (ECM) accumulation, and/or is systemic sclerosis (SSc), fibrosis, solid organ fibrosis or scleroderma.

In some embodiments, the present invention provides methods to treat cancer, such as, for example, a solid cancer with a fibrotic core, and/or a cancer of epithelial origin and/or a cancer which has, or is undergoing epithelial to mesenchymal transition (EMT). In some embodiments, the cancer is breast cancer or sarcoma, and in some embodiments, the subject has Her2+ breast cancer. In some embodiments, a subject amenable to treatment is identified to have a cancer which is characterized by increased expression of ACLP (e.g., the subject has been identified to have increased ACLP polypeptide expression in a cancer biopsy or tissue sample obtained from the subject). In all aspects of the invention, the subject is mammalian, e.g., a human subject.

These and other aspects of this invention will be apparent upon reference to the following detailed description. To that end, certain patent and other documents are cited herein to more specifically set forth various aspects of this invention. Each of these documents are hereby incorporated by reference in their entirety.

BRIEF DESCRIPTION OF THE DRAWINGS

FIG. 1A is a schematic of the domains of the human ACLP protein, showing (i) the N-terminal Pro-fibrotic domain (PFD) which interacts with the TGFβRII, comprising four Tsp motifs, (ii) the middle discoidin domain (collagen binding domain which functions to enhance fibroblast EMC contraction and (iii) the C-terminal carboxypeptidase domain (catalytically inactive). A C-terminal myc-His Tag was attached to the mouse recombinant ACLP protein (rA-CLP) assist in the purification of the recombinant ACLP (rACLP) protein (not shown). The second N-terminal Tsp motif (Tsp2) comprises a 4-repeat of a unique 11-amino acid sequence (4×11 amino acid sequence) that is lysine, proline and glutamic acid amino acid rich), FIG. 1B shows recombinant ACLP (rACLP) was purified from conditioned media of AD293 cells stably transfected with an ACLP expression construct. The rACLP protein was washed with a sodium carbonate buffer of pH 10.8 and eluted off the column with buffer containing 250 μM Imidazole. FIG. 1C shows ACLP protein (1 μg) prior to a sodium carbonate wash, 1p g of recombinant ACLP after a sodium carbonate wash, 0.4 ng of TGFβ were analyzed by SDS-PAGE and Western Blot with an antibody against TGFβ. FIG. 1D shows 1p g of rACLP was stained with Coomassie Blue.

FIG. 2A shows IMR90 human lung fibroblast cells were treated in low serum media with 3.75 μg/ml rACLP or 1 nM TGFβ for 48 hours and analyzed by SDS-PAGE and Western blot with antibodies against Collagen I, SMA and GAPDH. FIG. 2B is a graph of the data of FIG. 2A showing the fold increase in SMA expression with recombinant mouse ACLP protein. FIG. 2C shows mouse lung fibroblasts were transfected with either non-targeting control (NTC) siRNA or siRNA targeting ACLP one day after isolation. Protein was harvested 2 days after transfection and analyzed by SDS-PAGE and Western blot with antibodies against ACLP, SMA, collagen and pan-actin. Data presented are representative of 3 separate experiments. FIG. 2D is a graph of the data of FIG. 2C showing the decrease in expression of ACLP, SMA and collagen proteins with siRNA targeting mouse ACLP mRNA.

FIG. 5A is a schematic drawing showing three recombinant mouse ACLP (rACLP) proteins generated; (i) the whole mouse ACLP protein referred to as "ACLP (28-1128)", (ii) the N-terminal PFD of mouse ACLP protein (amino acids 28-373 of mouse ACLP protein) which comprises the four Tsp motifs (Tsp1, Tsp2, Tsp3 and Tsp4) and is referred to as "Tsp (28-373)", and (iii) the C-terminal domain of mouse ACLP protein containing a discoidin domain and a carboxypeptidase domain (amino acids 374-1128 of mouse ACLP protein) and referred to as "C-terminal (374-1128)". FIG. 5B shows mink lung epithelial cells stably transfected with the PAI-1 promoter luciferase construct treated with the indicated amounts of purified N-terminal PFD of ACLP, and FIG. 5C shows mink lung epithelial cells stably transfected with the PAI-1 promoter luciferase construct treated with the indicated amounts of purified C-terminal ACLP. rACLP (3.75 μg/ml) or 1 nM TGFβ were used as controls in FIGS. 5B and 5C. Luciferase activity was measured after 24 hours. Results are plotted as fold change compared to untreated controls. * indicates significance (p<0.05) versus control treated cells. Data representative of 3 separate experiments.

FIG. 8A is a I-TASSER modeling of the N-terminal PFD of human ACLP predicts 4 thrombospondin-like motifs, referred to as Tsp1, Tsp2, Tsp3 and Tsp4. FIG. 8B shows a similar predicted structure as FIG. 8A, showing the highly conserved Tsp2 motif, which is highly conserved across species in blue. Inhibition of one or more of the Tsp motifs, including but not limited to inhibition of Tsp2 is encompassed in the methods and compositions as disclosed herein.

FIGS. 9A-9B shows the anti-ACLP polyclonal antibody generated using the peptide of SEQ ID NO: 8 (TKKPKEKPPKATKKPKEKPPKA), which is a portion of the Tsp2 motif of the human ACLP protein, with the 11-amino acid repeating unit of SEQ ID NO: 3 highlighted by bold underlined). This peptide comprises part of the unique 11-amino acid sequence that is repeated 4 times in Tsp2. This antibody specifically recognizes, and specifically binds to, recombinant fragments of mammalian ACLP protein, including mouse (shown in FIG. 9A) and human recombinant ACLP protein and native human ACLP protein. FIG. 9A shows a Western blot analysis of recombinant protein of the N-terminus of ACLP and a deletion mutant which lacks the epitope. FIG. 9B shows the polyclonal antibody recognition of endogenous mouse ACLP protein in total cell lysates or conditioned media from mouse vascular smooth muscle cells (MASMC).

FIG. 10 is a schematic showing the interaction of the pro-fibrotic domain (PFD) (showing the four Tsp motifs) of ACLP with the TGFβ receptor (TGFβRII). Tsp2 comprises a unique 11-aa sequence which is repeated four times. An ACLP inhibitor encompassed for use in the methods, compositions and kits as disclosed herein can prevent the interaction of the pro-fibrotic domain (PFD) of ACLP with the TGFβ receptor (TGFβRII). Such an inhibitor can, for example, bind to at least one or more of, (i) TGFβRII at the ACLP binding site (i.e., serving as a competitive inhibitor), or (ii) one or more Tsp motifs in the PFD of ACLP protein (including but not limited to the Tsp2 motif) thereby preventing the PFD from interacting with a member of the TGFβ R superfamily (e.g., TGFBRII or BMP RII), or (iii) a portion, such as a loop region, of the discoidin domain of ACLP protein thereby serving as non-competitive inhibitor of ACLP, or (iv) interacting and binding to the ACLP protein at a site independent of the PFD (or a Tsp motif), thereby inducing a stoichiometric change in the ACLP protein to change the conformation of the Tsp motif to decrease the binding affinity of the PFD with a member of the TGFβ R superfamily (e.g., TGFBRII or BMP RII).

FIG. 11A shows that TGFβ receptor-Fc (TOR-Fc) decoy decreases pSmad3 expression in the presence of mouse rACLP in IMR90 human lung fibroblast cells treated for 90 mins. FIG. 11B shows that TGFβ receptor-Fc (TOR-Fc) decoy decreases ACLP-induced SMA and SM-MHC expression in the presence of rACLP in human lung fibroblast cells treated for 48 hours.

FIGS. 12A-12B shows the sequence of domains of human ACLP protein. FIG. 12A is a multiple sequence alignment of the amino acid sequence of mammalian ACLP proteins generated by Clustal W. Shown are the alignment of human ACLP (hum-ACLP), mouse ACLP (mus-ACLP), rat ACLP (rat-ACLP) and *Macaca fascicularis* ACLP (cyn-ACLP), showing homology of the 3 domains, the PFD, the discoidin domain and the C-terminal carboxypeptidase domain. The N-terminal pro-fibrotic domain (PFD) is shown in red, comprising the four Tsp motifs. Tsp 2, which comprises 4×11 amino acid unique sequence repeat is underlined and in italics. The discoidin (DS) domain is shown in green, and the inactive C-terminal carboxypeptidase (also known as metallocarboxypeptidase) domain is shown in purple text. The amino acids underlined in the discoidin and carboxypeptidase regions can optimally be N-linked glycosylated. The last row shows homology between sequences, where "*" is identity, with ":"and"." indicating descending similarity. FIG. 12B shows the sequence of human ACLP protein of SEQ ID NO: 1, showing (i) the amino acids of the PFD (underlined) comprising the Tsp2 motif (bold), (ii) the amino acids of the discoidin (DS) domain comprising the 4 loop regions (underlined bold), and (iii) the amino acids of the C-terminal domain of human ACLP protein.

FIGS. 13A-13C show the structure and sequence of discoidin domain (DS) of ACLP, and that inhibitors that have binding affinity to the DS are useful in combination with inhibitors to the PFD of ALCP. FIG. 13A shows the predicted structure of the human ACLP discoidin (DS) domain (Swiss-Model) showing the 4 loops (1-4) on one face of the DS domain, which are binding site targets for inhibitors the discoidin domain of the ACLP protein. FIG. 13B shows the alignment of a portion of the Discoidin domain of DDR1, DDR2, human ACLP and Factor V (FV) by Clustal W, indicating the variability of the loops 1-4, shown in boxes. Accordingly, inhibitor that bind to any one, or more, of loops 1, 2, 3, or 4 of the discoidin domain of human ACLP are encompassed for use in the compositions, methods and kits as disclosed herein, and can be used alone, or in combination with an inhibitor which binds to at least one region in the PFD, e.g., an inhibitor which bind to at least one or more of Tsp1, Tsp2, Tsp3 or Tsp4. FIG. 13C shows the discoidin (DS) domain of ACLP enhances myofibroblast differentiation in the presence of collagen. While in normal in vitro assays the discoidin domain is normally non-functional, the inventors surprisingly demonstrate, that in the presence of collagen (and on a tissue stiffness similar to that of fibrotic tissue), the discoidin domain potentiates TGFβRII signaling. Such discoidin-mediated potentiating of TGFβ signaling did not occur in the absence of collagen. Collagen gels of 4 and 25 kPa were coated overnight with 23 nM rACLP or discoidin (DS, referred to as Disc in the drawing) protein in DPBS at 37° C. Mouse IMR90 fibroblasts were plated on gels, allowed to adhere and grown in 0.5% FBS DMEM for 48 hrs. Protein was harvested and analyzed by SDS-PAGE and Western blot with antibodies against collagen I, SMA and GAPDH.

FIG. 14 shows elevated ACLP levels correlate with reduced relapse free survival in breast cancer patients. Kaplan-Meier survival curves of low vs. high ACLP expression plotted versus probability of relapse free survival (RFS) on Her2+ breast tumors (n=127). Data were generated using KM plotter.

FIG. 15A shows a Western blot of ACLP expression in normal mammary fibrosis and CAF. FIG. 15B shows in ACLP expression by Western blot in condition media from CAF. FIG. 15C shows mouse Her2+ ductal carcinomas stained with anti-ACLP, showing significant ACLP expression in the tumor margin and in the fibrotic/necrotic core.

DETAILED DESCRIPTION

As discussed herein, the present invention provides methods and compositions comprising use of an ACLP inhibitor, in particular an inhibitor of the pro-fibrotic domain (PFD) of ACLP, for the treatment of cancer and other proliferative diseases, such as, for example, fibrosis, or scleroderma. In some embodiments, an inhibitor which binds to at least part of the PFD, e.g., to one or more of the Tsp motifs in the PFD, can be used in combination with an inhibitor which binds to at least part of the discoidin (DS) domain of ACLP, e.g., for the treatment of cancer and other proliferative diseases, such as, for example, fibrosis, or scleroderma.

Previously, the inventors have previously identified a large collagen-binding secreted protein, aortic carboxypeptidase-like protein (ACLP), which is expressed highly in human fibrotic lungs and its absence in mice protects against experimentally induced lung fibrosis. Herein, the inventors have discovered the mechanisms of ACLP action as both a collagen binding protein, which alters matrix structure, and as TGFβ receptor dependent and independent signaling activator. Importantly, the inventors have therefore discovered that ACLP as a novel profibrotic molecule that accelerates multiple non-inflammatory aspects of fibrosis including collagen and myofibroblast contractile gene expression, cell proliferation, and collagen matrix contraction. Based on these discoveries, inhibition of ACLP will reduce the generation of matrix producing cells leading to a delay in SSc disease progression. The inventors have localized this effect to a discrete N-terminal domain which can be disrupted with antibodies or small molecules.

In particular, the present invention relates to inhibitors of the ACLP protein to inhibit fibroproliferation in diseases including cardiovascular, cancer, and fibrosis (including solid organ and scleroderma). Specifically, the inventors have discovered a defined region of the ACLP protein that stimulates transforming growth factor signaling. Accordingly, the inventors have discovered the ability to specifically inhibit ACLP action/function, they can use inhibitors, such as, for example peptides or blocking antibodies generated against the N-terminal domain, which is a pro-fibrotic domain (PFD). In addition, the present invention also encompasses blocking peptides or small molecules to inhibit ACLP induced stimulation of fibrotic changes.

ACLP (gene name AEBP1) is highly expressed in many fibroproliferative states and cancer. Previous published studies indicate that an absence of ACLP protects against experimental fibrosis.

Figure 8A:
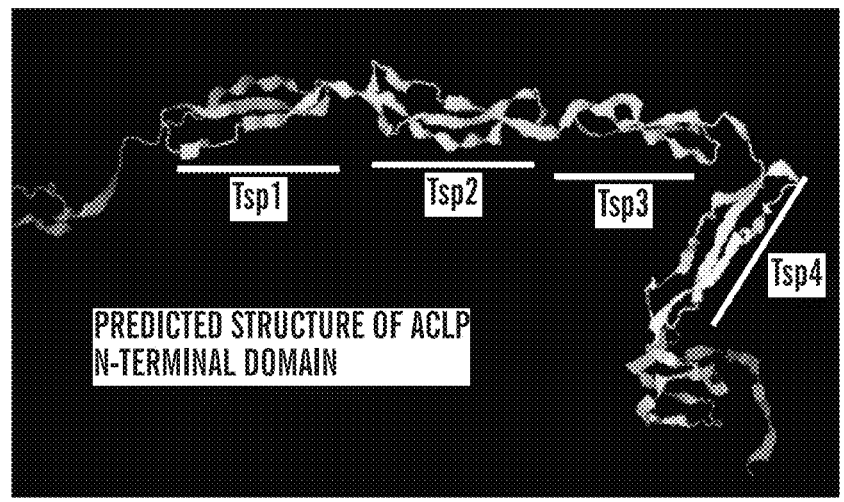
FIGS. 8A-8B shows the predicted structure of the N-terminus PFD of human ACLP protein.
Figure 8B:
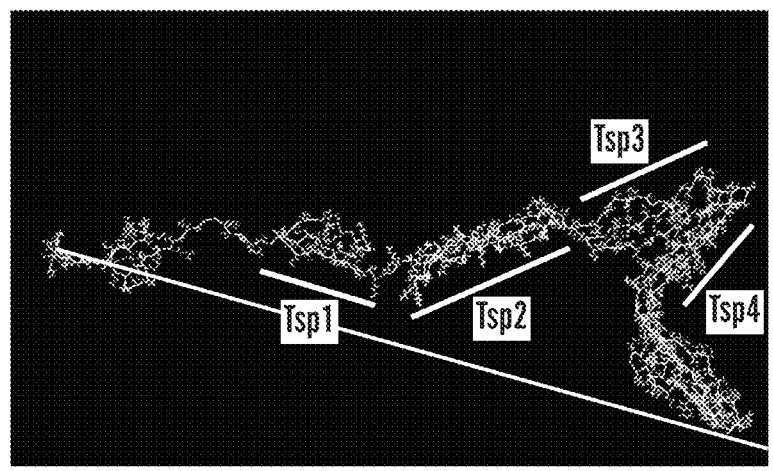
Figure 13A:
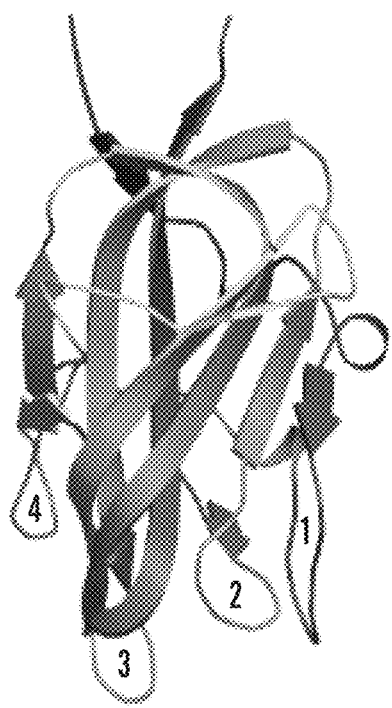
Figure 13C:
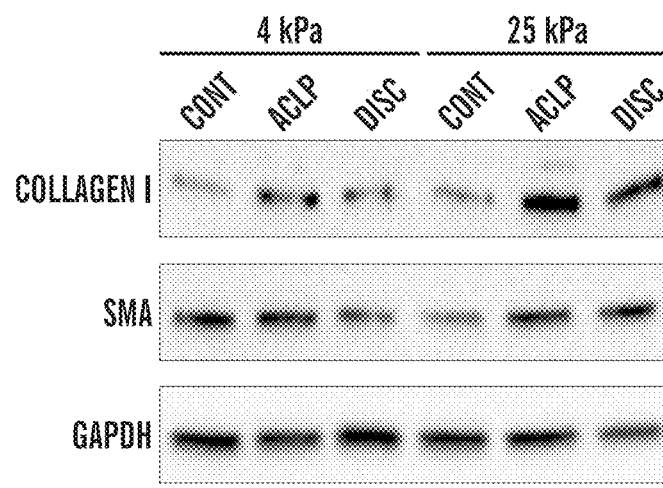

Herein, the inventors have generated a predicted structure of the N-terminus of ACLP and determined that it folds into a thrombospondin fold (e.g., see FIG. 8A-8B). Signaling experiments determined that the N-terminus PFD is necessary and required to activate pro-fibrotic TGFβ signaling (FIG. 5A), and that the discoidin (DS) domain can enhance or potentiate such TGFβ signaling (FIG. 13C).

Figure 6:
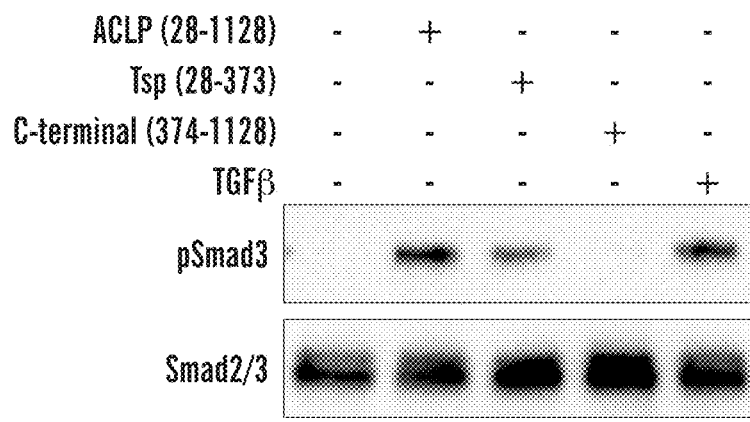
FIG. 6 shows the N-terminal PFD of mACLP induces Smad3 phosphorylation in human cells. IMR90 human lung fibroblasts were serum starved overnight and treated with 30 nM of full length ACLP, purified N-terminal PFD domain, purified C-terminal domain, or 1 nM TGFβ for 30 min. Protein lysate was harvested and analyzed by Western blot with antibodies against phospho-Smad3 and total Smad2/3. Data presented are representative of 3 separate experiments.
Figure 7:
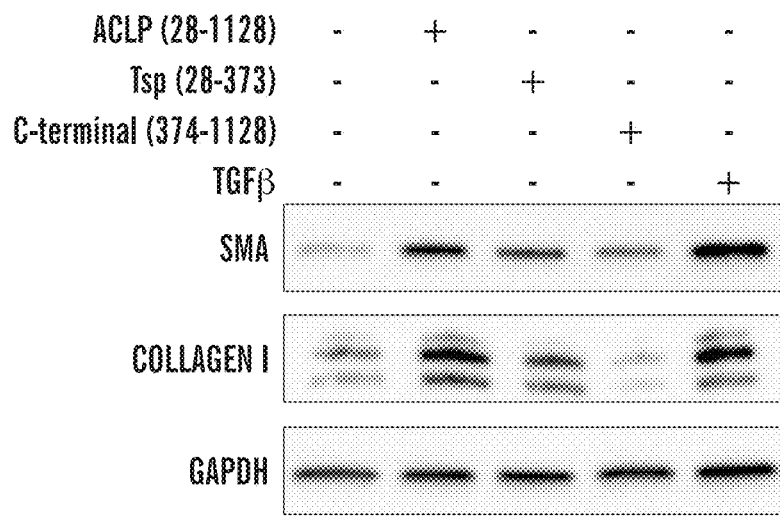
FIG. 7 shows the N-terminal PFD of mACLP induces SMA and collagen protein expression in human cells. IMR90 human lung fibroblasts were treated with 30 nM of full length ACLP, purified N-terminal PFD, purified C-terminal domain, or 1 nM TGFβ for 48 h. Protein lysate was harvested and analyzed with antibodies against SMA, collagen 1, and GAPDH. Data presented are representative of 3 separate experiments.

The inventors have demonstrated that in human IMR90 cells, that elimination of this domain reduced TGFβ-SMAD signaling and inhibited smooth muscle actin and collagen expression (FIGS. 6 and 7). Taken together, the inventors have discovered a novel mechanism driving profibrotic changes and developed a novel strategy to inhibit ACLP action to reduce fibroproliferation. Inhibitors of ACLP encompassed for use in this invention include, but are not limited to includes antibodies, peptides, and small molecule that inhibit the function of the N-terminal pro-fibrotic domain (PFD) of ACLP.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "ACLP inhibitor" generally refers to an agent or molecule that inhibits the activity or expression of ACLP. ACLP inhibitors can be of synthetic or biological origins. They can be, for example, organic or inorganic molecules (e.g., small molecules), peptides, antibodies or antisense RNA that inhibit the function and/or expression of ACLP. Inhibitors of ACLP as disclosed herein encompass chemical entities or molecules that can inhibit expression of ACLP and/or biological activity of ACLP. In some embodiments, an ACLP inhibitor is an inhibitor or entity which binds to at least one Tsp motif in the PFD of ACLP and inhibits the PFD domain from interacting with a member of the TGFβ receptor superfamily. In some embodiments, a ACLP inhibitor for use in the method, compositions and kits as disclosed herein is an inhibitor or entity which binds to a part of the discoidin (DS) domain of ACLP. One or more ACLP inhibitors can be used together, e.g., an ACLP inhibitor which binds to one or more Tsp motifs in combination with an ACLP inhibitor which binds to a region of the discoidin domain of the ACLP protein. ACLP inhibitors include, for example but are not limited to, RNAi agents, antisense nucleic acids, dominant negative proteins (decoy molecules), large polypeptides, or modified RNA (modRNA) which express decoy proteins, and enantiomers, prodrugs, derivatives and pharmaceutically acceptable salts thereof, which are discussed further in the section.

The term "PFD inhibitor" or "PFDi" generally refers to an agent or molecule that inhibits the pro-fibrotic domain (PFD) of the ACLP protein, e.g., inhibits ACLP-mediated TGFβ signaling. In some embodiments, a PFDi binds to the PFD domain, and/or prevents the PFD domain from interacting with a member of the TGFβ receptor superfamily. In some embodiments, a PFDi binds to the PFD-binding site on a ligand, e.g., the PFD binding site on a member of the TGFβ R superfamily domain and/or prevents the PFD domain from interacting with a member of the TGFβ receptor superfamily. PFD inhibitors can be of synthetic or biological origins. They can be organic, or inorganic molecules (e.g. small molecules), or peptides, antibodies (e.g., blocking or neutralizing antibodies), antibody fragments and antigen binding proteins that inhibit the activity of the pro-fibrotic domain (PFD) of ACLP. Inhibitors of PFD encompassed for use herein can be chemical entities or molecules that can inhibit the biological activity of the pro-fibrotic domain of ACLP. PFD inhibitors include, for example, dominant negative proteins (decoy molecules), large polypeptides, or modified RNA (modRNA) which express decoy proteins, and enantiomers, prodrugs, derivatives and pharmaceutically acceptable salts thereof, which are discussed further in the section.

The term "discoidin inhibitor" or "DSi" generally refers to an agent or molecule that inhibits the discoidin (DS) domain of the ACLP protein. DS inhibitors can be of synthetic or biological origins. They can be organic, or inorganic molecules (e.g. small molecules), or peptides, antibodies (e.g., blocking or neutralizing antibodies), antibody fragments and antigen binding proteins that inhibit the activity of the pro-fibrotic domain (PFD) of ACLP. Inhibitors of DS encompassed for use herein include chemical entities or molecules that can inhibit the biological activity of the discoidin domain of ACLP in the presence of collagen. DS inhibitors include, for example, antibodies or antibody fragments, antigen binding proteins, dominant negative proteins (decoy molecules), large polypeptides, or modified RNA (modRNA) which express decoy proteins etc.

The term "antagonist" is used herein to refer a compound or moiety that reduces a biological activity of another compound. Within the present invention, an "ACLP antagonist" is a compound that reduces the signaling or biological activity (e.g., activation of TGFβ and/or profibrotic activity) of ACLP in a target cell, tissue, or organism. Antagonists may exert their action by competing with ACLP for binding sites on a cell-surface receptor, by binding to ACLP, e.g., to the PFD domain and preventing it participating in cell signaling, or by otherwise interfering with receptor function, by reducing production of ACLP, or by other means. An antagonist is also referred to as an inhibitor. An ACLP antagonist can be determined by one of ordinary skill in the art as a molecule or entity that inhibits ACLP-mediated TGFβRII signaling as compared to in the absence of such an inhibitor.

The term TGF beta receptor superfamily, also referred to as TGFβ receptor superfamily includes, comprises two groups, the type I and the type II serine/threonine kinases, which are type I transmembrane proteins, and the two subgroups (Type I and type II) are distinguished by the presence of a glycine/serine-rich juxta-membrane domain found in the type I receptors. Whether the type I or the type II receptorbinds first is ligand-dependent, and the second type I or type II receptor is then recruited to form a heteromeric signaling complex. A functional receptor complex has one dimeric ligand interacting with two type I and two type II receptors. Type I receptors are referred to as the Activin-like Kinases (ALKs), while the type II receptors are named for the ligands they bind. The TGFβR superfamily is summarized as follows in Table 1.

TABLE 1

| TGFB type II Receptor | TGFB Type I Receptor | Ligand | Co-receptor |
|---|---|---|---|
| TGFβRII | ALK-5 | TGFβ | Betaglycan (TGF-β2+), endoglin (ALK-1 specific), CD109 |
|  | ALK-2 |  |  |
|  | ALK-1 |  |  |
| Act RII/IIB | ALK-4 | Activin |  |
|  | ALK-2 |  |  |
| Act RII/IIB BMP RII/IIB |  | Inhibin | Betaglycan |
| BMP RII/IIB | ALK-1 | BMP | RGM-A, RGM-B, RGM-C |
|  | ALK-2 |  |  |
|  | ALK-3 |  |  |
|  | ALK-6 |  |  |
| Act RII/IIB | ALK-4 | BMP | RGM-A, RGM-B, RGM-C |
|  | ALK-5 |  |  |
|  | ALK-7 |  |  |
|  | ALK-2 |  |  |
| BMP RII | ALK-5 | GDF | Crypto (GDF1, GDF-3) |
|  | ALK-6 |  |  |
| Act RII/IIB | ALK-4 |  |  |
|  | ALK-5 |  |  |
|  | ALK-6 |  |  |
| Act RII/IIB | ALK-4 | Nodal | Crypto+ |
|  | ALK-7 |  |  |
| Act RII/IIB |  | Lefty | Crypto (+nodal) |
| MIS RII | ALK-2 | MIS |  |
|  | ALK-3 |  |  |
|  | ALK-6 |  |  |

The term "extracellular matrix" or "ECM" is a complex mixture of macromolecules and proteins that accumulates within tissues and bone. EMC which is close to the cell surface is often referred to as "matricellular" and is included in the definition of EMC. ECM contains secreted macromolecules such as collagens I, III and IV; fibronectin; laminins; and various proteoglycans. These macromolecules can be organized to provide cohesion to the tissue and can contribute to its structural and mechanical properties.

An "inhibitory polynucleotide" is a DNA or RNA molecule that reduces or prevents expression (transcription or translation) of a second (target) polynucleotide. Inhibitory polynucleotides include antisense polynucleotides, ribozymes, and external guide sequences. The term "inhibitory polynucleotide" further includes DNA and RNA molecules, e.g., RNAi that encode the actual inhibitory species, such as DNA molecules that encode ribozymes.

As used herein, "gene silencing" or "gene silenced" in reference to an activity of an RNAi molecule, for example a siRNA or miRNA refers to a decrease in the mRNA level in a cell for a target gene (e.g. ACLP mRNA) by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene. By way of an example only, in some embodiments RNAi agents which serve to inhibit or gene silence are useful in the methods, kits and compositions disclosed herein to inhibit the ACLP mRNA.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "gene product(s)" as used herein refers to include RNA transcribed from a gene, or a polypeptide encoded by a gene or translated from RNA.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

When "decrease" or "inhibition" is used in the context of the level of expression or activity of a gene (e.g., ACLP gene) or a protein, (e.g. ACLP protein) herein, it refers to a reduction in protein or nucleic acid level or activity in the ECM. For example, such a decrease may be due to reduced RNA stability, transcription, or translation, increased protein degradation, or RNA interference. In some embodiments, an ACLP or PFD inhibitor which is a small-molecule as disclosed herein can decrease the activity or expression of ACLP protein. Preferably, this decrease is at least about 5%, at least about 10%, at least about 25%, at least about 50%, at least about 75%, at least about 80%, or even at least about 90% of the level of expression or activity under control conditions. The term "level" as used herein in reference to ACLP refers to expression or activity of ACLP.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

The term "fragment" of a peptide, polypeptide or molecule as used herein refers to any contiguous polypeptide subset of the molecule. The term "protein fragment" as used herein includes both synthetic and naturally-occurring amino acid sequences derivable from the naturally occurring amino acid sequence. Accordingly, a "fragment" of a molecule, is meant to refer to any polypeptide subset of the molecule.

The term "non-functional" as used herein in conjunction with a "non-functional TGFβ receptor" refers to a polypeptide which comprises at least a portion of the TGFβ receptor, but is not the full-length TGFβ protein and does not retain the natural function of TGFβ receptor of triggering TGFβ signalling. In some embodiments, a non-functional TGFβ receptor can bind to, and inhibit the pro-fibrotic domain (PFD). In some embodiments, a non-functional TGFβ receptor is a fragment of the TGFβ receptor which interacts with PFD, and in some embodiments, such a non-functional TGFβ receptor fragment comprises an ectopic mutation or amino acid change that allows it to still binds to the PFD of the ACLP protein, thereby preventing ACLP-mediated intracellular signaling, including activation of TGFβ signalling. In some embodiments, the term "non-functional" as used herein in conjunction with a "non-fragment of ACLP" refers to a polypeptide which comprises at least a portion of the ACLP protein of SEQ ID NO:1 but cannot bind to TGFβ RII and/or does not retain the natural function of ACLP of triggering TGFβ signalling. In some embodiments, a non-functional fragment of ACLP comprises a mimetic of the pro-fibrotic domain (PFD) which has an ectopic mutation or amino acid change that allows it to still binds to the native receptor of ACLP (e.g., TGFβRII) but does not allow ACLP-mediated intracellular signaling, including activation of TGFβ signalling.

The term "linker" refers to any means to join two or more entities, for example anon-functional fragment of ACLP (e.g., comprising a portion of pro-fibrotic domain (PFD) polypeptide with a ectopic mutation) as disclosed herein with a first fusion partner (e.g. Fc). A linker can be a covalent linker or a non-covalent linker. Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like.

To provide for linking, the effector molecule and/or the probe can be modified by oxidation, hydroxylation, substitution, reduction etc. to provide a site for coupling. It will be appreciated that modification which do not significantly decrease the function of a decoy receptor (e.g., decoy TGFβII receptor), or a decoy ligand (e.g., non-functional PFD mimetic) or other peptide inhibitor (e.g., peptide of a loop of discoidin domain e.g., peptide of SEQ ID NO: 12-47), as disclosed herein or the first fusion partner (e.g. Fc) are preferred.

The term "antibody" is meant to include any of a variety of forms of antibodies that specifically bind an antigen of interest, including complete antibodies, fragments thereof (e.g., F(ab')2, Fab, etc.), modified antibodies produced therefrom (e.g., antibodies modified through chemical, biochemical, or recombinant DNA methodologies), single chain antibodies, and the like, with the proviso that the antibody fragments and modified antibodies retain antigen binding characteristics sufficient to facilitate specific detection of an antigen of interest (e.g., PFD and DS domains of ACLP). The term "antibody" is meant to be an immunoglobulin protein that is capable of binding an antigen. Antibody as used herein is meant to include antibody fragments, e.g. $F(ab')_2$, Fab', Fab, capable of binding the antigen or antigenic fragment of interest.

The term "labeled antibody", or "detectably labeled" as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of biomarkers present in the tissue samples correlate to the intensity of the signal emitted from the detectably labeled antibody.

The terms "monoclonal antibody" (mAb) or "monoclonal antibody composition" as used herein refer to a preparation of antibody molecules of single molecular composition. A monoclonal antibody composition displays a single binding specificity and affinity for a particular epitope.

The term "epitope" means a protein determinant present on the surface of a peptide or polypeptide capable of being specifically bind by an antibody or antigen-binding moiety or molecule. Epitopes can comprise amino acids (e.g., consecutive and non-consecutive amino acids), and sometimes also comprise of chemically active surface groupings of molecules such as amino acids or sugar side chains and usually have specific three dimensional structural characteristics, as well as specific charge characteristics.

The phrases "an antibody recognizing an antigen" and "an antibody specific for an antigen" are used interchangeably herein with the term "an antibody which binds specifically to an antigen" or "an antibody which binds specifically to an epitope"

The term "antigen-binding moiety" is used interchangeably herein with "antigen-binding molecule" or"protein binding entity" and refers to any entity which has specific affinity for a protein, e.g., any entity or agent that can specifically bind to an epitope on a polypeptide (e.g., ACLP). Antigen-binding molecules are not limited to polypeptides, but also include small molecules, antibody-based binding moieties, immunoglobulin molecules and immunologically active determinants of immunoglobulin molecules, e.g., molecules that contain an antigen binding site which specifically binds (immunoreacts with) to a portion of the ACLP protein.

The term "antigen-binding portion" of an antibody (or simply "antibody portion"), as used herein, refers to one or more fragments of an intact antibody that retain the ability to specifically bind to an antigen (e.g., an antigen which binds a lectin,) or retains the ability to displace a bound lectin molecule from a glycoprotein. It has been shown that the antigen-binding function of an antibody can be performed by fragments of a full-length antibody. Examples of binding include (i) a Fab fragment, a monovalent fragment consisting of the VL, VH, CL and CH1 domains; (ii) a F (ab)'2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341: 544-546), which consists of a VH domain; and (vi) an isolated complementarity determining region (CDR); and (vii) a nanobody, a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Huston et al (1988) Proc. Natl. Acad. Sc USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

The term "fragments" as used with respect to "antibody fragments" refer to sequences sharing at least 40% amino acids in length with the respective sequence of the intact or full length anti-ACLP antibody, e.g., monoclonal antibodies (native). These sequences can be used as long as they exhibit the same properties as the native sequence from which they derive. Preferably these sequences share more than 70%, preferably more than 80%, in particular more than 90% amino acids in length with the respective sequence the intact or full length anti-ACLP antibody, e.g., monoclonal antibodies. In some embodiments, the term "fragments" as used herein, when used in reference to fragments anti-ACLP monoclonal antibodies, or monoclonal antibody fragments or antigen binding portions or fragments usually refers to a portion of at least 2, or at least about 5, or at least about 6, or at least about 8, or at least about 10 or more consecutive amino acids of the epitope binding region of an antibody. In some embodiments, a fragment includes at least 2, or at least about 5, or at least about 6, or at least about 8, or at least about 10 or more consecutive amino acids of the epitope binding region of an anti-ACLP antibody. In some embodiments, a fragment is a CDR region. In the case of an anti-ACLP antibody, e.g., monoclonal antibody of the invention, useful fragments include, but are not limited to: a CDR region, especially a CDR3 region of the heavy or light chain; a variable domain of a heavy or light chain; a portion of an antibody chain or just its variable region including two CDRs; and the like.

Suitable anti-ACLP antibodies, e.g., monoclonal antibody, or fragments of the invention are immunologically functional immunoglobulins. The term "immunologically functional immunoglobulin fragment" as used herein refers to a polypeptide fragment that contains at least a CDR of the immunoglobulin heavy and/or light chains. An immunologically functional immunoglobulin fragment of the invention is capable of specifically binding to at least Tsp repeat in the PFD of the human ACLP protein. In some embodiments, a fragment of an anti-ACLP can bind specifically to and/or modulate the biological activity of a glycoprotein, where the glycoprotein is located in the PFD of the human ACLP protein. In some embodiments, an immunologically functional immunoglobulin fragment specifically binds to a glycoprotein at the PFD of the ACLP protein.

As used herein, "specific binding" or "specifically binds" or "binds specifically" refers to antibody binding to a predetermined antigen. Typically, the antibody binds with a affinity constant (KD) of $10^{-6}$ M or a higher affinity for the Fab fragment, and binds to the predetermined antigen with a KD that is at least ten-fold less than its KD for binding to a non-specific antigen (e. g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The term "Kassoc" or "Ka", as used herein, is intended to refer to the association rate of a particular antibody-antigen interaction, whereas the term "Ks" or "Kd" is intended to refer to the dissociation rate of a particular antibody-antigen interaction. The term "high affinity" for an IgG antibody refers to an affinity constant (KD) for the Fab fragment of at least about $10^{-6}$ M, at least about $10^{-7}$ M, at least about $10^{-8}$ M, at least about $10^{-9}$ M, at least about $10^{-10}$ M, at least about $10^{-1}$ M, or at least about $10^{-12}$ M, or at least about $10^{-13}$ M, or at least about $10^{-4}$ M, or at least about $10^{-15}$ M or greater, e. g., up to $10^{-16}$M or $10^{-17}$ M or greater. However, "high affinity" binding can vary for other antibody isotypes.

The term "humanized antibody" is used herein to describe complete antibody molecules, i.e. composed of two complete light chains and two complete heavy chains, as well as antibodies consisting only of antibody fragments, e.g. Fab, Fab', F(ab')$_2$, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human subject.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species. In some embodiments, a variable region is derived from a non-human mammalian species and the constant region is derived from a human species. Specifically, the chimeric antibody is preferably produced from a 9 nucleotide sequence from a non-human mammal encoding a variable region and a nucleotide sequence from a human encoding a constant region of an antibody.

The terms "subject" and "individual" are used interchangeably herein, and refer to an animal, for example a human, to whom treatment for cancer or a proliferative disorder, including therapeutic treatment or prophylactic treatment, with a pharmaceutical composition comprising an inhibitor ACLP or PFD as disclosed herein can be administered. The term "subject" as used herein includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term "non-human animals" includes all vertebrates, e.g., mammals, such as non-human primates, (particularly higher primates), sheep, dog, rodent (e.g. mouse, rat, guinea pig), goat, pig, cat, rabbits, cows, and non-mammals such as chickens, amphibians, reptiles etc. In one embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. In one embodiment, the subject is human. In another embodiment, the subject is an experimental animal or animal substitute as a disease model, including transgenic non-human animal species.

The term "tissue" is intended to include intact cells, blood, blood preparations such as plasma and serum, bones, joints, muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, or other affection.

The term "cancer" and "malignancy" are used interchangeably herein, refers to diseases that are characterized by uncontrolled, abnormal growth of cells. In some embodiments, the term cancer encompasses cancer cells which have spread locally or through the bloodstream and lymphatic system to other parts of the body, referred to herein as "metastatic cancer". The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the terms "metastases" or "metastatic tumor" "metastatic cancer" are used interchangeably herein and refer to a secondary tumor that grows separately elsewhere in the body from the primary tumor and has arisen from detached cancer cells from the primary tumor which have been transported to a separate location, and where the primary tumor is a solid tumor. The primary tumor, as used herein, refers to a tumor that originated in the location or organ in which it is present and did not metastasize to that location from another location. As used herein, a "malignant tumor" or "metastatic cancer" is one having the properties of invasion and metastasis and showing a high degree of anaplasia. Anaplasia is the reversion of cells to an immature or a less differentiated form, and it occurs in most malignant tumors.

As used herein, the terms "treat" or "treatment" or "treating" refers to therapeutic treatment, wherein the object is to prevent or slow the development of the disease, such as slow down the development of a tumor, the spread of cancer, or reducing at least one effect or symptom of a condition, disease or disorder associated with inappropriate proliferation or a cell mass, for example cancer. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop secondary tumors due to metastasis.

The terms "treat" and "treatment" are used broadly to denote therapeutic and prophylactic interventions that favorably alter a pathological state. Treatments include procedures that moderate or reverse the progression of, reduce the severity of prevent, or cure a disease.

In particular, the term "prophylactic treatment" refers to the prevention of the development of cancer in a subject when the subject is at a high risk of developing cancer, such as, for example, a predisposition to cancer where the subject has a genetic mutation or polymorphism known to increase occurrence of a cancer, or a family history of cancer. In some embodiments, prophylactic treatment is used in a subject who has been successfully therapeutically treated for cancer and where the cancer has been eliminated or the subject has gone into remission, and is administered prophylactic treatment with comprising an ACLP inhibitor (e.g., an inhibitor of the pro-fibrotic domain of ACLP) to prevent a cancer relapse.

The term "effective amount" as used herein refers to the amount of therapeutic agent of a comprising an ACLP or PFD inhibitor as disclosed herein, to alleviate at least one or more symptom of the disease or disorder, and relates to a sufficient amount of pharmacological composition to provide the desired effect, e.g., to stop or reduce or lessen at least one symptom of the disease or disorder or cancer. The phrase "therapeutically effective amount" as used herein, e.g., a pharmaceutical composition comprising at least one ACLP or PFD inhibitor as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylactically significant reduction in a symptom or clinical marker associated with a cancer or a cancer-mediated condition.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

With reference to the treatment of a subject with a cancer with a pharmaceutical composition comprising at least one inhibitor of ACLP or PFD as disclosed herein, the term "therapeutically effective amount" refers to the amount that is safe and sufficient to prevent or delay the development and further growth of a tumor or the spread of metastases in cancer patients. The amount can thus cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastases. The effective amount for the treatment of cancer depends on the tumor to be treated, the severity of the tumor, the drug resistance level of the tumor, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of cancer and tumor, for example treatment of a rodent with a cancer, and any treatment or administration of the compositions or formulations that leads to a decrease of at least one symptom of the cancer, for example a reduction in the size of the tumor or a slowing or cessation of the rate of growth of the tumor indicates effective treatment. In embodiments where the compositions are used for the treatment of cancer, the efficacy of the composition can be judged using an experimental animal model of cancer, e.g., wild-type mice or rats, or preferably, transplantation of tumor cells. When using an experimental animal model, efficacy of treatment is evidenced when a reduction in a symptom of the cancer, for example a reduction in the size of the tumor or a slowing or cessation of the rate of growth of the tumor occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the term "treating" when used in reference to a cancer treatment is used to refer to the reduction of a symptom and/or a biochemical marker of cancer, for example a reduction in at least one biochemical marker of cancer by at least about 10% would be considered an effective treatment. Common examples of such biochemical markers of cancer include, but are not limited to, CD44, telomerase, TGF-α, TGF-β, erbB-2, erbB-3, MUC1, MUC2, CK20, PSA, CA125 and FOBT, but any biochemical marker for a specific cancer can be used as a marker of treating by one of ordinary skill in the art. In some embodiments, biomarkers of fibroproliferative diseases include PAR-2, TGF-01, TNF-α and IL-4Rα, and other biomarkers as disclosed in Karsdal et al, Aliment Pharmacol Ther. 2014 August; 40(3):233-49; The efficacy of biomarkers in chronic fibroproliferative diseases—early diagnosis and prognosis, with liver fibrosis as an exemplar, which is incorporated herein in its entirety by reference. A reduction in the rate of proliferation of the cancer cells by at least about 10% would also be considered effective treatment by the methods as disclosed herein. As alternative examples, a reduction in a symptom of cancer, for example, a slowing of the rate of growth of the cancer by at least about 10% or a cessation of the increase in tumor size, or a reduction in the size of a tumor by at least about 10% or a reduction in the tumor spread (i.e. tumor metastasis) by at least about 10% would also be considered as affective treatments by the methods as disclosed herein. In some embodiments, it is preferred, but not required that the therapeutic agent actually kill the tumor.

As used herein, the terms "administering," and "introducing" are used interchangeably herein and refer to the placement of the pharmaceutical compositions of the present invention comprising an inhibitor of ACLP or PFD as disclosed herein into a subject by a method or route which results in at least partial localization of the inhibitor of ACLP or PFD at a desired site. The compounds of the present invention can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. The phrases "systemic administration," "administered systemically", "peripheral administration" and "administered peripherally" as used herein mean the administration of the pharmaceutical compositions of the present invention comprising an inhibitor of ACLP or PFD and optionally other agents or material other than directly into the central nervous system, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; or other mode of administration. The pharmaceutical composition contains a compound of the invention in combination with one or more pharmaceutically acceptable ingredients. The carrier can be in the form of a solid, semi-solid or liquid diluent, cream or a capsule.

The terms "composition" or "pharmaceutical composition" used interchangeably herein refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) *Remington: The Science and Practice of Pharmacy with Facts and Comparisons*, 21st Ed.

The term "agent" or "compound" as used herein refers to a chemical entity or biological product, or combination of chemical entities or biological products, administered to a subject to treat or prevent or control a disease or condition. In some embodiments, a biological product is a protein (e.g., polypeptide) or peptide. In some embodiments, a chemical entity or biological product is a low molecular weight compound, but may also be a larger compound, or any organic or inorganic molecule, including modified and unmodified nucleic acids such as antisense nucleic acids, RNAi, such as siRNA or shRNA, peptides, peptidomimetics, receptors, ligands, and antibodies, aptamers, polypeptides, nucleic acid analogues or variants thereof. For example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

ACLP Inhibitors

As mentioned above, the present invention is directed to inhibitors of ACLP, in particular, to inhibitors of the N-terminal pro-fibrotic domain (PFD) of ACLP. Such inhibitors of ACLP, and/or inhibitors of the pro-fibrotic domain of ACLP can be used for the treatment and/or prevention of cancers, and fibroproliferation, including cardiovascular, cancer, fibrosis (including but not limited to, solid tissue fibrosis and scleroderma).

Accordingly, the present invention relates in part to methods and compositions to inhibit ACLP, in particular, to inhibitors of the N-terminal pro-fibrotic domain (PFD) of ACLP. In some embodiments, ACLP inhibitors as disclosed herein can be used to inhibit the pro-fibrotic domain (PFD) activity. In some embodiments, ACLP inhibitors as disclosed herein can decrease expression (level) of ACLP. In some embodiments, the ACLP inhibitors inhibit the interaction of the pro-fibrotic domain with other proteins, such as members of the transforming growth factor family, including TGFβ.

The ability of a compound to inhibit ACLP can be assessed by measuring a decrease in fibrotic activity of ACLP as compared to the activity of ACLP in the absence of the inhibitor. A decrease in fibrotic activity can be measured using the assays as described herein (see FIG. 5-7), showing a decrease in TGFβ signaling or decrease in pSmad3 and/or SMA and/or collagen I on inhibition of the pro-fibrotic domain of ACLP. In some embodiments, the ability of a compound to inhibit the pro-fibrotic domain of ACLP can be assessed by measuring a decrease in the biological activity (e.g., protein activity), e.g., TGFβ signaling as compared to the level of ACLP activity and/or expression in the absence of ACLP or PFD inhibitors.

In some embodiments, an ACLP inhibitor is an anti-ACLP antibody or antibody fragment. Antibodies and antibody fragments are well known in the art, and are commercially available. In some embodiments, an anti-ACLP blocking antibody binds to, or interacts with a portion of the pro-fibrotic domain of ACLP, in particular, to any portion of the PDF domain of amino acids 25-381 of SEQ ID NO: 1 which comprises the PFD of human ACLP protein (see FIG. 12B). In some embodiments, the antibody, antibody fragment or antigen binding moiety binds to any portion, or at least 5 consecutive amino acids of amino acids of 25-381 of SEQ ID NO: 1.

In some embodiments, an antibody or antibody fragment or antigen binding moiety binds to any portion of amino acids 120-163 of the human ACLP protein corresponding to SEQ ID NO: 1. In some embodiments, the antibody binds to any portion, or at least 5 consecutive amino acids of amino acids 120-163 of SEQ ID NO: 1, e.g., KEKPPKATKKPKEKPPKATKKPKEKPPKATKKPKEKPPKATKK (SEQ ID NO: 4)

In avoidance of any doubt, the amino acid sequence of human ACLP protein corresponds to NP_001120.3 (SEQ ID NO: 1) and as is follows, with the amino acids of Tsp2 comprising four 11-amino acid repeating sequences underlined and highlighted in bold:

```
                                                      (SEQ ID NO: 1)
MAAVRGAPLLSCLLALLALCPGGRPQTVLTDDEIEEFLEGFLSE

LEPEPREDDVEAPPPPEPTPRVRKAQAGGKPGKRPGTAAEVPPEKTKDKGKKGKKDKG

PKVPKESLEGSPRPPKKGKEKPPKATKKPKEKPPKATKKPKEKPPKATKKPKEKPPKA

TKKPPSGKRPPILAPSETLEWPLPPPPSPGPEELPQEGGAPLSNNWQNPGEETHVEAR

EHQPEPEEETEQPTLDYNDQIEREDYEDFEYIRRQKQPRPPPSRRRRPERVWPEPPEE

KAPAPAPEERIEPPVKPLLPPLPPDYGDGYVIPNYDDMDYYFGPPPPQKPDAERQTDE

EKEELKKPKKEDSSPKEETDKWAVEKGKDHKEPRKGEELEEEWTPTEKVKCPPIGMES

HRIEDNQIRASSMLRHGLGAQRGRLNMQTGATEDDYYDGAWCAEDDARTQWIEVDTRR

TTRFTGVITQGRDSSIHDDFVTTFFVGFSNDSQTWVMYTNGYEEMTFHGNVDKDTPVL

SELPEPVVARFIRIYPLTWNGSLCMRLEVLGCSVAPVYSYYAQNEVVATDDLDFRHHS

YKDMRQLMKVVNEECPTITRTYSLGKSSRGLKIYAMEISDNPGEHELGEPEFRYTAGI

HGNEVLGRELLLLLMQYLCREYRDGNPRVRSLVQDTRIHLVPSLNPDGYEVAAQMGSE

FGNWALGLWTEEGFDIFEDFPDLNSVLWGAEERKWVPYRVPNNNLPIPERYLSPDATV

STEVRAIIAWMEKNPFVLGANLNGGERLVSYPYDMARTPTQEQLLAAAMAAARGEDED

EVSEAQETPDHAIFRWLAISFASAHLTLTEPYRGGCQAQDYTGGMGIVNGAKWNPRTG

TINDFSYLHTNCLELSFYLGCDKFPHESELPREWENNKEALLTFMEQVHRGIKGVVTD

EQGIPIANATISVSGINHGVKTASGGDYWRILNPGEYRVTAHAEGYTPSAKTCNVDYD

IGATQCNFILARSNWKRIREIMAMNGNRPIPHIDPSRPMTPQQRRLQQRRLQHRLRLR

AQMRLRRLNATTTLGPHTVPPTLPPAPATTLSTTIEPWGLIPPTTAGWEESETETYTE

VVTEFGTEVEPEFGTKVEPEFETQLEPEFETQLEPEFEEEEEEKEEEIATGQAFPFT

TVETYTVNFGDF
```

In some embodiments, an anti-ACLP antibody, or fragment thereof, or antigen-binding moiety can bind to any region in the PFD, which comprises amino acids 25-381 of SEQ ID NO: 1 (see FIG. 12B), which is shown below:

```
                                                     (SEQ ID NO: 10)
PQTVLTDDEIEEFLEGFLSELEPEPREDDVEAPPPPEPTPRVRKAQGGKPGKRPGTAAEVPPEKTKDK

GKKGKKDKGPKVPKESLEGSPRPPKKGKEKPPKATKKPKEKPPKATKKPKEKPPKATKKPKEKPPKAT

KKPPSGKRPPILAPSETLEWPLPPPPSPGPEELPQEGGAPLSNNWQNPGEETHVEAREHQPEPEEETE

QPTLDYNDQIEREDYEDFEYIRRQKQPRPPPSRRRRPERVWPEPPEEKAPAPAPEERIEPPVKPLLPP

LPPDYGDGYVIPNYDDMDYYFGPPPPQKPDAERQTDEEKEELKKPKKEDSSPKEETDKWAVEKGKDHK

EPRKGEELEEEWTPTEK.
```

In some embodiments, the antibody, antibody fragment or antigen binding moiety binds to any portion, or at least 5 consecutive amino acids of SEQ ID NO: 10, or at least 5 consecutive amino acids of amino acid residues 25-381 of SEQ ID NO: 1.

The pro-fibrotic domain of human ACLP protein comprises 4 Tsp repeats, Tsp1, Tsp2, Tsp3 and Tsp4, where Tsp 2 comprises a highly conserved region of 4-repeats of a unique amino acid sequence of KEKPPKATKKP (SEQ ID NO: 3), as underlined in SEQ ID NO: 1 and SEQ ID NO: 10 (see also FIGS. 12A and 12B). Accordingly, in some embodiments, an anti-ACLP antibody specifically binds to a region within amino acids 120-163 of SEQ ID NO: 1. Accordingly, in some embodiments, the anti-ACLP antibody specifically binds to an epitope comprising at least part of, or all of the following amino acid sequence: KEKPPKATKKP (SEQ ID NO: 3). In some embodiments, an anti-ACLP antibody specifically binds to an epitope comprising at least part of, or all of the following amino acid sequence: KEKPPKATKKPKEKPPKATKKPKEKPPKATKKPKEKPPKATKK (SEQ ID NO: 4). In some embodiments, an anti-ACLP antibody specifically binds to an epitope comprising at least 4 or at least 5 or more consecutive amino acids of SEQ ID NO: 4. In some embodiments, an anti-ACLP antibody specifically binds to an epitope comprising at least 4 or at least 5 or more amino acids of SEQ ID NO: 4, where the amino acids can be any combination of non-consecutive and consecutive amino acids, where the amino acids are located spatially together to create an antibody binding epitope. In some embodiments, an anti-ACLP antibody specifically binds to an epitope comprising at least 2 or more amino acids in SEQ ID NO: 4 which are located on the exterior of the ACLP protein.

In some embodiments, an anti-ACLP antibody specifically binds to at least one hydroxylated amino acid within any one of the regions comprising amino acids residues 25-381 of SEQ ID NO: 1, or amino acid residues 120-163 of SEQ ID NO: 1 or amino acid residues of 384-539 of SEQ ID NO: 1. Accordingly, in some embodiments, an anti-ACLP antibody specifically bind to an epitope comprising at least part of, or all of the amino acid sequence of: KEKPPKATKKPKEKPPKATKKPKEKPPKATKKPKEKPPKATKK (SEQ ID NO: 4) where the epitope comprises at least one hydroxylated amino acid (e.g., OH-K and/or OH-Pro) and/or at least one other modified amino acid. For example, an anti-ACLP antibody can specifically bind to an epitope comprising at least part of, or all of the amino acid sequence of KEKPPKATKKPKEKPPKATKKPKEKPPKATKKPKEKPPKATKK (SEQ ID NO: 4) which comprises at least one lysine (K) is hydroxylysine (OH-Lys or OH-K) and/or at least one proline is hydroxyproline (also referred to as; OH-Pro, OH-P or Hyp). Similarly, in some embodiments, an anti-ACLP antibody can specifically bind to an epitope comprising at least one hydroxylated amino acid within the following sequence: KEKPPKATKKP (SEQ ID NO: 3), where at least one lysine (K) is hydroxylysine (OH-Lys or OH-K) and/or at least one proline is hydroxyproline (e.g., OH-Pro, OH-P or Hyp).

In some embodiments, an anti-ACLP antibody specifically binds to an epitope comprising at least part of, or all of amino acid residues 25-381 of SEQ ID NO: 1, or amino acid residues 120-163 of SEQ ID NO: 1 or amino acid residues of 384-539 of SEQ ID NO: 1, wherein at least one amino acid is glycosylated or is has a glycan attached. N-linked glycans can be attached to a nitrogen of asparagine (Asp or N) or arginine (Arg or R) side-chains. O-linked glycans attached to the hydroxyl oxygen of serine (S), threonine (Thr or T), tyrosine (Tyr or Y), hydroxylysine (OH-K or OH-Lys), or hydroxyproline (OH-Pro or OH-P) side-chains, or to oxygens on lipids such as ceramide. Phospho-glycans linked through the phosphate of a phospho-serine (P-ser); C-linked glycans, a rare form of glycosylation where a sugar is added to a carbon on a tryptophan side-chain. Glypiation, which is the addition of a GPI anchor that links proteins to lipids through glycan linkages. Accordingly, in some embodiments, an anti-ACLP antibody specifically bind to an epitope within any one of the regions comprising amino acid residues 25-381 of SEQ ID NO: 1, or amino acid residues 120-163 of SEQ ID NO: 1 or amino acid residues of 384-539 of SEQ ID NO: 1 where the epitope comprises at least one glycan or glycosylated amino acid. In some embodiments, an anti-ACLP antibody specifically bind to an epitope comprising at least part of, or all of the amino acid sequence of: KEKPPKATKKPKEKPPKATKKPKEKPPKATKKPKEKPPKATKK (SEQ ID NO: 4) where the epitope comprises at least one glycan or glycosylated amino acid. For example, an anti-ACLP antibody can specifically bind to an epitope comprising at least part of, or all of the amino acid sequence of KEKPPKATKKPKEKPPKATKKPKEKPPKATKKPKEKPPKATKK (SEQ ID NO: 4) which comprises at least one glycan attached to any one or more of T, OH-K or OH-P. Similarly, in some embodiments, an anti-ACLP antibody can specifically bind to an epitope comprising at least one hydroxylated amino acid within the following sequence: KEKPPKATKKP (SEQ ID NO: 3), which comprises at least one glycan attached to any one or more of T, OH-K or OH-P.

Similarly, in some embodiments, an anti-discoidin antibody can specifically bind to an epitope comprising at least one hydroxylated amino acid, or one glycosylated amino acid located within the region of amino acid residues 384-539 of SEQ ID NO: 1, or any of MLRHGLG (SEQ ID NO: 12), QTGATEDDYYDGA (SEQ ID NO: 13), DARTQ (SEQ ID NO: 14) or RDSSIHDD (SEQ ID NO: 15), where at least one glycan is attached to any one or more of T, OH-K or OH-P. In some embodiments, an anti-discoidin antibody can specifically bind to an epitope comprising at least one hydroxylated amino acid, or one glycosylated amino acid located within any of the following sequences; MLRHGLG (SEQ ID NO: 12); MLRHGLGA (SEQ ID NO: 16); MLRHGLGAQ (SEQ ID NO: 17); SMLRHGLG (SEQ ID NO: 18); SMLRHGLG (SEQ ID NO: 19); SMLRHGLGA (SEQ ID NO: 20); SMLRHGLGAQ (SEQ ID NO: 21); SSMLRHGLGA (SEQ ID NO: 22); SSMLRHGLGAQ (SEQ ID NO: 23); QTGATEDDYYDGA (SEQ ID NO: 13); QTGATEDDYYDGAW (SEQ ID NO: 24); QTGATEDDYYDGAWC (SEQ ID NO: 25); MQTGATEDDYYDGA (SEQ ID NO: 26); NMQTGATEDDYYDGA (SEQ ID NO: 27); MQTGATEDDYYDGAW (SEQ ID NO: 28); MQTGATEDDYYDGAWC (SEQ ID NO: 29); NMQTGATEDDYYDGAW (SEQ ID NO: 30); NMQTGATEDDYYDGAWC (SEQ ID NO: 31); DARTQ (SEQ ID NO: 14); DARTQW (SEQ ID NO: 32); DARTQWI (SEQ ID NO: 33); DDARTQ (SEQ ID NO: 34); EDDARTQ (SEQ ID NO: 35); DDARTQW (SEQ ID NO: 36); DDARTQWI (SEQ ID NO: 37); EDDARTQW (SEQ ID NO: 38); EDDARTQWI (SEQ ID NO: 39); RDSSIHDD (SEQ ID NO: 15); RDSSIHDDF (SEQ ID NO: 40); RDSSIHDDFV (SEQ ID NO: 41); GRDSSIHDD (SEQ ID NO: 42); QGRDSSIHDD (SEQ ID NO: 43); GRDSSIHDDF (SEQ ID NO: 44); GRDSSIHDDFV (SEQ ID NO: 45); QGRDSSIHDDF (SEQ ID NO: 46); or QGRDSSIHDDFV (SEQ ID NO: 47), where at least one glycan is attached to any one or more of T, OH-K or OH-P.

Similarly to the pro-fibrotic domain (PFD) of human ACLP protein, the Tsp2 motif of the PFD of mouse ACLP (mus-ACLP) protein comprises 4-repeats of a unique sequence of SEQ ID NO: 3, where the last repeat (repeat 3 of 4) comprises KEKPPKATKRP (SEQ ID NO: 5). Accordingly, in some embodiments, the anti-ACLP antibody binds to, or interacts with at least the following sequence: KEKPPKATKRP (SEQ ID NO: 5). In some embodiments, an anti-ACLP antibody targets at least a portion of, or a fragment of, a unique sequence of ACLP: TKKPKEKPPKA TKKPKEKPPKA TKKPKEKPPKA TKKPKEKPPKA (SEQ ID NO: 6).

In alternative embodiments, an anti-ACLP antibody binds to a region that corresponds to amino acids 120-163 of an ACLP protein variant, where the ACLP protein variant has a different amino acid sequence as a result of a SNP in the mRNA coding region which encodes amino acids 120-163 of SEQ ID NO: 1. In such embodiments, an anti-ACLP antibody can specifically binds to a region in repeating region of amino acids of 120-163 in a ACLP protein which is encoded by the a mRNA that carries a coding SNPS shown in Table 2. For example, in some embodiments, an anti-ACLP antibody specifically binds to a region within, or at least a portion within, the amino acid sequence: KEKPPKATKKPKEKPPKATKKPKEKPPKATKKPKE-KPPKASKK (SEQ ID NO: 9), where Thr (T) has been changed to Ser (S) amino acid at position 41 of SEQ ID NO: 9 (e.g a Thr→Ser change at position 161 of SEQ ID NO: 1) as a result of rs112053839 SNP.

Table 2 shows ACLP protein variants with amino acid sequence variations in regions 120-163 of ACLP of SEQ ID NO: 1:

acid. (See also world wide web: "ncbi.nlm.nih.gov/projects/SNP/snp_ref.cgi?geneId=165)"

As disclosed herein, the inventors demonstrate that the discoidin (DS) domain potentiates TGFβRII signaling in the presence of collagen (see FIG. 13C). The discoidin domain of human ACLP protein comprises amino acid residues 384-539 of SEQ ID NO: 1 (see FIG. 12B), or SEQ ID NO: 11.

Accordingly, in some embodiments, an anti-ACLP antibody can bind to an epitope comprising at least part of, or the full-length of the discoidin (DS) domain following amino acid sequence, where the underlined bold amino acids identify amino acids which make up loops 1, 2, 3 and 4 of the discoidin domain:

(SEQ ID NO: 11)
CPPIGMESHRIEDNQIRASSMLRHGLGAQRGRLNMQTGATEDDYYDGAWC

AEDDARTQWIEVDTRRTTRFTGVITQGRDSSIHDDFVTTFFVGFSNDSQT

WVMYTNGYEEMTFHGNVDKDTPVLSELPEPVVARFIRIYPLTWNGSLCMR

LEVLGC

In some embodiments, an antibody, antibody fragment or antigen binding moiety binds to any portion, or at least 5 consecutive amino acids of SEQ ID NO: 11, or at least 5 consecutive amino acids of amino acid residues 384-539 of SEQ ID NO: 1.

The discoidin domain comprises 4 loops which are the likely binding site for collagen; loop 1 corresponding to amino acids 404-410 of SEQ ID NO: 1 or MLRHGLG (SEQ ID NO: 12); loop 2 corresponding to amino acids 419-431

| dbSNP rs# cluster id | Heterozygosity | Function | dbSNP allele | Protein residue | Codon pos | Amino acid pos | Chr. position | mRNA pos |
|---|---|---|---|---|---|---|---|---|
| rs201227189 | 0.004 | synonymous | A | Pro [P] | 3 | 116 | 44106640 | 653 |
| | | contig reference | G | Pro [P] | 3 | 116 | | |
| rs200224104 | 0.004 | synonymous | G | Thr [T] | 3 | 128 | 44106676 | 689 |
| | | contig reference | C | Thr [T] | 3 | 128 | | |
| rs199689593 | 0.001 | synonymous | A | Lys [K] | 3 | 132 | 44106688 | 701 |
| | | contig reference | G | Lys [K] | 3 | 132 | | |
| rs201151753 | 0.002 | synonymous | A | Glu [E] | 3 | 155 | 44106757 | 770 |
| | | contig reference | G | Glu [E] | 3 | 155 | | |
| rs112053839 | 0.5 | missense | T | Ser [S] | 1 | 161 | 44106773 | 786 |
| | | contig reference | A | Thr [T] | 1 | 161 | | |
| rs201982646 | 0.001 | synonymous | A | Lys [K] | 3 | 163 | 44106781 | 794 |
| | | contig reference | G | Lys [K] | 3 | 163 | | |
| rs140913379 | 0 | missense | T | Leu [L] | 2 | 165 | 44106786 | 799 |
| | | contig reference | C | Pro [P] | 2 | 165 | | |
| rs144974496 | 0.001 | synonymous | A | Pro [P] | 3 | 165 | 44106787 | 800 |
| | | contig reference | G | Pro [P] | 3 | 165 | | |
| rs200698594 | 0.002 | synonymous | A | Arg [R] | 3 | 169 | 44106799 | 812 |
| | | contig reference | G | Arg [R] | 3 | 169 | | |

In some embodiments, an anti-ACLP antibody can bind to an epitope comprising at least part of, or the full-length of the following amino acid sequence, KEKPPKATKKPKEKPPKATKKPKEKPPKATKKPKEK-PPKAT/SKK (SEQ ID NO: 4) where the bold highlighted amino acids can be different amino acid due to SNP in the coding region, where T at position 8, K at positions 12 and 43, E at position 35 and T at position 41 of SEQ ID NO: 4 can be a different amino acid. For example, an anti-ACLP antibody can specifically bind to a region within, or at least a portion within, the amino acid sequence: KEKPPKAXKKPXEKPPKATKKPKEKPPKATKKPKXK-PPKAXKX (SEQ ID NO: 9) where X represents any amino of SEQ ID NO: 1 or QTGATEDDYYDGA (SEQ ID NO: 13); loop 3 corresponding to amino acids 437-441 of SEQ ID NO: 1 or DARTQ (SEQ ID NO: 14); loop 4 corresponding to amino acids 461-468 of SEQ ID NO: 1 or RDSSIHDD (SEQ ID NO: 15).

Accordingly, in some embodiments, an anti-ACLP antibody, antibody fragment, or antigen binding moiety can bind to an epitope that is at least part of one, or more loops (e.g., 2, or 3 or all 4 loops) of the discoidin domain. In some embodiments, an anti-ACLP antibody, antibody fragment, or antigen binding moiety can bind to one or more amino acids of loop 1 (MLRHGLG; SEQ ID NO: 12) and/or loop 2 (QTGATEDDYYDGA; SEQ ID NO: 13), and/or loop 3 (DARTQ; SEQ ID NO: 14) and/or loop 4 (RDSSIHDD; SEQ ID NO: 15). In some embodiments, an anti-ACLP antibody, antibody fragment, or antigen binding moiety can bind to epitope comprising at least 2, or at least 3, or at least 4 or at least 5 or more amino acids of loop 1 (MLRHGLG; SEQ ID NO: 12) and/or loop 2 (QTGATEDDYYDGA; SEQ ID NO: 13), and/or loop 3 (DARTQ; SEQ ID NO: 14) and/or loop 4 (RDSSIHDD; SEQ ID NO: 15), where the amino acids can be any combination of non-consecutive and consecutive amino acids in loop 1-4, or where the amino acids are located spatially together to create an antibody binding epitope.

In some embodiments, an anti-ACLP antibody, antibody fragment, or antigen binding moiety can bind to one or more amino acids in the sequences 12, 13, 14, 15, and 16-23, and/or 24-31 and/or 32-39 and/or 40-47 as shown in Table 3.

TABLE 3

Amino acids for targeting neutralizing antibodies or blocking peptides on the discoidin domain of human ACLP.

| Loop of the Discoidin domain | |
|---|---|
| Loop 1 | MLRHGLG (SEQ ID NO: 12) |
|  | MLRHGLGA (SEQ ID NO: 16) |
|  | MLRHGLGAQ (SEQ ID NO: 17) |
|  | SMLRHGLG (SEQ ID NO: 18) |
|  | SSMLRHGLG (SEQ ID NO: 19) |
|  | SMLRHGLGA (SEQ ID NO: 20) |
|  | SMLRHGLGAQ (SEQ ID NO: 21) |
|  | SSMLRHGLGA (SEQ ID NO: 22) |
|  | SSMLRHGLGAQ (SEQ ID NO: 23) |
| Loop 2 | QTGATEDDYYDGA (SEQ ID NO: 13) |
|  | QTGATEDDYYDGAW (SEQ ID NO: 24) |
|  | QTGATEDDYYDGAWC (SEQ ID NO: 25) |
|  | MQTGATEDDYYDGA (SEQ ID NO: 26) |
|  | NMQTGATEDDYYDGA (SEQ ID NO: 27) |
|  | MQTGATEDDYYDGAW (SEQ ID NO: 28) |
|  | MQTGATEDDYYDGAWC (SEQ ID NO: 29) |
|  | NMQTGATEDDYYDGAW (SEQ ID NO: 30) |
|  | NMQTGATEDDYYDGAWC (SEQ ID NO: 31) |
| Loop 3 | DARTQ (SEQ ID NO: 14) |
|  | DARTQW (SEQ ID NO: 32) |
|  | DARTQWI (SEQ ID NO: 33) |
|  | DDARTQ (SEQ ID NO: 34) |
|  | EDDARTQ (SEQ ID NO: 35) |
|  | DDARTQW (SEQ ID NO: 36) |
|  | DDARTQWI (SEQ ID NO: 37) |
|  | EDDARTQW (SEQ ID NO: 38) |
|  | EDDARTQWI (SEQ ID NO: 39) |
| Loop 4 | RDSSIHDD (SEQ ID NO: 15) |
|  | RDSSIHDDF (SEQ ID NO: 40) |
|  | RDSSIHDDFV (SEQ ID NO: 41) |
|  | GRDSSIHDD (SEQ ID NO: 42) |
|  | QGRDSSIHDD (SEQ ID NO: 43) |
|  | GRDSSIHDDF (SEQ ID NO: 44) |
|  | GRDSSIHDDFV (SEQ ID NO: 45) |
|  | QGRDSSIHDDF (SEQ ID NO: 46) |
|  | QGRDSSIHDDFV (SEQ ID NO: 47) |

It has been reported that blocking antibodies of FV and FVIII targeted to the discoidin-like C2 domain, and/or blocking peptides to the same region can be used to inhibit protein function (disclosed in Foster et al., Blood. 1990, 75(10):1999-2004, "Synthetic factor VIII peptides with amino acid sequences contained within the C2 domain of factor VIII inhibit factor VIII binding to phosphatidylserine"; Foster et al., Thromb Haemost. 1990, 63(3):403-6 "A synthetic factor VIII peptide of eight amino acid residues (1677-1684) contains the binding region of an anti-factor VIII antibody which inhibits the binding of factor VIII to von Willebrand factor"; which are incorporated herein in their entirety by reference).

Accordingly, in some embodiments, a ACLP inhibitor useful in the methods and composition as disclosed herein can comprise peptides selected from, for example, any of SEQ ID NO: 12-47. In such embodiments, such peptide inhibitors of the discoidin domain of ACLP (e.g., a peptide of SEQ ID NO: 12-47) can be modified to increase stability by methods commonly known by one of ordinary skill in the art, as disclosed herein e.g., Fc attached, PEGylation etc. In some embodiments, such peptides inhibitors of the discoidin domain of ACLP (e.g., a peptide of any of SEQ ID NO: 12-47) can be used alone, or in combination with an ACLP inhibitor which binds to the PFD of ACLP or inhibits the binding of the PFD to a member of the TGFβ receptor superfamily.

In some embodiments, the PFD of the human ACLP protein is glycosylated. Accordingly, in some embodiments, an anti-ACLP antibody binds to, or interacts with a glycosylated amino acid in the Pro-fibrotic domain of ACLP, and can, in some embodiments, interact with at least one sugar and not the amino acid in the pro-fibrotic domain of the ACLP protein.

In some embodiments, the human ACLP protein is glycosylated. Accordingly, in some embodiments, an anti-ACLP antibody binds to, or interacts with a glycosylated amino acid on an amino acid residue of the human ACLP protein, and can, in some embodiments, interact with at least one sugar attached to an amino acid of the ACLP protein. In some embodiments, the human ACLP protein is glycosylated on one or more of the following amino acids 479, 527 and 1098 of SEQ ID NO: 1 (see FIG. 12B). Accordingly, in some embodiments, an anti-ACLP antibody binds to, or interacts with at least one glycosylated amino acid of amino acid residues 479 and/or 527 and/or 1098 of SEQ ID NO: 1.

In some embodiments, an anti-ACLP antibody is a commercially available antibody.

In some embodiments, a targeting moiety useful in the methods as disclosed herein is an antibody, for example an antibody including not just complete or full length antibodies, but also antibody derivatives, such as a single chain antibody, a Fab portion of an antibody or a (Fab')₂ segment. In some embodiments, a binding moiety useful in the methods as disclosed herein is a protein or a nucleic acid binding domain of a protein, and in some embodiments the binding moiety is fused to the carboxyl terminus of the targeting moiety, and in some embodiments, the binding moiety is the protein protamine or nucleic acid binding fragment of protamine.

Blocking antibodies used as ACLP inhibitors antagonists include antibodies that specifically bind to the pro-fibrotic domain, e.g., a least a portion of SEQ ID NO 10, or SEQ ID NO: 3 or 4 and, by so binding, reduce ACLP-mediated activation of TGBβRII signalling and, consequently, reduce or block the fibrotic activity of ACLP.

Blocking antibodies used as ACLP inhibitors antagonists also include antibodies that specifically bind to the discoidin domain, e.g., a least a portion of SEQ ID NO 11, and/or any sequence selected from SEQ ID NO: 12-47, and by binding, reduce ACLP-mediated activation of TGBβRII signalling and, consequently, reduce or block the fibrotic activity of ACLP.

In some embodiments, blocking antibodies that bind to a least a portion of SEQ ID NO 10, or SEQ ID NO: 3 or 4, can be used alone, or in combination with antibodies which bind to at least a portion of SEQ ID NO 11, and/or any sequence selected from SEQ ID NO: 12-47.

As used herein, the term "antibodies" includes polyclonal antibodies, affinity-purified polyclonal antibodies, monoclonal antibodies, and antigen-binding fragments, such as F(ab')2 and Fab proteolytic fragments. Genetically engineered intact antibodies or fragments, such as chimeric antibodies, Fv fragments, single chain antibodies, and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Monoclonal antibodies can also be produced in mice that have been genetically altered to produce antibodies that have a human structure.

Methods for preparing and isolating polyclonal and monoclonal antibodies are well known in the art. See, for example, Cooligan et al. (eds.), Current Protocols in Immunology, National Institutes of Health, John Wiley and Sons, Inc., 1995; Sambrook et al., Molecular Cloning: A Laboratory Manual, second edition, Cold Spring Harbor, N.Y., 1989; and Hurrell (ed.), Monoclonal Hybridoma Antibodies: Techniques and Applications, CRC Press, Inc., Boca Raton, Fla., 1982. As would be evident to one of ordinary skill in the art, polyclonal antibodies can be generated by inoculating a variety of warm-blooded animals such as horses, cows, goats, sheep, dogs, chickens, rabbits, mice, and rats with an ACLP polypeptide or a fragment thereof.

Immunogenic polypeptides will comprise an epitope-bearing portion of a ACLP polypeptide (e.g., as shown in SEQ ID NO: 1) or receptor. In some embodiments, immunogenic polypeptides will comprise an epitope-bearing portion of the pro-fibrotic domain of ACLP polypeptide (e.g., as shown in SEQ ID NO: 3 or 4). An "epitope" is a region of a protein to which an antibody can bind. See, for example, Geysen et al., Proc. Natl. Acad. Sci. USA 81:3998-4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., Science 219:660-666, 1983. Immunogenic, epitope-bearing polypeptides contain a sequence of at least six, often at least nine, more often from 15 to about 30 contiguous amino acid residues of a ACLP protein, e.g., of 120-163 of SEQ ID NO: 1 or N-terminal PFD of the ACLP protein. Polypeptides comprising a larger portion of a ACLP protein or receptor, i.e. from 30 to 50 residues up to the entire sequence are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Exemplary longer peptide immunogens include peptides comprising residues (i) 120-163 of SEQ ID NO: 1. Peptides can be prepared with an additional C-terminal Cys residues and/or with an additional N-terminal Cys residue to facilitate coupling.

The immunogenicity of a polypeptide immunogen may be increased through the use of an adjuvant, such as alum (aluminum hydroxide) or Freund's complete or incomplete adjuvant. Polypeptides useful for immunization also include fusion polypeptides, such as fusions of an ACLP polypeptide or a portion thereof with an immunoglobulin polypeptide or with maltose binding protein. If the polypeptide portion is "hapten-like", such portion may be advantageously joined or linked to a macromolecular carrier (such as keyhole limpet hemocyanin (KLH), bovine serum albumin (BSA), or tetanus toxoid) for immunization.

Alternative techniques for generating or selecting antibodies include in vitro exposure of lymphocytes to a polypeptide immunogen, and selection of antibody display libraries in phage or similar vectors (for instance, through use of immobilized or labeled polypeptide). Techniques for creating and screening such random peptide display libraries are known in the art (e.g., Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698), and random peptide display libraries and kits for screening such libraries are available commercially, for instance from Clontech Laboratories (Palo Alto, Calif), Invitrogen Inc. (San Diego, Calif.), New England Biolabs, Inc. (Beverly, Mass.), and other commercial sources. Random peptide display libraries can be screened using the ACLP sequences disclosed herein to identify proteins that bind to ACLP.

Antibodies are determined to be specifically binding if they bind to their intended target (e.g., the pro-fibrotic domain of ACLP) with an affinity at least 10-fold greater than the binding affinity to control (e.g., non-ACLP or pro-fibrotic domains) polypeptide or protein. Due to the high level of amino acid sequence identity expected between ACLP orthologs, antibodies specific for human ACLP may also bind to ACLP or the pro-fibrotic domain of ACLP from other species. The binding affinity of an antibody can be readily determined by one of ordinary skill in the art, for example, by Scatchard analysis (Scatchard, G., Ann. NY Acad. Sci. 51: 660-672, 1949). Methods for screening and isolating specific antibodies are well known in the art. See, for example, Paul (ed.), Fundamental Immunology, Raven Press, 1993; Getzoff et al., Adv. in Immunol. 43:1-98, 1988; Goding (ed.), Monoclonal Antibodies: Principles and Practice, Academic Press Ltd., 1996; and Benjamin et al., Ann. Rev. Immunol. 2:67-101, 1984.

A variety of assays known to those skilled in the art can be utilized to detect antibodies that specifically bind to the pro-fibrotic domain of the ACLP protein. Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assays, inhibition or competition assays, sandwich assays and surface plasmon resonance (SPR).

For therapeutic applications it is generally preferred to use neutralizing antibodies. As used herein, the team "neutralizing antibody" is also referred to as a "blocking antibody" herein and refers to an antibody that inhibits at least 50% of the biological activity of the ACLP protein and/or inhibits at least 50% of the binding of the human ACLP protein to a member of the TGFβ receptor superfamily, such as, for example, TGFβRII when the antibody is added at a 1000-fold molar excess. In some embodiments, a blocking antibody refers to an antibody that results in a decrease by at least 10%, or at least 15%, or at least 20% decrease in ACLP mediated fibrosis, as measured in an in vivo model of fibrosis. In some embodiments, a blocking antibody is a low affinity binding blocking antibody. In some embodiments, a blocking antibody is a high affinity binding blocking antibody. Those of skill in the art will recognize that greater neutralizing activity is sometimes desirable, and neutralizing antibodies (either low affinity or high affinity) that provide at least a 50% inhibition of ACLP-mediated activation of a member of the TGFβ receptor superfamily, or a 20% decrease in ACLP-mediated fibrosis at a 100-fold or 10-fold molar access may be advantageously employed and are encompassed for use in the present invention.

An ACLP inhibitor which is an anti-ACLP antibody, e.g., binds to one or more Tsp repeats on the human ACLP protein, e.g., anti-ACLP monoclonal antibody according to the present invention is not limited to the whole molecule, and may be a fragment of the antibody or the modified product thereof, as long as it still binds to one or more Tsp repeats on the human ACLP protein and inhibits the interaction of ACLP with TGFβRII.

Multivalent, preferably bivalent, antibody and a monovalent antibody are included. Examples of the fragment of an antibody include Fab, F(ab)'2, Fv, Fab/c having one Fab and a complete Fc, and a single chain Fv (scFv) wherein the Fv of the H-chain or the L-chain is ligated with an appropriate linker. Specifically, an antibody fragment is synthesized by treating the antibody with an enzyme such as papain, pepsin or ficin, or genes encoding these antibody fragments are constructed, the genes are introduced into expression vectors, and the genes are then expressed by appropriate host cells (see e g, Rousseaux, J et al, Methods in Enzymology (1989) 121, 663-669, and Bird, R E et al, TIBTECH (1991)9, 132-137).

scFv is obtained by linking the H-chain V-region and the L-chain V-region of antibodies. In the scFv, the H-chain V-region and the L-chain V-region are linked via a linker, or preferably a peptide linker (Huston, J. S. et al., Proc. Natl. Acad. Sci. U.S.A. (1988) 85, 5879-5883). The H-chain V-region and the L-chain V-region in scFv may be derived from any of those described as antibodies in this specification. As a peptide linker to link the V-regions, for example, any single-stranded peptide comprising 12 to 19 amino acid residues is used.

According to an embodiment of the invention, an anti-ACLP antibody, e.g., an anti-ACLP antibody which specifically binds to one or more Tsp repeats on the human ACLP protein, e.g., an anti-ACLP monoclonal antibody or isolated monoclonal antibody fragments or antigen binding portions or fragments thereof may present an antibody heavy chain selected among: IgG, IgM, IgA, IgE, single chain antibody and other immunoglobulin-derived constructs or non antibody binding proteins.

As used herein, "isotype" refers to the antibody class (e. g., IgM, IgA, IgE or IgG) that is encoded by heavy chain constant region genes.

Usually, the non antibody binding proteins comprise adnectins (fibronectin-based reagents), Affibody (protein A-based reagents), DARPins (ankyrin-based reagents), avimers (cysteine rich cell surface receptor proteins), anticalins (lipocalin-derived reagents), and nucleotide-based reagents and the like (see for example Nutall & Walsh 2008 Curr Op Pharmacol 8:609).

In some embodiments, an anti-ACLP antibody, e.g., an anti-ACLP antibody which specifically binds to one or more Tsp repeats on the human ACLP protein there can be an IgG antibody heavy chain the latter may be selected among: IgG1, IgG2, IgG3 or IgG4, mutated IgG1 that is no longer recognized by FcR; mutated IgG4 sequence that no longer undergoes heavy chain swapping; mutated IgG to modify glycosylation; PEGylated IgG and the like. It is acknowledged that all possible "isotype switching" known to the person skilled in the art may be envisioned in the context of the present invention.

As used herein, "isotype switching" refers to the phenomenon by which the class, or isotype, of an antibody changes from one Ig class to one of the other Ig classes.

Among the list of antibody-based scaffolds, VNAR, which are lamprey-derived single domain antibodies may be advantageously used.

The present invention further provides at least an anti-ACLP antibody, e.g., an anti-ACLP antibody which specifically binds to an epitope created by one or more Tsp repeats of SEQ ID NO: 3 or SEQ ID NO: 4 of the human ACLP protein, or an amino acid sequence that differ from SEQ ID NO: 3 or 4 by one or more conservative amino acid substitutions; or amino acid sequences having at least 95% sequence identity to SEQ ID NO: 3 or SEQ ID NO: 4.

The term "sequence identity/similarity" has its ordinary meaning in the field. The terms "identical" or percent "identity" in the context of two or more polypeptide sequences, refer to two or more sequences that are the same, or have a specified percentage of amino acid residues that are the same (i.e., at least 70% identity, preferably at least 75%, 80%, 85%, 90%, even more preferably at least 95% or 98% or even 99% identity over a specified region), when compared and aligned for maximum correspondence. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (e.g., human and mouse sequences), compared to species more distantly related (e.g., human and non-mammalian ACLP sequences).

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:23744, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol Biol. 215:403-10, 1990, presents a detailed consideration of sequence alignment methods and homology calculations. The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md.

20894) and on the Internet, for use in connection with the sequence analysis programs blastp, blastn, blastx, tblastn and tblastx, and can be easily performed by one or ordinary skill in the art. Proteins with even greater similarity to the reference sequence will show increasing percentage identities when assessed by this method, such as at least 70%, 75%, 80%, 85%, 90%, 92%, 95%, 98%, 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site. Homologs of an anti-ACLP antibody, e.g., an anti-ACLP antibody which specifically binds to an epitope comprising at least part of one or more Tsp repeats on the human ACLP proteins are typically characterized by possession of at least 70%, preferably of at least 95%, and more preferably of at least 98% sequence identity sequence identity counted over the full-length alignment with the disclosed amino acid sequences using the NCBI Blast, or using the manual alignment as described above. Proteins with even greater similarity to the anti-ACLP antibody will show increasing percentage identities when assessed by this method, such as at least 75%, 80%, 85%, 90%, 95% or even 98% sequence identity. When less than the entire sequence is being compared for sequence identity, homologs will typically possess at least 75% sequence identity over short windows of 10-20 amino acids, and can possess sequence identities of at least 85%, 90%, 95% or even 98% depending on their similarity to the reference sequence. One of skill in the art will appreciate that these sequence identity ranges are provided for guidance only; it is possible that strongly significant homologs could be obtained that fall outside the ranges provided.

The present invention also includes variants of an anti-ACLP antibody, e.g., an anti-ACLP antibody which specifically binds to one or more Tsp repeats on the human ACLP protein. The term "variants" or derivatives or equivalents of an anti-ACLP antibody refer to polypeptides having amino acid sequences that differ to some extent from a native sequence polypeptide that is amino acid sequences that vary from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence. Typically, such variants possess at least 90%, preferably at least 95%, and very particularly preferably at least 98%, sequence identity with the native sequence. Variants which are particularly preferred in this connection are replacement variants which typically contain less than 10, preferably less than 5, and very particularly preferably less than 3, replacements as compared with the respective disclosed sequences.

In addition or alternative to modifications made within the framework or CDR regions, an anti-ACLP antibody, e.g., an anti-ACLP antibody which specifically binds to one or more Tsp repeats on the human ACLP protein useful herein can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody.

Variants, derivatives and equivalents of an anti-ACLP antibody, e.g., an anti-ACLP antibody which specifically binds to one or more Tsp repeats on the human ACLP protein useful in the compositions and methods as disclosed herein have substantially the same, or a greater biological activity than the anti-ACLP antibody they are derived from. In some embodiments, the biological activity of an anti-ACLP antibody, e.g., an anti-ACLP antibody which specifically binds to an epitope comprising at least part of one or more Tsp repeats on the human ACLP protein can be determined by one of ordinary skill in the art, for example, using an assay such as that disclosed herein in the Examples, such as an in vitro assay to assess if the variant antibody can inhibit ACLP-mediated collagen I or SMA expression or inhibit ACLP-induced phosphorylation of Smad3 in IMR90 cells.

Glycosylation of an anti-ACLP antibody can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of an anti-ACLP antibody for the PFD antigen of the ACLP protein. Such an approach is described in U.S. Pat. Nos. 5,714,350 and 6,350,861 by Co et al, which are incorporated herein in its entirety by reference.

Additionally or alternatively, an anti-ACLP antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express an anti-ACLP antibody, e.g., an anti-ACLP antibody which specifically binds to an epitope comprising at least part of one or more Tsp repeats on the human ACLP protein to produce an anti-ACLP antibody with altered glycosylation. Alternatively, the fucose residues of the antibody may be cleaved off using a fucosidase enzyme.

Another modification of an anti-ACLP antibody encompassed for use herein is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (Cl-ClO) alkoxy- or aryloxy-polyethylene glycol or polyethylene glycol-maleimide. In certain embodiments, the antibody to be pegylated is a glycosylated antibody. Methods for pegylating proteins are known in the art and can be applied to the antibodies of the invention. See for example, EP 0 154 316 by Nishimura et al. and EP 0 401 384 by Ishikawa et al, which are incorporated herein in their entirety by reference.

In another embodiment, an anti-ACLP antibody, e.g., an anti-ACLP antibody which specifically binds to an epitope comprising at least part of one or more Tsp repeats on the human ACLP protein does not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain.

In another embodiment, antibodies useful in the methods and compositions as disclosed herein are selected that do not rapidly degrade. Fragmentation of an anti-ACLP antibody, e.g., an anti-ACLP antibody which specifically binds to an epitope comprising at least part of one or more Tsp repeats on the human ACLP protein may be measured using capillary electrophoresis (CE) and MALDI-MS, as is well understood in the art (Alexander A J and Hughes D E (1995) Anal Chem 67:3626-32). In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

In addition to the above described monoclonal antibodies, an anti-ACLP antibody, e.g., an anti-ACLP antibody which specifically binds to an epitope comprising at least part of one or more Tsp repeats on the human ACLP protein can be a recombinant antibody such as a chimeric antibody or humanized antibody, for example, to lower its antigenicity in a human subject. These altered antibodies can be produced using a known method.

Chimeric anti-ACLP antibodies can e.g., be obtained by ligating the DNA encoding the antibody V-region to a DNA encoding a human antibody C-region, incorporating the product into an expression vector, and then introducing the vector into a host to cause the host to produce the antibodies. Using this known method, chimeric an anti-ACLP antibody, e.g., an anti-ACLP antibody which specifically binds to an epitope comprising at least part of one or more Tsp repeats on the human ACLP protein can be obtained.

Humanized antibodies are also referred to as reshaped human antibodies, which are prepared by grafting an antibody CDR (complementarity determining region) of a mammal other than a human, such as a mouse, to the CDR of a human antibody. The general gene recombination technique thereof is also known (see European Patent Application Publication EP 125023 and WO 96/02576, or any one of their US counterparts, e.g. U.S. Pat. No. 6,068,040, which are incorporated herein in their entirety by reference).

The term "humanized antibody" is intended to refer to antibodies in which CDR sequences derived from the germline of another mammalian species, such as a mouse, have been grafted onto human framework sequences. Additional framework region modifications may be made within the human framework sequences.

Chimeric or humanized anti-ACLP antibodies useful in the methods and compositions as disclosed herein can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al, which are incorporated herein in their entirety by reference). To create a humanized monoclonal antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al, which are incorporated herein in their entirety by reference). In some embodiments, an anti-ACLP antibody useful in the methods and compositions as disclosed herein is a human monoclonal antibody, for example, a human monoclonal anti-ACLP antibody which specifically binds to an epitope comprising at least part of one or more Tsp repeats on the human ACLP protein.

Given a specific variable domain region sequence, one of ordinary skill can easily screen for complementary variable domain region sequences using methods well known in the art. See, for example, Klimka et al., British Journal of Cancer (2000) 93: 252-260; Beboer et al., J. Mol. Biol. (2000) 296: 833-849; Radar et al., PNAS (1998) 95:8910-8915; Portolano et al, J. Immuno. (193) 150: 880-887; and Clarkson et al., Nature (1991) 352: 624-628, contents of all of which is herein incorporated by reference. For example, a heavy chain variable domain sequence comprising 1, 2, or 3 of the heavy chain CDR amino acid sequences described herein can be screened against a library of light chain variable domain sequences to obtain antibodies that bind the PFD of human and/or mouse ACLP protein which are is the binding site for TGFβRII. Alternatively, a light chain variable domain sequence comprising 1, 2, or 3 of the light chain CDRs described herein can be screened against a library of heavy chain variable domain sequences to obtain antibodies that bind PFD of human and/or mouse ACLP protein at a region which is binds to a member of the TGFβ receptor superfamily as disclosed herein, e.g., TGFβRII, or to obtain antibodies which bind to the discoidin domain at a region which binds to collagen. Without wishing to be bound by theory, this methodology can be used to humanize any known antibody. For example, a non-human variable domain sequence can be screened against human variable domain sequences and then the identified human variable domain sequences screened against a second set of human variable domain sequences.

Chimeric antibodies are antibodies whose light and heavy chain genes have been constructed, typically by genetic engineering, from antibody variable and constant region genes belonging to different species. For example the variable region of the genes from a mouse monoclonal antibody may be joined to human constant regions, such as gamma 1, gamma 2, gamma 3 and gamma 4.

The term "fusion protein" as used herein refers to a polypeptide which comprises protein domains from at least two different proteins. For example, a fusion protein may comprise an antigen-binding portion or fragment of an antibody and a non-antibody protein.

Conjugation of Antibodies with Ligand/Tags

A wide variety of ligands or tags can be coupled (i.e. linked) with the antibodies described herein. In some embodiments, antibodies described herein can be conjugated to either other peptides or other molecules to tailor, for example, the bioavailability, serum half-life or shelf-life of the antibodies, as well as immunogenicity, tolerance by human body, or to affect the solubility of the antibodies in pharmaceutically acceptable carriers. In some embodiments, antibodies as disclosed herein can be coupled to form a fusion protein with a molecule or peptide to provide an additional functionality to the antibody, for example, enhanced therapeutic function such as coupling to a toxin. Although, conjugation with ligands and tags is discussed in reference to antibodies herein, it is to be understood that antibody fragments and antigen binding portions and fragments are also amenable to conjugation with ligands and tags.

In some embodiments, an antibody as disclosed herein can be fused with another molecule, for example, an anti-ACLP antibody can be fused to at least one or more additional molecules, for example for therapeutic use and/or diagnostic use of antibodies. In some embodiments, an anti-ACLP antibody, e.g., an anti-ACLP antibody which specifically binds to an epitope comprising at least part of one or more Tsp repeats on the human ACLP protein, or fragments thereof can be fused or conjugated to different proteins or molecules, for example to produce, but not limited to, bi-specific antibodies, antibody-drug conjugates (ADCs), antibody-radioisotope conjugates (e.g., radioimmunoconjugates), antibody-toxin fusion proteins (e.g., immunotoxins), antibody-enzyme fusion proteins for prodrug activation in Antibody Directed Enzyme Prodrug Therapy (ADEPT), and antibodies used for targeting gene delivery or drug-delivery systems.

In some embodiments, an anti-ACLP antibody, e.g., an anti-ACLP antibody which specifically binds to an epitope comprising at least part of one or more Tsp repeats on the human ACLP protein (e.g., binds to at least part of residues 25-381 of SEQ ID NO: 1) or specifically binds to an epitope located within amino residues 384-539 of SEQ ID NO: 1, or fragments thereof can be fused or conjugated to different ligands, including but not limited to, naturally occurring molecules, in some embodiments, a ligand can be a recombinant or synthetic molecules. Exemplary ligands include, but are not limited to, polylysine (PLL), poly L aspartic acid, poly L-glutamic acid, styrene-maleic acid anhydride copolymer, poly(L-lactide-co-glycolide) copolymer, divinyl ether-maleic anhydride copolymer, N-(2-hydroxypropyl) methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazene, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases, lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), dinitrophenyl, HRP, AP, hormones and hormone receptors, lectins, carbohydrates, multivalent carbohydrates, natural or recombinant low density lipoprotein (LDL), natural or recombinant high-density lipoprotein (HDL), bovine serum albumin (BSA), ovalbumin, keyhole limpet hemocyanin (KLH), and a cell-permeation agent (e.g., a helical cell-permeation agent).

Ligands can be used for any number of reasons including, but no limited to, targeting, PK modulation, and labeling/tagging. A targeting ligand can provide enhanced affinity for a selected target, e.g., a cell, cell type, tissue, organ, region of the body, or a compartment, e.g., a cellular, tissue or organ compartment. A PK modulating ligand can modulate pharmacokinetics of an antibody in vivo.

In some embodiments, an anti-ACLP antibody, e.g., an anti-ACLP antibody which specifically binds to an epitope comprising at least part of one or more Tsp repeats on the human ACLP protein is conjugated with a label/tag, such as a fluorescent label or a biotin label. Without wishing to be bound by theory, such labeling allows one to easily track the anti-ACLP antibody, if necessary or to assist in purification of the antibody.

One can also design the ligand in such a way that is can be removed from the anti-ACLP antibody after purification of the antibody is complete. For example, the ligand can be attached to the antibody via a linker that can be is easily cleavable under the appropriate conditions. Such conditions can include acid or basic pH, heating, sonication, enzymatic cleavage, and the like.

As used herein, the term "label" refers to a composition capable of producing a detectable signal indicative of the presence of a target. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods and devices described herein. For example, the antibody can be labeled with a detectable tag which can then be detected using an antibody specific to the label.

Exemplary fluorescent labels, and agents used to attach a fluorescent label include, but are not limited to, Hydroxycoumarin Succinimidyl ester, Aminocoumarin, Methoxycoumarin, CASCADE BLUE™, Hydrazide, PACIFIC BLUE™, Maleimide, PACIFIC ORANGE™, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-TEXAS RED®, PerCP, Peridinin chlorophyll protein, TRURED™ (PerCP-Cy5.5 conjugate), FluorX, Fluoresceinisothyocyanate (FITC), BODIPY-FL, TRITC, X-Rhodamine (XRITC), Lissamine Rhodamine B, TEXAS RED®, Allophycocyanin (APC), an APC-Cy7 conjugate, ALEXA FLUOR®350, ALEXA FLUOR® 405, ALEXA FLUOR® 430, Alexa Fluor® 488, Alexa Fluor® 500, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, ALEXA FLUOR® 790, Cy2, Cy3, Cy3B, Cy3.5, Cy5, Cy5.5 or Cy7.

The ligands can be conjugated, either directly or through a linker, to the N-terminal, C-terminal, or the amino acid side chains of the heavy and/or light chain of the antibody. A ligand can be present on an amino acid when said amino acid is incorporated into the antibody heavy and/or light during synthesis. In some embodiments, the ligand can be incorporated via coupling to a "precursor" amino acid after said "precursor" amino acid has been incorporated into the antibody heavy and/or light chain. For example, a ligand having an electrophilic group, e.g., a pentafluorophenyl ester or aldehyde group, can be conjugated to the N-terminal of heavy and/or light chain of the antibody.

In another example, a monomer having a chemical group suitable for taking part in Click Chemistry reaction can be incorporated, e.g., an azide or alkyne group. In a subsequent operation, i.e., after incorporation of the precursor monomer antibody heavy and/or light chain, a ligand having complementary chemical group, e.g., an alkyne or azide can be attached to the precursor monomer by coupling the alkyne and the azide together.

In some embodiments, the covalent linkages between the antibody and a ligand is mediated by a linker. This linker can be cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the antibody after transport to the desired target. The intended nature of the conjugation or coupling interaction, or the desired biological effect, will determine the choice of linker group.

As used herein, the term "non-peptide linker" means an organic moiety that connects two parts of the peptide and such a moiety is not a peptide. Linkers typically comprise a direct bond or an atom such as oxygen or sulfur, a unit such as NR1, C(O), C(O)NH, SO, SO2, SO2NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO2, N(R1)2, C(O), cleavable linking group, substituted or unsubstituted aryl, substituted or unsubstituted heteroaryl, substituted or unsubstituted heterocyclic; where R1 is hydrogen, acyl, aliphatic or substituted aliphatic. The two parts of the compound can be linked together by providing on each part of the molecule complementary chemical functionalities that undergo a coupling reaction.

In some embodiments, linkers can be non-covalent coupling of two parts of a compound or two different molecules. Such non-covalent coupling can be achieved through, for example, ionic interactions, H-bonding, van der Waals interactions and affinity of one molecule for another. When non-covalent coupling is used, each part of the compound can be conjugated with a moiety that has complementary to another moiety that is conjugated to the second part of the compound. One example of such complementary coupling is the biotin/avidin coupling. Other examples include, affinity of an oligonucleotide for its complementary strand, receptor/ligand binding, aptamer/ligand binding and antibody/antigen binding.

Many strategies are known in the art for conjugating peptides to peptides and other molecules. For example, Hermanson, G. T., Bioconjugate Techniques, 2nd Ed., Academic Press (2008) and Niemeyr, C. M., Bioconjugation Protocols: Strategies and Methods (Methods in Molecular Biology), Humana Press (2004) provide a number of methods and techniques for conjugating peptides to other molecules. Contents of both of these are herein incorporated by reference in their entirety for all purposes. For a review of site-specific introduction of non-natural amino acids into peptides for conjugation see A. J. de Graaf, et al., Bioconjugate Chemistry (2009) 20(7):1281-1295, contents of which are herein incorporated in its entirety. Int. Pat. App. Pub. No.: WO92/13095, contents of which are herein incorporated in its entirety, describes methods for PEGylation of peptides.

One conjugation strategy is the biotin-sandwich method (Davis, et al., Proc. Natl. Acad. Sci. USA 103:8155-8160 (2006)) in which a peptide is biotinylated and bound to biotinylated ligand using tetravalent streptavidin as a linker. To accomplish this, the peptide may be coupled to the sequence of an acceptor peptide (AP) for biotinylation (disclosed in Chen, et al., Nat. Methods 2:99-104 (2005), which is incorporated herein in its entirety by reference). Fusion proteins can be made by incorporating the extra sequences at the N- or the C-terminus of the peptide of the AP peptide. The acceptor peptide sequence allows site-specific biotinylation by the *E. coli* enzyme biotin ligase (BirA; Chen, et al., Nat. Methods 2:99-104 (2005)). A ligand peptide can be similarly biotinylated for conjugation with a peptide described herein. Many commercial kits are available for biotinylating proteins. Non-peptidyl ligands agents can also be conjugated with biotin using methods well known in the art for conjugating biotin to non-peptide molecules, e.g. small organic molecules. In order to prevent steric interference between the biotin/avidin groups and the peptides or the ligands, a spacer may be included between them.

The linkers and linking methods described herein can also be used for linking together heavy chain and light chain of an anti-ACLP antibody, two or more Fv domains, and fragments thereof.

Mimetic and Decoy Inhibitors of ACLP

In some embodiments, an ACLP inhibitor encompassed for use in the present invention is a decoy molecule, e.g., a non-functional mimetic of the TGFβ receptor or a peptide or fragment of the TGFβ receptor, which can bind to the pro-fibrotic domain of the ACLP protein but cannot activate the TGFβ receptor signaling. Such decoy receptor molecules of TGFβ receptor are referred to herein as "decoyTGFβRII".

In such an embodiment, such a TGFβ receptor mimetic or non-functional fragment of the TGFβ receptor serves as a competitive inhibitor to prevent the pro-fibrotic domain of the ACLP polypeptide from binding to the native TGFβ receptor.

One of ordinary skill in the art can generate a non-functional mimetic of the TGFβ receptor or a non-functional fragment of the TGFβ receptor to serve a decoy receptor to bind to the pro-fibrotic domain of the ACLP protein but cannot activate the TGFβ receptor signaling for use in the methods and compositions as disclosed herein. For example, previous research indicates that peptides against betaglycan (TGFB RIII) seem to work in fibrosis (Hermida et al., (2009). A synthetic peptide from transforming growth factor-β1 type III receptor prevents myocardial fibrosis in spontaneously hypertensive rats. Cardiovasc Res 81, 601-9, which is incorporated herein in its entirety by reference).

Zhang et al., Nature Gene Therapy, 2013, 20; 575-580, which is incorporated herein in its entirety by reference, disclose a TGF-β-dominant-negative receptor II (DNRII) and two secreted soluble TGF-0 receptors: soluble TGF-0 receptor II (sRII) and the sRII fused with mouse IgG Fc domain (sRIIFc), which are encompassed for use in the present invention.

In an alternative embodiment, an ACLP inhibitor is a decoy ligand of the TGFβ receptor, e.g., a decoy TGFβRII, for example a mimetic of the pro-fibrotic domain of the ACLP protein that is a non-functional mimetic and binds to the TGFβ receptor but does not activate TGFβ signaling (thereby the decoy ligand which is a non-functional mimetic of pro-fibrotic domain of the ACLP protein acts as a competitive inhibitor and preventing endogenous ACLP protein binding). In some embodiments, such a mimetic comprises SEQ ID NO: 4 or a fragment thereof, comprising at least one ectopic mutation, whereby the ectopic mutation results in a non-functional pro-fibrotic domain of the ACLP protein which can bind to TGFβ receptor but can not activate TGFβ signaling. In some embodiments, the mimetic comprises at least one repeat of SEQ ID NO:3, wherein at least one repeat comprises at least one ectoptic mutation that results in a non-functional pro-fibrotic domain of the ACLP protein.

In some embodiments, such a mimetic can bind the normal receptor or ligand for ACLP (e.g., TGFβ receptor, e.g., TGFβRII), but cannot activate signaling, such as TGFβ signaling.

In some embodiments, an ACLP inhibitor which is a decoy receptor (e.g., a decoyTGFβRII), e.g., a non-functional mimetic of the TGFβ receptor, a non-functional fragment of the TGFβ receptor or decoy ligand, e.g., a non-functional mimetic of the pro-fibrotic domain of the ACLP protein, or other peptide inhibitor (e.g., peptide of a loop of discoidin domain e.g., peptide of SEQ ID NO: 12-47), is conjugated to a fusion partner, e.g., a fusion protein which increase the stability of the mimetic or decoy protein. In some embodiments, the fusion partner is an IgG1 Fc, e.g., human IgG1 Fc. In particular embodiments, an ACLP inhibitor is a non-functional mimetic of the TGFβ receptor fused to Fc, or a non-functional fragment of the TGFβ receptor fused to Fc. In some embodiments, Fc, or a fragment of Fc can be SEQ ID NO: 48 or functional variants or functional derivatives thereof, where SEQ ID NO: 48 is as follows:

(SEQ ID NO: 48)

LELVPRGSGDPIEGRGGGGGDPKSCDKPHTCPLCPAPELLGGPSVFLFPP

KPKDTLMISRTPEVTCVVVDVSHEDPEVKFNWYVDGVEVHNAKTKPREEQ

-continued

YNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKATP

PVLDSDGSFFLYSKLTVDKSRWQQGNVFSCSVMHEALHNHYTQKSLSLSP

GK

In some embodiments, an ACLP inhibitor which is a decoy receptor (e.g., a decoyTGFβRII; (e.g., a non-functional mimetic of the TGFβ receptor, a non-functional fragment of the TGFβ receptor) or decoy ligand (e.g., a non-functional mimetic of the pro-fibrotic domain of the ACLP protein) can be fused to a second fusion partner, such as a carrier molecule to enhance its bioavailability. Such carriers are known in the art and include poly (alkyl) glycol such as poly ethylene glycol (PEG). Fusion to serum albumin can also increase the serum half-life of therapeutic polypeptides.

In some embodiments, an ACLP inhibitor which is a decoy receptor (e.g., decoy TGFβII receptor), or a decoy ligand (e.g., non-functional PFD mimetic) can also be fused to a second fusion partner, for example, to a polypeptide that targets the product to a desired location, or, for example, a tag that facilitates its purification, if so desired. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use.

In some embodiments, an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), or antibody or other antigen-binding moiety can be modified to achieve adequate circulating half-lives, which impact dosing, drug administration and efficacy. Many approaches have been undertaken with the aim to increase the half-life of biotherapeutics. Small proteins below 60 kD are cleared rapidly by the kidney and therefore do not reach their target. This means that high doses are needed to reach efficacy. The modifications to a decoy receptor (e.g., decoy TGFβII receptor), or a decoy ligand (e.g., non-functional PFD mimetic) encompassed in the methods of the present invention to increase the half-life of proteins in circulation include: PEGylation; conjugation or genetic fusion with proteins, e.g., transferrin (WO06096515A2), albumin, growth hormone (US2003104578AA); conjugation with cellulose (Levy and Shoseyov, 2002); conjugation or fusion with Fc fragments; glycosylation and mutagenesis approaches (Carter, 2006), which are incorporated herein by reference.

In the case of PEGylation, polyethylene glycol (PEG) is conjugated to an ACLP inhibitor which is a decoy receptor (e.g., decoy TGFβII receptor), or a decoy ligand (e.g., non-functional PFD mimetic) can be for example a plasma protein, antibody or antibody fragment. The first studies regarding the effect of PEGylation of antibodies were performed in the 1980s. The conjugation can be done either enzymatically or chemically and is well established in the art (Chapman, 2002; Veronese and Pasut, 2005). With PEGylation the total size can be increased, which reduces the chance of renal filtration. PEGylation further protects from proteolytic degradation and slows the clearance from the blood. Further, it has been reported that PEGylation can reduce immunogenicity and increase solubility. The improved pharmacokinetics by the addition of PEG is due to several different mechanisms: increase in size of the molecule, protection from proteolysis, reduced antigenicity, and the masking of specific sequences from cellular receptors. In the case of antibody fragments (Fab), a 20-fold increase in plasma half-life has been achieved by PEGylation (Chapman, 2002).

To date there are several approved PEGylated drugs, e.g., PEG-interferon alpha2b (PEG-INTRON™) marketed in 2000 and alpha2a (PEGASYS®) marketed in 2002. A PEGylated antibody fragment against TNF alpha, called CIMZIA® (also known as Certolizumab Pegol), was filed for FDA approval for the treatment of Crohn's disease in 2007 and has been approved on Apr. 22, 2008. A limitation of PEGylation is the difficulty in synthesizing long monodisperse species, especially when PEG chains over 1000 kD are needed. For many applications, polydisperse PEG with a chain length over 10000 kD is used, resulting in a population of conjugates having different length PEG chains, which need extensive analytics to ensure equivalent batches between productions. The different length of the PEG chains may result in different biological activities and therefore different pharmacokinetics. Another limitation of PEGylation is a decrease in affinity or activity as it has been observed with alpha-interferon Pegasys, which has only 7% of the antiviral activity of the native protein, but has improved pharmacokinetics due to the enhanced plasma half-life.

In some embodiments, an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), or antibody or other antigen-binding moiety can be conjugated with a long lived protein, e.g. albumin, which is 67 kD and has plasma half-life of 19 days in human (Dennis et al., 2002). Albumin is the most abundant protein in plasma and is involved in plasma pH regulation, but also serves as a carrier of substances in plasma. In the case of CD4, increased plasma half-life has been achieved after fusing it to human serum albumin (Yeh et al., 1992). Other examples for fusion proteins are insulin, human growth hormone, transferrin and cytokines (Ali et al., 1999; Duttaroy et al., 2005; Melder et al., 2005; Osborn et al., 2002a; Osborn et al., 2002b; Sung et al., 2003) and see (US2003104578A1, WO06096515A2, and WO07047504A2, herein incorporated in entirety by reference).

The effect of glycosylation on plasma half-life and protein activity has also been extensively studied. In the case of tissue plasminogen activator (tPA) the addition of new glycosylation sites decreased the plasma clearance, and improved the potency (Keyt et al., 1994). Glycoengineering has been successfully applied for a number of recombinant proteins and immunoglobulins (Elliott et al., 2003; Raju and Scallon, 2007; Sinclair and Elliott, 2005; Umana et al., 1999). Further, glycosylation influences the stability of immunoglobulins (Mimura et al., 2000; Raju and Scallon, 2006).

In some embodiments, an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), can be fused to the Fc fragment of an IgG (Ashkenazi and Chamow, 1997). The Fc fusion approach has been utilized, for example in the Trap Technology developed by Regeneron (e.g. IL1 trap and VEGF trap). The use of albumin to extend the half-life of peptides has been described in US2004001827A1. Positive effects of albumin have also been reported for Fab fragments and scFv-HSA fusion protein (Smith et al., 2001). It has been demonstrated that the prolonged serum half-life of albumin is due to a recycling process mediated by the FcRn (Anderson et al., 2006; Chaudhury et al., 2003; Smith et al., 2001).

In some embodiments, an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), can be conjugated to a biotinylated Fc protein, as disclosed in US application 2010/0209424, which is incorporated herein in its entirety by reference.

As used herein, the term "conjugate" or "conjugation" refers to the attachment of two or more entities to form one entity. For example, the methods of the present invention provide conjugation of a peptide comprising at least one repeat of SEQ ID NO: 3 which comprises at least one ectopic mutation (to result in a non-functional PDF) is joined with another entity, for example a moiety such as a first fusion partner that makes the decoy receptor (e.g., decoy TGFβII receptor), or a decoy ligand (e.g., non-functional PFD mimetic) protein stable, such as Ig carrier particle, for example IgG1 Fc. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

According to the present invention, an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), can be linked to the first fusion partner via any suitable means, as known in the art, see for example U.S. Pat. Nos. 4,625,014, 5,057,301 and 5,514,363, which are incorporated herein in their entirety by reference. For example, an non-functional ACLP mimetic protein (e.g., a non-functional mimetic of SEQ ID NO: 3 or SEQ ID NO: 4) can be covalently conjugated to the IgG1 Fc, either directly or through one or more linkers. In one embodiment, an ACLP inhibitor which is a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), as disclosed herein is conjugated directly to the first fusion partner (e.g. Fc), and in an alternative embodiment, they can be conjugated to a first fusion partner (such as IgG1 Fc) via a linker, e.g. a transport enhancing linker.

A large variety of methods for conjugation of an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), as disclosed herein, with a first fusion partner (e.g. Fc) are known in the art. Such methods are e.g. described by Hermanson (1996, Bioconjugate Techniques, Academic Press), in U.S. Pat. Nos. 6,180,084 and 6,264,914 which are incorporated herein in their entirety by reference and include e.g. methods used to link haptens to carriers proteins as routinely used in applied immunology (see Harlow and Lane, 1988, "Antibodies: A laboratory manual", Cold Spring Harbor Laboratory Press, Cold Spring Harbor, NY). It is recognized that, in some cases, an ACLP inhibitor which is a decoy receptor (e.g., decoy TGFβII receptor), or a decoy ligand (e.g., non-functional PFD mimetic) can lose efficacy or functionality upon conjugation depending, e.g., on the conjugation procedure or the chemical group utilized therein. However, given the large variety of methods for conjugation the skilled person is able to find a conjugation method that does not or least affects the efficacy or functionality of the receptor decoy or ligand decoy such that it still binds but retains its non-functional activity.

Suitable methods for conjugation of an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), as disclosed herein, with a first fusion partner (e.g. Fc) include e.g. carbodiimide conjugation (Bauminger and Wilchek, 1980, Meth. Enzymol. 70: 151-159). Alternatively, a moiety can be coupled to a targeting agent as described by Nagy et al., Proc. Natl. Acad. Sci. USA 93:7269-7273 (1996), and Nagy et al., Proc. Natl. Acad. Sci. USA 95:1794-1799 (1998), each of which are incorporated herein by reference. Another method for conjugating one can use is, for example sodium periodate oxidation followed by reductive alkylation of appropriate reactants and glutaraldehyde crosslinking.

One can use a variety of different linkers to conjugate an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), as disclosed herein, with a first fusion partner (e.g. Fc), for example but not limited to aminocaproic horse radish peroxidase (HRP) or a heterobifunctional cross-linker, e.g. carbonyl reactive and sulfhydryl-reactive cross-linker. Heterobifunctional cross linking reagents usually contain two reactive groups that can be coupled to two different function targets on proteins and other macromolecules in a two or three-step process, which can limit the degree of polymerization often associated with using homobifunctional cross-linkers. Such multi-step protocols can offer a great control of conjugate size and the molar ratio of components.

In some embodiments, an ACLP inhibitor which is peptide based, e.g., a decoy receptor (e.g., decoy TGFβII receptor), or a decoy ligand (e.g., non-functional PFD mimetic), or other peptide inhibitor (e.g., peptide of a loop of discoidin domain e.g., peptide of SEQ ID NO: 12-47), useful in the present invention, can be modified at their amino termini, for example, so as to increase their hydrophilicity. Increased hydrophobicity enhances exposure of the peptides on the surfaces of lipid-based carriers into which the parent peptide-lipid conjugates have been incorporated.

Polar groups suitable for attachment to peptides so as to increase their hydrophilicity are well known, and include, for example and without limitation: acetyl ("Ac"), 3-cyclohexylalanyl ("Cha"), acetyl-serine ("Ac Ser"), acetyl-seryl-serine ("Ac-Ser-Ser-"), succinyl ("Suc"), succinyl-serine ("Suc-Ser"), succinyl-seryl-serine ("Suc-Ser-Ser"), methoxy succinyl ("MeO-Suc"), methoxy succinyl-serine ("MeO-Suc-Ser"), methoxy succinyl-seryl-serine ("MeO-Suc-Ser-Ser") and seryl-serine ("Ser-Ser-") groups, polyethylene glycol ("PEG"), polyacrylamide, polyacrylomorpholine, polyvinylpyrrolidine, a polyhydroxyl group and carboxy sugars, e.g., lactobionic, N-acetyl neuraminic and sialic acids, groups. The carboxy groups of these sugars would be linked to the N-terminus of the peptide via an amide linkage. Presently, the preferred N-terminal modification is a methoxy-succinyl modification.

Inhibitors to ACLP, or the pro-fibrotic domain of ACLP also include soluble receptors, peptides, or decoy molecules (aka dominant negative inhibitors). As used herein, a "soluble TGFβ receptor" is a TGFβ receptor which can bind the pro-fibrotic domain of the ACLP polypeptide but cannot activate TGFβ signalling. Soluble receptors are most commonly receptor polypeptides that comprise at least a portion of the extracellular, ligand binding domain sufficient to bind ligand but lack transmembrane and cytoplasmic domains. Many cell-surface receptors have naturally occurring, soluble counterparts that are produced by proteolysis. Receptor polypeptides are said to be substantially free of transmembrane and intracellular polypeptide segments when they lack sufficient portions of these segments to provide membrane anchoring or signal transduction, respectively. Soluble receptors can comprise additional amino acid residues, such as affinity tags that provide for purification of the polypeptide or provide sites for attachment of the polypeptide to a substrate, or immunoglobulin constant region sequences. Dimeric and higher order multimeric soluble receptors are preferred for their ability to bind ligand with high affinity. A soluble receptor can be prepared as a fusion to a dimerizing protein as disclosed in U.S. Pat. Nos. 5,155,027 and 5,567,584. Dimerizing proteins in this regard include, for example, immunoglobulin fragments comprising constant region and hinge domains (e.g., IgG Fc fragments).

The pro-fibrotic domain of ACLP has been found to be an active species of the molecule that activates TGFβ signaling. Proteolytic processing to remove the N-terminal portion of the ACLP molecule is also encompassed in the present invention, e.g., an agent which removes and/or catalytically cleaves and destroys the N-terminal pro-fibrotic domain of ACLP is encompassed in this present invention.

RNAi Inhibitors of ACLP

As discussed herein, the inventors have discovered that inhibition of ACLP, or in particular, inhibition of the pro-fibrotic domain of ACLP can be used in the methods and compositions as disclosed herein. In some embodiments, an inhibitor of ACLP, or the pro-fibrotic domain of ACLP is a protein inhibitor, and in some embodiments, the inhibitor is any agent which inhibits the pro-fibrotic domain or function of ACLP or the expression of ACLP from its gene. In some embodiments, an inhibitor of ACLP is a gene silencing agent. Without wishing to be bound by theory, ACLP is an aortic carboxypeptidase-like protein (ACLP) (the gene is also referred to by synonyms ACLP1, AEBP1 (AE binding protein 1) or adipocyte enhancer binding protein 1). ACLP protein is highly expressed in human fibrotic lungs.

The human ACLP protein is encoded by the ACLP gene comprising nucleic acid sequence NM_001129.4 (SEQ ID NO: 2), and the human ACLP protein has an amino acid of NP_001120.3 (SEQ ID NO: 1).

ACLP inhibitors further include antisense polynucleotides, which can be used to inhibit ACLP gene transcription and thereby inhibit cell activation and/or proliferation in vivo. Polynucleotides that are complementary to a segment of an ACLP-encoding polynucleotide (e.g., a polynucleotide as set forth in SEQ ID NO: 2) are designed to bind to ACLP-encoding mRNA and to inhibit translation of such mRNA. Antisense polynucleotides can be targeted to specific tissues using a gene therapy approach with specific vectors and/or promoters, such as viral delivery systems as disclosed in more detail below.

Inhibition of the ACLP mRNA can be by gene silencing RNAi molecules according to methods commonly known by a skilled artisan. For example, a gene silencing siRNA oligonucleotide duplexes targeted specifically to human ACLP (GenBank No: NM_001129.4) can readily be used to knockdown ACLP expression. ACLP mRNA can be successfully targeted using siRNAs; and other siRNA molecules may be readily prepared by those of skill in the art based on the known sequence of the target mRNA. Accordingly, in avoidance of any doubt, one of ordinary skill in the art can design nucleic acid inhibitors, such as RNAi (RNA silencing) agents to the nucleic acid sequence of NM_001129.4 which is as follows:

```
                                                               (SEQ ID NO: 2)
   1 cggctatccg cgcgggagtg cgccacgcgg ggccggagcg cctattagcc gccaggacct
  61 cggagcgccc cgaccacccc tgagcccctc tggcttcgga gcccccagc accccttccc
 121 gggtcccctc gcccaccta atccactctc cctcccttc ccggattccc tcgctcaccc
 181 catcctctct cccgcccctt cctggattcc ctcacccgtc tcgatcccct ctccgcccct
 241 tcccagagac ccagagcccc tgaccccccg cgccctcccc ggagcccccc gcgcgtgccg
 301 cggccatggc ggccgtgcgc ggggcgcccc tgctcagctg cctcctggcg ttgctggccc
 361 tgtgccctgg agggcgcccg cagacggtgc tgaccgacga cgagatcgag gagttcctcg
 421 agggcttcct gtcagagcta gaacctgagc cccgggagga cgacgtggag gccccgcgc
 481 ctcccgagcc caccccgcgg gtccgaaaag cccaggcggg gggcaagcca gggaagcggc
 541 cagggacggc cgcagaagtg cctccggaaa agaccaaaga caaagggaag aaaggcaaga
 601 aagacaaagg ccccaaggtg cccaaggagt ccttggaggg gtcccccagg ccgcccaaga
 661 aggggaagga gaagccaccc aaggccacca agaagcccaa ggagaagcca cctaaggcca
 721 ccaagaagcc caaggagaag ccacccaagg ccaccaagaa gcccaaagag aagccaccca
 781 aggccaccaa gaagcccccg tcagggaaga ggccccccat tctggctccc tcagaaaccc
 841 tggagtggcc actgccccca cccccagcc ctggccccga ggagctaccc caggagggag
 901 gggcgcccct ctcaaataac tggcagaatc caggagagga gacccatgtg gaggcacggg
 961 agcaccagcc tgagccggag gaggagaccg agcaacccac actggactac aatgaccaga
1021 tcgagaggga ggactatgag gactttgagt acattcggcg ccagaagcaa cccaggccac
1081 ccccaagcag aaggaggagg cccgagcggg tctggccaga gcccctgag gagaaggccc
1141 cggcccccage cccggaggag aggattgagc ctcctgtgaa gcctctgctg cccccgctgc
1201 cccctgacta tggtgatggt tacgtgatcc ccaactacga tgacatggac tattactttg
1261 ggcctcctcc gccccagaag cccgatgctg agcgccagac agacgaagag aaggaggagc
1321 tgaagaaacc caaaaaggag gacagcagcc ccaaggagga gaccgacaag tgggcagtgg
1381 agaagggcaa ggaccacaaa gagcccgaa agggcgagga gttggaggag gagtggacgc
1441 ctacggagaa agtcaagtgt ccccccattg ggatggagtc acaccgtatt gaggacaacc
1501 agatccgagc ctcctccatg ctgcgccacg gctgggggc acagcgcggc cggctcaaca
1561 tgcagaccgg tgccactgag gacgactact atgatggtgc gtggtgtgcc gaggacgatg
1621 ccaggaccca gtggatagag gtggacacca ggaggactac ccggttcaca ggcgtcatca
1681 cccagggcag agactccagc atccatgacg attttgtgac caccttcttc gtgggcttca
1741 gcaatgacag ccagacatgg gtgatgtaca ccaacggcta tgaggaaatg acctttcatg
1801 ggaacgtgga caaggacaca cccgtgctga gtgagctccc agagccggtg gtggctcgtt
```

-continued

```
1861 tcatccgcat ctacccactc acctggaatg gcagcctgtg catgcgcctg gaggtgctgg
1921 ggtgctctgt ggcccctgtc tacagctact acgcacagaa tgaggtggtg gccaccgatg
1981 acctggattt ccggcaccac agctacaagg acatgcgcca gctcatgaag gtggtgaacg
2041 aggagtgccc caccatcacc cgcacttaca gcctgggcaa gagctcacga ggcctcaaga
2101 tctatgccat ggagatctca gacaaccctg gggagcatga actgggggag cccgagttcc
2161 gctacactgc tgggatccat ggcaacgagg tgctgggccg agagctgttg ctgctgctca
2221 tgcagtacct gtgccgagag taccgcgatg gaacccacg tgtgcgcagc ctggtgcagg
2281 acacacgcat ccacctggtg ccctcactga accctgatgg ctacgaggtg gcagcgcaga
2341 tgggctcaga gtttgggaac tgggcgctgg gactgtggac tgaggagggc tttgacatct
2401 ttgaagattt cccggatctc aactctgtgc tctggggagc tgaggagagg aaatgggtcc
2461 cctaccgggt ccccaacaat aacttgccca tccctgaacg ctacctttcg ccagatgcca
2521 cggtatccac ggaggtccgg gccatcattg cctggatgga aagaacccc ttcgtgctgg
2581 gagcaaatct gaacggcggc gagcggctag tatcctaccc ctacgatatg gcccgcacgc
2641 ctacccagga gcagctgctg gccgcagcca tggcagcagc ccgggggggag gatgaggacg
2701 aggtctccga ggcccaggag actccagacc acgccatctt ccggtggctt gccatctcct
2761 tcgcctccgc acacctcacc ttgaccgagc cctaccgcgg aggctgccaa gcccaggact
2821 acaccggcgg catgggcatc gtcaacgggg ccaagtggaa cccccggacc gggactatca
2881 atgacttcag ttacctgcat accaactgcc tggagctctc cttctacctg gctgtgaca
2941 agttccctca tgagagtgag ctgccccgcg agtgggagaa caacaaggag gcgctgctca
3001 ccttcatgga gcaggtgcac cgcggcatta aggggggtggt gacggacgag caaggcatcc
3061 ccattgccaa cgccaccatc tctgtgagtg gcattaatca cggcgtgaag acagccagtg
3121 gtggtgatta ctggcgaatc ttgaacccgg gtgagtaccg cgtgacagcc cacgcggagg
3181 gctacacccc gagcgccaag acctgcaatg ttgactatga catcggggcc actcagtgca
3241 acttcatcct ggctcgctcc aactggaagc gcatccggga gatcatggcc atgaacggga
3301 accggcctat cccacacata gacccatcgc gccctatgac cccccaacag cgacgcctgc
3361 agcagcgacg cctacaacac cgcctgcggc ttcgggcaca gatgcggctg cggcgcctca
3421 acgccaccac cacccctaggc ccccacactg tgcctccac gctgccccct gccctgcca
3481 ccaccctgag cactaccata gagccctggg gcctcatacc gccaaccacc gctggctggg
3541 aggagtcgga gactgagacc tacacagagg tggtgacaga gtttgggacc gaggtggagc
3601 ccgagtttgg gaccaaggtg gagcccgagt ttgagaccca gttggagcct gagtttgaga
3661 cccagctgga acccgagttt gaggaagagg aggaggagga gaaagaggag gagatagcca
3721 ctggccaggc attccccttc acaacagtag agacctacac agtgaacttt ggggacttct
3781 gagatcagcg tcctaccaag accccagccc aactcaagct acagcagcag cacttcccaa
3841 gcctgctgac cacagtcaca tcacccatca gcacatggaa ggcccctggt atggacactg
3901 aaaggaaggg ctggtcctgc ccctttgagg gggtgcaaac atgactggga cctaagagcc
3961 agaggctgtg tagaggctcc tgctccacct gccagtctcg taagagatgg ggttgctgca
4021 gtgttggagt aggggcagag ggaggagcc aaggtcactc aataaaaca agctcatggc
4081 acggacaaaa aaaaaaaaaa aa
```

In some embodiments, the ACLP protein is encoded by a variant of the ACLP gene of SEQ ID NO: 2, where the variant comprises one or more nucleic acid changes due to SNPs in the coding regions. Such variants of ACLP gene are well known to persons of ordinary skill in the art, for example, as shown in Table 4, and at world wide web site: "ncbi.nlm.nih.gov/projects/SNP/snp_refcgi?geneId=165". Accordingly, encompassed for use in the methods and compositions as disclosed herein is a siRNA that inhibits the expression of the ACLP gene of SEQ ID NO: 2 or any variant thereof comprising a SNP as disclosed in Table 4.

TABLE 4

SNPs variants of ACLP gene of SEQ ID NO: 2
Table 4: SNPs variants of ACLP gene of SEQ ID NO: 2

| dbSNP rs# cluster id | Heterozygosity | Function | dbSNP allele | Protein residue | Codon pos | Amino acid pos | mRNA pos |
|---|---|---|---|---|---|---|---|
| rs28362521 | 0.032 | missense | A | Glu [E] | 2 | 7 | 325 |
|  |  | contig reference | C | Ala [A] | 2 | 7 |  |
| rs13241299 | N.D. | missense | T | Leu [L] | 2 | 21 | 367 |
|  |  | contig reference | C | Pro [P] | 2 | 21 |  |
| rs375195748 | N.D. | missense | A | Met [M] | 1 | 28 | 387 |
|  |  | contig reference | G | Val [V] | 1 | 28 |  |
| rs201978706 | 0.001 | synonymous | T | Phe [F] | 3 | 41 | 428 |
|  |  | contig reference | C | Phe [F] | 3 | 41 |  |
| rs141126404 | 0.001 | missense | G | Gly [G] | 2 | 48 | 448 |
|  |  | contig reference | A | Glu [E] | 2 | 48 |  |
| rs112298043 | N.D. | frameshift | — | Ala [A] | 3 | 73 | 518 |
|  |  | contig reference | G | Gly [G] | 3 | 73 |  |
| rs75107445 | 0.003 | missense | T | Leu [L] | 2 | 87 | 565 |
|  |  | contig reference | C | Pro [P] | 2 | 87 |  |
| rs139078339 | 0.001 | missense | C | Asn [N] | 3 | 89 | 572 |
|  |  | contig reference | G | Lys [K] | 3 | 89 |  |
| rs371412622 | N.D. | missense | C | His [H] | 1 | 92 | 579 |
|  |  | contig reference | G | Asp [D] | 1 | 92 |  |
| rs145109144 | 0 | missense | G | Arg [R] | 2 | 104 | 616 |
|  |  | contig reference | A | Lys [K] | 2 | 104 |  |
| rs375250739 | N.D. | missense | A | Glu [E] | 2 | 112 | 640 |
|  |  | contig reference | G | Gly [G] | 2 | 112 |  |
| rs201227189 | 0.004 | synonymous | A | Pro [P] | 3 | 116 | 653 |
|  |  | contig reference | G | Pro [P] | 3 | 116 |  |
| rs200224104 | 0.004 | synonymous | G | Thr [T] | 3 | 128 | 689 |
|  |  | contig reference | C | Thr [T] | 3 | 128 |  |
| rs199689593 | 0.001 | synonymous | A | Lys [K] | 3 | 132 | 701 |
|  |  | contig reference | G | Lys [K] | 3 | 132 |  |
| rs201151753 | 0.002 | synonymous | A | Glu [E] | 3 | 155 | 770 |
|  |  | contig reference | G | Glu [E] | 3 | 155 |  |
| rs112053839 | 0.5 | Missense | T | Ser [S] | 1 | 161 | 786 |
|  |  | contig reference | A | Thr [T] | 1 | 161 |  |
| rs201982646 | 0.001 | synonymous | A | Lys [K] | 3 | 163 | 794 |
|  |  | contig reference | G | Lys [K] | 3 | 163 |  |
| rs140913379 | 0 | missense | T | Leu [L] | 2 | 165 | 799 |
|  |  | contig reference | C | Pro [P] | 2 | 165 |  |
| rs144974496 | 0.001 | synonymous | A | Pro [P] | 3 | 165 | 800 |
|  |  | contig reference | G | Pro [P] | 3 | 165 |  |
| rs200698594 | 0.002 | synonymous | A | Arg [R] | 3 | 169 | 812 |
|  |  | contig reference | G | Arg [R] | 3 | 169 |  |
| rs200193837 | 0.002 | missense | G | Arg [R] | 2 | 187 | 865 |
|  |  | contig reference | C | Pro [P] | 2 | 187 |  |
| rs376847554 | N.D. | synonymous | T | Pro [P] | 3 | 191 | 878 |
|  |  | contig reference | C | Pro [P] | 3 | 191 |  |
| rs368973524 | N.D. | missense | A | Lys [K] | 1 | 192 | 879 |
|  |  | contig reference | G | Glu [E] | 1 | 192 |  |
| rs139352566 | 0.046 | missense | T | Val [V] | 2 | 200 | 904 |
|  |  | contig reference | C | Ala [A] | 2 | 200 |  |
| rs369661351 | N.D. | missense | G | Arg [R] | 2 | 201 | 907 |
|  |  | contig reference | C | Pro [P] | 2 | 201 |  |
| rs34982915 | N.D. | frame shift | A | Arg [R] | 3 | 210 | 932 |
|  |  | contig reference | — | Gly [G] | 3 | 210 |  |
| rs200342317 | 0.001 | missense | G | Ala [A] | 1 | 224 | 975 |
|  |  | contig reference | C | Pro [P] | 1 | 224 |  |
| rs367737639 | N.D. | missense | C | Asp [D] | 3 | 226 | 983 |
|  |  | contig reference | G | Glu [E] | 3 | 226 |  |
| rs148932183 | 0 | synonymous | T | Thr [T] | 3 | 228 | 989 |
|  |  | contig reference | C | Thr [T] | 3 | 228 |  |
| rs372015098 | N.D. | missense | T | Tyr [Y] | 1 | 234 | 1005 |
|  |  | contig reference | G | Asp [D] | 1 | 234 |  |
| rs375315010 | N.D. | missense | A | Glu [E] | 3 | 237 | 1016 |
|  |  | contig reference | C | Asp [D] | 3 | 237 |  |
| rs142763648 | 0 | missense | A | Lys [K] | 1 | 238 | 1017 |
|  |  | contig reference | C | Gln [Q] | 1 | 238 |  |

TABLE 4-continued

SNPs variants of ACLP gene of SEQ ID NO: 2
Table 4: SNPs variants of ACLP gene of SEQ ID NO: 2

| dbSNP rs# cluster id | Heterozygosity | Function | dbSNP allele | Protein residue | Codon pos | Amino acid pos | mRNA pos |
|---|---|---|---|---|---|---|---|
| rs151068311 | 0 | missense | C | Ser [S] | 3 | 241 | 1028 |
|  |  | contig reference | G | Arg [R] | 3 | 241 |  |
| rs201963190 | 0.001 | missense | A | Lys [K] | 1 | 245 | 1038 |
|  |  | contig reference | G | Glu [E] | 1 | 245 |  |
| rs141311453 | 0 | missense | C | Leu [L] | 1 | 247 | 1044 |
|  |  | contig reference | T | Phe [F] | 1 | 247 |  |
| rs145045450 | 0.001 | synonymous | A | Arg [R] | 3 | 251 | 1058 |
|  |  | contig reference | G | Arg [R] | 3 | 251 |  |
| rs200279382 | N.D. | missense | A | His [H] | 2 | 252 | 1060 |
|  |  | contig reference | G | Arg [R] | 2 | 252 |  |
| rs368747482 | N.D. | synonymous | T | Pro [P] | 3 | 266 | 1103 |
|  |  | contig reference | C | Pro [P] | 3 | 266 |  |
| rs2537188 | 0.435 | missense | A | Thr [T] | 1 | 273 | 1122 |
|  |  | contig reference | C | Pro [P] | 1 | 273 |  |
| rs374676651 | N.D. | synonymous | A | Glu [E] | 3 | 284 | 1157 |
|  |  | contig reference | G | Glu [E] | 3 | 284 |  |
| rs144144167 | 0.001 | synonymous | T | Pro [P] | 3 | 296 | 1193 |
|  |  | contig reference | C | Pro [P] | 3 | 296 |  |
| rs200809130 | 0.004 | synonymous | A | Pro [P] | 3 | 297 | 1196 |
|  |  | contig reference | G | Pro [P] | 3 | 297 |  |
| rs376019197 | N.D. | missense | T | Ser [S] | 1 | 299 | 1200 |
|  |  | contig reference | C | Pro [P] | 1 | 299 |  |
| rs376262022 | N.D. | missense | G | Cys [C] | 2 | 302 | 1210 |
|  |  | contig reference | A | Tyr [Y] | 2 | 302 |  |
| rs138067786 | 0.003 | missense | A | Met [M] | 1 | 307 | 1224 |
|  |  | contig reference | G | Val [V] | 1 | 307 |  |
| rs369540170 | N.D. | missense | G | Gly [G] | 2 | 307 | 1225 |
|  |  | contig reference | T | Val [V] | 2 | 307 |  |
| rs376785882 | N.D. | missense | G | Cys [C] | 2 | 317 | 1255 |
|  |  | contig reference | A | Tyr [Y] | 2 | 317 |  |
| rs141003956 | 0.001 | missense | T | Leu [L] | 2 | 322 | 1270 |
|  |  | contig reference | C | Pro [P] | 2 | 322 |  |
| rs371155958 | N.D. | synonymous | A | Pro [P] | 3 | 322 | 1271 |
|  |  | contig reference | G | Pro [P] | 3 | 322 |  |
| rs374505155 | N.D. | missense | T | Leu [L] | 2 | 330 | 1294 |
|  |  | contig reference | G | Arg [R] | 2 | 330 |  |
| rs2595701 | 0.332 | synonymous | G | Thr [T] | 3 | 332 | 1301 |
|  |  | contig reference | A | Thr [T] | 3 | 332 |  |
| rs138623215 |  | synonymous | T | Asp [D] | 3 | 333 | 1304 |
|  |  | contig reference | C | Asp [D] | 3 | 333 |  |
| rs149248982 | 0 | missense | A | Lys [K] | 1 | 334 | 1305 |
|  |  | contig reference | G | Glu [E] | 1 | 334 |  |
| rs377324824 | N.D. | missense | T | Asp [D] | 3 | 335 | 1310 |
|  |  | contig reference | G | Glu [E] | 3 | 335 |  |
| rs199942462 | 0.001 | missense | G | Arg [R] | 3 | 347 | 1346 |
|  |  | contig reference | C | Ser [S] | 3 | 347 |  |
| rs75175945 | 0.004 | missense | A | Gln [Q] | 2 | 368 | 1408 |
|  |  | contig reference | G | Arg [R] | 2 | 368 |  |
| rs200190216 | 0.001 | missense | A | Ser [S] | 1 | 370 | 1413 |
|  |  | contig reference | G | Gly [G] | 1 | 370 |  |
| rs376053706 | N.D. | synonymous | A | Thr [T] | 3 | 378 | 1439 |
|  |  | contig reference | G | Thr [T] | 3 | 378 |  |
| rs202186949 | 0.001 | missense | C | Gln [Q] | 1 | 381 | 1446 |
|  |  | contig reference | G | Glu [E] | 1 | 381 |  |
| rs144457398 | 0 | missense | T | Leu [L] | 2 | 392 | 1480 |
|  |  | contig reference | C | Ser [S] | 2 | 392 |  |
| rs111888664 | 0.5 | missense | A | His [H] | 2 | 394 | 1486 |
|  |  | contig reference | G | Arg [R] | 2 | 394 |  |
| rs376044473 | N.D. | synonymous | A | Leu [L] | 3 | 410 | 1535 |
|  |  | contig reference | G | Leu [L] | 3 | 410 |  |
| rs376270715 | N.D. | missense | C | Ala [A] | 2 | 411 | 1537 |
|  |  | contig reference | G | Gly [G] | 2 | 411 |  |
| rs137891711 | 0 | missense | T | Cys [C] | 1 | 414 | 1545 |
|  |  | contig reference | C | Arg [R] | 1 | 414 |  |
| rs368135596 | N.D. | missense | A | Gln [Q] | 2 | 416 | 1552 |
|  |  | contig reference | G | Arg [R] | 2 | 416 |  |
| rs369588798 | N.D. | synonymous | T | Thr [T] | 3 | 421 | 1568 |
|  |  | contig reference | C | Thr [T] | 3 | 421 |  |
| rs373830686 | N.D. | missense | T | Tyr [Y] | 1 | 427 | 1584 |
|  |  | contig reference | G | Asp [D] | 1 | 427 |  |
| rs143568325 | 0.001 | missense | G | Gly [G] | 2 | 430 | 1594 |
|  |  | contig reference | A | Asp [D] | 2 | 430 |  |

TABLE 4-continued

SNPs variants of ACLP gene of SEQ ID NO: 2
Table 4: SNPs variants of ACLP gene of SEQ ID NO: 2

| dbSNP rs# cluster id | Heterozygosity | Function | dbSNP allele | Protein residue | Codon pos | Amino acid pos | mRNA pos |
|---|---|---|---|---|---|---|---|
| rs372850520 | N.D. | synonymous | A | Ala [A] | 3 | 432 | 1601 |
| | | contig reference | G | Ala [A] | 3 | 432 | |
| rs376165441 | N.D. | missense | A | Lys [K] | 1 | 436 | 1611 |
| | | contig reference | G | Glu [E] | 1 | 436 | |
| rs370857030 | N.D. | missense | G | Glu [E] | 1 | 442 | 1629 |
| | | contig reference | C | Gln [Q] | 1 | 442 | |
| rs61737461 | 0.029 | missense | T | Leu [L] | 1 | 444 | 1635 |
| | | contig reference | A | Ile [I] | 1 | 444 | |
| rs140926602 | 0.001 | contig reference | A | Glu [E] | 3 | 445 | 1640 |
| | | | G | Glu [E] | 3 | 445 | |
| rs375790313 | N.D. | synonymous | A | Arg [R] | 3 | 450 | 1655 |
| | | contig reference | G | Arg [R] | 3 | 450 | |
| rs144784842 | 0.001 | missense | A | Gln [Q] | 2 | 453 | 1663 |
| | | contig reference | G | Arg [R] | 2 | 453 | |
| rs199564337 | 0.001 | missense | A | Asp [D] | 2 | 461 | 1687 |
| | | contig reference | G | Gly [G] | 2 | 461 | |
| rs150909656 | 0.001 | missense | A | Asn [N] | 1 | 469 | 1710 |
| | | contig reference | G | Asp [D] | 1 | 469 | |
| rs139397017 | 0.001 | missense | G | Ser [S] | 2 | 473 | 1723 |
| | | contig reference | C | Thr [T] | 2 | 473 | |
| rs192685042 | 0.001 | synonymous | T | Tyr [Y] | 3 | 488 | 1769 |
| | | contig reference | C | Tyr [Y] | 3 | 488 | |
| rs199596276 | 0.001 | nonsense | G | | 3 | 492 | 1781 |
| | | contig reference | T | Tyr [Y] | 3 | 492 | |
| rs376721512 | N.D. | missense | A | Gln [Q] | 3 | 498 | 1799 |
| | | contig reference | T | His [H] | 3 | 498 | |
| rs201501212 | 0.001 | synonymous | T | Asn [N] | 3 | 500 | 1805 |
| | | contig reference | C | Asn [N] | 3 | 500 | |
| rs150055229 | 0 | missense | G | Arg [R] | 2 | 503 | 1813 |
| | | contig reference | A | Lys [K] | 2 | 503 | |
| rs370022508 | N.D. | missense | G | Ala [A] | 1 | 505 | 1818 |
| | | contig reference | A | Thr [T] | 1 | 505 | |
| rs372825522 | N.D. | missense | A | Met [M] | 1 | 507 | 1824 |
| | | contig reference | G | Val [V] | 1 | 507 | |
| rs374647057 | N.D. | missense | A | Asn [N] | 2 | 509 | 1831 |
| | | contig reference | G | Ser [S] | 2 | 509 | |
| rs200076938 | N.D. | missense | T | Leu [L] | 2 | 514 | 1846 |
| | | contig reference | C | Pro [P] | 2 | 514 | |
| rs75738447 | 0.005 | synonymous | G | Leu [L] | 3 | 525 | 1880 |
| | | contig reference | C | Leu [L] | 3 | 525 | |
| rs141206792 | 0 | missense | T | Cys [C] | 1 | 534 | 1905 |
| | | contig reference | C | Arg [R] | 1 | 534 | |
| rs143744776 | 0.001 | missense | A | Ile [I] | 1 | 545 | 1938 |
| | | missense | C | Leu [L] | 1 | 545 | |
| rs146802668 | 0 | contig reference | G | Val [V] | 1 | 545 | 1952 |
| | | synonymous | T | Tyr [Y] | 3 | 549 | |
| rs376114999 | N.D. | contig reference | C | Tyr [Y] | 3 | 549 | 1953 |
| | | missense | A | Thr [T] | 1 | 550 | |
| rs141019167 | 0 | contig reference | G | Ala [A] | 1 | 550 | 1976 |
| | | synonymous | T | Thr [T] | 3 | 557 | |
| rs143113716 | 0 | contig reference | C | Thr [T] | 3 | 557 | 1977 |
| | | missense | A | Asn [N] | 1 | 558 | |
| rs199515795 | 0.002 | contig reference | G | Asp [D] | 1 | 558 | 1992 |
| | | missense | T | Trp [W] | 1 | 563 | |
| rs148240925 | 0 | contig reference | C | Arg [R] | 1 | 563 | 2001 |
| | | missense | G | Gly [G] | 1 | 566 | |
| rs140411744 | 0 | contig reference | A | Ser [S] | 1 | 566 | 2013 |
| | | missense | G | Val [V] | 1 | 570 | |
| rs200867650 | 0.001 | contig reference | A | Met [M] | 1 | 570 | 2017 |
| | | missense | A | His [H] | 2 | 571 | |
| rs200212819 | 0.001 | contig reference | G | Arg [R] | 2 | 571 | 2021 |
| | | missense | C | His [H] | 3 | 572 | |
| rs150374163 | 0.001 | contig reference | G | Gln [Q] | 3 | 572 | 2024 |
| | | synonymous | T | Leu [L] | 3 | 573 | |
| rs368488702 | N.D. | contig reference | C | Leu [L] | 3 | 573 | 2031 |
| | | missense | A | Met [M] | 1 | 576 | |
| rs200666867 | 0.002 | contig reference | G | Val [V] | 1 | 576 | 2034 |
| | | missense | A | Met [M] | 1 | 577 | |
| rs137956957 | 0 | contig reference | G | Val [V] | 1 | 577 | 2101 |
| | | missense | G | Ser [S] | 2 | 599 | |
| rs143372513 | 0 | contig reference | T | Ile [I] | 2 | 599 | 2161 |
| | | missense | A | His [H] | 2 | 619 | |

TABLE 4-continued

SNPs variants of ACLP gene of SEQ ID NO: 2
Table 4: SNPs variants of ACLP gene of SEQ ID NO: 2

| dbSNP rs# cluster id | Heterozygosity | Function | dbSNP allele | Protein residue | Codon pos | Amino acid pos | mRNA pos |
|---|---|---|---|---|---|---|---|
| rs368996866 | N.D. | contig reference | G | Arg [R] | 2 | 619 | 2162 |
|  |  | synonymous | T | Arg [R] | 3 | 619 |  |
| rs375474488 | N.D. | contig reference | C | Arg [R] | 3 | 619 | 2236 |
|  |  | missense | T | Leu [L] | 2 | 644 |  |
| rs11770649 | N.D. | contig reference | G | Arg [R] | 2 | 644 | 2249 |
|  |  | missense | A | Glu [E] | 3 | 648 |  |
| rs374944511 | N.D. | contig reference | T | Asp [D] | 3 | 648 | 2281 |
|  |  | missense | T | Val [V] | 2 | 659 |  |
| rs199581509 | 0.044 | contig reference | A | Asp [D] | 2 | 659 | 2292 |
|  |  | missense | A | Asn [N] | 1 | 663 |  |
| rs369402824 | N.D. | contig reference | C | His [H] | 1 | 663 | 2307 |
|  |  | synonymous | T | Leu [L] | 1 | 668 |  |
| rs373373055 | N.D. | contig reference | C | Leu [L] | 1 | 668 | 2315 |
|  |  | synonymous | G | Pro [P] | 3 | 670 |  |
| rs181697573 | 0.001 | contig reference | T | Pro [P] | 3 | 670 | 2324 |
|  |  | nonsense | G |  | 3 | 673 |  |
| rs184719396 | 0.001 | contig reference | C | Tyr [Y] | 3 | 673 | 2325 |
|  |  | missense | A | Lys [K] | 1 | 674 |  |
| rs201455144 | 0.001 | contig reference | G | Glu [E] | 1 | 674 | 2363 |
|  |  | missense | C | Cys [C] | 3 | 686 |  |
| rs200174513 | 0.002 | contig reference | G | Trp [W] | 3 | 686 | 2422 |
|  |  | missense | T | Ile [I] | 2 | 706 |  |
| rs374341905 | N.D. | contig reference | A | Asn [N] | 2 | 706 | 2455 |
|  |  | missense | C | Ser [S] | 2 | 717 |  |
| rs377753845 | N.D. | contig reference | G | Trp [W] | 2 | 717 | 2476 |
|  |  | missense | G | Ser [S] | 2 | 724 |  |
| rs145884426 | 0.001 | contig reference | A | Asn [N] | 2 | 724 | 2499 |
|  |  | missense | T | Cys [C] | 1 | 732 |  |
| rs138705367 | 0.001 | contig reference | C | Arg [R] | 1 | 732 | 2539 |
|  |  | missense | C | Pro [P] | 2 | 745 |  |
| rs149410697 | 0.001 | contig reference | G | Arg [R] | 2 | 745 | 2594 |
|  |  | synonymous | T | Asn [N] | 3 | 763 |  |
| rs370216167 | N.D. | contig reference | C | Asn [N] | 3 | 763 | 2597 |
|  |  | synonymous | T | Gly [G] | 3 | 764 |  |
| rs201912634 | N.D. | contig reference | C | Gly [G] | 3 | 764 | 2601 |
|  |  | missense | C | Gln [Q] | 1 | 766 |  |
| rs201492258 | 0.002 | contig reference | G | Glu [E] | 1 | 766 | 2627 |
|  |  | synonymous | C | Asp [D] | 3 | 774 |  |
| rs144799697 | 0.005 | contig reference | T | Asp [D] | 3 | 774 | 2632 |
|  |  | missense | T | Val [V] | 2 | 776 |  |
| rs200626782 | 0.001 | contig reference | C | Ala [A] | 2 | 776 | 2668 |
|  |  | missense | T | Val [V] | 2 | 788 |  |
| rs374013273 | N.D. | contig reference | C | Ala [A] | 2 | 788 | 2683 |
|  |  | missense | C | Pro [P] | 2 | 793 |  |
| rs142028646 | 0 | contig reference | G | Arg [R] | 2 | 793 | 2684 |
|  |  | synonymous | T | Arg [R] | 3 | 793 |  |
| rs377008639 | N.D. | contig reference | G | Arg [R] | 3 | 793 | 2690 |
|  |  | synonymous | A | Glu [E] | 3 | 795 |  |
| rs150691639 | 0 | contig reference | G | Glu [E] | 3 | 795 | 2694 |
|  |  | missense | C | Gln [Q] | 1 | 797 |  |
| rs140025413 | 0 | contig reference | G | Glu [E] | 1 | 797 | 2748 |
|  |  | missense | G | Val [V] | 1 | 815 |  |
| rs143544464 | 0.001 | contig reference | C | Leu [L] | 1 | 815 | 2790 |
|  |  | missense | A | Thr [T] | 1 | 829 |  |
| rs200145109 | 0.001 | contig reference | C | Pro [P] | 1 | 829 | 2841 |
|  |  | missense | A | Ile [I] | 1 | 846 |  |
| rs201478823 | 0.001 | contig reference | G | Val [V] | 1 | 846 | 2866 |
|  |  | missense | T | Leu [L] | 2 | 854 |  |
| rs146820958 | 0 | contig reference | G | Arg [R] | 2 | 854 | 2870 |
|  |  | synonymous | A | Thr [T] | 3 | 855 |  |
| rs139591184 | 0 | contig reference | C | Thr [T] | 3 | 855 | 2888 |
|  |  | missense | A | Leu [L] | 3 | 861 |  |
| rs150005580 | N.D. | contig reference | C | Phe [F] | 3 | 861 | 2894 |
|  |  | synonymous | T | Tyr [Y] | 3 | 863 |  |
| rs200012664 | 0.001 | contig reference | C | Tyr [Y] | 3 | 863 | 2895 |
|  |  | missense | A | Met [M] | 1 | 864 |  |
| rs145586647 | 0.002 | contig reference | C | Leu [L] | 1 | 864 | 2909 |
|  |  | synonymous | T | Cys [C] | 3 | 868 |  |
| rs200487092 | 0.001 | contig reference | C | Cys [C] | 3 | 868 | 3064 |
|  |  | missense | C | Thr [T] | 2 | 920 |  |
| rs75837861 | N.D. | contig reference | T | Ile [I] | 2 | 920 | 3143 |
|  |  | missense | T | Phe [F] | 3 | 946 |  |

TABLE 4-continued

SNPs variants of ACLP gene of SEQ ID NO: 2
Table 4: SNPs variants of ACLP gene of SEQ ID NO: 2

| dbSNP rs# cluster id | Heterozygosity | Function | dbSNP allele | Protein residue | Codon pos | Amino acid pos | mRNA pos |
|---|---|---|---|---|---|---|---|
| rs201507217 | 0.001 | contig reference synonymous | G A | Leu [L] Glu [E] | 3 3 | 946 950 | 3155 |
| rs148876034 | 0 | contig reference synonymous | G T | Glu [E] Arg [R] | 3 3 | 950 952 | 3161 |
| rs372595583 | N.D. | contig reference nonsense | C A | Arg [R] | 3 3 | 952 971 | 3218 |
| rs367704352 | N.D. | contig reference missense | T C | Tyr [Y] Ser [S] | 3 2 | 971 980 | 3244 |
| rs147631109 | 0 | contig reference synonymous | T T | Phe [F] Ile [I] | 2 3 | 980 981 | 3248 |
| rs141977965 | 0.001 | contig reference synonymous | C T | Ile [I] Arg [R] | 3 3 | 981 984 | 3257 |
| rs371157380 | N.D. | contig reference synonymous | C A | Arg [R] Arg [R] | 3 3 | 984 991 | 3278 |
| rs200154504 | 0.002 | contig reference missense | G A | Arg [R] Glu [E] | 3 2 | 991 998 | 3298 |
| rs4724285 | 0.014 | contig reference missense | G T | Gly [G] Leu [L] | 2 2 | 998 1001 | 3307 |
| rs200791707 | 0.002 | contig reference missense | C T | Pro [P] Leu [L] | 2 2 | 1001 1015 | 3349 |
| rs146344486 | 0.001 | contig reference missense | A A | Gln [Q] Thr [T] | 2 1 | 1015 1031 | 3396 |
| rs200356275 | N.D. | contig reference missense | G A | Ala [A] Gln [Q] | 1 2 | 1031 1036 | 3412 |
| rs376181075 | N.D. | contig reference missense | G T | Arg [R] Ile [I] | 2 2 | 1036 1042 | 3430 |
| rs202072841 | 0.001 | contig reference synonymous | C C | Thr [T] Val [V] | 2 3 | 1042 1049 | 3452 |
| rs113676804 | 0.5 | contig reference missense | G T | Val [V] Pro [P] | 3 3 | 1049 1054 | 3467 |
| rs201065802 | 0.001 | contig reference missense | C G | Pro [P] Gly [G] | 3 2 | 1054 1066 | 3502 |
| rs61736256 | 0.053 | contig reference synonymous | A G | Glu [E] Gly [G] | 2 3 | 1066 1077 | 3536 |
| rs138297087 | 0.001 | contig reference missense | C A | Gly [G] Lys [K] | 3 1 | 1077 1079 | 3540 |
| rs149601977 | 0 | contig reference missense | G T | Glu [E] Ile [I] | 1 2 | 1079 1085 | 3559 |
| rs148505735 | 0 | contig reference synonymous | C A | Thr [T] Gln [Q] | 2 3 | 1085 1112 | 3641 |
| rs199622819 | 0.001 | contig reference missense | G G | Gln [Q] Gly [G] | 3 2 | 1112 1130 | 3694 |
| rs142895757 | 0.001 | contig reference | A A | Glu [E] Glu [E] | 2 3 | 1130 1130 | 3695 |
| rs13928 | 0.474 | contig reference missense | G G | Glu [E] Glu [E] | 3 1 | 1130 1133 | 3702 |
| rs34841625 | N.D. | contig reference frame shift | A C | Lys [K] Leu [L] | 1 3 | 1133 1145 | 3737 |
| rs13898 | 0.03 | contig reference missense | — A | Phe [F] Ile [I] | 3 1 | 1145 1148 | 3747 |
| rs113791881 | 0.011 | missense synonymous | G C | Val [V] Phe [F] | 1 3 | 1148 1155 | 3770 |

In some embodiments, an ACLP inhibitor is a siRNA, thereby inhibiting the mRNA of ACLP. In some embodiments, a ACLP siRNA inhibitor is (GGCUCAAGAUC-UACGCAAU) (SEQ ID NO: 7) which inhibits mouse ACLP expression or a fragment or a homologue thereof of at least 50%, or at least 60% or at least 70% or at least 80% or at least 90% identical thereto. In some embodiments, an ACLP inhibitor is a commercially available siRNA, such as available from Santa Cruz (cat #sc-40327). In some embodiments, siRNA or RNAi targeting ACLP can be delivered in a vector, for example a lentiviral vector, such as commercially available ACLP shRNA lentivial vectors from Santa Cruz.

Also siRNAs/RNAis, antisense molecules and ribozymes directed against nucleic acid molecules encoding ACLP are envisaged as ACLP inhibitors for the use and the method of the present invention. The above-mentioned antagonist/inhibitor of ACLP may also be a co-suppressive nucleic acid.

An siRNA approach is, for example, disclosed in Elbashir ((2001), Nature 41 1, 494-498)). It is also envisaged in accordance with this invention that for example short hairpin RNAs (shRNAs) are employed in accordance with this invention as pharmaceutical composition. The shRNA approach for gene silencing is well known in the art and may comprise the use of st (small temporal) RNAs; see, inter alia, Paddison (2002) Genes Dev. 16, 948-958.

As mentioned above, approaches for gene silencing are known in the art and comprise "RNA"-approaches like RNAi (iRNA) or siRNA. Successful use of such approaches has been shown in Paddison (2002), Elbashir (2002) Methods 26, 199-213; Novina (2002) Mat. Med. Jun. 3, 2002; Donze (2002) Nucl. Acids Res. 30, e46; Paul (2002) Nat. Biotech 20, 505-508; Lee (2002) Nat. Biotech. 20, 500-505; Miyagashi (2002) Nat. Biotech. 20, 497-500; Yu (2002) PNAS 99, 6047-6052 or Brummelkamp (2002), Science 296, 550-553. These approaches may be vector-based, e.g. the pSUPER vector, or RNA polIII vectors may be employed as illustrated, inter alia, in Yu (2002) loc. cit.; Miyagishi (2002) loc. cit. or Brummelkamp (2002).

In some embodiments, a RNAi or siRNA is targeted to a tumor or cancer cell. In some embodiments, the ACLP RNAi agent, e.g., an anti-ACLP RNAi complementary to, or complementary in part, to the ACLP mRNA of SEQ ID NO: 2, can further comprise a binding moiety and a targeting moiety, and in some embodiments the binding moiety binds the ACLP RNAi agent to the targeting moiety. In some embodiments, a targeting moiety is a cell surface receptor ligand or antigen-binding fragment thereof, for example a cell surface receptor or ligand which is expressed on cells expressing the ACLP protein.

In some embodiments, an ACLP inhibitor agent, e.g., a peptide inhibitor of ACLP or a ACLP RNAi agent, e.g., an anti-ACLP RNAi complementary to, or complementary in part, to the ACLP of SEQ ID NO: 2 is encoded by a nucleic acid in a vector, for example, a plasmid, cosmid, phagemid, or virus or variants thereof, and in some embodiments the ACLP inhibitor agent, e.g., a peptide inhibitor of ACLP or a ACLP RNAi agent is operatively linked to a promoter. In some embodiments, the vector further comprises one or more in vivo expression elements for expression in human cells, such as a promoter or enhancer and combinations thereof.

In some embodiments, administration of an ACLP inhibitor agent, e.g., a peptide inhibitor of ACLP or a ACLP RNAi agent (e.g., an anti-ACLP RNAi complementary to, or complementary in part, to the ACLP of SEQ ID NO: 2) can be intravenous, intradermal, intramuscular, intraarterial, intralesional, percutaneous, subcutaneous, or by aerosol administration, or combinations thereof. In some embodiments, administration is prophylactic administration, and in alternative embodiments, administration is therapeutic administration. Antimirs have been effective in vivo to block miRNA mediated gene suppression when administered a variety of ways, in particular, intravenous, subcutaneous, intraperitonial (i.p) and other administration routes. In some embodiments, where the ACLP RNAi agent is a locked nucleic acid (LNA), the LNA is administered to a subject intravenously, for example at a dose of about 10 mg/kg, or at least about 2 mg/kg, or at about at least 5 mg/kg, or at least about 10 mg/kg. Intravenous administration of LNA has been demonstrated to be effective to inhibit mRNA mediated gene suppression in vivo (Obad et al, Nature Genetics, 2011; 43; 371-378, which is incorporated herein in its entirety by reference).

In some embodiments, the methods and compositions as disclosed herein can be administered to a subject, where the subject is, for example, a mammal such as a human.

In some embodiments, a ACLP inhibitor agent as disclosed herein can be, for example a small molecule, nucleic acid, nucleic acid analogue, aptamer, ribozyme, peptide, protein, antibody, or variants and fragments thereof. In some embodiments, a nucleic acid agent can be DNA, RNA, nucleic acid analogue, peptide nucleic acid (PNA), pseudo-complementary PNA (pcPNA), locked nucleic acid (LNA) or analogue thereof, and in embodiments where the nucleic acid agent is RNA, the RNA can be a small inhibitory RNA (RNAi), siRNA, microRNA, shRNA, miRNA and analogues and homologues and variants thereof effective in gene silencing. In some embodiments, an ACLP inhibitor (e.g., an inhibitor of the pro-fibrotic domain of ACLP) is a LNA oligonucleotide which is complementary to part of the ACLP mRNA of SEQ ID NO: 2.

In some embodiments, an ACLP inhibitor agent is a Tiny LNA oligonucleotide which is complementary to at least part of SEQ ID NO: 2.

In some embodiments, an ACLP inhibitor is an antagomir, fully 2'-O-methoxyethyl (2'-MOE), 2'-F/MOE mixmer, LNA/DNA mixmer, a tiny LNA or a combination thereof, which are complementary to, or complementary in part, to of SEQ ID NO: 2. As used herein, the term "tiny LNA" refers to a short, e.g., 6, 7, 8, 9, 10, 11 or 12-mer oligonucleotide that is comprised entirely of locked nucleic acid monomers. Tiny LNAs are described in Obad et al., (Nature Genetics, 2010, 43(4): 371-380, content of which is incorporated herein by reference. In some embodiments, the tiny LNA comprises phosphorothioate inter-sugar linkages at all positions. In some embodiments, the tiny LNA is 8 nucleotides in length and comprises phosphorothioate inter-sugar linkages at all positions.

In some embodiments, an ACLP inhibitory agent comprises a modification selected from the group consisting of nucleobase modifications, sugar modifications, inter-sugar linkage modifications, backbone modifications, and any combinations thereof. In some embodiments, an ACLP inhibitor agent is from about 11 to about 30 nucleotides in length. In some embodiments, an ACLP inhibitor agent is single-stranded. In some embodiments, an ACLP inhibitor agent is formulated in a lipid delivery vehicle, e.g., liposomes, lipid particles, other compositions used for oligonucleotide delivery. In some embodiments, an ACLP inhibitor agent is encoded by an expression vector.

As used herein, the term "oligonucleotide" refers to a polymer or an oligomer of nucleotide or nucleoside monomers consisting of naturally occurring bases, sugars and intersugar linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The oligonucleotide can be single-stranded or double-stranded. A single-stranded oligonucleotide can have double-stranded regions and a double-stranded oligonucleotide can have single-stranded regions. The oligonucleotide can have a hairpin structure or have a dumbbell structure. The oligonucleotide can be, e.g., wherein the 5'end of the oligonucleotide is linked to the 3' end of the oligonucleotide.

The oligonucleotides described herein can comprise any oligonucleotide modification described herein and below. In some embodiments, the oligonucleotide comprises at least one modification. In some embodiments, the modification is selected from the group consisting of a sugar modification, a non-phosphodiester inter-sugar (or inter-nucleoside) linkage, nucleobase modification, and ligand conjugation.

In some embodiments, the oligonucleotide comprises at least two different modifications selected from the group consisting of a sugar modification, a non-phosphodiester inter-sugar linkage, nucleobase modification, and ligand conjugation. In some embodiments, the at least two different modifications are present in the same subunit of the oligonucleotide, e.g. present in the same nucleotide.

As used herein, an oligonucleotide can be of any length. In some embodiments, oligonucleotides can range from about 6 to 100 nucleotides in length. In various related embodiments, the oligonucleotide can range in length from about 10 to about 50 nucleotides, from about 10 to about 35 nucleotides, from about 15 to about 30 nucleotides, from about 20 to about 30 nucleotides in length. In some embodiments, oligonucleotide is from about 8 to about 39 nucleotides in length. In some embodiments, the oligonucleotide is 10 to 25 nucleotides in length (e.g., 10, 11, 12, 13, 14, 15, 16, 18, 19, 20, 21, 22, 23, or 24 nucleotides in length). In some embodiments the oligonucleotide is 25-30 nucleotides. In some embodiments, the single-stranded oligonucleotide is 15 to 29 nucleotides in length. In some other embodiments, the oligonucleotide is from about 18 to about 25 nucleotides in length. In some embodiments, the oligonucleotide is about 23 nucleotides in length.

The oligonucleotide can be completely DNA, completely RNA, or comprise both RNA and DNA nucleotides. It is to be understood that when the oligonucleotide is completely DNA, RNA or a mix of both, the oligonucleotide can comprise one or more oligonucleotide modifications described herein.

An oligonucleotide can be a chimeric oligonucleotide. As used herein, a "chimeric" oligonucleotide" or "chimera" refers to an oligonucleotide which contains two or more chemically distinct regions, each made up of at least one monomer unit, i.e., a modified or unmodified nucleotide in the case of an oligonucleotide. Chimeric oligonucleotides can be described as having a particular motif. In some embodiments, the motifs include, but are not limited to, an alternating motif, a gapped motif, a hemi-mer motif, a uniformly fully modified motif and a positionally modified motif. As used herein, the phrase "chemically distinct region" refers to an oligonucleotide region which is different from other regions by having a modification that is not present elsewhere in the oligonucleotide or by not having a modification that is present elsewhere in the oligonucleotide. An oligonucleotide can comprise two or more chemically distinct regions. As used herein, a region that comprises no modifications is also considered chemically distinct.

A chemically distinct region can be repeated within an oligonucleotide. Thus, a pattern of chemically distinct regions in an oligonucleotide can be realized such that a first chemically distinct region is followed by one or more second chemically distinct regions. This sequence of chemically distinct regions can be repeated one or more times. Preferably, the sequence is repeated more than one time. Both strands of a double-stranded oligonucleotides can comprise these sequences. Each chemically distinct region can actually comprise as little as a single nucleotide. In some embodiments, each chemically distinct region comprises 1, 2, 3, 4, 5, 6, 7, 8, 9, 10, 11, 12, 13, 14, 15, 16, 17 or 18 nucleotides.

In some embodiments, alternating nucleotides comprise the same modification, e.g. all the odd number nucleotides in a strand have the same modification and/or all the even number nucleotides in a strand have the similar modification to the first strand. In some embodiments, all the odd number nucleotides in an oligonucleotide have the same modification and all the even numbered nucleotides have a modification that is not present in the odd number nucleotides and vice versa.

When the oligonucleotide is double-stranded and both strands of the double-stranded oligonucleotide comprise the alternating modification patterns, nucleotides of one strand can be complementary in position to nucleotides of the second strand which are similarly modified. In an alternative embodiment, there is a phase shift between the patterns of modifications of the first strand, respectively, relative to the pattern of similar modifications of the second strand. Preferably, the shift is such that the similarly modified nucleotides of the first strand and second strand are not in complementary position to each other. In some embodiments, the first strand has an alternating modification pattern wherein alternating nucleotides comprise a 2'-modification, e.g., 2'-O-Methyl modification. In some embodiments, the first strand comprises an alternating 2'-O-Methyl modification and the second strand comprises an alternating 2'-fluoro modification. In other embodiments, both strands of a double-stranded oligonucleotide comprise alternating 2'-O-methyl modifications. When both strands of a double-stranded oligonucleotide comprise alternating 2'-O-methyl modifications, such 2'-modified nucleotides can be in complementary position in the duplex region. Alternatively, such 2'-modified nucleotides may not be in complementary positions in the duplex region.

In some embodiments, the oligonucleotide comprises two chemically distinct regions, wherein each region is 1-10 nucleotides in length.

In other embodiments, the oligonucleotide comprises three chemically distinct regions. The middle region is about 5-15, (e.g., 5, 6, 7, 8, 9, 10, 11, 12, 13, 14 or 15) nucleotide in length and each flanking or wing region is independently 1-10 (e.g., 1, 2, 3, 4, 5, 6, 7, 8, 9 or 10) nucleotides in length.

All three regions can have different modifications or the wing regions can be similarly modified to each other. In some embodiments, the wing regions are of equal length, e.g. 1, 2, 3, 4, 5, 6, 7, 8, 9 or 10 nucleotides long.

As used herein the term "alternating motif" refers to an oligonucleotide comprising at least two different chemically distinct regions that alternate for essentially the entire sequence of the oligonucleotide. In an alternating motif length of each region is independent of the length of other regions.

As used herein, the term "uniformly fully modified motif" refers to an oligonucleotide wherein all nucleotides in the oligonucleotide have at least one modification that is the same.

As used herein, the term "hemi-mer motif" refers to an oligonucleotide having two chemically distinct regions, wherein one region is at the 5' end of the oligonucleotide and the other region is at the 3 end of the oligonucleotide. In some embodiments, length of each chemically distinct region is independently 1 nucleotide to 1 nucleotide less than the length of the oligonucleotide.

As used herein the term "gapped motif" refers to an oligonucleotide having three chemically distinct regions. In some embodiments, the gapped motif is a symmetric gapped motif, wherein the two outer chemically distinct regions (wing regions) are identically modified. In another embodiment, the gapped motif is an asymmetric gaped motif in that the three regions are chemically distinct from each other As used herein the term "positionally modified motif" refers to an oligonucleotide having three or more chemically distinct regions. Positionally modified oligonucleotides are distinguished from gapped motifs, hemi-mer motifs, blockmer motifs and alternating motifs because the pattern of regional substitution defined by any positional motif does not fit into the definition provided herein for one of these other motifs. The term positionally modified oligomeric compound includes many different specific substitution patterns.

In some embodiments, oligonucleotide comprises two or more chemically distinct regions and has a structure as described in International Application No. PCT/US09/

038433, filed Mar. 26, 2009, content of which is incorporated herein by reference in its entirety. In some embodiments, the single-stranded oligonucleotide has a ZXY structure, such as is described in International Application No. PCT/US2004/07070 filed on Mar. 8, 2004, content of which is incorporated herein by reference in its entirety.

Ribozymes can also be used as ACLP inhibitors within the present invention. Ribozymes are RNA molecules that contains a catalytic center and a target RNA binding portion. The term includes RNA enzymes, self-splicing RNAs, self-cleaving RNAs, and nucleic acid molecules that perform these catalytic functions. A ribozyme selectively binds to a target RNA molecule through complementary base pairing, bringing the catalytic center into close proximity with the target sequence. The ribozyme then cleaves the target RNA and is released, after which it is able to bind and cleave additional molecules. A nucleic acid molecule that encodes a ribozyme is termed a "ribozyme gene." Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). An expression vector can be constructed in which a regulatory element is operably linked to a nucleotide sequence that encodes a ribozyme.

In another approach, expression vectors can be constructed in which a regulatory element directs the production of RNA transcripts capable of promoting RNase P-mediated cleavage of mRNA molecules that encode a ACLP polypeptide. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053; Yuan et al., Science 263:1269, 1994; Pace et al., WIPO Publication No. WO 96/18733; George et al., WIPO Publication No. WO 96/21731; and Werner et al., WIPO Publication No. WO 97/33991). An external guide sequence generally comprises a ten- to fifteen-nucleotide sequence complementary to ACLP mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

Method of Treatment of a Subject

The present invention relates generally to a method of treating cancers and fibroproliferative diseases or disorders in a subject, where the proliferative disease or disorder is a cancer, e.g., breast cancer, sarcoma, sarcoderma, fibroproliferative disorders (e.g., of the lung, heart, kidney, skin and vasculature). Thus, by using the methods of the present invention, one can intervene in the fibroproliferative disease, for example cancer, ameliorate the symptoms, and in some cases cure the disease.

In a related embodiment, the invention contemplates the practice of the method in conjunction with other therapies such as conventional chemotherapy directed against solid tumors and for control of establishment of metastases. The administration of the compounds described herein is typically conducted prior to and/or at the same time and/or after chemotherapy, although it is also encompassed within the present invention to inhibit cell proliferation after a regimen of chemotherapy at times where the tumor tissue will be responding to the toxic assault by inducing angiogenesis to recover by the provision of a blood supply and nutrients to the tumor tissue. In addition, the pharmaceutical compositions of the invention for the treatment of proliferative disorders, for example cancer, can be administrated prophylatically and/or before the development of a tumor, if the subject has been identified as to have a risk of developing cancer, for example to subjects that are positive for biomarkers of cancer cells or tumors. Insofar as the present methods apply to inhibition of cell proliferation, the methods can also apply to inhibition of tumor tissue growth, to inhibition of tumor metastases formation, and to regression of established tumors.

Fibroproliferative Disorders (FPD)

Fibroproliferative disorders (FPD) are characterized by the abnormal accumulation of fibrous tissue ("fibrosis") or extracellular matrix (ECM) that can occur as a part of the wound-healing process in damaged tissue. Fibroproliferation has been estimated to be causative of 50% of all deaths, such as in cardiovascular diseases, fibrosis and cancer. Such tissue damage may result from physical injury, inflammation, infection, exposure to toxins, and other causes. The fibroproliferative condition includes both a cell growth component and an extensive phase characterized by extracellular matrix (ECM) accumulation. Examples of fibroproliferative disorders include, but are not limited to, dermal scar formation, keloids, liver fibrosis, lung fibrosis (e.g., silicosis, asbestosis), kidney fibrosis (including diabetic nephropathy), and glomerulosclerosis. Benign and malignant fibroproliferative disorders (FPDs) include idiopathic pulmonary fibrosis, hepatic cirrhosis, myelofibrosis, systemic sclerosis (SSc), Dupuytren's contracture, hypertrophic scars, and keloids.

A variety of renal diseases can be classified as fibroproliferative. Glomerular (usually mesangial) cell proliferation occurs in many types of glomerulonephritides in conjunction with increased extracellular matrix accumulation (Iida et al., Proc. Natl. Acad. Sci. USA 88:6560-6564, 1991). For example, mesangial cell proliferation precedes glomerulosclerosis in the remnant kidney model (Floege et al., Kidney International 41:297-309, 1992), and experimental overexpression of growth factors such as PDGF-B and TGF-beta in the kidney induces cell proliferation, matrix accumulation, and glomerulosclerosis (Isaka et al., J. Clin. Invest. 92:2597-2601, 1993; Cybulsky, Curr. Opin. Nephropathy and Hypert. 9:217-223, 2000).

A number of vascular pathologies result from a combination of mesenchymal cell proliferation (smooth muscle and fibroblast-like) and extensive accumulation of extracellular matrix components. Such artery wall diseases as arteriosclerotic lesions, arteritis of various origins, and the vascular re-stenotic lesions that frequently follow angioplasty (Riessen et al., Am. Heart J. 135:357-364, 1998; Plenz et al., Arterioscler. Thromb. Vasc. Biol. 17:2489-2499, 1997; McCaffrey, Cytokine Growth Factor Rev. 11:103-114, 2000) are considered fibroproliferative. Other fibroproliferative responses include the fibroproliferative responses that occur in organs following transplant (e.g., heart transplants), at sites of vascular anastamosis, and at areas around catheter placements (e.g., arterio-venous shunts used for dialysis).

Bone formation, both physiologic and pathologic, can be described as the interplay between bone formation that results from proliferation of osteoblasts and production by them of extracellular matrix, and the replication of osteoclasts and their modulation of this matrix. Diseases where there is aberrant and ectopic bone formation, such as that occurring with prostate tumor metastases to the axial skeleton, are commonly characterized by active proliferation of the major cell types participating in bone formation as well as by elaboration by them of a complex bone matrix. These diseases can therefore be viewed as fibroproliferative.

Pulmonary fibrosis is a major cause of morbidity and mortality. Pulmonary fibrosis is associated with the use of high-dose antineoplastic agents (e.g., bleomycin) in chemotherapy and with bone marrow transplantation for cancer treatment. The development of lung disease is the major dose-limiting side effect of bleomycin. See, Tran et al., J. Clin. Invest. 99:608-617, 1997. Idiopathic pulmonary fibrosis (IPF) is another lung fibrotic disease characterized by a fibroproliferative response. Various factors, including aspiration and exposure to environmental pollutants may result in IPF (Egan, The Lancet 354:1839-1840, 1999). The standard treatment for IPF is oral glucocorticoids. However, lung function improves in less than 30 percent of patients who receive this treatment, and, regardless of treatment, the median survival is four to five years after the onset of symptoms. The proliferation of fibroblasts and the accumulation of interstitial collagens are the hallmarks of progressive organ fibrosis, however the biochemical mechanism of induction of lung fibrosis remains unclear (Ziesche et al., New Eng. J. Med. 341:1264-1269, 1999; Kuwano et al., J. Clin Invest. 104:13-19, 1999). Pulmonary hypertension results from a variety of initiating stimuli. Its progression is associated with pulmonary vascular sclerosis, which includes abnormal endothelial morphology and function, muscularization of normally nonmuscular peripheral arteries related to differentiation of pericytes, and medial hypertrophy and neointimal formation in muscular arteries as a consequence of hypertrophy, proliferation, and migration of resident smooth muscle cells and increased production of extracellular matrix components. These components include collagen, elastin, fibronectin, and tenascin-C. This fibroproliferative response can progress to life-threatening pulmonary arterial obstructive disease (Cowan et al., J. Clin. Invest. 105:21-34, 2000).

Liver (hepatic) fibrosis occurs as a part of the wound-healing response to chronic liver injury. Fibrosis occurs as a complication of haemochromatosis, Wilson's disease, alcoholism, schistosomiasis, viral hepatitis, bile duct obstruction, toxin exposure, and metabolic disorders. This formation of scar tissue is believed to represent an attempt by the body to encapsulate the injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

There have been significant advances in the understanding of the cellular and biochemical mechanisms underlying liver fibrosis (reviewed by Li and Friedman, J. Gastroenterol. Hepatol. 14:618-633, 1999). Stellate (Ito) cells are believed to be a major source of extracellular matrix in the liver and respond to a variety of cytokines present in the liver. Friedman, Seminars in Liver Disease 19:129-140, 1999).

The actual and proposed therapeutic strategies for liver fibrosis include removal of the underlying cause (e.g., toxin or infectious agent), suppression of inflammation (using, e.g., corticosteroids, IL-1 receptor antagonists, or other agents), down-regulation of stellate cell activation (using, e.g., gamma interferon or antioxidants), promotion of matrix degradation, or promotion of stellate cell apoptosis. Despite recent progress, many of these strategies are still in the experimental stage, and existing therapies are aimed at suppressing inflammation rather than addressing the underlying biochemical processes. Thus, there remains a need in the art for materials and methods for treating fibroproliferative disorders, including liver fibrosis.

Fibroproliferative disorders are characterized by excessive connective tissue accumulation and slow but continuous tissue contraction that lead to progressive deterioration in the normal structure and function of affected organs. The main cells involved in FPDs are fibroblasts and myofibroblasts. Signalling pathways involved in FPD include integrins, transforming growth factor-β/Smad, mitogen-activated protein kinase, RhoA/ROCK, Wnt/β-catenin, and tumor necrosis factor-α/nuclear factor kappa-light-chain-enhancer of activated B cells pathways.

Fibroproliferative disorders of the kidney include, without limitation, glomerulonephritis (including membranoproliferative, diffuse proliferative, rapidly progressive, and chronic), diabetic glomerulosclerosis, focal glomerulosclerosis, diabetic nephropathy, lupus nephritis, tubulointerstitial fibrosis, membranous nephropathy, amyloidosis (which affects the kidney among other tissues), renal arteriosclerosis, and nephrotic syndrome. The glomerulus is a major target of many types of renal injury, including immunologic (e.g., immune-complex- or T-cell-mediated), hemodynamic (systemic or renal hypertension), metabolic (e.g., diabetes), "atherosclerotic" (accumulation of lipids in the glomerulus), infiltrative (e.g., amyloid), and toxic (e.g., snake venom) injuries (Johnson, Kidney Mt. 45:1769-1782, 1994). The renal structural changes in patients with diabetic nephropathy include hypertrophy of the glomerulus, thickening of the glomerular and tubular membranes (due to accumulated matrix), and increased amounts of matrix in the mesangium and tubulointerstitium (Ziyadeh et al., Proc. Natl. Acad. Sci. USA 97:8015-8020, 2000). Glomerular hypertension due to intrarenal hemodynamic changes in diabetes can contribute to the progression of diabetic nephropathy (Ishida et al., Diabetes 48:595-602, 1999). Autoimmune nephritis can also lead to altered mesangial cell growth responses (Liu and Ooi, J. Immunol. 151:2247-2251, 1993). Infection by hepatitis-C virus can also result in idiopathic membranoproliferative glomerulonephritis (Johnson et al., N. Engl. J. Med. 328:465-470, 1993).

Fibroproliferative disorders of the lung include, for example, silicosis, asbestosis, idiopathic pulmonary fibrosis, bronchiolitis obliterans-organizing pneumonia, pulmonary fibrosis associated with high-dose chemotherapy, idiopathic pulmonary fibrosis, and pulmonary hypertension. These diseases are characterized by cell proliferation and increased production of extracellular matrix components, such as collagens, elastin, fibronectin, and tenascin-C.

Fibrosis of the liver can result from damage due to chronic liver disease, including chronic active hepatitis (including hepatitis C) and many other types of cirrhosis. Widespread, massive necrosis, including destruction of virtually the entire liver, can be caused by, inter alia, fulminant viral hepatitis; overdoses of the analgesic acetaminophen; exposure to other drugs and chemicals such as halothane, monoamine oxidase inhibitors, agents employed in the treatment of tuberculosis, phosphorus, carbon tetrachloride, and other industrial chemicals. Conditions associated with ultrastructural lesions that do not necessarily produce obvious liver cell necrosis include Reye's syndrome in children, tetracycline toxicity, and acute fatty liver of pregnancy. Cirrhosis, a diffuse process characterized by fibrosis and a conversion of normal architecture into structurally abnormal nodules, can come about for a variety reasons including alcohol abuse, post necrotic cirrhosis (usually due to chronic active hepatitis), biliary cirrhosis, pigment cirrhosis, cryptogenic cirrhosis, Wilson's disease, and alpha-1-antitrypsin deficiency. In cases of liver fibrosis it may be beneficial to administer an ACLP antagonist to suppress the activation of stellate cells, which have been implicated in the production of extracellular matrix in fibrotic liver (Li and Friedman, J. Gastroenterol. Hepatol. 14:618-633, 1999).

Diseases of the skeleton that are due to modified growth and matrix production in the bone include, but are not limited to, osteopetrosis, hyperostosis, osteosclerosis, osteoarthritis, and ectopic bone formation in metastatic prostate cancer, sarcoma. Fibroproliferative disorders of bone are characterized by aberrant and ectopic bone formation, commonly seen as active proliferation of the major cell types participating in bone formation as well as elaboration by those cells of a complex bone matrix. Exemplary of such bone disorders is the fibrosis that occurs with prostate tumor metastases to the axial skeleton. In prostate tumor-related cancellous bone growth, prostate carcinoma cells can interact reciprocally with osteoblasts to produce enhanced tumor growth and osteoblastic action when they are deposited in bone (Zhau et al., Cancer 88:2995-3001, 2000; Ritchie et al., Endocrinology 138:1145-1150, 1997). It has been reported in U.S. Pat. No. 8,834,879 (which is incorporated herein in its entirety by reference) that mice receiving a ACLP-encoding adenovirus vector displayed a similar pathology as that observed in prostate cancer patients who display tumor metastases in the axial skeleton and consequent formation of endosteal bone. In addition, a panel of mouse prostate cell lines (epithelial and stromal) propagated in culture were found to express very high levels of ACLP messenger RNA, suggesting that ACLP is involved (via autocrine and/or paracrine mechanisms) in prostate tumor growth, metastasis, and effects in bone. Fibroproliferative responses of the bone originating in the skeleton per se include osteopetrosis and hyperstosis. A defect in osteoblast differentiation and function is thought to be a major cause in osteopetrosis, an inherited disorder characterized by bone sclerosis due to reduced bone resorption, wherein marrow cavities fail to develop, resulting in extramedullary hematopoiesis and severe hematologic abnormalities associated with optic atrophy, deafness, and mental retardation (Lajeunesse et al., J. Clin Invest. 98:1835-1842, 1996). In osteoarthritis, bone changes are known to occur, and bone collagen metabolism is increased within osteoarthritic femoral heads. The greatest changes occur within the subchondral zone, supporting a greater proportion of osteoid in the diseased tissue (Mansell and Bailey, J. Clin. Invest. 101:1596-1603, 1998).

Fibroproliferative disorders of the vasculature include, for example, transplant vasculopathy, which is a major cause of chronic rejection of heart transplantation. Transplant vasculopathy is characterized by accelerated atherosclerotic plaque formation with diffuse occlusion of the coronary arteries, which is a "classic" fibroproliferative disease. See, Miller et al., Circulation 101:1598-1605, 2000).

The inventive methods disclosed herein provide for the parenteral and oral administration of the compounds of the present invention, e.g., an ACLP inhibitor (e.g., an inhibitor of the pro-fibrotic domain of ACLP) as disclosed herein in combination with other pharmaceutical compositions to subjects in need of such treatment. Parenteral administration includes, but is not limited to, intravenous (IV), intramuscular (IM), subcutaneous (SC), intraperitoneal (IP), intranasal, and inhalant routes. In the method of the present invention, the ACLP inhibitors thereof are preferably administered orally. IV, IM, SC, and IP administration may be by bolus or infusion, and may also be by slow release implantable device, including, but not limited to pumps, slow release formulations, and mechanical devices. The formulation, route and method of administration, and dosage will depend on the disorder to be treated and the medical history of the subject. In general, a dose that is administered by subcutaneous injection will be greater than the therapeutically-equivalent dose given intravenously or intramuscularly.

The methods of the present invention for treating a fibroproliferative disease and/or cancer comprising contacting a tissue in which proliferation is occurring, or is at risk for occurring, with the compositions of the present invention comprising a therapeutically effective amount of an ACLP inhibitor (e.g., an inhibitor of the pro-fibrotic domain of ACLP) as disclosed herein or functional derivatives thereof.

In some embodiments, the subject treated by the methods of the present invention in its many embodiments is a human subject, although it is to be understood that the principles of the invention indicate that the invention is effective with respect to all mammals. In this context, a mammal is understood to include any mammalian species in which treatment of diseases associated with cancer or a proliferative-related disorder is desirable, particularly agricultural and domestic mammalian species, as well as transgenic animals.

In some embodiments, a subject amenable for treatment has breast cancer. In some embodiments, the subject has Her2+ breast cancer, or liver cancer. In some embodiments, the subject has sarcoma.

Administration of Pharmaceutical Compositions

A physician or veterinarian having ordinary skill in the art can readily determine and prescribe the effective amount of the pharmaceutical composition of an ACLP inhibitor (e.g., an inhibitor of the pro-fibrotic domain of ACLP) as disclosed herein which is required. For example, the physician or veterinarian could start doses of the compounds of the invention employed in the pharmaceutical composition at levels lower than that required in order to achieve the desired therapeutic effect and gradually increase the dosage until the desired effect is achieved.

After formulation of an ACLP inhibitor (e.g., an inhibitor of the pro-fibrotic domain of ACLP) as disclosed herein with an appropriate pharmaceutically acceptable carrier in a desired dosage, the pharmaceutical compositions of this invention can be administered to a subject. The pharmaceutical compositions as disclosed herein can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular, or nasal routes.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

When the compounds of the present invention, for example an ACLP inhibitor (e.g., an inhibitor of the pro-fibrotic domain of ACLP) as disclosed herein are administered as pharmaceuticals, to humans and mammals, they can be given per se or as a pharmaceutical composition containing, for example, 0.1 to 99.5% (more preferably, 0.5 to 90%) of active ingredient, i.e., at least one ACLP inhibitor (e.g., an inhibitor of the pro-fibrotic domain of ACLP) as disclosed herein and/or derivative thereof, in combination with a pharmaceutically acceptable carrier.

In general, a suitable daily dose of an ACLP inhibitor (e.g., an inhibitor of the pro-fibrotic domain of ACLP) as disclosed herein will be that amount of the compound which is the lowest dose effective to produce a therapeutic effect. Such an effective dose will generally depend upon the factors described above. Generally, intravenous and subcutaneous doses of the compounds of this invention for a patient, will range from about 0.1 mg to about 250 mg per kilogram of body weight per day, more preferably from about 1 mg to about 60 mg per kg per day.

If desired, the effective daily dose of the active compound may be administered as two, three, four, five, six or more sub-doses administered separately at appropriate intervals throughout the day, optionally, in unit dosage forms.

Pharmaceutical compositions comprising an ACLP inhibitor (e.g., an inhibitor of the pro-fibrotic domain of ACLP) as disclosed herein can include a "therapeutically effective amount" or a "prophylactically effective amount" of one or more of the compounds of the present invention, or functional derivatives thereof. An "effective amount" is the amount as defined herein in the definition section and refers to an amount effective, at dosages and for periods of time necessary, to achieve the desired therapeutic result, e.g., a diminishment or prevention of effects associated with the fibroproliferative disease states or conditions, such as cancer. A therapeutically effective amount of an ACLP inhibitor (e.g., an inhibitor of the pro-fibrotic domain of ACLP) as disclosed herein or functional derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylatically or therapeutically effective amount is also one in which any toxic or detrimental effects of the compound are outweighed by the beneficial effects.

Antibodies are preferably administered parenterally, such as by bolus injection or infusion (intravenous, intramuscular, intraperitoneal, or subcutaneous) over the course of treatment. Antibodies are generally administered in an amount sufficient to provide a minimum circulating level of antibody throughout the treatment period of between approximately 20 µg and 1 mg/kg body weight. In this regard, it is preferred to use antibodies having a circulating half-life of at least 12 hours, preferably at least 4 days, more preferably up to 14-21 days. Chimeric and humanized antibodies are expected to have circulatory half-lives of up to four and up to 14-21 days, respectively. In many cases it will be preferable to administer daily doses during a hospital stay, followed by less frequent bolus injections during a period of outpatient treatment. Antibodies can also be delivered by slow-release delivery systems, pumps, and other known delivery systems for continuous infusion. Dosing regimens may be varied to provide the desired circulating levels of a particular antibody based on its pharmacokinetics. Thus, doses will be calculated so that the desired circulating level of therapeutic agent is maintained. Daily doses referred to above may be administered as larger, less frequent bolus administrations to provide the recited dose averaged over the term of administration.

Those skilled in the art will recognize that the same principles will guide the use of other ACLP inhibitors (e.g., inhibitors of the pro-fibrotic domain of ACLP). The dosing regimen for a given antagonist will be determined by a number of factors including potency, pharmacokinetics, and the physicochemical nature of the antagonist. For example, non-peptidic ACLP inhibitors (e.g., inhibitors of the pro-fibrotic domain of ACLP) may be administered enterally.

Therapeutic polynucleotides, such as antisense polynucleotides, can be delivered to patients or test animals by way of viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., Meth. Cell Biol. 43:161-189, 1994; and Douglas and Curiel, Science & Medicine 4:44-53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters, including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. When intravenously administered to intact animals, adenovirus primarily targets the liver. If the adenoviral delivery system has an El gene deletion, the virus cannot replicate in the host cells. However, the host's tissue (e.g., liver) will express and process (and, if a signal sequence is present, secrete) the heterologous protein.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter, by methods commonly known by one of ordinary skill in the art. See, e.g., Wu et al., J. Biol. Chem. 263:14621-14624, 1988; Wu et al., J. Biol. Chem. 267:963-967, 1992; and Johnston and Tang, Meth. Cell Biol. 43:353-365, 1994.

ACLP inhibitors (e.g., inhibitors of the pro-fibrotic domain of ACLP) can be analyzed for inhibition of TGFβ signaling (e.g., by a decrease in pSmad3, or levels of SMA and/or collagen I) by a variety of methods that are well known in the art, including receptor competition assays (Bowen-Pope and Ross, Methods Enzymol. 109:69-100, 1985) and through the use of soluble receptors, including receptors produced as IgG fusion proteins (U.S. Pat. No.

5,750,375). The receptors can be naturally present in the cell, or can be recombinant receptors expressed by genetically engineered cells.

Activity of ACLP inhibitors (e.g., inhibitors of the pro-fibrotic domain of ACLP) can be measured in vitro using cultured cells in assays designed to measure ACLP activity. Antagonists will reduce the effects of ACLP within the assay. Mitogenic activity can be measured using known assays, including 3H-thymidine incorporation assays which are well known in art (e.g., as disclosed by, e.g., Wagner et al., Veterinary Immunology and Immunopathology, 1999, 70; 151-159), dye incorporation assays and MTT assays (as disclosed by, for example, Hamid et al., Toxicology in vitro; 2004; 18(5); Lobner et al., J. Neurosci methods, 2000; 96(2); 147-152; Chiba et al., Toxicology in vitro, 1998; 12(3); 251-258) or cell counts.

The biological activities of ACLP inhibitors (e.g., inhibitors of the pro-fibrotic domain of ACLP) can be studied in non-human animals by administration of exogenous compounds, by expression of ACLP inhibitory polynucleotides, and by suppression of endogenous ACLP expression through knock-out techniques. Viral delivery systems (disclosed above) can be employed. ACLP inhibitors (e.g., inhibitors of the pro-fibrotic domain of ACLP) can be administered or expressed individually, in combination with other ACLP inhibitors (e.g., inhibitors of the pro-fibrotic domain of ACLP), or in combination other compounds, including other growth factor antagonists. Test animals are monitored for changes in such parameters as clinical signs, body weight, blood cell counts, clinical chemistry, histopathology, and the like.

Effects of ACLP inhibitors (e.g., inhibitors of the pro-fibrotic domain of ACLP) on liver and kidney fibrosis can be tested in known animal models, such as the db/db mouse model disclosed by Cohen et al., Diabetologia 39:270-274, 1996 and Cohen et al., J. Clin. Invest. 95:2338-2345, 1995, or transgenic animal models (Imai et al., Contrib. Nephrol. 107:205-215, 1994).

Effects on lung fibrosis can also be assayed in a mouse model using bleomycin. The chemotherapy agent bleomycin is a known causative agent of pulmonary fibrosis in humans and can induce interstitial lung disease in mice, including an increase in the number of fibroblasts, enhanced collagen deposition, and dysregulated matrix remodeling. C57Bl/6 mice are administered bleomycin by osmotic minipump for 1 week or by intratracheal injection. There follows a period of inflammation, with cutaneous toxicity beginning approximately 4-7 days after bleomycin administration and continuing for about a week, after which the mice appear to regain health. About 3-4 weeks after the finish of bleomycin delivery, the mice are euthanized, and the lungs are examined histologically for signs of fibrosis. Scoring is based on the extent of lung fibrotic lesions and their severity. Serum is assayed for lactic dehydrogenase, an intracellular enzyme that is released into the circulation upon general cell death or injury. Lung tissue is assayed for hydroxyproline as a measure of collagen deposition.

Mice and other animals expressing ACLP protein using a viral vector, e.g., an ACLP-expressing adenovirus or AAV vector are also useful models for testing ACLP inhibitors (e.g., inhibitors of the pro-fibrotic domain of ACLP) and other antifibroproliferative agents.

The term "synergy" or "synergistic" as used herein, refers to the interaction of two or more agents so that their combined effect is greater than each of their individual effects at the same dose alone. In some embodiments, a ACLP inhibitor that targets the PFD domain (e.g., an agent which inhibits the PFD domain from interacting with a member of the TGFβ R superfamily, e.g., TGFβRII), can be used synergistically with an ACLP inhibitor which targets the discoidin domain of ACLP (e.g., a discoidin inhibitor or DSi). As such, their combined effect of such PFDi and DSi inhibitors together is greater, e.g., at least about 5%, or at least about 10%, or at least about 15%, or greater than 15%, than their individual effects alone (e.g., a PFDi alone or a DSi alone) at inhibiting ACLP-mediated fibrosis and/or ACLP-mediated activation of a member of the TGFβ receptor superfamily, e.g., TGFβRII.

Dosage regimens may be adjusted to provide the optimum desired response (e.g. a therapeutic or prophylactic response). For example, a single bolus may be administered, several divided doses may be administered over time or the dose may be proportionally reduced or increased as indicated by the exigency of the therapeutic situation. It is especially advantageous to formulate parenteral compositions in dosage unit form for ease of administration and uniformity of dosage. Actual dosage levels of the active ingredients in the pharmaceutical compositions comprising one or more ACLP inhibitors (e.g., inhibitors of the pro-fibrotic domain of ACLP) may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound, an ACLP inhibitor (e.g., an inhibitor of the pro-fibrotic domain of ACLP) and/or derivative thereof and the particular therapeutic or prophylactic effect to be achieved, and (b) the limitations inherent in the art of compounding such an active compound for the treatment of sensitivity in individuals.

In some embodiments, therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount of an ACLP inhibitor (e.g., an inhibitor of the pro-fibrotic domain of ACLP) as disclosed herein is sufficient to reduce or inhibit cell proliferation in a subject suffering from a fibroproliferative disorder, for example cancer. In some embodiments, the therapeutically effective amount is sufficient to eliminate the proliferative cells, for example eliminate the cancer cells and/or tumor in a subject suffering cancer and/or a proliferative disease.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of an ACLP inhibitor (e.g., an inhibitor of the pro-fibrotic domain of ACLP) as disclosed herein or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more an ACLP inhibitor (e.g., an inhibitor of the pro-fibrotic domain of ACLP) as disclosed herein or functional derivatives thereof are optionally tested in one or more appropriate in vitro and/or in vivo animal models of disease, such as models of cancer, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of an ACLP inhibitor (e.g., an inhibitor of the pro-fibrotic domain of ACLP) as disclosed herein or functional derivatives thereof at various concentrations, e.g., as applied to the mass and overall health of the patient. Administration can be accomplished via single or divided doses.

In vitro models can be used to determine the effective doses of an ACLP inhibitor (e.g., an inhibitor of the pro-fibrotic domain of ACLP) as disclosed herein or functional derivatives thereof as a potential cancer treatment. Suitable in vitro models include, but are not limited to, proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., I J. Natl. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. J. Dev. Biol., 40: 1189-97 (1999) and Li et al., Clin. Exp. Metastasis, 17:423-9 (1999), respectively. Suitable tumor cells lines are available, e.g. from American Type Tissue Culture Collection catalogs.

In vivo models are the preferred models to determine an effective dose of an ACLP inhibitor (e.g., an inhibitor of the pro-fibrotic domain of ACLP) as disclosed herein or functional derivatives thereof as disclosed herein as potential cancer treatments. Suitable in vivo models include, but are not limited to, mice that carry a mutation in the KRAS oncogene (Lox-Stop-Lox K-RasGi2D mutants, Kras24TYj) available from the National Cancer Institute (NCI) Frederick Mouse Repository. Other mouse models known in the art and that are available include but are not limited to models for breast cancer, gastrointestinal cancer, hematopoietic cancer, lung cancer, mammary gland cancer, nervous system cancer, ovarian cancer, prostate cancer, skin cancer, cervical cancer, oral cancer, and sarcoma cancer (see world-wide web address: "emice.nci.nih. gov/mouse_models/").

In determining the effective amount of an ACLP inhibitor (e.g., an inhibitor of the pro-fibrotic domain of ACLP) as disclosed herein or a functional derivative thereof to be administered in the treatment or prophylaxis of disease the physician evaluates circulating plasma levels, formulation toxicities, and progression of the disease.

Figure 4:
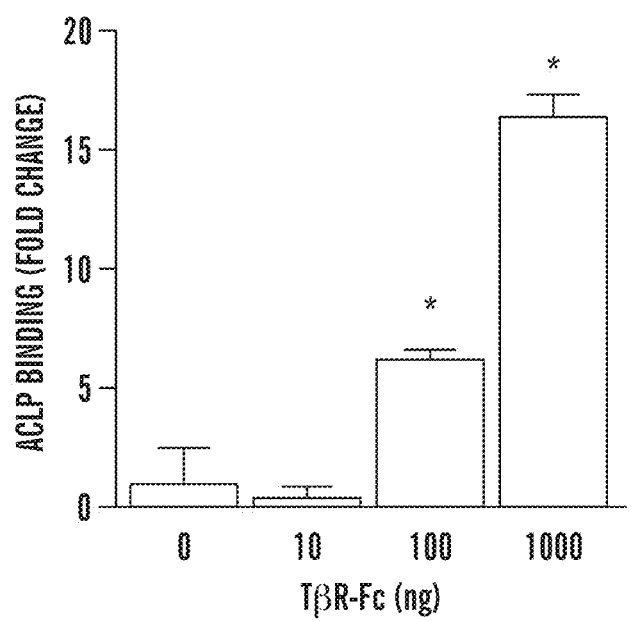
FIG. 4 shows ACLP binds directly to the TGFβ receptor. rACLP was biotinylated and immobilized to streptavidin-coated plates. The wells were blocked, incubated with increasing amounts of Tβ-RII Fc (TOR-Fc) fusion chimera (1, 10, 100, 1000 ng), followed by human anti-Ig-HRP and TMB substrate. The reaction was quenched with 2M $H_2SO_4$ and binding was measured by reading the absorbance at 450 nm. * indicates significance (P<0.05) versus control treated cells. Data presented are representative of 3 separate experiments.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. In some embodiments, the compounds of the present invention have an $ED_{50}$ value ranging from 0.01 µM-10 nM or 10-100 ng in an in vitro assay for inhibition of ACLP-mediated TGFβ signaling (see FIGS. 4 and 11A).

The dose of agents, e.g., antibodies and peptide can be calculated based on the human-equivalent doses (HED) as recommended in Sharma et al., Br J Pharmacol. 2009 July; 157(6): 907-921, and in "Estimating the maximum Safe Starting dose in Initial Clinical Trials for Therapeutics in Adult Healthy Volunteers" by US Department of Health and Human Services, CDER, 2005 (available at world-wide-web at "fda.gov/downloads/Drugs/Guidances/UCM078932.pdf") (which are incorporated herein in their entirety by reference), which recommend that where a drug or agent is assessed in a rat model, with a NOAEL (no observed adverse effect levels) of 15 mg·kg$^{-1}$·day$^{-1}$, the HED according to FDA guidelines is as follows: HED=animal mg·kg$^{-1}$·day$^{-1}$×animal weight kg/human weight kg)$^{0033}$=15×(0.35/60)$^{0.33}$=3.4 mg·kg$^{-1}$·day$^{-1}$. Assuming the human weight is 60 kg, the HED is 206 mg·kg$^{-1}$·day$^{-1}$. Applying a safety factor of 10, the starting dose in humans is 20.6 mg·kg$^{-1}$·day$^{-1}$, so a dose of 20 mg·kg$^{-1}$·day$^{-1}$ would be selected. As disclosed herein, the inventors demonstrate that at least 100 ng of TpR-Fc inhibited ACLP binding to TGFβ-RII in vitro, therefore one can use at least 50 ng of a peptide or polypeptide ACLPi in the methods and compositions as disclosed herein.

In some embodiments, where an ACLPi (e.g., a PDFi) or a DCi is an antibody or antibody-binding fragment or an antigen-binding molecule, the dose can be calculated as disclosed in Mulshine et al., Cancer Res. 1992 May 1; 52(9 Suppl):2743s-2746s. (which is incorporated herein in its entirety by reference.) In some embodiments, where an ACLPi (e.g., a PDFi) or a DCi is an antibody or antibody-binding fragment or an antigen-binding molecule, or peptide, the dose can be, for example, at least about 0.1 mg/kg, or at least about 0.3 mg/kg, or at least about 1 mg/kg or at least about 3 mg/kg or at least about 10 mg/kg, or at least about 30 mg/kg body weight. In some embodiments, the treatment is twice a day, or once a day, or by weekly, or three-times a week, or every 5-days, or every 10-days or every 14 days, or once a month, or every 3 months, or every 6 months or every 1 year, or once in a lifetime, or any interval in between.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

An exemplary, non-limiting range for a therapeutically or prophylactically effective amount of a compound of the present invention, for example an ACLP inhibitor (e.g., an inhibitor of the pro-fibrotic domain of ACLP and/or an inhibitor of the DS domain of ACLP) as disclosed herein and/or functional derivatives thereof of the invention is 0.1-250 mg/kg, and in some embodiments, the dosage is 1-60 mg/kg. In some embodiments, the dose of an ACLP inhibitor (e.g., an inhibitor of the pro-fibrotic domain of ACLP) as disclosed herein is between 30-600 mg/kg/day, or between about 10-1000 mg/kg/day, or between about 50-500 mg/kg/day, or between about 100-100 mg/kg/day, or between about 30-100 mg/kg/day. In some embodiments, the dose is about 30 mg/kg/day. In some embodiments, the dose is about 600 mg/kg/day. In some embodiments, the human equivalent dose (HED) of an ACLP inhibitor (e.g., an inhibitor of the pro-fibrotic domain of ACLP) (which, if used in mice at 30 mg/kg/day and 600 mg/kg/day) is between about between 2.5-5 mg/kg/day, or between about 1-10 mg/kg/day, or between about 2-5 mg/kg/day, or between about 1-2.5 mg/kg/day, or between about 2-7.5 mg/kg/day. In some embodiments, the dose is about 2.5 mg/kg/day. In some embodiments, the dose is about 5 mg/kg/day. In some embodiments, where the PFDi or DSi is an antibody, antigen-binding molecule or antibody fragment, the dosages range are as follows; for a subject weighing between 10 kg (22 lb) to <15 kg (33 lb) dosages range from 10 mg every day, or 10 mg every other day, or 10 mg every week, or 10 mg every 2 weeks or 10 mg every 3 weeks, or 10 mg every month, or 10 mg every 2 months, or 10 mg every 3 months, or 10 mg every 4 months, or 10 mg every 6 months, or 10 mg every 12 months; for a subject weighing between 15 kg (33 lb) to <30 kg (66 lb) dosages range from 20 mg every day, or 20 mg every other day, or 20 mg every week, or 20 mg every 2 weeks or 20 mg every 3 weeks, or 20 mg every month, or 20 mg every 2 months, or 20 mg every 3 months, or 20 mg every 4 months, or 20 mg every 6 months, or 20 mg every 12 months; for a subject weighing greater than 30 kg (66 lb) dosages range from 40 mg every day, or 40 mg every other day, or 40 mg every week, or 40 mg every 2 weeks or 40 mg every 3 weeks, or 40 mg every month, or 40 mg every 2 months, or 40 mg every 3 months, or 40 mg every 4 months, or 40 mg every 6 months, or 40 mg every 12 months.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The invention features an article of manufacture that contains packaging material and compounds of the present invention, for example an ACLP inhibitor (e.g., an inhibitor of the pro-fibrotic domain of ACLP), and optionally a DCi, as disclosed herein and/or functional derivatives thereof in a formulation contained within the packaging material. In some embodiments, a formulation can contain at least one of the compounds of the present invention, for example at least one an ACLP inhibitor (e.g., an inhibitor of the pro-fibrotic domain of ACLP) as disclosed herein and/or functional derivatives thereof and the packaging material contains a label or package insert indicating that the formulation can be administered to the subject to treat one or more conditions as described herein, in an amount, at a frequency, and for a duration effective to treat or prevent such condition(s). In some embodiments, the PFDi and/or DSi in such kits and admixture is in lyophilized form. Such conditions are mentioned throughout the specification and are incorporated herein by reference.

More specifically, the invention features an article of manufacture that contains packaging material and at least one of the compounds of the present invention, for example at least one an ACLP inhibitor (e.g., an inhibitor of the pro-fibrotic domain of ACLP), and optionally, at least on DCi inhibitor as disclosed herein or a functional derivative thereof contained within the packaging material. The packaging material contains a label or package insert indicating that the formulation can be administered to the subject to alleviate a proliferative disorder, for example cancer in an amount, at a frequency, and for a duration effective treat or prevent symptoms associated with such disease states or conditions discussed throughout this specification.

Pharmaceutical Compositions

In another embodiment of the invention, a pharmaceutical composition can contain one or more compounds as disclosed, e.g., an ACLP inhibitor (e.g., an inhibitor of the pro-fibrotic domain of ACLP) as disclosed herein. For purpose of administration, an ACLP inhibitor (e.g., an inhibitor of the pro-fibrotic domain of ACLP) as disclosed herein is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Preferably, a pharmaceutical composition of the present invention can include an ACLP inhibitor (e.g., an inhibitor of the pro-fibrotic domain of ACLP) as disclosed herein in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in Remington's Pharmaceutical Sciences, Gennaro, Ed., Mack Publishing Co., Easton, Pa. 1990.

While it is possible for compounds of the present invention, for example an ACLP inhibitor (e.g., an inhibitor of the pro-fibrotic domain of ACLP) as disclosed herein and/or functional derivatives thereof, to be administered alone, it is preferable to administer the compound as a pharmaceutical composition.

Formulations of the invention can be prepared by a number or means known to persons skilled in the art. In some embodiments the formulations can be prepared by combining (i) at least an ACLP inhibitor (e.g., an inhibitor of the pro-fibrotic domain of ACLP) as disclosed herein and/or functional derivatives thereof in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches, that comprise one or more of the compounds of the present invention, and/or their functional derivatives thereof for oral or subcutaneous administration. In some embodiments, a PFDi and/or DSi, as disclosed herein for use in the methods, compositions, kits and admixtures is in lyophilized form.

In certain embodiments, the compounds of the present invention, for example an ACLP inhibitor (e.g., an inhibitor of the pro-fibrotic domain of ACLP) as disclosed herein or functional derivatives thereof are administered to a subject as a pharmaceutical composition with a pharmaceutically acceptable carrier. In certain embodiments, these pharmaceutical compositions optionally further comprise one or more additional therapeutic agents. In certain embodiments, the additional therapeutic agent or agents are anti-cancer agents. In some embodiments, the therapeutic agents are chemotherapeutic agents, for example but not limited to, cisplatin, paclitaxel etc. In some embodiments, the therapeutic agents are radiotherapeutic agents.

In some embodiments the pharmaceutical composition comprises compounds of the present invention, for example an ACLP inhibitor (e.g., an inhibitor of the pro-fibrotic domain of ACLP) as disclosed herein and/or functional derivatives thereof, alone or in any plurality of combinations. In other embodiments, the pharmaceutical compositions optionally further comprise one or more additional therapeutic agents including but not limited to chemotherapeutic agents. Examples of chemotherapeutic agents in the pharmaceutical compositions of this invention are, but are not limited to, for example, any or any combination of paclitaxel, cisplatin (e.g., the combination of doxorubicin and paclitaxel), vermurafib, nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon, platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective and encompassed for use in the methods of the present invention.

Patient(s) may also be subject to co-therapy/co-treatment with an ACLP inhibitor (e.g., an inhibitor of the pro-fibrotic domain of ACLP) and a further compound/drug (e.g. an agent for the treatment of fibroproliferative disorders)). Of course, co-therapy/combination therapy to be used in context of the present invention may also comprise radiation therapy, conventional chemotherapy and the like.

The following relates to pharmaceutical compositions and drug combinations. In one embodiment, the present invention relates to an ACLP inhibitor (e.g., an inhibitor of the pro-fibrotic domain of ACLP) as defined herein for use in treating, ameliorating and/or preventing fibroproliferative disorders. Accordingly, also the use of an ACLP inhibitor (e.g., an inhibitor of the pro-fibrotic domain of ACLP) for the preparation of a pharmaceutical composition for the treatment, amelioration and/or prevention of any fibroproliferative disorder disclosed herein is envisaged in context of the present invention.

In accordance with the above, the present invention relates to drug combinations and pharmaceutical compositions comprising at least one ACLP inhibitor (e.g., an inhibitor of the pro-fibrotic domain of ACLP) as active ingredient together with at least one pharmaceutically acceptable carrier, excipient and/or diluent and optionally together with one or more other anti-tumor agents As used herein the term "drug combination" refers to a combination of at least to pharmaceutically active agents or therapeutic agents with or without further ingredients, carrier, diluents and/or solvents. As used herein the term "pharmaceutical composition" refers to a galenic formulation of at least one pharmaceutically active agent together with at least one further ingredient, carrier, diluent and/or solvent.

An ACLP inhibitor (e.g., an inhibitor of the pro-fibrotic domain of ACLP) may be administered as the sole pharmaceutical agent or in combination with one or more additional therapeutic agents, wherein the drug combination causes no unacceptable adverse effects. This combination therapy includes administration of a single pharmaceutical dosage formulation, which contains an ACLP inhibitor (e.g., an inhibitor of the pro-fibrotic domain of ACLP) and one or more additional therapeutic agents in form of a single pharmaceutical composition, as well as administration of an ACLP inhibitor (e.g., an inhibitor of the pro-fibrotic domain of ACLP) and each additional therapeutic agent in its own separate pharmaceutical dosage formulation, i.e. in its own separate pharmaceutical composition. For example, an ACLP inhibitor (e.g., an inhibitor of the pro-fibrotic domain of ACLP) and a therapeutic agent may be administered to the patient together in a single oral dosage composition such as a tablet or capsule, or each agent may be administered in separate pharmaceutical compositions. Where separate pharmaceutical compositions are used, an ACLP inhibitor (e.g., an inhibitor of the pro-fibrotic domain of ACLP) and one or more additional therapeutic agents may be administered at essentially the same time (e.g., concurrently) or at separately staggered times (e.g., sequentially).

In particular, an ACLP inhibitor (e.g., an inhibitor of the pro-fibrotic domain of ACLP) to be used in accordance with the present invention may be used in fixed or separate pharmaceutical compositions with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other antitumor drugs.

In this regard, the following is a non-limiting list of examples of secondary agents that may be used in combination with an ACLP inhibitor (e.g., an inhibitor of the pro-fibrotic domain of ACLP), including but not limited to; Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, and mitolactol; platinum-coordinated alkylating compounds include, but are not limited to, cisplatin, carboplatin, eptaplatin, lobaplatin, nedaplatin, oxaliplatin, and satraplatin; Anti-metabolites include, but are not limited to, methotrexate, 6-mercaptopurine riboside, mercaptopurine, 5-fluorouracil alone or in combination with leucovorin, tegafur, doxifluri-dine, carmofur, cytarabine, cytarabine ocfosfate, enocitabine, gemcitabine, fludarabin, 5-azacytidine, capecitabine, cladribine, clofarabine, decitabine, eflomithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine; Hormonal therapy agents include, but are not limited to, exemestane, LUPRON® (leuprolide), anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, TRELSTAR® (Triptorelin Pamoate), toremifene, raloxifene, lasofoxifene, letrozole, anti-androgens such as bicalutamide, flutamide, mifepristone, nilutamide, CASODEX® (bicalutamide), and anti-progesterones and combinations thereof, Plant-derived anti-tumor substances include, e.g., those selected from mitotic inhibitors, for example epothilones such as sagopilone, ixabepilone and epothilone B, vinblastine, vinfiunine, docetaxel, and paclitaxel; Cytotoxic topoisomerase inhibiting agents include, but are not limited to, aclarubicin, doxorubicin, amonafide, belotecan, camptothecin, 10-hydroxycamptothecin, 9-aminocampto-thecin, difiomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof, Immunologicals include interferons such as interferon alpha, interferon alpha-2a, interferon alpha-2b, interferon beta, interferon gamma-la and interferon gamma-nl, and other immune enhancing agents such as L19-IL2 and other IL2 derivatives, filgrastim, lentinan, sizofilan, THERACYS® (BCG live intravesical), ubenimex, aldesleukin, alemtuzumab, BAM-002, dacarbazine, daclizumab, deni-leukin, gemtuzumab, ozogamicin, ibritumomab, imiquimod, lenograstim, lentinan, melanoma vaccine, molgramostim, sargramostim, tasonermin, tecleukin, thymalasin, tositumomab, VIML-IZIM® (elosulfase alfa), epratuzumab, mitumomab, oregovomab, pemtumomab, and SIPULEUCEL-T® (Provenge); Merial melanoma vaccine; biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, PROMUNE® (Sutherlandia Extract), and ubenimex.

Anti-angiogenic compounds for cancer treatment include, but are not limited to, acitretin (bestatin), aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafe ib, vatalanib, squalamine, sunitinib, telatinib, thalidomide, ukrain, and vitaxin; Antibodies include, but are not limited to, trastuzumab, cetuximab, bevacizumab, rituximab, ticilimumab, ipilimumab, lumiliximab, catumaxomab, atacicept, oregovomab, and alemtuzumab; VEGF inhibitors such as, e.g., sorafenib, DAST, bevacizumab, sunitinib, recentin, axitinib, aflibercept, telatinib, brivanib alaninate, vatalanib, pazopanib, and rambizumab; PALLADIA® (toceranib phosphate) EGFR (HER1) inhibitors such as, e.g., cetuximab, panitumumab, vectibix, gefitmib, erlotinib, and ZACTIMA® (vandetanib) Zactima; HER2 inhibitors such as, e.g., lapatinib, tratuzumab, and pertuzumab.

Other anti-cancer agents include, mTOPv inhibitors such as, e.g., temsirolimus, sirolimus/Rapamycin, and everolimus; c-Met inhibitors; PI3K and AKT inhibitors; CDK inhibitors; HSP90 and HSP70 inhibitors; Proteasome inhibitors such as bortezomib and carfilzomib; Serine/threonine kinase inhibitors including ME inhibitors (such as e.g. RDEA 1 19) and Raf inhibitors such as sorafenib; Farnesyl transferase inhibitors such as, e.g., tipifarnib; HDAC inhibitors such as, e.g., panobinostat, vorinostat, MS275, belinostat, and LBH589; Spindle assembly checkpoints inhibitors and targeted anti-mitotic agents such as PL inhibitors, Aurora inhibitors (e.g. Hesperadin), checkpoint kinase inhibitors, and KSP inhibitors; Vitamin D receptor agonists; Bcl-2 protein inhibitors such as obatoclax, oblimersen sodium, and gossypol; Cluster of differentiation 20 receptor antagonists such as, e.g., rituximab; Ribonucleotide reductase inhibitors such as, e.g., gemcitabine; Tumor necrosis apoptosis inducing ligand receptor 1 agonists such as, e.g., mapatumumab; 5-Hydroxytryptamine receptor antagonists such as, e.g., rEV598, xaliprode, palonosetron hydrochloride, granisetron, ZINDOL® (enhanced ginger product), and AB-1001; Integrin inhibitors including alpha5-betal integrin inhibitors such as, e.g., E7820, JSM 6425. volociximab, and endostatin; Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide; Aromatase inhibitors such as, e.g., anastrozole, letrozole, testolactone, exemestane, amino-glutethimide, and formestane; Matrix metalloproteinase inhibitors; and Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, rambizumab, vatalanib, cetuximab, panitumumab, vectibix, gefitinib, erlotinib, lapatinib, tratuzumab, pertuzumab, and c-Kit inhibitors; PALLADIA® (toceranib phosphate), masitini.

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegasparga.se, pentostatin, tazaroten, velcade, gallium nitrate, canfosfamide, darinaparsin, and tretinoin.

Of course, other chemotherapeutic agents which are known to those of ordinary skill in the art can readily be substituted as this list should not be considered exhaustive or limiting.

An ACLP inhibitor (e.g., an inhibitor of the pro-fibrotic domain of ACLP) may also be employed in cancer treatment in conjunction with radiation therapy and/or surgical intervention. Furthermore, an ACLP inhibitor (e.g., an inhibitor of the pro-fibrotic domain of ACLP) may be utilized, as such or in compositions, in research and diagnostics, or as analytical reference standards, and the like, which are well known in the art. Thus, another aspect of the present invention relates to drug combinations comprising at least one inventive ACLP inhibitor (e.g., an inhibitor of the pro-fibrotic domain of ACLP) and/or pharmaceutically acceptable salts thereof together with at least one anti-retroviral drug, especially at least one of the drugs mentioned above.

In some embodiments, the pharmaceutical composition comprising an ACLP inhibitor (e.g., an inhibitor of the pro-fibrotic domain of ACLP) as disclosed herein or derivatives thereof as disclosed herein can supplement the treatment of any known additional therapy, including, but not limited to, antibody administration, vaccine administration, administration of cytotoxic agents, natural amino acid polypeptides, nucleic acids, nucleotide analogues, and biologic response modifiers. In some embodiments, additional therapy is, for example, surgery, chemotherapy, radiotherapy, thermotherapy, immunotherapy, hormone therapy and laser therapy. In some embodiments, the additional therapy is chemotherapy. Two or more combined compounds may be used together or sequentially with the pharmaceutical composition comprising an ACLP inhibitor (e.g., an inhibitor of the pro-fibrotic domain of ACLP) as disclosed herein or a derivative thereof. In some embodiments, an ACLP inhibitor (e.g., an inhibitor of the pro-fibrotic domain of ACLP) as disclosed herein or derivatives thereof can be administered before the additional therapy, after the additional therapy or at the same time as the additional therapy. In some embodiments, an ACLP inhibitor (e.g., an inhibitor of the pro-fibrotic domain of ACLP) as disclosed herein or a functional derivative thereof are administered a plurality of times, and in other embodiments, the additional therapies are also administered a plurality of times.

In some embodiments, an ACLP inhibitor (e.g., an inhibitor of the pro-fibrotic domain of ACLP) as disclosed herein or a functional derivative thereof can also be administered in therapeutically effective amounts as a portion of an anti-cancer cocktail. An anti-cancer cocktail is a mixture, for example at least one ACLP inhibitor (e.g., an inhibitor of the pro-fibrotic domain of ACLP) as disclosed herein or functional derivatives thereof is combined with one or more additional anti-cancer agents in addition to a pharmaceutically acceptable carrier for delivery. The use of anti-cancer cocktails as a cancer treatment is routine. Anti-cancer agents that are well known in the art and can be used as a treatment in combination with an ACLP inhibitor (e.g., an inhibitor of the pro-fibrotic domain of ACLP) as disclosed herein or functional derivatives thereof as disclosed herein include, but are not limited to: Actinomycin D, Aminoglutethimide, Asparaginase, Bleomycin, Busulfan, Carboplatin, Carmustine, Chlorambucil, Cisplatin (cis-DDP), Cyclophospharnide, Cytarabine HCl (Cytosine arabinoside), Dacarbazine, Dactinomycin, Daunorubicin HCl, Doxorubicin HCl, Estramustine phosphate sodium, Etoposide (V16-213), Flosuridine, S-Fluorouracil (5-Fu), Flutamide, Hydroxyurea (hydroxycarb amide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Ockeotide, Paclitaxel; Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate, and analogues thereof. In some embodiments, the anti-cancer agent is selected from the group consisting of paclitaxel, cisplatin, doxorubicin and paclitaxel, vermurafib.

In certain embodiments, the pharmaceutical compositions comprising an ACLP inhibitor (e.g., an inhibitor of the pro-fibrotic domain of ACLP) as disclosed herein or functional derivatives thereof can optionally further comprise one or more additional therapies or agents. In certain embodiments, the additional agent or agents are anti-cancer agents. In some embodiments, the therapeutic agents are chemotherapeutic agents, for example cisplatin, paclitaxel etc. In some embodiments, the therapeutic agents are radiotherapeutic agents. Examples of chemotherapeutic agents in the pharmaceutical compositions of this invention are, for example nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; *vinca* alkaloids such as vinblastine; epipodophyllotoxins such as etoposide and teniposide; antibiotics such as actinomycin D, doxorubicin, bleomycin, and mithramycin; biological response modifiers such as interferon, platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective. Of course, other chemotherapeutic agents which are known to those of ordinary skill in the art can readily be substituted as this list should not be considered exhaustive or limiting.

In some embodiments, an ACLP inhibitor (e.g., an inhibitor of the pro-fibrotic domain of ACLP) as disclosed herein or functional derivatives thereof is administered to a subject with other anti-cancer therapies, for example cancer therapies to which the cancer was previously resistant or refractory.

In some embodiments, the methods of the present invention are directed to use of an ACLP inhibitor (e.g., an inhibitor of the pro-fibrotic domain of ACLP) as disclosed herein and functional derivatives thereof with other therapeutic agents, for example chemotherapy agents as disclosed herein can be used at a lower dose that results in decreased side effects.

In certain embodiments, the endogenous compounds are isolated and/or purified or substantially purified by one or more purification methods described herein or known by those skilled in the art. Generally, the purities are at least 90%, in particular 95% and often greater than 99%. In certain embodiments, the naturally occurring compound is excluded from the general description of the broader genus.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. The term "pharmaceutically acceptable carriers" is intended to include all solvents, diluents, or other liquid vehicle, dispersion or suspension aids, surface active agents, isotonic agents, thickening or emulsifying agents, preservatives, solid binders, lubricants and the like, as suited to the particular dosage form desired. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its functional derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

As used herein, "pharmaceutically acceptable salts or prodrugs are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use. These compounds include the zwitterionic forms, where possible, of compounds of the invention.

The term "prodrug" refers to compounds that are rapidly transformed in vivo to yield the compounds of the invention, for example the pyrazoloathrone and functional derivatives thereof of the invention, by hydrolysis in blood. A thorough discussion is provided in T. Higachi and V. Stella, "Prodrugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. The prodrug may be designed to alter the metabolic stability or the transport characteristics of a compound, to mask side effects or toxicity, to improve the flavor of a compound or to alter other characteristics or properties of a compound. By virtue of knowledge of pharmacodynamic processes and drug metabolism in vivo, once a pharmaceutically active compound is identified, those of skill in the pharmaceutical art generally can design prodrugs of the compound (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

In other embodiments of the present invention, an ACLP inhibitor (e.g., an inhibitor of the pro-fibrotic domain of ACLP) as disclosed herein or a functional derivative thereof are conjugated or covalently attached to another targeting agent to increase the specificity of an ACLP inhibitor (e.g., an inhibitor of the pro-fibrotic domain of ACLP) and functional derivatives thereof targeting the cell, for example a cancer cell. Targeting agents can include, for example without limitation, antibodies, cytokines and receptor ligands. In some embodiments, the targeting agent is overexpressed on the cells to be targeted, for example the cancer cells as compared to normal cells. In alternative embodiments, an ACLP inhibitor (e.g., an inhibitor of the pro-fibrotic domain of ACLP) can be conjugated or covalently attached to compounds that elicit an immune response, such as for example but without limitation, cytokines.

In some embodiments, an ACLP inhibitor (e.g., an inhibitor of the pro-fibrotic domain of ACLP) as disclosed herein can be conjugated to, by covalent linkage or any other means, to another agent, for example a chemotherapy agent or antibody targeting a cancer cell or cancer stem cell. In some embodiments, an ACLP inhibitor (e.g., an inhibitor of the pro-fibrotic domain of ACLP) as disclosed herein can be conjugated to a targeting moiety, for example a cancer cell targeting moiety to target the compounds of the present invention to a cancer cell. Such targeting moieties and methods are well known by persons of ordinary skill in the art and are encompassed for use in the methods of the present invention. The conjugation may be a permanent or reversible conjugation.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some instances, pharmaceutical compositions comprising the ACLP inhibitors as disclosed herein be in a formulation suitable for rectal or vaginal administration, for example as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore release the active compound. Suitable carriers and formulations for such administration are known in the art.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

More specifically, the invention features an article of manufacture or kit that contains packaging material and at least one compound of the present invention, for example an ACLP inhibitor (e.g., an inhibitor of the pro-fibrotic domain of ACLP, or PFDi) as disclosed herein or a functional derivative thereof are contained within the packaging material. In some embodiments, the kit or article of manufacture comprises a DCi as disclosed herein. The packaging material can comprise a label or package insert with relevant information, including but not limited to the formulation can be administered to the subject for the treatment of a subject with a fibroproliferative disease or disorder, or a subject with cancer, as disclosed herein, in an amount, at a frequency, and for a duration effective treat or prevent symptoms associated with such disease states or conditions discussed throughout this specification. In some embodiments, the fibroproliferative disorder is a cancer, e.g., a subject with breast cancer, or Her2+ cancer.

Remington's Pharmaceutical sciences Ed. Germany, Merk Publishing, Easton, PA, 1 995 (the contents of which are hereby incorporated by reference), discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its functional derivatives such as sodium carboxymethyl cellulose, ethyl cellulose and cellulose acetate; malt; gelatin; talc; excipients such as cocoa butter and: suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; water; isotonic saline; Ringer's solution, ethyl alcohol, and phosphate buffer solutions, as well as other non-toxic compatible lubricants such as sodium lauryl sulfate and magnesium sulfate, as well as coloring agents, releasing agents, coating agents, sweetening, flavoring and perfuming agents, preservatives and antioxidants can also be present in the composition, according to the judgment of the formulator.

Oligonucleotide Formulations:

A formulated oligonucleotide composition can assume a variety of states. In some examples, the composition can be at least partially crystalline, uniformly crystalline, and/or anhydrous (e.g., less than 80, 50, 30, 20, or 10% water). In another example, the oligonucleotide is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a micro particle as can be appropriate for a crystalline composition). Generally, the oligonucleotide composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An oligonucleotide preparation can be formulated in combination with another agent, e.g., another therapeutic agent or an agent that stabilizes the oligonucleotide, e.g., a protein that complex with oligonucleotide to form an oligonucleotide-protein complex. Still other agents include chelators, e.g., EDTA (e.g., to remove divalent cations such as Mg2+), salts, DNAse inhibitors, RNAse inhibitors (e.g., a broad specificity RNAse inhibitor such as RNAsin) and so forth.

In some embodiments, the oligonucleotide preparation includes at least a second therapeutic agent (e.g., an agent other than RNA or DNA). Exemplary therapeutic agents that can formulated with an oligonucleotide preparation include, but are not limited to, those found in Harrison's Principles of Internal Medicine, 17th Edition, 2008, McGraw-Hill N.Y., NY; Physicians Desk Reference, 63rd Edition, 2008, Thomson Reuters, N.Y., N.Y.; Goodman & Gilman's The Pharmacological Basis of Therapeutics, 11th Edition, 2005, McGraw-Hill N.Y., NY; United States Pharmacopeia, The National Formulary, USP-32 NF-27, 2008, U.S. Pharmacopeia, Rockville, MD, the complete contents of all of which are incorporated herein by reference.

In some embodiments, the second therapeutic agent is an anti-hypertension agent or anti-hypertensive.

Exemplary Oligonucleotide Formulations

Liposomes: The oligonucleotides of the invention can be formulated in liposomes. As used herein, a liposome is a structure having lipid-containing membranes enclosing an aqueous interior. Liposomes can have one or more lipid membranes. In some embodiments, liposomes have an average diameter of less than about 100 nm. More preferred embodiments provide liposomes having an average diameter from about 30-70 nm and most preferably about 40-60 nm. Oligolamellar large vesicles and multilamellar vesicles have multiple, usually concentric, membrane layers and are typically larger than 100 nm. Liposomes with several noncon-centric membranes, i.e., several smaller vesicles contained within a larger vesicle, are termed multivesicular vesicles.

Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach ligands onto the liposome surface. Any of a number of additional lipids and/or other components can be present, including amphipathic, neutral, cationic, anionic lipids, and programmable fusion lipids. Such lipids and/or components can be used alone or in combination. One or more components of the liposome can comprise a ligand, e.g., a targeting ligand.

Liposome compositions can be prepared by a variety of methods that are known in the art. See e.g., U.S. Pat. Nos. 4,235,871; 4,737,323; 4,897,355 and 5,171,678; published International Applications WO 96/14057 and WO 96/37194; Felgner, P. L. et al., Proc. Natl. Acad. Sci., USA (1987) 8:7413-7417, Bangham, et al. M. Mol. Biol. (1965) 23:238, Olson, et al. Biochim. Biophys. Acta (1979) 557:9, Szoka, et al. Proc. Natl. Acad. Sci. (1978) 75: 4194, Mayhew, et al. Biochim. Biophys. Acta (1984) 775:169, Kim, et al. Biochim. Biophys. Acta (1983) 728:339, and Fukunaga, et al. Endocrinol. (1984) 115:757.

Micelles and other Membranous Formulations: The oligonucleotides of the invention can be prepared and formulated as micelles. As used herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

In some embodiments, the formulations comprises micelles formed from an oligonucleotide of the invention and at least one amphiphilic carrier, in which the micelles have an average diameter of less than about 100 nm, preferably. More preferred embodiments provide micelles having an average diameter less than about 50 nm, and even more preferred embodiments provide micelles having an average diameter less than about 30 nm, or even less than about 20 nm.

Micelle formulations can be prepared by mixing an aqueous solution of the oligonucleotide composition, an alkali metal C8 to C22 alkyl sulphate, and an amphiphilic carrier. The amphiphilic carrier can be added at the same time or after addition of the alkali metal alkyl sulphate. Micelles will form with substantially any kind of mixing of the ingredients but vigorous mixing in order to provide smaller size micelles.

Emulsions: The oligonucleotides of the present invention can be prepared and formulated as emulsions. As used herein, "emulsion" is a heterogenous system of one liquid dispersed in another in the form of droplets. Emulsions are often biphasic systems comprising two immiscible liquid phases intimately mixed and dispersed with each other. Either of the phases of the emulsion can be a semisolid or a solid, as is the case of emulsion-style ointment bases and creams. The oligonucleotide can be present as a solution in either the aqueous phase, oily phase or itself as a separate phase.

In some embodiments, the compositions are formulated as microemulsions. As used herein, "microemulsion" refers to a system of water, oil and amphiphile which is a single optically isotropic and thermodynamically stable liquid solution. Microemulsions also include thermodynamically stable, isotropically clear dispersions of two immiscible liquids that are stabilized by interfacial films of surface-active molecules.

The application of emulsion formulations via dermatological, oral and parenteral routes and methods for their manufacture have been reviewed in the literature, for example see Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., volume 1, p. 245; and Block, in Pharmaceutical Dosage Forms, Lieberman, Rieger and Banker (Eds.), 1988, Marcel Dekker, Inc., New York, N.Y., volume 1, p. 335, contents of which are herein incorporated by reference in their entirety.

Lipid Particles: The oligonucleotides of the present invention can be prepared and formulated as lipid particles, e.g., formulated lipid particles (FLiPs) comprising (a) an oligonucleotide of the invention, where said oligonucleotide has been conjugated to a lipophile and (b) at least one lipid component, for example an emulsion, liposome, isolated lipoprotein, reconstituted lipoprotein or phospholipid, to which the conjugated oligonucleotide has been aggregated, admixed or associated.

The stoichiometry of oligonucleotide to the lipid component can be 1:1. Alternatively the stoichiometry can be 1:many, many:1 or many:many, where many is two or more.

The FLiP can comprise triacylglycerols, phospholipids, glycerol and one or several lipid-binding proteins aggregated, admixed or associated via a lipophilic linker molecule with an oligonucleotide. Surprisingly, it has been found that due to said one or several lipid-binding proteins in combination with the above mentioned lipids, the FLiPs show affinity to liver, gut, kidney, steroidogenic organs, heart, lung and/or muscle tissue. These FLiPs can therefore serve as carrier for oligonucleotides to these tissues. For example, lipid-conjugated oligonucleotides, e.g., cholesterol-conjugated oligonucleotides, bind to HDL and LDL lipoprotein particles which mediate cellular uptake upon binding to their respective receptors thus directing oligonucleotide delivery into liver, gut, kidney and steroidogenic organs, see Wolfrum et al. Nature Biotech. (2007), 25:1145-1157.

The FLiP can be a lipid particle comprising 15-25% triacylglycerol, about 0.5-2% phospholipids and 1-3% glycerol, and one or several lipid-binding proteins. FLiPs can be a lipid particle having about 15-25% triacylglycerol, about 1 2% phospholipids, about 2-3% glycerol, and one or several lipid-binding proteins. In some embodiments, the lipid particle comprises about 20% triacylglycerol, about 1.2% phospholipids and about 2.25% glycerol, and one or several lipid-binding proteins.

Another suitable lipid component for FLiPs is lipoproteins, for example isolated lipoproteins or more preferably reconstituted lipoproteins. Exemplary lipoproteins include chylomicrons, VLDL (Very Low Density Lipoproteins), IDL (Intermediate Density Lipoproteins), LDL (Low Density Lipoproteins) and HDL (High Density Lipoproteins). Methods of producing reconstituted lipoproteins are known in the art, for example see A. Jones, Experimental Lung Res. 6, 255-270 (1984), U.S. Pat. Nos. 4,643,988 and 5,128,318, PCT publication WO87/02062, Canadian Pat. No. 2,138, 925. Other methods of producing reconstituted lipoproteins, especially for apolipoproteins A-I, A-II, A-IV, apoC and apoE have been described in A. Jonas, Methods in Enzymology 128, 553-582 (1986) and G. Franceschini et al. J. Biol. Chem., 260(30), 16321-25 (1985).

One preferred lipid component for FLiP is Intralipid. Intralipid® is a brand name for the first safe fat emulsion for human use. Intralipid® 20% (a 20% intravenous fat emulsion) is made up of 20% soybean oil, 1.2% egg yolk phospholipids, 2.25% glycerin, and water for injection. It is further within the present invention that other suitable oils, such as safflower oil, can serve to produce the lipid component of the FLiP.

FLiP can range in size from about 20-50 nm or about 30-50 nm, e.g., about 35 nm or about 40 nm. In some embodiments, the FLiP has a particle size of at least about 100 nm. FLiPs can alternatively be between about 100-150 nm, e.g., about 110 nm, about 120 nm, about 130 nm, or about 140 nm, whether characterized as liposome- or emulsion-based. Multiple FLiPs can also be aggregated and delivered together, therefore the size can be larger than 100 nm.

The process for making the lipid particles comprises the steps of: (a) mixing a lipid components with one or several lipophile (e.g. cholesterol) conjugated oligonucleotides that can be chemically modified; and (b) fractionating this mixture. In some embodiments, the process comprises the additional step of selecting the fraction with particle size of 30-50 nm, preferably of about 40 nm in size.

Some exemplary lipid particle formulations amenable to the invention are described in U.S. patent application Ser. No. 12/412,206, filed Mar. 26, 2009, contents of which are herein incorporated by reference in their entirety.

Yeast cell wall particles: In some embodiments, the oligonucleotide is formulated in yeast cell wall particles ("YCWP"). A yeast cell wall particle comprises an extracted yeast cell wall exterior and a core, the core comprising a payload (e.g., oligonucleotides). Exterior of the particle comprises yeast glucans (e.g. beta glucans, beta-1,3-glucans, beta-1,6-glucans), yeast mannans, or combinations thereof. Yeast cell wall particles are typically spherical particles about 1-4 μm in diameter.

Preparation of yeast cell wall particles is known in the art, and is described, for example in U.S. Pat. Nos. 4,992,540; 5,082,936; 5,028,703; 5,032,401; 5,322,841; 5,401,727; 5,504,079; 5,607,677; 5,741,495; 5,830,463; 5,968,811; 6,444,448; and 6,476,003, U.S. Pat. App. Pub. Nos. 2003/0216346 and 2004/0014715, and Int. App. Pub. No. WO 2002/12348, contents of which are herein incorporated by reference in their entirety. Applications of yeast cell like particles for drug delivery are described, for example in U.S. Pat. Nos. 5,032,401; 5,607,677; 5,741,495; and 5,830,463, and U.S. Pat. Pub Nos. 2005/0281781 and 2008/0044438, contents of which are herein incorporated by reference in their entirety. U.S. Pat. App. Pub. No. 2009/0226528, contents of which are herein incorporated by reference, describes formulation of nucleic acids with yeast cell wall particles for delivery of oligonucleotide to cells.

Additional exemplary formulations for oligonucleotides are described in U.S. Pat. Nos. 4,897,355; 4,394,448; 4,235, 871; 4,231,877; 4,224,179; 4,753,788; 4,673,567; 4,247, 411; 4,814,270; 5,567,434; 5,552,157; 5,565,213; 5,738, 868; 5,795,587; 5,922,859; and 6,077,663, Int. App. Nos. PCT/US07/079203, filed Sep. 21, 2007; PCT/US07/080331, filed Oct. 3, 2007; U.S. patent application Ser. No. 12/123, 922, filed May 28, 2008; U.S. Pat. Pub. Nos. 2006/0240093 and 2007/0135372 and U.S. Provisional App. Nos. 61/018, 616, filed Jan. 2, 2008; 61/039,748, filed Mar. 26; 2008; 61/045,228, filed Apr. 15, 2008; 61/047,087, filed Apr. 22, 2008; 61/051,528, filed May 21, 2008; and 61/113,179 (filed Nov. 10, 2008), contents of which are herein incorporated by reference in their entirety. Behr (1994) Bioconjugate Chem. 5:382-389, and Lewis et al. (1996) PNAS 93:3176-3181), also describe formulations for oligonucleotides that are amenable to the invention, contents of which are herein incorporated by reference in their entirety.

Vectors: Vectors can be used to deliver an ACLP inhibitor (e.g., an inhibitor of the pro-fibrotic domain of ACLP) that is a RNAi or oligonucleotide, e.g., a nucleic acid sequence encoding a decoy protein or a fragment thereof. Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; marine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA.

Retroviruses have been approved for human gene therapy trials. Genetically altered retroviral expression vectors have general utility for the high efficiency transduction of nucleic acids in viva. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular L Biology," vol. 7, Humana Press, Inc., Clifton, N.J. (1991).

In some embodiments the "in vivo expression elements" are any regulatory nucleotide sequence, such as a promoter sequence or promoter-enhancer combination, which facilitates the efficient expression of the nucleic acid to produce the RNAi or decoy protein inhibitor of ACLP. The in vivo expression element may, for example, be a mammalian or viral promoter, such as a constitutive or inducible promoter and/or a tissue specific promoter. Examples of which are well known to one of ordinary skill in the art. Constitutive mammalian promoters include, but are not limited to, polymerase promoters as well as the promoters for the following genes: hypoxanthine phosphoribosyl transferase (HPTR), adenine deaminase, pyruvate kinase, and beta-actin. Exemplary viral promoters which function constitutively in eukaryotic cells include, but are not limited to, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include, but are not limited to, metal-inducible promoters and steroid-regulated promoters. For example, the metallothionein promoter is induced to promote transcription in the presence of certain metal ions. Other inducible promoters are known to those of ordinary skill in the art.

In some embodiments, the tissue specific promoter is derived from the 5' region of a mammalian ACLP (AEBP1) gene, such as that of the mouse ACLP/AEBP1 gene. In some embodiments, a tissue-specific promoter can be all of, or part of SEQ ID NO:3 as disclosed in U.S. Pat. No. 7,094,878, which is incorporated herein in its entirety by reference, and relates to the mouse ACLP promoter/enhancer.

In alterative embodiments, other tissue-specific promoters can be used and are well known in the art, for example, include but are not limited to, the promoter for creatine kinase, which has been used to direct expression in muscle and cardiac tissue and immunoglobulin heavy or light chain promoters for expression in B cells. Other tissue specific promoters include the human smooth muscle alpha-actin promoter. Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol 7-alpha hydroxylase (CYP-7) promoter, beta-galactosidase promoter, insulin-like growth factor binding protein (IGFBP-1) promoter, aldolase B promoter, human transferrin promoter, and collagen type I promoter. Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1). Exemplary tissue-specific expression elements for gastric tissue include but are not limited to the human H+/K+-ATPase alpha subunit promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include, but are not limited to, the uteroglobin promoter. Exemplary tissue-specific expression elements for adrenal cells include, but are not limited to, cholesterol side-chain cleavage (SCC) promoter. Exemplary tissue-specific expression elements for the general nervous system include, but are not limited to, gamma-gamma enolase (neuron-specific enolase, NSE) promoter. Exemplary tissue-specific expression elements for the brain include, but are not limited to, the neurofilament heavy chain (NF-H) promoter. Exemplary tissue-specific expression elements for lymphocytes include, but are not limited to, the human CGL-1/granzyme B promoter, the terminal deoxy transferase (TdT), lambda 5, VpreB, and lck (lymphocyte specific tyrosine protein kinase p561ck) promoter, the humans CD2 promoter and its 3'transcriptional enhancer, and the human NK and T cell specific activation (NKG5) promoter. Exemplary tissue-specific expression elements for the colon include, but are not limited to, pp60c-src tyrosine kinase promoter, organ-specific neoantigens (OSNs) promoter, and colon specific antigen-P promoter.

In some embodiments, tissue-specific expression elements for breast cells include, but are not limited to, the human alpha-lactalbumin promoter. Exemplary tissue-specific expression elements for the lung include, but are not limited to, the cystic fibrosis transmembrane conductance regulator (CFTR) gene promoter.

Other elements aiding specificity of expression in a tissue of interest can include secretion leader sequences, enhancers, nuclear localization signals, endosmolytic peptides, etc. Preferably, these elements are derived from the tissue of interest to aid specificity. In general, the in vivo expression element shall include, as necessary, 5' non-transcribing and 5' non-translating sequences involved with the initiation of transcription. They optionally include enhancer sequences or upstream activator sequences.

An ACLP inhibitor (e.g., an inhibitor of the pro-fibrotic domain of ACLP), e.g., a ACLP RNAi agent or ACLP decoy protein either alone, or expressed as a viral vector or complexed to targeting moieties can be delivered using any delivery system such as topical administration, subcutaneous, intramuscular, intraperitoneal, intrathecal and intravenous injections, catheters.

Uses

In another embodiment, the present invention provides a method for treating a variety of conditions by administering an effective amount of example an ACLP inhibitor (e.g., an inhibitor of the pro-fibrotic domain of ACLP) as disclosed herein or a functional derivative thereof to a subject in need thereof. Conditions that may be treated by the compounds of this invention, or a pharmaceutical composition containing the same, include any condition which is treated or results in the reduction of a symptom by administration of an ACLP inhibitor (e.g., an inhibitor of the pro-fibrotic domain of ACLP), and thereby benefit from administration of an ACLP inhibitor (e.g., an inhibitor of the pro-fibrotic domain of ACLP) as disclosed herein. Representative conditions in this regard include, for example, but not limited to, fibroproliferative disorders and cancers, such as breast cancer, or other cancers overexpressing ACLP. Such fibroproliferative disorders include, but are not limited to, fibroproliferative disorders of the lung, heart, liver, kidney orvasculature, systemic sclerosis (SSc), fibrosis, solid fibrosis, scleroderma, as well as fibroproliferative disorders of the kidney, such as membranoproliferative glomerulonephritis, diffuse proliferative glomerulonephritis, diabetic nephrology or lupus nephritis. In some embodiments, the methods as disclosed herein are useful in the treatment of any fibroproliferative disorder which is characterized by extracellular matrix accumulation. In some embodiments, fibroproliferative disorders include, but are not limited to, dermal scar formation, keloids, liver fibrosis, lung fibrosis (e.g., silicosis, asbestosis), kidney fibrosis (including diabetic nephropathy), and glomerulosclerosis. Benign and malignant fibroproliferative disorders (FPDs) include idiopathic pulmonary fibrosis, hepatic cirrhosis, myelofibrosis, systemic sclerosis (SSc), Dupuytren's contracture, hypertrophic scars, and keloids.

Accordingly, the present invention relates to the use of an ACLP inhibitor (e.g., an inhibitor of the pro-fibrotic domain of ACLP) as disclosed herein or a functional derivative thereof for the treatment of any disorder where administration of an ACLP inhibitor is whole, or part, of the therapeutic regime.

Kits

In another embodiment, this invention provides kits for the practice of the methods of this invention. The kits preferably include one or more containers containing an ACLP inhibitor (e.g., an inhibitor of the pro-fibrotic domain of ACLP) and a pharmaceutically acceptable excipient. The kit may optionally contain additional therapeutics to be co-administered with the ACLP.

The kits may also optionally include appropriate systems (e.g. opaque containers) or stabilizers (e.g. antioxidants) to prevent degradation of the an ACLP inhibitor by light or other adverse conditions.

The kits may optionally include instructional materials containing directions (i.e., protocols) providing for the use of an ACLP inhibitor (e.g., an inhibitor of the pro-fibrotic domain of ACLP) in the treatment of a fibroproliferative disease or disorder, or cancer, such as breast cancer.

In Some Embodiments, the Present Invention May be Defined in any of the Following Numbered Paragraphs:

1. A method for treating a fibroproliferative disease or cancer in a subject comprising administering to the subject a therapeutically effective amount of a pharmaceutical composition comprising at least one ACLP in paragraph inhibitor, wherein the ACLP inhibitor inhibits the activity of the pro-fibrotic domain (PFD) of the ACLP polypeptide.
2. The method of paragraph 1, wherein the ACLP inhibitor is an antibody which binds to a region of the PFD of ACLP polypeptide from amino acids 25-381 of SEQ ID NO: 1.
3. The method of paragraph 1 or 2, wherein the ACLP inhibitor binds to at least one Tsp repeat located in amino acid residues 25-381 of SEQ ID NO: 1.
4. The method of any of paragraphs 1 to 3, wherein the ACLP inhibitor is an antibody that specifically binds to an epitope on SEQ ID NO: 1 from amino acid residues 121-163.
5. The method of any of paragraphs 1 to 4, wherein the ACLP inhibitor binds to at least 5 amino acids in KEKPPKATKKPKEKPPKATKKPKEKPPKATKKP-KEKPPKATKKP (SEQ ID NO: 4).
6. The method of any of paragraphs 1 to 5, wherein the ACLP inhibitor binds to at least part of the amino acid sequence KEKPPKATKKP (SEQ ID NO: 3).
7. The method of paragraph 1, wherein the ACLP inhibitor is a peptide or peptide analogue that inhibits the binding of the PFD of ACLP polypeptide to a member of the TGFβ receptor superfamily.
8. The method of paragraph 7, wherein the member of the TGFβ receptor superfamily is TGFβ R II or BMP RII.
9. The method of paragraph 7 or 8, wherein the peptide comprises at a portion of amino acids 25-381 of SEQ ID NO: 1.
10. The method of any of paragraphs 7 to 9, wherein the peptide comprises at least 5 consecutive amino acid of KEKPPKATKKPKEKPPKATKKPKEKPPKATKKP-KEKPPKATKKP (SEQ ID NO: 4).
11. The method of any of paragraphs 7 to 10, wherein the peptide is fused to Fc or fragment of SEQ ID NO: 48.
12. The method of any of paragraphs 1 to 11, further comprising a second ACLP inhibitor, wherein the second ACLP inhibitor inhibits the function of the discoidin (DS) domain of the ACLP polypeptide.
13. The method of paragraph 12, wherein the second ACLP inhibitor is an antibody which specifically binds to at least a region of amino acids 384-539 of SEQ ID NO: 1.
14. The method of paragraph 12 or 13, wherein the second ACLP inhibitor is an antibody which specifically binds to at least one loop region within amino acids 384-539 of SEQ ID NO: 1, wherein the loop regions are selected from amino acids; MLRHGLG (SEQ ID NO: 12), QTGATEDDYYDGA (SEQ ID NO: 13), DARTQ (SEQ ID NO: 14) or RDSSIHDD (SEQ ID NO: 15).
15. The method of any of paragraphs 2 to 14, wherein the antibody is a monoclonal antibody.
16. The method of any of paragraphs 2 to 15, wherein the antibody is a humanized antibody.
17. The method of any of paragraphs 2 to 16, wherein the antibody is a human antibody.
18. The method of any of paragraphs 2 to 17, wherein the antibody is a single-chain antibody.
19. The method of any of paragraphs 2 to 18, wherein the antibody is an antigen binding fragment selected from the group consisting of: F(ab')2 fragment of a Fab fragment.
20. The method of paragraph 12, wherein the second ACLP inhibitor is a peptide comprising at least 5 amino acids of residues 384-539 of SEQ ID NO: 1.
21. The method of paragraph 20, wherein the peptide comprises at least 5 amino consecutive from at least one loop region within amino acids 384-539 of SEQ ID NO: 1, wherein the loop regions are selected from amino acids; MLRHGLG (SEQ ID NO: 12), QTGATEDDYYDGA (SEQ ID NO: 13), DARTQ (SEQ ID NO: 14) or RDSSIHDD (SEQ ID NO: 15).
22. The method of paragraph 21, wherein the peptide is selected from the group consisting of,

```
                                         (SEQ ID NO: 12)
MLRHGLG;

(SEQ ID NO: 16)
MLRHGLGA;

(SEQ ID NO: 17)
MLRHGLGAQ;

(SEQ ID NO: 18)
SMLRHGLG;

(SEQ ID NO: 19)
SMLRHGLG;
```

-continued

SMLRHGLGA; (SEQ ID NO: 20)

SMLRHGLGAQ; (SEQ ID NO: 21)

SSMLRHGLGA; (SEQ ID NO: 22)

SSMLRHGLGAQ; (SEQ ID NO: 23)

QTGATEDDYYDGA; (SEQ ID NO: 13)

QTGATEDDYYDGAW; (SEQ ID NO: 24)

QTGATEDDYYDGAWC; (SEQ ID NO: 25)

MQTGATEDDYYDGA; (SEQ ID NO: 26)

NMQTGATEDDYYDGA; (SEQ ID NO: 27)

MQTGATEDDYYDGAW; (SEQ ID NO: 28)

MQTGATEDDYYDGAWC; (SEQ ID NO: 29)

NMQTGATEDDYYDGAW; (SEQ ID NO: 30)

NMQTGATEDDYYDGAWC; (SEQ ID NO: 31)

DARTQ; (SEQ ID NO: 14)

DARTQW; (SEQ ID NO: 32)

DARTQWI; (SEQ ID NO: 33)

DDARTQ; (SEQ ID NO: 34)

EDDARTQ; (SEQ ID NO: 35)

DDARTQW; (SEQ ID NO: 36)

DDARTQWI; (SEQ ID NO: 37)

EDDARTQW; (SEQ ID NO: 38)

EDDARTQWI; (SEQ ID NO: 39)

RDSSIHDD; (SEQ ID NO: 15)

RDSSIHDDF; (SEQ ID NO: 40)

RDSSIHDDFV; (SEQ ID NO: 41)

GRDSSIHDD; (SEQ ID NO: 42)

QGRDSSIHDD; (SEQ ID NO: 43)

GRDSSIHDDF; (SEQ ID NO: 44)

GRDSSIHDDFV; (SEQ ID NO: 45)

QGRDSSIHDDF; (SEQ ID NO: 46)

or

QGRDSSIHDDFV. (SEQ ID NO: 47)

23. The method of paragraph 22, wherein the peptide is fused to Fc or a fragment of SEQ ID NO: 48.

24. The method of any of paragraphs 7-11 or 22-23, wherein the peptide comprises one or more ectopic mutations from the sequence from which it is derived.

25. The method of paragraph 1, wherein the fibroproliferative disorder is selected from a fibroproliferative disorder of the lung, heart, liver, kidney or vasculature.

26. The method of paragraph 26, wherein the fibroproliferative disorder of the kidney is selected from the group consisting of: membranoproliferative glomerulonephritis, diffuse proliferative glomerulonephritis, diabetic nephrology or lupus nephritis.

27. The method of paragraph 1, wherein the fibroproliferative disorder is further characterized by extracellular matrix (ECM) accumulation.

28. The method of paragraph 1, wherein the fibroproliferative disorder is selected from; systemic sclerosis (SSc), fibrosis, solid organ fibrosis or scleroderma.

29. The method of paragraph 1, wherein the cancer is a solid cancer with a fibrotic core.

30. The method of paragraph 1, wherein the cancer is a cancer of epithelial origin and/or a cancer which has, or is undergo epithelial to mesenchymal transition (EMT).

31. The method of paragraph 1, wherein the cancer is breast cancer or sarcoma.

32. The method of paragraph 31, wherein the breast cancer is Her2+ breast cancer.

33. The method of paragraph 1, wherein the cancer is characterized by increased expression of ACLP.

34. The method of paragraph 1, wherein the subject is human.

35. A composition comprising at least one ACLP inhibitor, wherein the ACLP inhibitor inhibits the activity of the pro-fibrotic domain (PFD) of the ACLP polypeptide and a second ACLP inhibitor, where in the second ACLP inhibitor inhibits the function of the discoidin (DS) domain of the ACLP polypeptide.

36. The composition of paragraph 35, wherein the ACLP inhibitor is an antibody, antibody fragment or antigen-binding molecule that specifically binds to a region of the PFD of ACLP polypeptide from amino acids 25-381 of SEQ ID NO: 1.

37. The composition of claim 36, wherein the antibody, antibody fragment or antigen-binding molecule that specifically binds to any of:
  a. a region of the PFD of ACLP polypeptide from amino acids 25-381 of SEQ ID NO: 1;
  b. at least one Tsp repeat located in amino acid residues 25-381 of SEQ ID NO: 1;
  c. an epitope on SEQ ID NO: 1 from amino acid residues 121-163;
  d. at least 5 amino acids in KEKPPKATKKPKEKPPKATKKPKEKPPKATKKPKEKPPKATKKP (SEQ ID NO: 4); or e. at least part of the amino acid sequence KEKPPKATKKP (SEQ ID NO: 3).

38. The composition of any of paragraph 35, wherein the ACLP inhibitor is a peptide or peptide analogue that inhibits the binding of the PFD of ACLP polypeptide to a member of the TGFβ receptor superfamily.

39. The composition of paragraph 38, wherein the member of the TGFβ receptor superfamily is TGFβ R II or BMP RII.

40. The composition of paragraph 38, wherein the peptide comprises at least a portion of amino acids 25-381 of SEQ ID NO: 1, or at least 5 consecutive amino acid of KEKPPKATKKPKEKPPKATKKPKEKPPKATKKP-KEKPPKATKKP (SEQ ID NO: 4).

41. The composition of any of paragraphs 38 to 40, wherein the peptide is fused to Fc or fragment of SEQ ID NO: 48.

42. The composition of paragraph 35, wherein the second ACLP inhibitor is an antibody, antibody fragment or antigen-binding molecule which specifically binds to at least one of:
   a. a region of amino acids 384-539 of SEQ ID NO: 1; or
   b. at least one loop region within amino acids 384-539 of SEQ ID NO: 1, wherein the loop regions are selected from amino acids; MLRHGLG (SEQ ID NO: 12), QTGATEDDYYDGA (SEQ ID NO: 13), DARTQ (SEQ ID NO: 14) or RDSSIHDD (SEQ ID NO: 15).

43. The composition of any of paragraphs 35 to 41, wherein the antibody is selected from the group of; a monoclonal antibody, a humanized antibody, a human antibody, a single-chain antibody, an antigen binding fragment selected from the group consisting of: F(ab')2 fragment of a Fab fragment.

44. The composition of any of paragraphs 35 to 41, wherein the second ACLP inhibitor is a peptide comprising any of;
   a. at least 5 amino acids of residues 384-539 of SEQ ID NO: 1;
   b. at least 5 amino consecutive from at least one loop region within amino acids 384-539 of SEQ ID NO: 1, wherein the loop regions are selected from amino acids; MLRHGLG (SEQ ID NO: 12), QTGATED-DYYDGA (SEQ ID NO: 13), DARTQ (SEQ ID NO: 14) or RDSSIHDD (SEQ ID NO: 15); or
   c. selected from the group consisting of, MLRHGLG (SEQ ID NO: 12); MLRHGLGA (SEQ ID NO: 16); MLRHGLGAQ (SEQ ID NO: 17); SMLRHGLG (SEQ ID NO: 18); SMLRHGLG (SEQ ID NO: 19); SMLRHGLGA (SEQ ID NO: 20); SMLRHGLGAQ (SEQ ID NO: 21); SSMLRHGLGA (SEQ ID NO: 22); SSMLRHGLGAQ (SEQ ID NO: 23); QTGATEDDYYDGA (SEQ ID NO: 13); QTGATEDDYYDGAW (SEQ ID NO: 24); QTGATEDDYYDGAWC (SEQ ID NO: 25); MQT-GATEDDYYDGA (SEQ ID NO: 26); NMQT-GATEDDYYDGA (SEQ ID NO: 27); MQTGATED-DYYDGAW (SEQ ID NO: 28); MQTGATEDDYYDGAWC (SEQ ID NO: 29); NMQTGATEDDYYDGAW (SEQ ID NO: 30); NMQTGATEDDYYDGAWC (SEQ ID NO: 31); DARTQ (SEQ ID NO: 14); DARTQW (SEQ ID NO: 32); DARTQWI (SEQ ID NO: 33); DDARTQ (SEQ ID NO: 34); EDDARTQ (SEQ ID NO: 35); DDARTQW (SEQ ID NO: 36); DDARTQWI (SEQ ID NO: 37); EDDARTQW (SEQ ID NO: 38); EDDARTQWI (SEQ ID NO: 39); RDSSIHDD (SEQ ID NO: 15); RDSSIHDDF (SEQ ID NO: 40); RDSSIHDDFV (SEQ ID NO: 41); GRDSSIHDD (SEQ ID NO: 42); QGRDSSIHDD (SEQ ID NO: 43); GRDSSIHDDF (SEQ ID NO: 44); GRDSSIHDDFV (SEQ ID NO: 45); QGRDSSIHDDF (SEQ ID NO: 46); or QGRDSSIHDDFV (SEQ ID NO: 47).

45. The composition of any of paragraphs 35 to 44, wherein the peptide is fused to Fc or a fragment of SEQ ID NO: 48.

46. The composition of any of paragraphs 35 to 45, wherein the peptide comprises one or more ectopic mutations from the sequence from which it is derived.

47. The composition of any of paragraphs 35 to 46, for use in a method to treat a fibroproliferative disease or disorder or cancer.

48. The composition of paragraph 54, wherein the fibroproliferative disorder is selected from any of;
   a. a fibroproliferative disorder of the lung, heart, liver, kidney or vasculature,
   b. a fibroproliferative disorder of the kidney selected from the group consisting of: membranoproliferative glomerulonephritis, diffuse proliferative glomerulonephritis, diabetic nephrology or lupus nephritis;
   c. a fibroproliferative disorder characterized by extracellular matrix (ECM) accumulation; or
   d. a fibroproliferative disorder is selected from; systemic sclerosis (SSc), fibrosis, solid organ fibrosis or scleroderma.

49. The composition of paragraph 47, wherein the cancer is selected from; a solid cancer with a fibrotic core, a cancer of epithelial origin, a cancer which has or is undergoing epithelial to mesenchymal transition (EMT), or a cancer characterized by increased expression of ACLP.

50. The composition of paragraph 49, wherein the cancer is breast cancer or sarcoma.

51. The composition of paragraph 50, wherein the breast cancer is Her2+ breast cancer.

52. An admixture comprising an agent which inhibits the activity of the pro-fibrotic domain (PFD) of the ACLP polypeptide and an agent which inhibits the function of the discoidin (DS) domain of the ACLP polypeptide.

53. The admixture of paragraph 52, wherein the agent which inhibits the PFD domain is an antibody or antibody fragment or antigen-binding molecule which binds to the PFD domain of ACLP.

54. The admixture of paragraph 52, wherein the agent which inhibits the function of the discoidin (DS) domain is an antibody or antibody fragment or antigen-binding molecule which binds to the DS domain of the ACLP polypeptide.

55. The admixture of paragraph 53, wherein the antibody, antibody fragment or antigen-binding molecule which binds to the PFD domain of ACLP specifically binds to any of
   a. a region of the PFD of ACLP polypeptide from amino acids 25-381 of SEQ ID NO: 1;
   b. at least one Tsp repeat located in amino acid residues 25-381 of SEQ ID NO: 1;
   c. an epitope on SEQ ID NO: 1 from amino acid residues 121-163;
   d. at least 5 amino acids in KEKPPKATKKPKEKPPKATKKPKEKPPKATK-KPKEKPPKATKKP (SEQ ID NO: 4); or e. at least part of the amino acid sequence KEKPPKATKKP (SEQ ID NO: 3).
56. The admixture of any of paragraph 52 to 55, wherein the ACLP inhibitor is a peptide or peptide analogue that inhibits the binding of the PFD of ACLP polypeptide to a member of the TGFβ receptor superfamily.
57. The admixture of paragraph 56, wherein the member of the TGFβ receptor superfamily is TGFβ R II or BMP RII.
58. The admixture of paragraph 56, wherein the peptide comprises at least a portion of amino acids 25-381 of SEQ ID NO: 1, or at least 5 consecutive amino acid of KEKPPKATKKPKEKPPKATKKPKEKPPKATKKP-KEKPPKATKKP (SEQ ID NO: 4).
59. The admixture of any of paragraphs 56 to 58, wherein the peptide is fused to Fc or fragment of SEQ ID NO: 48.
60. The composition of paragraph 52, wherein the antibody, antibody fragment or antigen-binding molecule which binds to the DS domain of the ACLP polypeptide specifically binds to any of
 a. a region of amino acids 384-539 of SEQ ID NO: 1; or
 b. at least one loop region within amino acids 384-539 of SEQ ID NO: 1, wherein the loop regions are selected from amino acids; MLRHGLG (SEQ ID NO: 12), QTGATEDDYYDGA (SEQ ID NO: 13), DARTQ (SEQ ID NO: 14) or RDSSIHDD (SEQ ID NO: 15).
61. The admixture of any of paragraphs 52 to 60, wherein the antibody is selected from the group of; a monoclonal antibody, a humanized antibody, a human antibody, a single-chain antibody, an antigen binding fragment selected from the group consisting of: F(ab')2 fragment of a Fab fragment.
62. The admixture of any of paragraphs 52 to 41, wherein the agent which inhibits the function of the discoidin (DS) domain is a peptide comprising any of,
 a. at least 5 amino acids of residues 384-539 of SEQ ID NO: 1;
 b. at least 5 amino consecutive from at least one loop region within amino acids 384-539 of SEQ ID NO: 1, wherein the loop regions are selected from amino acids; MLRHGLG (SEQ ID NO: 12), QTGATED-DYYDGA (SEQ ID NO: 13), DARTQ (SEQ ID NO: 14) or RDSSIHDD (SEQ ID NO: 15); or
 c. selected from the group consisting of, MLRHGLG (SEQ ID NO: 12); MLRHGLGA (SEQ ID NO: 16); MLRHGLGAQ (SEQ ID NO: 17); SMLRHGLG (SEQ ID NO: 18); SMLRHGLG (SEQ ID NO: 19); SMLRHGLGA (SEQ ID NO: 20); SMLRHGLGAQ (SEQ ID NO: 21); SSMLRHGLGA (SEQ ID NO: 22); SSMLRHGLGAQ (SEQ ID NO: 23); QTGATEDDYYDGA (SEQ ID NO: 13); QTGATEDDYYDGAW (SEQ ID NO: 24); QTGATEDDYYDGAWC (SEQ ID NO: 25); MQTGATEDDYYDGA (SEQ ID NO: 26); NMQTGATEDDYYDGA (SEQ ID NO: 27); MQTGATED-DYYDGAW (SEQ ID NO: 28); MQTGATEDDYYDGAWC (SEQ ID NO: 29); NMQTGATEDDYYDGAW (SEQ ID NO: 30); NMQTGATEDDYYDGAWC (SEQ ID NO: 31); DARTQ (SEQ ID NO: 14); DARTQW (SEQ ID NO: 32); DARTQWI (SEQ ID NO: 33); DDARTQ (SEQ ID NO: 34); EDDARTQ (SEQ ID NO: 35); DDARTQW (SEQ ID NO: 36); DDARTQWI (SEQ ID NO: 37); EDDARTQW (SEQ ID NO: 38); EDDARTQWI (SEQ ID NO: 39); RDSSIHDD (SEQ ID NO: 15); RDSSIHDDF (SEQ ID NO: 40); RDSSIHDDFV (SEQ ID NO: 41); GRDSSIHDD (SEQ ID NO: 42); QGRDSSIHDD (SEQ ID NO: 43); GRDSSIHDDF (SEQ ID NO: 44); GRDSSIHDDFV (SEQ ID NO: 45); QGRDSSIHDDF (SEQ ID NO: 46); or QGRDSSIHDDFV (SEQ ID NO: 47).
63. The admixture of paragraph 63, wherein the peptide is fused to Fc or a fragment of SEQ ID NO: 48.
64. The admixture of any of paragraphs 52 to 63, wherein the peptide comprises one or more ectopic mutations from the sequence from which it is derived.
65. The admixture of any of paragraphs 52 to 64, for use in a method to treat a fibroproliferative disease or disorder or cancer.
66. The admixture of paragraph 65, wherein the fibroproliferative disorder is selected from any of;
 a. a fibroproliferative disorder of the lung, heart, liver, kidney or vasculature,
 b. a fibroproliferative disorder of the kidney selected from the group consisting of membranoproliferative glomerulonephritis, diffuse proliferative glomerulonephritis, diabetic nephrology or lupus nephritis;
 c. a fibroproliferative disorder characterized by extracellular matrix (ECM) accumulation; or
 d. a fibroproliferative disorder is selected from; systemic sclerosis (SSc), fibrosis, solid organ fibrosis or scleroderma.
67. The admixture of paragraph 65, wherein the cancer is selected from; a solid cancer with a fibrotic core, a cancer of epithelial origin, a cancer which has or is undergoing epithelial to mesenchymal transition (EMT), or a cancer characterized by increased expression of ACLP.
68. The admixture of paragraph 65, wherein the cancer is breast cancer or sarcoma.
69. The admixture of paragraph 68, wherein the breast cancer is Her2+ breast cancer.
70. A kit comprising a container comprising at least one ACLP inhibitor, wherein the ACLP inhibitor inhibits the activity of the pro-fibrotic domain (PFD) of the ACLP polypeptide and a container comprising a second ACLP inhibitor, where in the second ACLP inhibitor inhibits the function of the discoidin (DS) domain of the ACLP polypeptide.
71. The kit of paragraph 70, wherein the inhibitor which inhibits the activity of the PFD domain is an antibody or antibody fragment or antigen-binding molecule which binds to the PFD domain of ACLP.
72. The kit of paragraph 70, wherein the inhibitor which inhibits the function of the discoidin (DS) domain is an antibody or antibody fragment or antigen-binding molecule which binds to the DS domain of the ACLP polypeptide.
73. The kit of paragraph 70, wherein the antibody, antibody fragment or antigen-binding molecule which binds to the PFD domain of ACLP specifically binds to any of
 a. a region of the PFD of ACLP polypeptide from amino acids 25-381 of SEQ ID NO: 1;
 b. at least one Tsp repeat located in amino acid residues 25-381 of SEQ ID NO: 1;
 c. an epitope on SEQ ID NO: 1 from amino acid residues 121-163;

d. at least 5 amino acids in KEKPPKATKKPKEKPPKATKKPKEKPPKATK-KPKEKPPKATKKP (SEQ ID NO: 4); or
e. at least part of the amino acid sequence KEKPPKATKKP (SEQ ID NO: 3).

74. The kit of any of paragraph 70 to 71, wherein the ACLP inhibitor which inhibits the activity of the PFD domain, or the ACLP inhibitor which inhibits the activity of the DS domain is a peptide or peptide analogue that inhibits the binding of the PFD of ACLP polypeptide to a member of the TGFβ receptor superfamily.
75. The kit of paragraph 74, wherein the member of the TGFβ receptor superfamily is TGFβ R II or BMP RII.
76. The kit of paragraph 74, wherein the peptide comprises at least a portion of amino acids 25-381 of SEQ ID NO: 1, or at least 5 consecutive amino acid of KEKPPKATKKPKEKPPKATKKPKEKPPKATKKP-KEKPPKATKKP (SEQ ID NO: 4).
77. The kit of any of paragraphs 70 to 75, wherein the peptide is fused to Fc or fragment of SEQ ID NO: 48.
78. The kit of paragraph 72, wherein the antibody, antibody fragment or antigen-binding molecule which binds to the DS domain of the ACLP polypeptide specifically binds to any of:
a. a region of amino acids 384-539 of SEQ ID NO: 1; or
b. at least one loop region within amino acids 384-539 of SEQ ID NO: 1, wherein the loop regions are selected from amino acids; MLRHGLG (SEQ ID NO: 12), QTGATEDDYYDGA (SEQ ID NO: 13), DARTQ (SEQ ID NO: 14) or RDSSIHDD (SEQ ID NO: 15).
79. The kit of any of paragraphs 71 to 78, wherein the antibody is selected from the group of, a monoclonal antibody, a humanized antibody, a human antibody, a single-chain antibody, an antigen binding fragment selected from the group consisting of: F(ab')2 fragment of a Fab fragment.
80. The kit of any of paragraphs 72 to 79, wherein the ACLP inhibitor which inhibits the function of the discoidin (DS) domain is a peptide comprising any of,
a. at least 5 amino acids of residues 384-539 of SEQ ID NO: 1;
b. at least 5 amino consecutive from at least one loop region within amino acids 384-539 of SEQ ID NO: 1, wherein the loop regions are selected from amino acids; MLRHGLG (SEQ ID NO: 12), QTGATED-DYYDGA (SEQ ID NO: 13), DARTQ (SEQ ID NO: 14) or RDSSIHDD (SEQ ID NO: 15); or
c. selected from the group consisting of, MLRHGLG (SEQ ID NO: 12); MLRHGLGA (SEQ ID NO: 16); MLRHGLGAQ (SEQ ID NO: 17); SMLRHGLG (SEQ ID NO: 18); SMLRHGLG (SEQ ID NO: 19); SMLRHGLGA (SEQ ID NO: 20); SMLRHGLGAQ (SEQ ID NO: 21); SSMLRHGLGA (SEQ ID NO: 22); SSMLRHGLGAQ (SEQ ID NO: 23); QTGATEDDYYDGA (SEQ ID NO: 13); QTGATEDDYYDGAW (SEQ ID NO: 24); QTGATEDDYYDGAWC (SEQ ID NO: 25); MQT-GATEDDYYDGA (SEQ ID NO: 26); NMQT-GATEDDYYDGA (SEQ ID NO: 27); MQTGATED-DYYDGAW (SEQ ID NO: 28); MQTGATEDDYYDGAWC (SEQ ID NO: 29); NMQTGATEDDYYDGAW (SEQ ID NO: 30); NMQTGATEDDYYDGAWC (SEQ ID NO: 31); DARTQ (SEQ ID NO: 14); DARTQW (SEQ ID NO: 32); DARTQWI (SEQ ID NO: 33); DDARTQ (SEQ ID NO: 34); EDDARTQ (SEQ ID NO: 35); DDARTQW (SEQ ID NO: 36); DDARTQWI (SEQ ID NO: 37); EDDARTQW (SEQ ID NO: 38); EDDARTQWI (SEQ ID NO: 39); RDSSIHDD (SEQ ID NO: 15); RDSSIHDDF (SEQ ID NO: 40); RDSSIHDDFV (SEQ ID NO: 41); GRDSSIHDD (SEQ ID NO: 42); QGRDSSIHDD (SEQ ID NO: 43); GRDSSIHDDF (SEQ ID NO: 44); GRDSSIHDDFV (SEQ ID NO: 45); QGRDSSIHDDF (SEQ ID NO: 46); or QGRDSSIHDDFV (SEQ ID NO: 47).
81. The kit of paragraph 80, wherein the peptide is fused to Fc or a fragment of SEQ ID NO: 48.
82. The kit of any of paragraphs 72 to 81, wherein the peptide comprises one or more ectopic mutations from the sequence from which it is derived.
83. The kit of any of paragraphs 70 to 83, for use in a method to treat a fibroproliferative disease or disorder or cancer.
84. The kit of paragraph 83, wherein the fibroproliferative disorder is selected from any of,
a. a fibroproliferative disorder of the lung, heart, liver, kidney or vasculature,
b. a fibroproliferative disorder of the kidney selected from the group consisting of: membranoproliferative glomerulonephritis, diffuse proliferative glomerulonephritis, diabetic nephrology or lupus nephritis;
c. a fibroproliferative disorder characterized by extracellular matrix (ECM) accumulation; or
d. a fibroproliferative disorder is selected from; systemic sclerosis (SSc), fibrosis, solid organ fibrosis or scleroderma.
85. The kit of paragraph 83, wherein the cancer is selected from; a solid cancer with a fibrotic core, a cancer of epithelial origin, a cancer which has or is undergoing epithelial to mesenchymal transition (EMT), or a cancer characterized by increased expression of ACLP.
86. The kit of paragraph 83, wherein the cancer is breast cancer or sarcoma.
87. The kit of paragraph 86, wherein the breast cancer is Her2+ breast cancer.
88. The kit of any of paragraphs 70 to 87, wherein the ACLP inhibitor which inhibits the activity of the pro-fibrotic domain (PFD) of the ACLP polypeptide and/or the ACLP inhibitor which inhibits the function of the discoidin (DS) domain of the ACLP polypeptide is in lyophilized form.
89. The kit of any of paragraphs 70 to 88, wherein the ACLP inhibitor which inhibits the activity of the pro-fibrotic domain (PFD) of the ACLP polypeptide and/or the ACLP inhibitor which inhibits the function of the discoidin (DS) domain of the ACLP polypeptide comprises a detectable label.
90. The kit of any of paragraphs 70 to 88, wherein the antibody, antibody fragment or antigen-binding molecule which binds to the PFD domain of ACLP, or bind to the DS domain of ACLP is conjugated to an anti-cancer agent or exists as an antibody drug conjugate (ADC).

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The examples presented herein relate to use of an ACLP inhibitor (e.g., an inhibitor of the pro-fibrotic domain of ACLP) for the treatment of fibropoliferative diseases or disorders and cancers. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Materials and Methods

Recombinant protein. AD293 cells were used to generate recombinant full length mouse ACLP, N-terminal Tsp repeat domain, and C-terminal domain of ACLP. The full length vector was subcloned by William Monis (Layne Laboratory, Boston University School of Medicine). All constructs contain a BM40 (Sparc) signal sequence replacing the endogenous ACLP signal peptide and a C-terminal myc-His tag for detection and purification. The full-length protein contains amino acids 26-1128 of mouse ACLP. The N-terminal Tsp repeat domain of ACLP contains amino acids 26-373 and C-terminal discoidin and carboxypeptidase domains contain amino acids 374-1128. AD293 cells were transfected with each of these constructs using Mirus-293 (Fisher), and cells expressing the constructs were selected using 1 µg/ml puromycin.

Once 293 cells stably transfected with the ACLP constructs were generated, their ability to express and secrete full length ACLP, the Tsp repeat domain, or the C-terminal domain was confirmed. The ACLP expressing cells were grown in suspension in serum free media (HYCLONE™ SFM4HEK293) supplemented with 1% penicillin/streptomycin and incubated in a 5% $CO_2$ atmosphere at 37° C. Conditioned media was collected and dialyzed against 300 mM KCl, 50 mM $KH_2PO_4$, pH 8. Full length ACLP was dialyzed using 100,000 molecular weight cut off (MWCO) dialysis tubing and the N-terminal and C-terminal constructs were dialyzed using 12,000-14,000 MWCO dialysis tubing (Spectra/Por). The protein was bound to an immobilized metal affinity chromatography column (Bio-Rad Duo Flow) via its His tag, and washed exhaustively. During the final wash, the column was washed with a sodium carbonate buffer (pH 11) as described (1) to remove remaining contaminating proteins including potentially TGFβ which was not detected in final recombinant ACLP (rACLP) preparations. Protein was eluted off the column with 250 mM imidazole, concentrated 40× and dialyzed into 1×PBS with calcium and magnesium. Protein purity was determined by SDS-PAGE followed by Coomassie staining. Protein concentration was determined via a Bradford Assay. The concentration accuracy of the full-length protein was calibrated using amino acid analysis (Molecular Biology Core, Dana Farber Cancer Institute). Authenticity of the full length recombinant protein was also determined by mass spectrometry (Taplin Mass Spectrometry Facility, Harvard Medical School).

Cell Treatments. IMR90 human lung fibroblasts (ATCC) and AD293 cells (Stratagene) were grown in DMEM supplemented with 10% FBS and 1% penicillin/streptomycin and incubated in a 5% $CO_2$ atmosphere at 37° C. Mink lung epithelial cells stably transfected with the plasminogen activator inhibitor 1 (PAI-1) reporter construct driving luciferase expression (MLEC-TGFβ) (2) were grown in DMEM supplemented with 10% FBS and 1% penicillin/streptomycin, maintained in 250 µg/ml G418, and incubated in a 5% $CO_2$ atmosphere at 37° C.

IMR90 cells and MLEC-TGFβ cells were generally treated for 30 min, 24 h, or 48 h in low serum media containing 0.5% FBS and 1% penicillin/streptomycin and incubated in a 5% $CO_2$ atmosphere at 37° C. Cells were treated with 3.75 µg/ml (approximately 30 nM) rACLP (full length, Tsp, or C-terminal) or 1 nM TGFβ (R&D) (as a positive control), except where indicated. Cells treated for 30 min were serum starved in low serum media overnight preceding treatment.

siRNA. Differentiating primary lung fibroblasts were transfected with 2 nM small interfering RNA (siRNA) targeting ACLP (Dharmacon) (GGCUCAAGAUC-UACGCAAU) (SEQ ID NO: 5) on either day 1 or day 2 post-isolation. Fully differentiated primary lung myofibroblasts were transfected at passage 2 or 3 with 2 nM siRNA targeting ACLP. Non-targeting control (NTC) siRNA (UG-GUUUACAUGUCGACUAA, UGGUUUACAUGUUGU-GUGA, UGGUUUACAUGUUUUCCUA, UGGUUUA-CAUGUUUUCUGA) (SEQ ID NO: 6) was used as a control in all experiments. Transfections were performed using RNAiMAX (Invitrogen) according to manufacturer's instructions.

MLEC-TGFβ activity assay. To measure TGFβ signaling activity, 1×10⁴ MLEC-TGFβ cells/well were plated on white 96-well cell culture treated plates and allowed to adhere overnight. They were then treated with indicated amounts of rACLP or TGFβ in media containing 0.5% FBS and 1% penicillin/streptomycin and incubated in a 5% $CO_2$ atmosphere at 37° C. for 24 h. Cells were lysed in Reporter Lysis Buffer (Promega) according to manufacturer's instructions. Luciferase activity was measured on an auto-injecting BioTek Synergy HT plate reader using 50 µl of luciferase assay substrate (Promega).

ACLP binding assays. To determine if ACLP binds to TGFβ Receptor II (TORII), ACLP was biotinylated using an EZ-Link Sulfo-NHS-LC-Biotin kit (Thermo Scientific 21327) according to manufacturer's instructions. Briefly, rACLP (0.267 nM) was incubated with 20 fold molar excess of biotin for 30 min at room temperature. The protein was then dialyzed back into DPBS overnight. Biotinylated ACLP (1 µg/well) was immobilized on a PIERCE™ Streptavidin coated High-Binding Capacity Plate (Thermo-Scientific PI-15500) overnight at 4° C. in binding buffer made up of PBS with $Mg^{2+}$, $Ca^{2+}$, 0.1% BSA, and 0.05% Tween 20). The next day, the plates were washed with binding buffer, blocked with the same buffer containing 1% BSA at room temperature for 1 h, followed by incubation with increasing amounts of TβRII Fc (0, 10, 100, 1000 ng). Binding was detected with Human-IgG-HRP (GE Healthcare Life Sciences) followed by incubation with 3,3',5,5'-Tetramethylbenzidine (TMB, eBioscience). The reaction was quenched with 2 M $H_2SO_4$ and absorbance at 450 nm was measured on the BioTek Synergy HT system.

Rabbit polyclonal antibody against N-terminal repeat. Peptides were generated against the center of the human ACLP N-terminal repeat domain. TKKPKEKPPKATKKPKEKPPKA (SEQ ID NO: 8), where the highlighted (underlined and bolded) region identifies the 11 amino acid repeat sequence. Peptides were purified by HPLC and validated to CID MS/MS (mass spectrometry) and polyclonal antibodies were generated in rabbits. Antibodies were affinity purified and validated for specificity against recombinant and cellular proteins.

Example 1

Generation of Recombinant ACLP

Figure 1A:
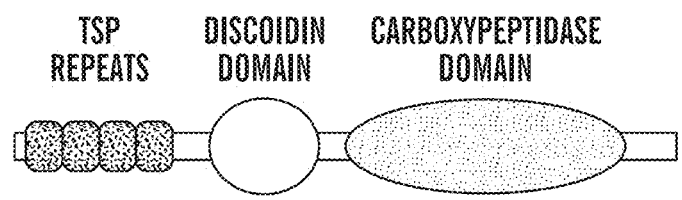
FIGS. 1A-1D show the structure of mammalian ACLP protein and purification of recombinant mouse ACLP protein.
Figure 1B:
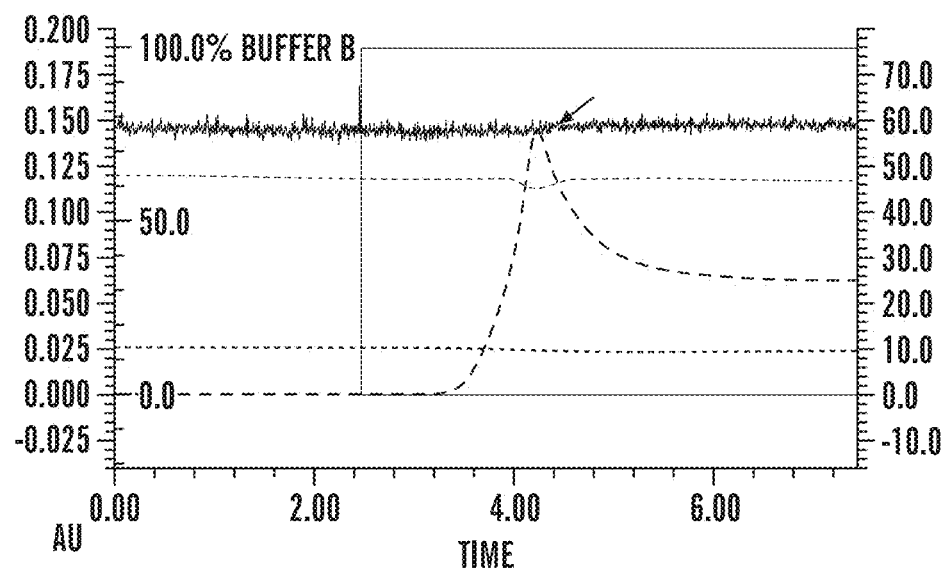
Figure 1C:
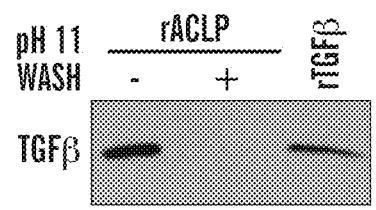
Figure 1D:
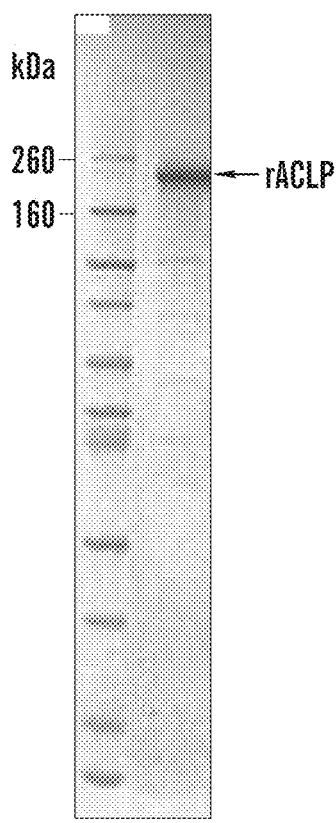

In order to elucidate the role of ACLP in the fibroblast to myofibroblast transition, recombinant ACLP was expressed and purified from mammalian cells for use in gain of function studies in fibroblasts (FIG. 1) (3). Purification was achieved by binding the protein to an immobilized metal affinity chromatography column (Bio-Rad BioLogic DUO FLOW™) via a C-terminal His tag (FIG. 1A). The column was washed exhaustively, including a sodium carbonate buffer (pH 11) wash as described (1) to remove trace amounts of TGFβ (FIG. 1C), protein was eluted off the column with 250 mM imidazole (FIG. 1B), dialyzed into 1×PBS with $Ca^{2+}$ and $Mg^{2+}$, and concentrated. Protein purity was determined by SDS-PAGE and Coomassie staining (FIG. 1D).

Figure 2A:
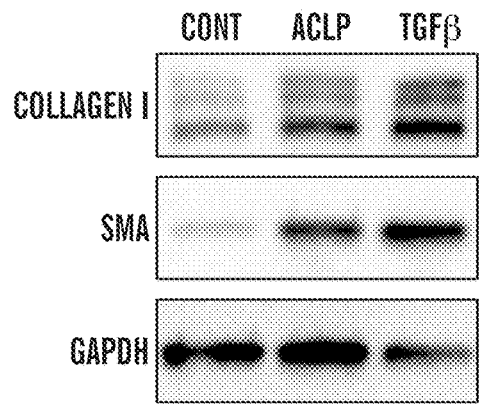
FIGS. 2A-2D shows rACLP promotes SMA and collagen I expression in human fibroblasts.

Recombinant ACLP induces myofibroblast gene and protein expression. To further define the role of ACLP in the fibroblast to myofibroblast differentiation process, IMR90 human lung fibroblast cells were treated with rACLP. IMR90 fibroblasts do not express endogenous ACLP and express very low basal levels of smooth muscle α actin (SMA) and type I collagen, two well established myofibroblast markers; therefore they are an excellent system to examine the effects of ACLP in gain of function studies. IMR90 cells were grown in media containing 3.75 µg/ml (30 nM) rACLP or 1 nM TGFβ as a positive control (FIG. 2A). Compared to control treated cells, rACLP induced an increase in both SMA and collagen protein expression in IMR90 cells after a 48 h treatment. These findings indicate that ACLP promotes the fibroblast to myofibroblast differentiation because it stimulates expression of SMA and collagen 1(3).

Figure 2B:
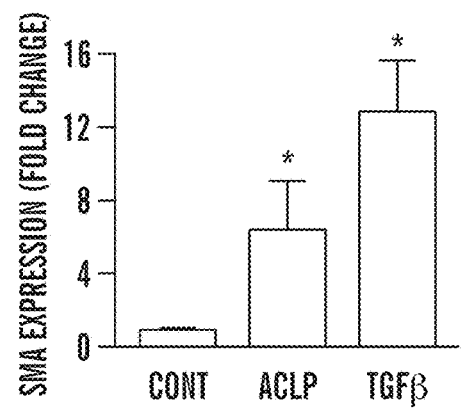
Figure 2C:
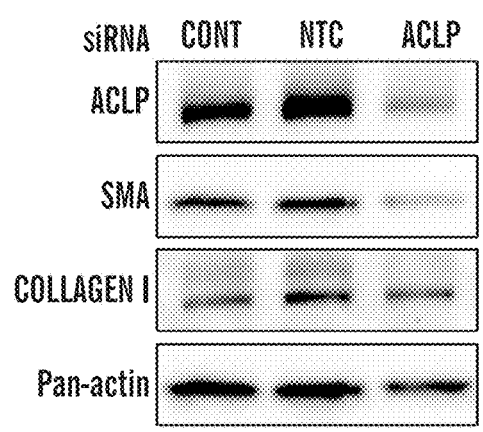
Figure 2D:
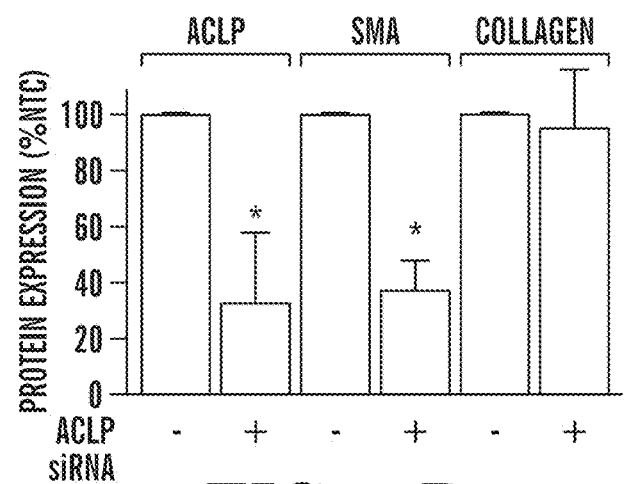
Figure 3:
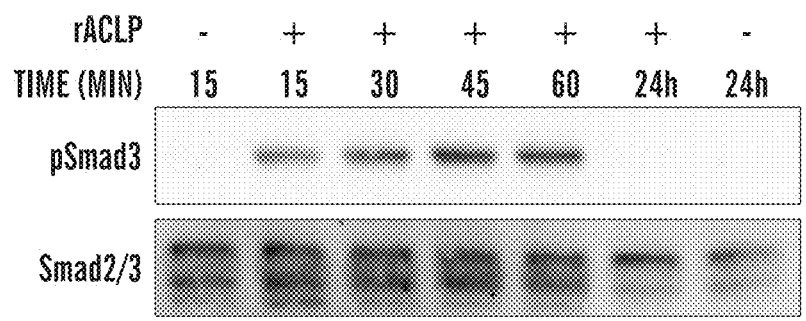
FIG. 3 shows ACLP stimulates transient Smad3 phosphorylation. IMR90 human lung fibroblasts were serum starved overnight and treated with 3.75 μg/ml rACLP for 15, 3-, 45 and 60 mins or 24 hours. Protein lysates were harvested and analyzed by SDS-PAGE and Western blot with antibodies against phospho-Smad3 and total Smad2/3. Data presented are representative of 3 separate experiments.

Knockdown of ACLP slows and partially reverts the fibroblast to myofibroblast transition. To determine if ACLP was required for fibroblast to myofibroblast differentiation, siRNA was used to knockdown ACLP expression during myofibroblast differentiation. Freshly isolated wildtype primary lung fibroblasts were transfected on day 1 post-isolation with siRNA targeting ACLP (FIG. 2B) (3). Cells transfected with ACLP siRNA (resulting in a 68% reduction in ACLP protein expression) exhibited a statistically significant 63% reduction in SMA protein expression as compared to cells transfected with NTC siRNA. Collagen I levels were reduced by only 5%, indicating that ACLP knockdown alone is insufficient to down regulate collagen at this time point.

rACLP stimulates canonical TGFβ signaling (Published Tumelty et al JBC 2014). Because ACLP increases TGFβ signaling in a reporter assay, the role of ACLP in canonical TGFβ signaling was investigated in detail. In pulmonary fibroblasts, TGFβ promotes the phosphorylation of Smad3 which then binds to Smad4 and translocates into the nucleus to promote transcription of myofibroblast marker genes (4,5). Therefore, the effects of ACLP on Smad3 phosphorylation were measured. Serum starved IMR90 cells were treated with rACLP for 15, 30, 45, or 60 min, or 24 h (FIG. 3) (3). Short-term rACLP treatment stimulated Smad3 phosphorylation first detected after 15 min, and this phosphorylation was transient and not detectable after 24 h.

Example 2

ACLP binds to the TGFβ-receptor II. Because ACLP stimulated TGFβ signaling but did not appear to directly interact with TGFβ in the inventors cell-free binding assay or activate latent TGFβ (data not shown), the inventors then assessed if ACLP interacts directly with TβRII (see FIG. 10). rACLP was biotinylated, immobilized on a streptavidin-coated plate, incubated with increasing amounts of TβRII Fc chimera (R&D), and binding was detected with human IgG-HRP (FIG. 4) (3). The TβRII Fc chimera contains the extracellular domain of mouse TβRII fused to the Fc domain of human IgG and has been used as a global inhibitor of TGFβ (6). In these assays, the TβRII Fc did not bind to streptavidin wells without ACLP. Compared to control-coated wells, wells with immobilized rACLP exhibited significantly more binding to the TβRII Fc chimera ($p<0.05$). These results indicate that ACLP binds to TβRII independent of the presence of TGFβ.

Example 3

Figure 5A:
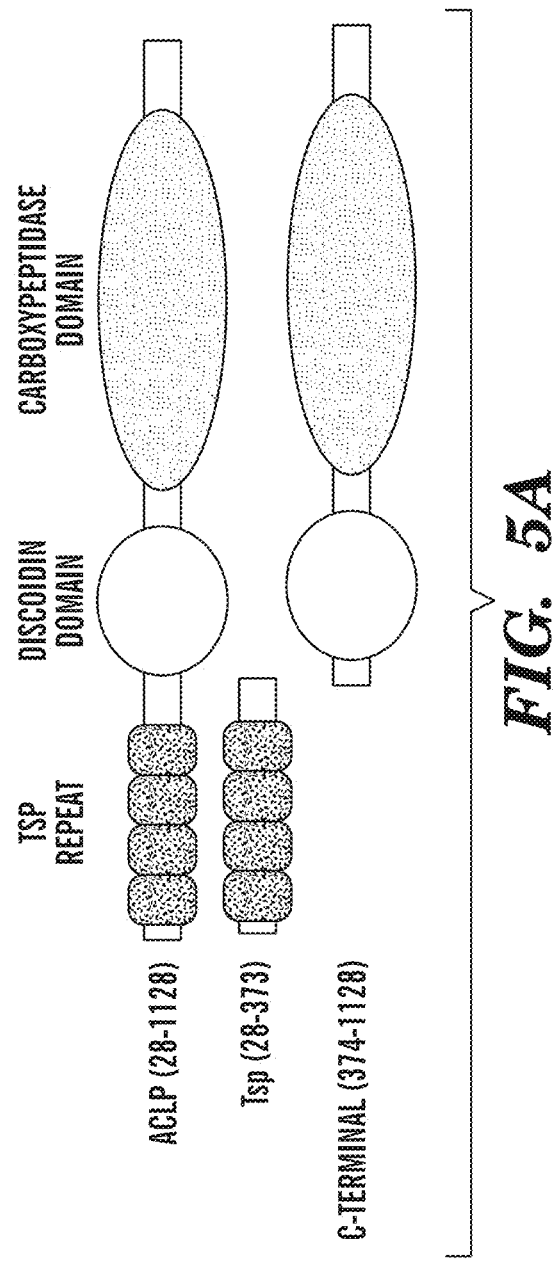
FIGS. 5A-5C show that the N-terminal PFD of mammalian ACLP protein, comprising the 4 Tsp motifs is responsible for binding to TGFβ receptor and stimulating TGFβ signaling.
Figures 5B, 5C:
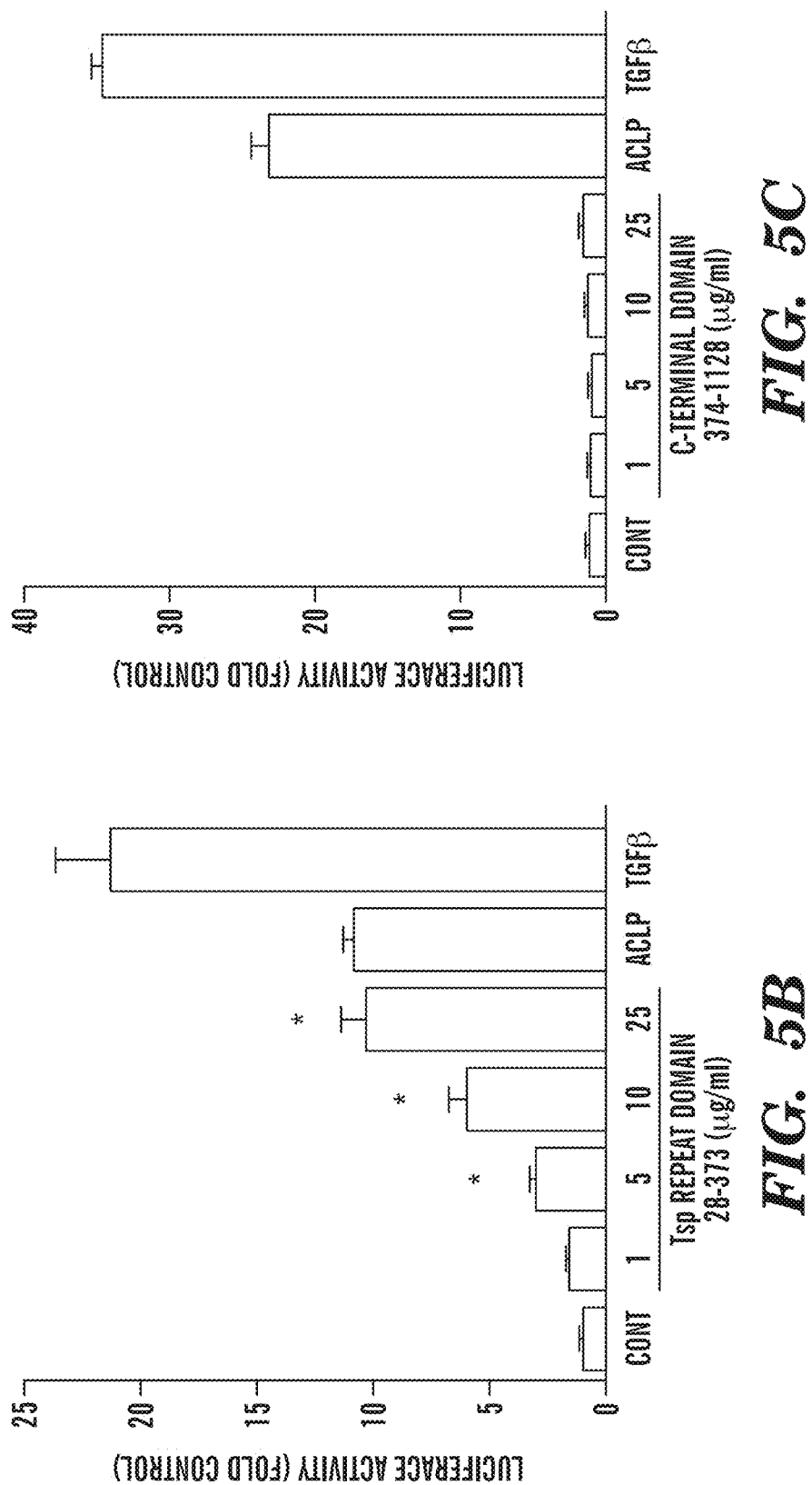

MAPPING THE FUNCTIONAL DOMAINS OF ACLP. The N-terminal domain of ACLP stimulates TGFβ signaling. ACLP is made up of an N-terminal Tsp repeat domain which is lysine, proline (i.e., the pro-fibrotic domain or PFD), and glutamic acid-rich, a discoidin domain (DS), and a catalytically inactive carboxypeptidase domain (7,8) (FIG. 1A). Because the inventors have previously reported that ACLP promotes the fibroblast to myofibroblast transition by binding to TβRII to promote Smad3 phosphorylation and nuclear translocation and subsequent SMA and collagen protein expression, the inventors herein assessed which domains of ACLP were responsible. The inventors purified recombinant mouse ACLP (mACLP) protein containing the N-terminal Tsp repeat domain (amino acids 26-373 of a mouse ACLP) or the C-terminal discoidin (DS) domain and carboxypeptidase domain (amino acids 374-1128 of mouse ACLP) (FIG. 5A). TGFβ responsive MLEC cells were treated overnight in low serum media containing increasing amounts of either the Tsp repeat domain (FIG. 5B) or the C-terminal domain (FIG. 5C). Interestingly, as little as 5 µg/ml of the Tsp repeat domain stimulated luciferase activity in this assay, whereas 25 µg/ml of C-terminal ACLP did not stimulate luciferase activity.

Serum starved IMR90 human lung fibroblasts were treated with equivalent molar amounts (~30 nM) of purified full-length, Tsp repeat domain, or C-terminal protein for 30 min in low serum media (FIG. 6). 30 nM of full length ACLP and Tsp repeat domain stimulated Smad3 phosphorylation, whereas the C-terminal domain of ACLP did not. Taken together, these results demonstrate that the N-terminal Tsp repeat domain of ACLP is required and sufficient to stimulate TGFβ signaling pathways.

The N-terminal domain of ACLP promotes myofibroblast marker protein expression. Because the inventors discovered that the N-terminal Tsp motifs of ACLP (e.g. the PFD) is the domain responsible for promoting TGFβ signaling, the inventors next assessed which domain of ACLP is responsible for increased SMA and collagen I expression in lung myofibroblasts. IMR90 lung fibroblasts were treated in low serum media containing equal molar amounts of full-length protein, the pro-fibrotic domain (PFD) of ACLP, and C-terminal ACLP (~30 nM) for 48 h (FIG. 7). Full-length ACLP (30 nM) and the pro-fibrotic domain (PFD) promoted an increase in SMA and collagen protein expression as compared to untreated control cells and cells treated with 30 nM of C-terminal ACLP. These results demonstrate that the N-terminal Tsp repeat domain of ACLP is responsible for promoting the fibroblast to myofibroblast transition by stimulating Smad3 phosphorylation and SMA and collagen expression.

Structural prediction of N-terminal domain. The N-terminal region of ACLP overall is extremely rich in proline, lysine, and glutamic acid residues with a 4-fold highly conserved repeat of KEKPPKATKKP (SEQ ID NO: 3), which depending where the repeat is started can be a 4-times repeat of the following sequence TKKPKEKPPKA (SEQ ID NO: 49) (see SEQ ID NO: 4). To develop a hypothesis regarding the function of this domain, the inventors used the I-TASSER protein structure modeler. The N-terminal domain is predicted with high confidence to contain 4 thrombospondin 1 repeats (Tsp 1) (FIG. 8A). Thrombospondins have been implicated in numerous profibrotic pathways and in cancer. The repeat in Tsp2 is highlighted in FIG. 8B. Taken together with our in vivo studies showing the absence of ACLP reduces SMA and collagen expression, this observation supports the central hypothesis of the project that inhibition of ACLP expression or function will reduce the generation of matrix producing cells leading to a reduced rate of fibrosis.

Example 4

Generation of polyclonal antibody against N-terminal PFD of ACLP. In order to more fully elucidate the role of the N-terminal PFD of ACLP in pro-fibrotic mechanisms, the inventors have generated a polyclonal antibody, which specifically recognizes the N-terminus of ACLP (FIG. 9). It recognizes a recombinant protein containing only the N-terminal domain of ACLP and does not detect anything when a protein lacking the N-terminal domain is probed (FIG. 9A). Additionally, when cell lysates from mouse aortic smooth muscle cells are probed, the antibody detects endogenous ACLP (FIG. 9B).

Figure 11A:
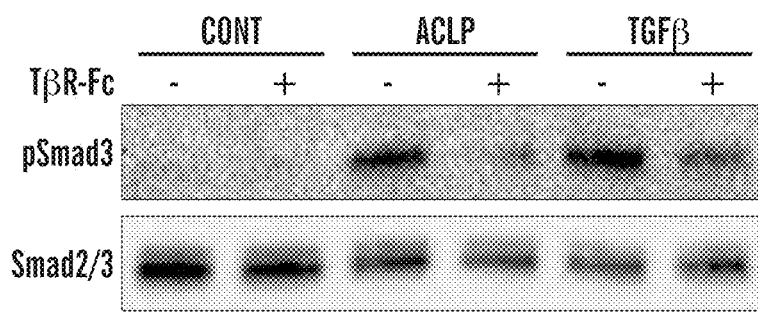
FIG. 11A-11B shows an exemplary ACLP inhibitor which is receptor decoy molecule comprising a portion of the TGFβRII protein bound to Fc (TGFβ receptor-Fc) which blocks ACLP signaling and myoblast differentiation.
Figure 11B:
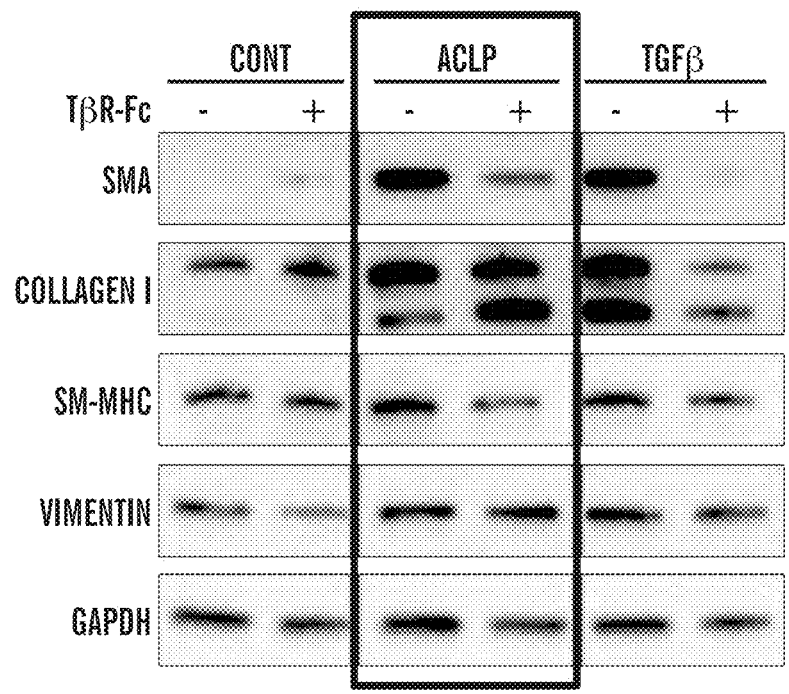

Accordingly, the inventors determined that the pro-fibrotic domain (PFD) (showing the four Tsp motifs) of ACLP interacts with the TGFβ receptor (TGFβRII) (FIG. 10), and TGFβ receptor-Fc (TOR-Fc) as an exemplary ACLP inhibitor, blocks ACLP signaling and myoblast differentiation (FIG. 11A, 11B). In particular, the inventors demonstrate that TpR-Fc decoy molecule decreases pSmad3 expression in the presence of mouse rACLP in IMR90 human lung fibroblast cells (FIG. 11A) and decreases ACLP-induced SMA and SM-MHC expression in the presence of rACLP in human lung fibroblast cells (FIG. 11B). Further, the inventors demonstrate that the amino acid sequence of the PFD domain, in particular Tsp2 motif in mammalian ACLP proteins is highly conserved (FIG. 12), and therefore an inhibitor that inhibits recombinant mouse ACLP protein, or the PFD of mouse ACLP, in particular the Tsp2 motif of mouse ACLP will also inhibit the PFD of human ACLP protein or the Tsp2 motif of human ACLP.

Example 5

Discoidin (DS) Domain Potentiates and Increases ACLP-Mediated TGFβRII Signaling in the Presence of Collagen.

The inventors next assessed if other regions of the ACLP polypeptide contributed to the ACLP-mediated TGFβRII signaling, which is dependent on the PFD of the ACLP polypeptide. The inventors discovered that inhibitors that have binding affinity to the DS are also useful in combination with inhibitors to the PFD of ALCP (e.g., PFDi), as the discoidin (DS) domain of ACLP enhances myofibroblast differentiation in the presence of collagen (FIG. 13C). In particular, in in vitro assays the discoidin domain is normally non-functional, whereas herein, the inventors surprisingly demonstrate that, in the presence of collagen (and on a tissue stiffness similar to that of fibrotic tissue), the discoidin domain potentiates TGFβRII signaling. Such discoidin-mediated potentiating of TGFβ signaling did not occur in the absence of collagen (FIG. 13C). Human ACLP discoidin (DS) domain is predicted to comprise 4 loops (1-4) on one face of the DS domain, which are binding site targets for inhibitors the discoidin domain of the ACLP protein (FIG. 13A). Accordingly, a discoidin domain inhibitor (DSi) that bind to any one, or more, of loops 1, 2, 3, or 4 of the discoidin domain of human ACLP are encompassed for use in the compositions, methods and kits as disclosed herein, and can be used alone, or in combination with an inhibitor which binds to at least one region in the PFD, e.g., an inhibitor which bind to at least one or more of Tsp1, Tsp2, Tsp3 or Tsp4. Additionally, as the discoidin domains of DDR1, DDR2, human ACLP and Factor V (FV) have high amino acid sequence similarly (see FIG. 13B), inhibitors of Factor V, DDR1, DDR2 that inhibit the discording domain of these proteins are also encompassed for use in the method, kits and compositions of the present invention, either alone, or in combination with a inhibitor which binds to at least one region in the PFD, e.g., an inhibitor which bind to at least one or more of Tsp1, Tsp2, Tsp3 or Tsp4.

Example 6

Role of ACLP in Cancer Prognosis and Cancer Progression.

Figure 14:
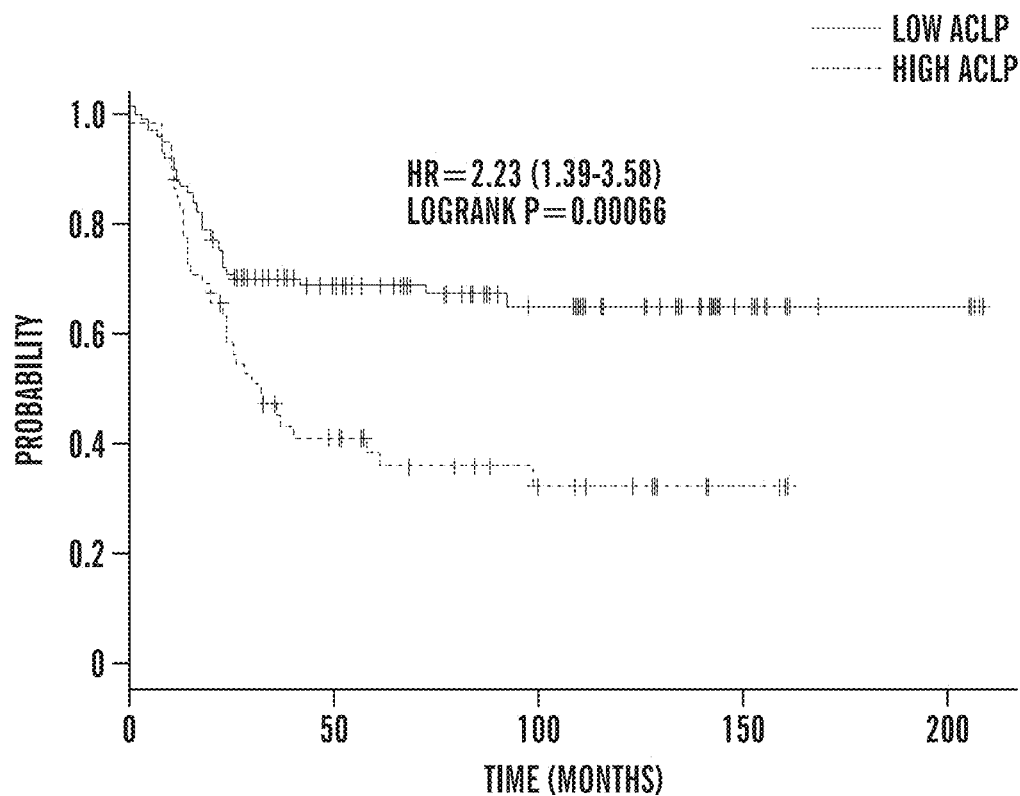
FIG. 14 shows elevated ACLP expression correlates with poor cancer prognosis and that inhibition of ACLP protein using inhibitors that specifically target the PFD and/or the discoidin domain of ACLP are useful in methods to treat cancers, as well as inhibit cancer progression.

Elevated ACLP expression correlates with poor prognosis. The inventors examined the correlation of ACLP expression with relapse free survival (RFS) in human patients that had human Her2+ breast tumors by Kaplan-Meier analysis. Importantly, the inventors discovered that there was a statistically significant correlation of elevated ACLP levels with a reduction in relapse free survival (RFS) with a calculated hazard ratio (HR) of 2.23 (FIG. 14).

Figure 15A:
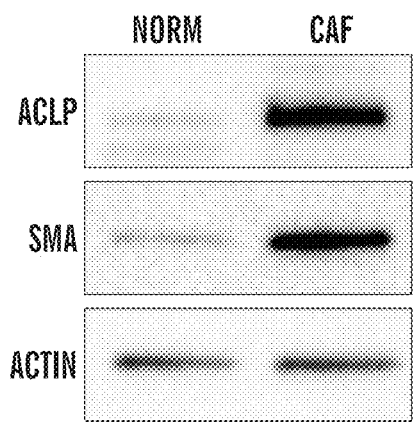
FIG. 15A-15C shows ACLP production in CAF (cancer-associated fibroblasts) and presence of ACLP in murine ductal carcinoma model.
Figure 15B:
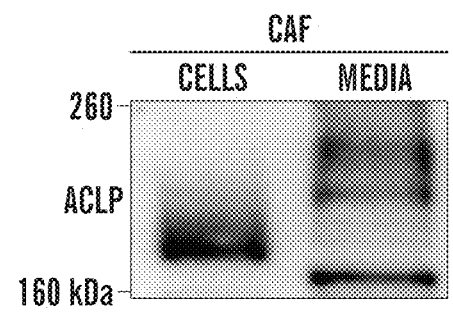
Figure 15C:
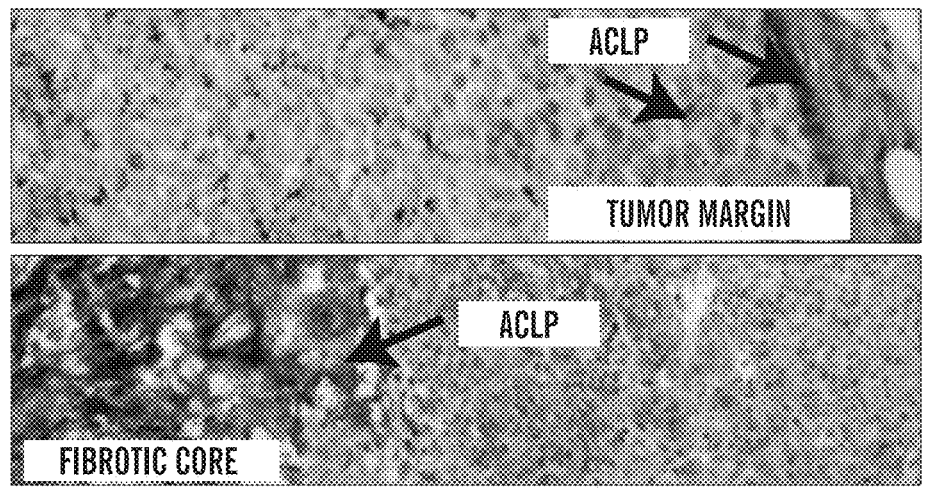

Cancer Associated fibroblasts secrete ACLP. The inventors assessed if, ACLP, a stromal derived proteins, directly alters epithelial cells and facilitates cancer progression. Compared to normal primary mammary gland fibroblasts which express low levels of ACLP, cancer associated fibroblasts (CAFs) derived from mouse ductal carcinomas exhibit elevated expression levels (FIG. 15A). Furthermore, CAF were discovered to secrete ACLP into the media (FIG. 15B). The inventors detected multiple bands which represent differential glycosylation and proteolytic processing of ACLP, possibly by MMPs. Using immunohistochemistry, the inventors detected the expression of ACLP in advanced tumors derived from the Her2/neu mouse model. Surprisingly, ACLP expression was detected in the peripheral stroma at the tumor margin (FIG. 15C, upper), and showed a gradient from that margin. Furthermore, very high levels of ACLP were detected in the tumor's fibrotic core and a gradient of expression extended into the tumor (FIG. 5C, lower), consistent with the Kaplan-Meier analysis (FIG. 14).

Figure 16:
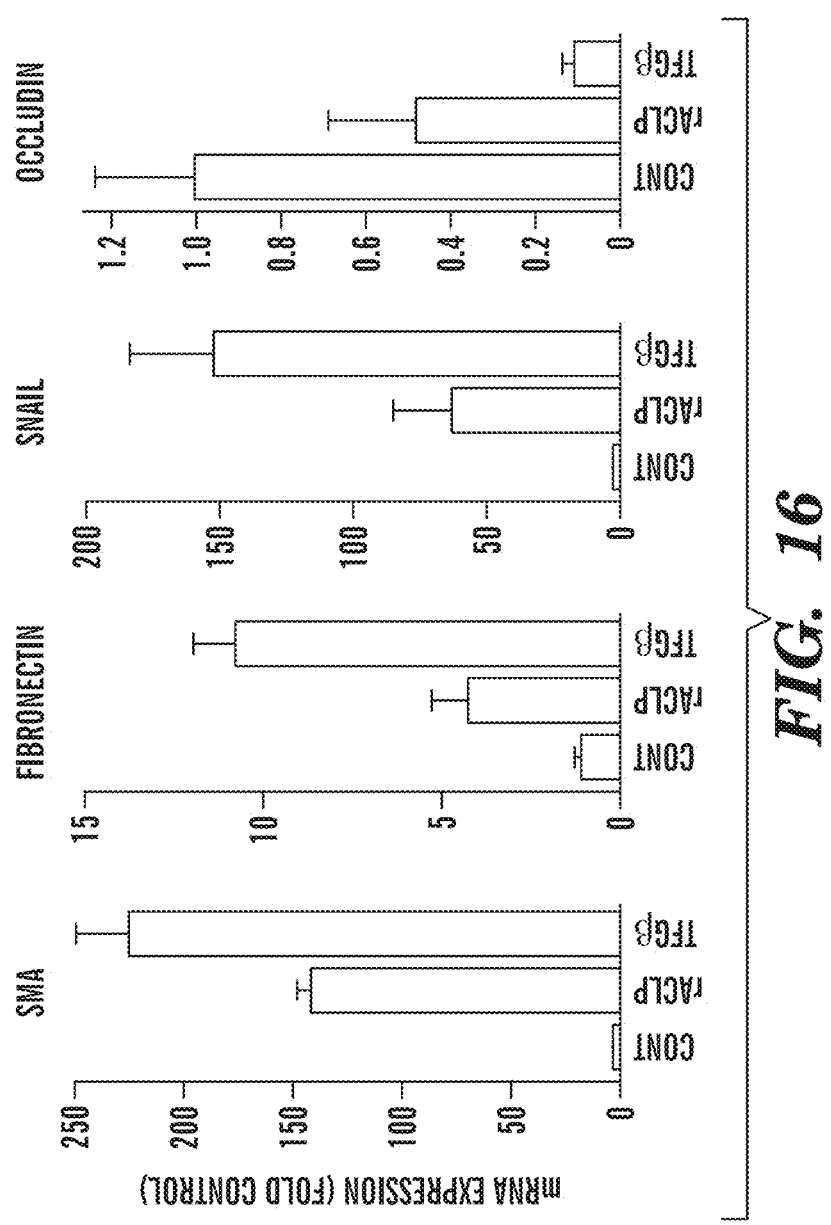
FIG. 16 shows ACLP expression in breast cancer induced an epithelial to mesenchymal transition (EMT) phenotype in mammary epithelial cells. Normal murine mammary gland epithelial cells (NMuMg) were treated with rACLP (30 nM) or TGFβ (1 nM) and RNA was analyzed by qPCR after 48 hours.

ACLP alters epithelial cell phenotype. Using purified recombinant ACLP (rACLP), which does not contain contaminating TGFβ, the inventors assessed the effect of ACLP, a CAF (cancer-associated fibroblast) secreted molecule, on normal epithelial cell gene expression and phenotype. The inventors discovered that rACLP enhanced the mesenchymal markers SMA, fibronectin, and Snail while decreasing the epithelial marker occludin (FIG. 16). The inventors also detected a change in cellular morphology in the ACLP treated cells consistent with EMT (epithelial to mesenchymal transition). Accordingly, the inventors have discovered that elevated ACLP expression is associated with reduced relapse free survival in human patients with Her2+ breast tumors, and that ACLP is secreted from CAF and is present within breast tumors. Furthermore, the inventors have discovered that ACLP alters epithelial phenotypes to a mesenchymal phenotype and that ACLP expression is part of a specific stromal gene expression signature that can predict resistance to several breast cancer chemotherapies. Thus, the inventors herein provide data for targeting inhibition of ACLP, by using inhibitors that bind to any one of Tsp motifs in the PFD and/or in combination with an inhibitor that binds to the discoidin (DS) domain for the treatment and delay of cancer progression, including solid cancers with a fibrotic core, such as breast cancers and other cancers if epithelial origin and/or under go EMT. In some embodiments, the cancer is breast cancer, e.g. Her2+ breast cancer.

REFERENCES

The references cited herein and throughout the application are incorporated herein in their entirety by reference.

1. Murphy-Ullrich, J. E., Schultz-Cherry, S., and Hook, M. (1992) Transforming Growth Factor-Beta Complexes with Thrombospondin. *Mol Biol Cell* 3, 181-188
2. Abe, M., Harpel, J. G., Metz, C. N., Nunes, I., Loskutoff, D. J., and Rifkin, D. B. (1994) An Assay for Transforming Growth Factor-Beta Using Cells Transfected with a Plasminogen Activator Inhibitor-1 Promoter-Luciferase Construct. *Analytical biochemistry* 216, 276-284
3. Tumelty, K. E., Smith, B. D., Nugent, M. A., and Layne, M. D. (2014) Aortic Carboxypeptidase-Like Protein Enhances Lung Myofibroblast Differentiation through Transforming Growth Factor β Receptor Dependent and Independent Pathways. *J Biol Chem* 289, 2526-36
4. Zhang, Y., Feng, X., We, R., and Derynck, R. (1996) Receptor-Associated Mad Homologues Synergize as Effectors of the Tgf-Beta Response. *Nature* 383, 168-172
5. Macias-Silva, M., Abdollah, S., Hoodless, P. A., Pirone, R., Attisano, L., and Wrana, J. L. (1996) Madr2 Is a Substrate of the Tgfbeta Receptor and Its Phosphorylation Is Required for Nuclear Accumulation and Signaling. *Cell* 87, 1215-1224
6. Horan, G. S., Wood, S., Ona, V., Li, D. J., Lukashev, M. E., Weinreb, P. H., Simon, K. J., Hahm, K., Allaire, N. E., Rinaldi, N. J., Goyal, J., Feghali-Bostwick, C. A., Matteson, E. L., O'hara, C., Lafyatis, R., Davis, G. S., Huang, X., Sheppard, D., and Violette, S. M. (2008) Partial Inhibition of Integrin Alpha(V)Beta6 Prevents Pulmonary Fibrosis without Exacerbating Inflammation. *Am J Respir Crit Care Med* 177, 56-65
7. Layne, M. D., Endege, W. O., Jain, M. K., Yet, S. F., Hsieh, C. M., Chin, M. T., Perrella, M. A., Blanar, M. A., Haber, E., and Lee, M. E. (1998) Aortic Carboxypeptidase-Like Protein, a Novel Protein with Discoidin and Carboxypeptidase-Like Domains, Is up-Regulated During Vascular Smooth Muscle Cell Differentiation. *J Biol Chem* 273, 15654-15660
8. Tumelty, K. E., and Layne, M. D. (2013) Adipocyte Enhancer Binding Protein 1 and Aortic Carboxypeptidase-Like Protein. In *Handbook of Proteolytic Enzymes* (Rawlings, N. D. and Salvesen, G. S., ed.) Academic Press, Oxford. pp 1348-1353.

Danzer E, Layne M D, Auber F, Shegu S, Kreiger P, Radu A, Volpe M, Adzick N S, Flake A W. Gastroschisis in mice lacking aortic carboxypeptidase-like protein (ACLP) is associated with a defect in neuromuscular development of the eviscerated intestine. Pediatr Res. 2010; 68(1):23-8.

Schissel S L, Dunsmore S E, Liu X L, Shine R W, Perrella M A, Layne M D. Aortic carboxypeptidase-like protein is expressed in fibrotic human lung and its absence protects against bleomycin-induced lung fibrosis. Am J Pathol. 2009; 174(3):818-28.

Ith B, Wei J, Yet S-F, Perrella M A, Layne M D. Aortic carboxypeptidase-like protein is expressed in collagen-rich tissues during mouse embryonic development. Gene Expr Patterns 2005; 5(4):533-537.

Gagnon A M, Landry A, Proulx J, Layne M D, Sorisky A. Aortic carboxypeptidase-like protein is regulated by transforming growth factor-β in 3T3-L1 preadipocytes. Exp Cell Res 2005; 308(2):265-72.

Layne M D, Yet S-F, Maemura K, Hsieh C-M, Liu X, Ith B, Lee M-E, Perrella M A. Characterization of the mouse aortic carboxypeptidase-like protein promoter reveals activity in both differentiated and dedifferentiated vascular smooth muscle cells. Circ Res 2002; 90:728-36.

Layne M D*, Yet S-F, Hsieh C-M, Maemura K, Bemfield M, Perrella M A, Lee M-E.

Impaired abdominal wall development and deficient wound healing in mice lacking aortic carboxypeptidase-like protein. Mol Cell Biol 2001; 21:5256-61.

Lee M-E, Layne M D, Yet S-F, inventors; Harvard University assignee. Aortic carboxypeptidase-like polypeptide. U.S. Pat. No. 6,468,766. 2002 Oct. 22.

Lee M-E, Layne M D, Yet S-F, inventors; Harvard University assignee. Aortic carboxypeptidase-like polypeptide. U.S. Pat. No. 7,094,878. 2006 Aug. 22.

The invention claimed is:

1. An admixture comprising:
   a) a first peptide that comprises at least 5 consecutive amino acids of the amino acid sequence of SEQ ID NO: 3 or SEQ ID NO: 4 and has at least 85% sequence identity to the amino acid sequence of SEQ ID NO: 3 or SEQ ID NO: 4; and
   b) a second peptide that comprises at least 5 consecutive amino acid residues of amino acids 384-539 of SEQ ID NO: 1.

2. The admixture of claim 1, wherein the first peptide, or second peptide, or both are fused to a Fc, wherein the Fc comprises the amino acid sequence of SEQ ID NO: 48 or a Fc variant having at least 85% sequence identity to SEQ ID NO: 48.

3. The admixture of claim 1, wherein first peptide comprises at least 5 consecutive amino acids of KEKPPKATKKPKEKPPKATKKPKEKPPKATKKPKEKPPKATKKP (SEQ ID NO: 4).

4. The admixture of claim 1, wherein the second peptide comprises:
   (i) at least 5 consecutive amino acids from at least one loop region within amino acids 384-539 of SEQ ID NO: 1, wherein the loop region is selected from: MLRHGLG (SEQ ID NO: 12), QTGATEDDYYDGA (SEQ ID NO: 13), DARTQ (SEQ ID NO: 14) and RDSSIHDD (SEQ ID NO: 15); or
   (ii) a peptide selected from the group consisting of: MLRHGLG (SEQ ID NO: 12); MLRHGLGA (SEQ ID NO: 16); MLRHGLGAQ (SEQ ID NO: 17); SMLRHGLG (SEQ ID NO: 18); SMLRHGLG (SEQ ID NO: 19); SMLRHGLGA (SEQ ID NO: 20); SMLRHGLGAQ (SEQ ID NO: 21); SSMLRHGLGA (SEQ ID NO: 22); SSMLRHGLGAQ (SEQ ID NO: 23); QTGATEDDYYDGA (SEQ ID NO: 13); QTGATEDDYYDGAW (SEQ ID NO: 24); QTGATEDDYYDGAWC (SEQ ID NO: 25); MQTGATEDDYYDGA (SEQ ID NO: 26); NMQTGATED- DYYDGA (SEQ ID NO: 27); MQTGATEDDYYD-GAW (SEQ ID NO: 28); MQTGATEDDYYDGAWC (SEQ ID NO: 29); NMQTGATEDDYYDGAW (SEQ ID NO: 30); NMQTGATEDDYYDGAWC (SEQ ID NO: 31); DARTQ (SEQ ID NO: 14); DARTQW (SEQ ID NO: 32); DARTQWI (SEQ ID NO: 33); DDARTQ (SEQ ID NO: 34); EDDARTQ (SEQ ID NO: 35); DDARTQW (SEQ ID NO: 36); DDARTQWI (SEQ ID NO: 37); EDDARTQW (SEQ ID NO: 38); EDDARTQWI (SEQ ID NO: 39); RDSSIHDD (SEQ ID NO: 15); RDSSIHDDF (SEQ ID NO: 40); RDSSIHDDFV (SEQ ID NO: 41); GRDSSIHDD (SEQ ID NO: 42); QGRDSSIHDD (SEQ ID NO: 43); GRDSSIHDDF (SEQ ID NO: 44); GRDSSIHDDFV (SEQ ID NO: 45); QGRDSSIHDDF (SEQ ID NO: 46); and QGRDSSIHDDFV (SEQ ID NO: 47).

5. The admixture of claim 1, for use in a method to treat a fibroproliferative disease or a solid cancer with a fibrotic core.

6. A kit comprising:
a first container comprising a first peptide that comprises at least 5 consecutive amino acids of the amino acid sequence of SEQ ID NO: 3 or SEQ ID NO: 4 and has at least 85% sequence identity to the amino acid sequence of SEQ ID NO: 3 or SEQ ID NO: 4, and
a second container comprising a second peptide comprising at least 5 consecutive amino acid residues of amino acids 384-539 of SEQ ID NO: 1.

7. The kit of claim 6, wherein the first peptide comprises at least 5 consecutive amino acids of KEKPPKATKKPKEKPPKATKKPKEKPPKATKKPKEKPPKATKKP (SEQ ID NO: 4), and can be optionally fused to a Fc comprising the amino acid sequence of SEQ ID NO: 48 or a fragment of SEQ ID NO: 48.

8. The kit of claim 6, wherein the second peptide is selected from the group consisting of:
(i) at least 5 consecutive amino acids from at least one loop region within amino acids 384-539 of SEQ ID NO: 1, wherein the loop region is selected from: MLRHGLG (SEQ ID NO: 12), QTGATEDDYYDGA (SEQ ID NO: 13), DARTQ (SEQ ID NO: 14) and RDSSIHDD (SEQ ID NO: 15); and
(ii) a peptide selected from the group consisting of: MLRHGLG (SEQ ID NO: 12); MLRHGLGA (SEQ ID NO: 16); MLRHGLGAQ (SEQ ID NO: 17); SMLRHGLG (SEQ ID NO: 18); SMLRHGLG (SEQ ID NO: 19); SMLRHGLGA (SEQ ID NO: 20); SMLRHGLGAQ (SEQ ID NO: 21); SSMLRHGLGA (SEQ ID NO: 22); SSMLRHGLGAQ (SEQ ID NO: 23); QTGATEDDYYDGA (SEQ ID NO: 13); QTGATEDDYYDGAW (SEQ ID NO: 24); QTGATEDDYYDGAWC (SEQ ID NO: 25); MQTGATEDDYYDGA (SEQ ID NO: 26); NMQTGATEDDYYDGA (SEQ ID NO: 27); MQTGATEDDYYDGAW (SEQ ID NO: 28); MQTGATEDDYYDGAWC (SEQ ID NO: 29); NMQTGATEDDYYDGAW (SEQ ID NO: 30); NMQTGATEDDYYDGAWC (SEQ ID NO: 31); DARTQ (SEQ ID NO: 14); DARTQW (SEQ ID NO: 32); DARTQWI (SEQ ID NO: 33); DDARTQ (SEQ ID NO: 34); EDDARTQ (SEQ ID NO: 35); DDARTQW (SEQ ID NO: 36); DDARTQWI (SEQ ID NO: 37); EDDARTQW (SEQ ID NO: 38); EDDARTQWI (SEQ ID NO: 39); RDSSIHDD (SEQ ID NO: 15); RDSSIHDDF (SEQ ID NO: 40); RDSSIHDDFV (SEQ ID NO: 41); GRDSSIHDD (SEQ ID NO: 42); QGRDSSIHDD (SEQ ID NO: 43); GRDSSIHDDF (SEQ ID NO: 44); GRDSSIHDDFV (SEQ ID NO: 45); QGRDSSIHDDF (SEQ ID NO: 46) and QGRDSSIHDDFV (SEQ ID NO: 47),
wherein the second peptide can be optionally fused to a Fc comprising the amino acid sequence of SEQ ID NO: 48 or a fragment of SEQ ID NO: 48.

9. The kit of claim 6, wherein the first peptide or the second peptide, or both is at least one of:
(a) in a lyophilized form;
(b) in a form comprising a detectable label; or
(c) is conjugated to an anti-cancer agent.

\* \* \* \* \*

SEQUENCE LISTING

```
<160> NUMBER OF SEQ ID NOS: 62

<210> SEQ ID NO 1
<211> LENGTH: 1158
<212> TYPE: PRT
<213> ORGANISM: Homo sapiens
```

<400> SEQUENCE: 1

```
Met Ala Ala Val Arg Gly Ala Pro Leu Leu Ser Cys Leu Leu Ala Leu
1               5                   10                  15

Leu Ala Leu Cys Pro Gly Gly Arg Pro Gln Thr Val Leu Thr Asp Asp
            20                  25                  30

Glu Ile Glu Glu Phe Leu Glu Gly Phe Leu Ser Glu Leu Glu Pro Glu
            35                  40                  45

Pro Arg Glu Asp Asp Val Ala Pro Pro Pro Glu Pro Thr Pro
    50                  55                  60

Arg Val Arg Lys Ala Gln Ala Gly Gly Lys Pro Gly Lys Arg Pro Gly
65                  70                  75                  80

Thr Ala Ala Glu Val Pro Pro Glu Lys Thr Lys Asp Lys Gly Lys Lys
                85                  90                  95

Gly Lys Lys Asp Lys Gly Pro Lys Val Pro Lys Glu Ser Leu Glu Gly
                100                 105                 110

Ser Pro Arg Pro Pro Lys Lys Gly Lys Glu Lys Pro Pro Lys Ala Thr
            115                 120                 125

Lys Lys Pro Lys Glu Lys Pro Pro Lys Ala Thr Lys Lys Pro Lys Glu
        130                 135                 140

Lys Pro Pro Lys Ala Thr Lys Lys Pro Lys Glu Lys Pro Pro Lys Ala
145                 150                 155                 160

Thr Lys Lys Pro Pro Ser Gly Lys Arg Pro Pro Ile Leu Ala Pro Ser
                165                 170                 175

Glu Thr Leu Glu Trp Pro Leu Pro Pro Pro Ser Pro Gly Pro Glu
            180                 185                 190

Glu Leu Pro Gln Glu Gly Gly Ala Pro Leu Ser Asn Asn Trp Gln Asn
            195                 200                 205

Pro Gly Glu Glu Thr His Val Glu Ala Arg Glu His Gln Pro Glu Pro
            210                 215                 220

Glu Glu Glu Thr Glu Gln Pro Thr Leu Asp Tyr Asn Asp Gln Ile Glu
225                 230                 235                 240

Arg Glu Asp Tyr Glu Asp Phe Glu Tyr Ile Arg Arg Gln Lys Gln Pro
                245                 250                 255

Arg Pro Pro Pro Ser Arg Arg Arg Pro Glu Arg Val Trp Pro Glu
            260                 265                 270

Pro Pro Glu Glu Lys Ala Pro Ala Pro Ala Pro Glu Glu Arg Ile Glu
            275                 280                 285

Pro Pro Val Lys Pro Leu Leu Pro Pro Leu Pro Pro Asp Tyr Gly Asp
            290                 295                 300

Gly Tyr Val Ile Pro Asn Tyr Asp Asp Met Asp Tyr Tyr Phe Gly Pro
305                 310                 315                 320

Pro Pro Pro Gln Lys Pro Asp Ala Glu Arg Gln Thr Asp Glu Glu Lys
                325                 330                 335

Glu Glu Leu Lys Lys Pro Lys Lys Glu Asp Ser Ser Pro Lys Glu Glu
            340                 345                 350

Thr Asp Lys Trp Ala Val Glu Lys Gly Lys Asp His Lys Glu Pro Arg
            355                 360                 365

Lys Gly Glu Glu Leu Glu Glu Trp Thr Pro Thr Glu Lys Val Lys
            370                 375                 380

Cys Pro Pro Ile Gly Met Glu Ser His Arg Ile Glu Asp Asn Gln Ile
385                 390                 395                 400
```

```
Arg Ala Ser Ser Met Leu Arg His Gly Leu Gly Ala Gln Arg Gly Arg
            405                 410                 415

Leu Asn Met Gln Thr Gly Ala Thr Glu Asp Asp Tyr Tyr Asp Gly Ala
            420                 425                 430

Trp Cys Ala Glu Asp Ala Arg Thr Gln Trp Ile Glu Val Asp Thr
        435                 440                 445

Arg Arg Thr Thr Arg Phe Thr Gly Val Ile Thr Gln Gly Arg Asp Ser
450                 455                 460

Ser Ile His Asp Asp Phe Val Thr Thr Phe Phe Val Gly Phe Ser Asn
465                 470                 475                 480

Asp Ser Gln Thr Trp Val Met Tyr Thr Asn Gly Tyr Glu Glu Met Thr
                485                 490                 495

Phe His Gly Asn Val Asp Lys Asp Thr Pro Val Leu Ser Glu Leu Pro
            500                 505                 510

Glu Pro Val Val Ala Arg Phe Ile Arg Ile Tyr Pro Leu Thr Trp Asn
            515                 520                 525

Gly Ser Leu Cys Met Arg Leu Glu Val Leu Gly Cys Ser Val Ala Pro
            530                 535                 540

Val Tyr Ser Tyr Tyr Ala Gln Asn Glu Val Val Ala Thr Asp Asp Leu
545                 550                 555                 560

Asp Phe Arg His His Ser Tyr Lys Asp Met Arg Gln Leu Met Lys Val
                565                 570                 575

Val Asn Glu Glu Cys Pro Thr Ile Thr Arg Thr Tyr Ser Leu Gly Lys
            580                 585                 590

Ser Ser Arg Gly Leu Lys Ile Tyr Ala Met Glu Ile Ser Asp Asn Pro
            595                 600                 605

Gly Glu His Glu Leu Gly Glu Pro Glu Phe Arg Tyr Thr Ala Gly Ile
610                 615                 620

His Gly Asn Glu Val Leu Gly Arg Glu Leu Leu Leu Leu Met Gln
625                 630                 635                 640

Tyr Leu Cys Arg Glu Tyr Arg Asp Gly Asn Pro Arg Val Arg Ser Leu
                645                 650                 655

Val Gln Asp Thr Arg Ile His Leu Val Pro Ser Leu Asn Pro Asp Gly
            660                 665                 670

Tyr Glu Val Ala Ala Gln Met Gly Ser Glu Phe Gly Asn Trp Ala Leu
            675                 680                 685

Gly Leu Trp Thr Glu Glu Gly Phe Asp Ile Phe Glu Asp Phe Pro Asp
            690                 695                 700

Leu Asn Ser Val Leu Trp Gly Ala Glu Glu Arg Lys Trp Val Pro Tyr
705                 710                 715                 720

Arg Val Pro Asn Asn Asn Leu Pro Ile Pro Glu Arg Tyr Leu Ser Pro
                725                 730                 735

Asp Ala Thr Val Ser Thr Glu Val Arg Ala Ile Ile Ala Trp Met Glu
            740                 745                 750

Lys Asn Pro Phe Val Leu Gly Ala Asn Leu Asn Gly Gly Glu Arg Leu
            755                 760                 765

Val Ser Tyr Pro Tyr Asp Met Ala Arg Thr Pro Thr Gln Glu Gln Leu
770                 775                 780

Leu Ala Ala Ala Met Ala Ala Arg Gly Glu Asp Glu Asp Glu Val
785                 790                 795                 800

Ser Glu Ala Gln Glu Thr Pro Asp His Ala Ile Phe Arg Trp Leu Ala
                805                 810                 815
```

Ile Ser Phe Ala Ser Ala His Leu Thr Leu Thr Glu Pro Tyr Arg Gly
            820                 825                 830

Gly Cys Gln Ala Gln Asp Tyr Thr Gly Gly Met Gly Ile Val Asn Gly
            835                 840                 845

Ala Lys Trp Asn Pro Arg Thr Gly Thr Ile Asn Asp Phe Ser Tyr Leu
            850                 855                 860

His Thr Asn Cys Leu Glu Leu Ser Phe Tyr Leu Gly Cys Asp Lys Phe
865                 870                 875                 880

Pro His Glu Ser Glu Leu Pro Arg Glu Trp Asn Asn Lys Glu Ala
            885                 890                 895

Leu Leu Thr Phe Met Glu Gln Val His Arg Gly Ile Lys Gly Val Val
            900                 905                 910

Thr Asp Glu Gln Gly Ile Pro Ile Ala Asn Ala Thr Ile Ser Val Ser
            915                 920                 925

Gly Ile Asn His Gly Val Lys Thr Ala Ser Gly Gly Asp Tyr Trp Arg
            930                 935                 940

Ile Leu Asn Pro Gly Glu Tyr Arg Val Thr Ala His Ala Glu Gly Tyr
945                 950                 955                 960

Thr Pro Ser Ala Lys Thr Cys Asn Val Asp Tyr Asp Ile Gly Ala Thr
            965                 970                 975

Gln Cys Asn Phe Ile Leu Ala Arg Ser Asn Trp Lys Arg Ile Arg Glu
            980                 985                 990

Ile Met Ala Met Asn Gly Asn Arg Pro Ile Pro His Ile Asp Pro Ser
            995                 1000                1005

Arg Pro Met Thr Pro Gln Gln Arg Arg Leu Gln Gln Arg Arg Leu
            1010                1015                1020

Gln His Arg Leu Arg Leu Arg Ala Gln Met Arg Leu Arg Arg Leu
            1025                1030                1035

Asn Ala Thr Thr Thr Leu Gly Pro His Thr Val Pro Pro Thr Leu
            1040                1045                1050

Pro Pro Ala Pro Ala Thr Thr Leu Ser Thr Thr Ile Glu Pro Trp
            1055                1060                1065

Gly Leu Ile Pro Pro Thr Thr Ala Gly Trp Glu Glu Ser Glu Thr
            1070                1075                1080

Glu Thr Tyr Thr Glu Val Val Thr Glu Phe Gly Thr Glu Val Glu
            1085                1090                1095

Pro Glu Phe Gly Thr Lys Val Glu Pro Glu Phe Glu Thr Gln Leu
            1100                1105                1110

Glu Pro Glu Phe Glu Thr Gln Leu Glu Pro Glu Phe Glu Glu Glu
            1115                1120                1125

Glu Glu Glu Glu Lys Glu Glu Ile Ala Thr Gly Gln Ala Phe
            1130                1135                1140

Pro Phe Thr Thr Val Glu Thr Tyr Thr Val Asn Phe Gly Asp Phe
            1145                1150                1155

<210> SEQ ID NO 2
<211> LENGTH: 4102
<212> TYPE: DNA
<213> ORGANISM: Homo sapiens

<400> SEQUENCE: 2
cggctatccg cgcgggagtg cgccacgcgg ggccggagcg cctattagcc gccaggacct      60
cggagcgccc cgaccacccc tgagcccctc tggcttcgga gccccccagc acccttccc     120 gggtcccctc gcccacccta atccactctc cctcccttc ccggattccc tcgctcaccc     180

```
catcctctct cccgcccctt cctggattcc ctcacccgtc tcgatccct ctccgcccttt     240
tcccagagac ccagagcccc tgaccccccg cgccctcccc ggagcccccc gcgcgtgccg     300
cggccatggc ggccgtgcgc ggggcgcccc tgctcagctg cctcctggcg ttgctggccc     360
tgtgccctgg agggcgcccg cagacggtgc tgaccgacga cgagatcgag gagttcctcg     420
agggcttcct gtcagagcta gaacctgagc cccggggagga cgacgtggag gccccgccgc     480
ctcccgagcc caccccgcgg gtccgaaaag cccaggcggg gggcaagcca gggaagcggc     540
cagggacggc cgcagaagtg cctccggaaa agaccaaaga caaagggaag aaaggcaaga     600
aagacaaagg cccaaggtg cccaaggagt ccttggaggg gtcccccagg ccgcccaaga     660
aggggaagga gaagccaccc aaggccacca agaagcccaa ggagaagcca cctaaggcca     720
ccaagaagcc caaggagaag ccacccaagg ccaccaagaa gcccaaagag aagccacca     780
aggccaccaa gaagcccccg tcagggaaga ggccccccat tctggctccc tcagaaaccc     840
tggagtggcc actgccccca cccccagcc ctggccccga ggagctaccc caggagggag     900
gggcgcccct ctcaaataac tggcagaatc caggagagga gacccatgtg gaggcacggg     960
agcaccagcc tgagccggag gaggagaccg agcaacccac actggactac aatgaccaga    1020
tcgagaggga ggactatgag gactttgagt acattcggcg ccagaagcaa cccaggccac    1080
ccccaagcag aaggaggagg cccgagcggg tctggccaga gccccctgag gagaaggccc    1140
cggccccagc cccggaggag aggattgagc ctcctgtgaa gcctctgctg ccccgctgc    1200
cccctgacta tggtgatggt tacgtgatcc caactacga tgacatggac tattactttg    1260
ggcctcctcc gccccagaag cccgatgctg agcgccagac agacgaagag aaggaggagc    1320
tgaagaaacc caaaaaggag gacagcagcc caaggaggag gaccgacaag tgggcagtgg    1380
agaagggcaa ggaccacaaa gagccccgaa agggcgagga gttggaggag gagtggacgc    1440
ctacggagaa agtcaagtgt cccccccattg ggatggagtc acaccgtatt gaggacaacc    1500
agatccgagc ctcctccatg ctgcgccacg gcctgggggc acagcgcggc cggctcaaca    1560
tgcagaccgg tgccactgag gacgactact atgatggtgc gtggtgtgcc gaggacgatg    1620
ccaggaccca gtggatagag gtggacacca ggaggactac ccggttcaca ggcgtcatca    1680
cccaggggcag agactccagc atccatgacg attttgtgac caccttcttc gtgggcttca    1740
gcaatgacag ccagacatgg gtgatgtaca ccaacggcta tgaggaaatg acctttcatg    1800
ggaacgtgga caaggacaca cccgtgctga gtgagctccc agagccggtg gtggctcgtt    1860
tcatccgcat ctacccactc acctggaatg gcagcctgtg catgcgcctg gaggtgctgg    1920
ggtgctctgt ggcccctgtc tacagctact acgcacagaa tgaggtggtg gccaccgatg    1980
acctggattt ccggcaccac agctacaagg acatgcgcca gctcatgaag gtggtgaacg    2040
aggagtgccc caccatcacc cgcacttaca gcctgggcaa gagctcacga ggcctcaaga    2100
tctatgccat ggagatctca gacaacccctg gggagcatga actgggggag cccgagttcc    2160
gctacactgc tgggatccat ggcaacgagg tgctgggccg agagctgttg ctgctgctca    2220
tgcagtacct gtgccgagag taccgcgatg ggaacccacg tgtgcgcagc ctggtgcagg    2280
acacacgcat ccacctggtg ccctcactga acctgatgg ctacgaggtg cagcgcagga    2340
tgggctcaga gtttgggaac tgggcgctgg gactgtggac tgaggagggc tttgacatct    2400
ttgaagattt cccggatctc aactctgtgc tctgggagc tgaggagagg aaatgggtcc    2460
cctaccgggt ccccaacaat aacttgccca tccctgaacg ctacctttcg ccagatgcca    2520
```

```
cggtatccac ggaggtccgg gccatcattg cctggatgga gaagaacccc ttcgtgctgg    2580
gagcaaatct gaacggcggc gagcggctag tatcctaccc ctacgatatg cccgcacgc     2640 ctacccagga gcagctgctg ccgcagcca tggcagcagc ccggggggag gatgaggacg     2700
aggtctccga ggcccaggag actccagacc acgccatctt ccggtggctt gccatctcct   2760
tcgcctccgc acacctcacc ttgaccgagc cctaccgcgg aggctgccaa gcccaggact   2820
acaccggcgg catgggcatc gtcaacgggg ccaagtggaa ccccggacc gggactatca    2880 atgacttcag ttacctgcat accaactgcc tggagctctc cttctacctg gctgtgaca    2940 agttccctca tgagagtgag ctgccccgcg agtgggagaa caacaaggag cgctgctca    3000 ccttcatgga gcaggtgcac cgcggcatta agggggtggt gacggacgag caaggcatcc   3060
ccattgccaa cgccaccatc tctgtgagtg gcattaatca cggcgtgaag acagccagtg   3120
gtggtgatta ctggcgaatc ttgaacccgg gtgagtaccg cgtgacagcc cacgcggagg   3180
gctacacccc gagcgccaag acctgcaatg ttgactatga catcggggcc actcagtgca   3240
acttcatcct ggctcgctcc aactggaagc gcatccggga gatcatggcc atgaacggga   3300
accggcctat cccacacata gacccatcgc gccctatgac ccccaacag cgacgcctgc    3360 agcagcgacg cctacaacac cgcctgcggc ttcgggcaca gatgcggctg cggcgcctca   3420
acgccaccac caccctaggc ccccacactg tgcctcccac gctgccccct gcccctgcca   3480
ccaccctgag cactaccata gagccctggg gcctcatacc gccaaccacc gctggctggg   3540
aggagtcgga gactgagacc tacacagagg tggtgacaga gtttgggacc gaggtggagc   3600
ccgagtttgg gaccaaggtg gagcccgagt ttgagaccca gttggagcct gagtttgaga   3660
cccagctgga acccgagttt gaggaagagg aggaggagga gaaagaggag gagatagcca   3720
ctggccaggc attccccttc acaacagtag agacctacac agtgaacttt ggggacttct   3780
gagatcagcg tcctaccaag accccagccc aactcaagct acagcagcag cacttcccaa   3840
gcctgctgac cacagtcaca tcacccatca gcacatggaa ggcccctggt atggacactg   3900
aaaggaaggg ctggtcctgc cccttgagg gggtgcaaac atgactggga cctaagagcc    3960
agaggctgtg tagaggctcc tgctccacct gccagtctcg taagagatgg ggttgctgca   4020
gtgttggagt aggggcagag ggagggagcc aaggtcactc caataaaaca agctcatggc   4080
acggacaaaa aaaaaaaaaa aa                                            4102

<210> SEQ ID NO 3
<211> LENGTH: 11
<212> TYPE: PRT
<213> ORGANISM: Homo sapiens

<400> SEQUENCE: 3

Lys Glu Lys Pro Pro Lys Ala Thr Lys Lys Pro
1               5                   10

<210> SEQ ID NO 4
<211> LENGTH: 44
<212> TYPE: PRT
<213> ORGANISM: Homo sapiens

<400> SEQUENCE: 4

Lys Glu Lys Pro Pro Lys Ala Thr Lys Lys Pro Lys Glu Lys Pro Pro
1               5                   10                  15

Lys Ala Thr Lys Lys Pro Lys Glu Lys Pro Pro Lys Ala Thr Lys Lys
                20                  25                  30
```

Pro Lys Glu Lys Pro Pro Lys Ala Thr Lys Lys Pro
         35                  40

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Glu Lys Pro Pro Lys Ala Thr Lys Arg Pro
1               5                  10

<210> SEQ ID NO 6
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Thr Lys Lys Pro Lys Glu Lys Pro Pro Lys Ala Thr Lys Lys Pro Lys
1               5                  10                  15

Glu Lys Pro Pro Lys Ala Thr Lys Lys Pro Lys Glu Lys Pro Pro Lys
            20                  25                  30

Ala Thr Lys Lys Pro Lys Glu Lys Pro Pro Lys Ala
         35                  40

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggcucaagau cuacgcaau                                                19

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Lys Lys Pro Lys Glu Lys Pro Pro Lys Ala Thr Lys Lys Pro Lys
1               5                  10                  15

Glu Lys Pro Pro Lys Ala
            20

<210> SEQ ID NO 9
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Lys Glu Lys Pro Pro Lys Ala Thr Lys Pro Lys Glu Lys Pro Pro
1               5                   10                  15

Lys Ala Thr Lys Lys Pro Lys Glu Lys Pro Pro Lys Ala Thr Lys Lys
            20                  25                  30

Pro Lys Glu Lys Pro Pro Lys Ala Ser Lys Lys
            35                  40
```

<210> SEQ ID NO 10
<211> LENGTH: 357
<212> TYPE: PRT
<213> ORGANISM: Homo sapiens

<400> SEQUENCE: 10

```
Pro Gln Thr Val Leu Thr Asp Asp Glu Ile Glu Glu Phe Leu Glu Gly
1               5                   10                  15

Phe Leu Ser Glu Leu Glu Pro Glu Pro Arg Glu Asp Asp Val Glu Ala
            20                  25                  30

Pro Pro Pro Pro Glu Pro Thr Pro Arg Val Arg Lys Ala Gln Gly Gly
            35                  40                  45

Lys Pro Gly Lys Arg Pro Gly Thr Ala Ala Glu Val Pro Pro Glu Lys
50                  55                  60

Thr Lys Asp Lys Gly Lys Lys Gly Lys Asp Lys Gly Pro Lys Val
65                  70                  75                  80

Pro Lys Glu Ser Leu Glu Gly Ser Pro Arg Pro Pro Lys Lys Gly Lys
                85                  90                  95

Glu Lys Pro Pro Lys Ala Thr Lys Lys Pro Lys Glu Lys Pro Pro Lys
            100                 105                 110

Ala Thr Lys Lys Pro Lys Glu Lys Pro Pro Lys Ala Thr Lys Lys Pro
            115                 120                 125

Lys Glu Lys Pro Pro Lys Ala Thr Lys Lys Pro Pro Ser Gly Lys Arg
            130                 135                 140

Pro Pro Ile Leu Ala Pro Ser Glu Thr Leu Glu Trp Pro Leu Pro Pro
145                 150                 155                 160

Pro Pro Ser Pro Gly Pro Glu Glu Leu Pro Gln Glu Gly Gly Ala Pro
                165                 170                 175

Leu Ser Asn Asn Trp Gln Asn Pro Gly Glu Glu Thr His Val Glu Ala
            180                 185                 190

Arg Glu His Gln Pro Glu Pro Glu Glu Glu Thr Glu Gln Pro Thr Leu
            195                 200                 205

Asp Tyr Asn Asp Gln Ile Glu Arg Glu Asp Tyr Glu Asp Phe Glu Tyr
            210                 215                 220

Ile Arg Arg Gln Lys Gln Pro Arg Pro Pro Ser Arg Arg Arg
225                 230                 235                 240

Pro Glu Arg Val Trp Pro Glu Pro Glu Glu Lys Ala Pro Ala Pro
                245                 250                 255

Ala Pro Glu Glu Arg Ile Glu Pro Val Lys Pro Leu Leu Pro Pro
            260                 265                 270

Leu Pro Pro Asp Tyr Gly Asp Gly Tyr Val Ile Pro Asn Tyr Asp Asp
            275                 280                 285

Met Asp Tyr Tyr Phe Gly Pro Pro Pro Lys Pro Asp Ala Glu
            290                 295                 300

Arg Gln Thr Asp Glu Glu Lys Glu Glu Leu Lys Lys Pro Lys Lys Glu
305                 310                 315                 320
```

```
Asp Ser Ser Pro Lys Glu Glu Thr Asp Lys Trp Ala Val Glu Lys Gly
                325                 330                 335

Lys Asp His Lys Glu Pro Arg Lys Gly Glu Leu Glu Glu Trp
            340                 345                 350

Thr Pro Thr Glu Lys
        355

<210> SEQ ID NO 11
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Cys Pro Pro Ile Gly Met Glu Ser His Arg Ile Glu Asp Asn Gln Ile
1               5                   10                  15

Arg Ala Ser Ser Met Leu Arg His Gly Leu Gly Ala Gln Arg Gly Arg
            20                  25                  30

Leu Asn Met Gln Thr Gly Ala Thr Glu Asp Asp Tyr Tyr Asp Gly Ala
        35                  40                  45

Trp Cys Ala Glu Asp Ala Arg Thr Gln Trp Ile Glu Val Asp Thr
    50                  55                  60

Arg Arg Thr Thr Arg Phe Thr Gly Val Ile Thr Gln Gly Arg Asp Ser
65                  70                  75                  80

Ser Ile His Asp Asp Phe Val Thr Thr Phe Phe Val Gly Phe Ser Asn
                85                  90                  95

Asp Ser Gln Thr Trp Val Met Tyr Thr Asn Gly Tyr Glu Glu Met Thr
            100                 105                 110

Phe His Gly Asn Val Asp Lys Asp Thr Pro Val Leu Ser Glu Leu Pro
        115                 120                 125

Glu Pro Val Val Ala Arg Phe Ile Arg Ile Tyr Pro Leu Thr Trp Asn
    130                 135                 140

Gly Ser Leu Cys Met Arg Leu Glu Val Leu Gly Cys
145                 150                 155

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Leu Arg His Gly Leu Gly
1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Thr Gly Ala Thr Glu Asp Asp Tyr Tyr Asp Gly Ala
1               5                   10
```

```
<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ala Arg Thr Gln
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Asp Ser Ser Ile His Asp Asp
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Leu Arg His Gly Leu Gly Ala
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Leu Arg His Gly Leu Gly Ala Gln
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Met Leu Arg His Gly Leu Gly
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 19

Ser Ser Met Leu Arg His Gly Leu Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Met Leu Arg His Gly Leu Gly Ala
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Met Leu Arg His Gly Leu Gly Ala Gln
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ser Met Leu Arg His Gly Leu Gly Ala
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ser Met Leu Arg His Gly Leu Gly Ala Gln
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Thr Gly Ala Thr Glu Asp Asp Tyr Tyr Asp Gly Ala Trp
1               5                   10

<210> SEQ ID NO 25
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 25

Gln Thr Gly Ala Thr Glu Asp Asp Tyr Tyr Asp Gly Ala Trp Cys
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Gln Thr Gly Ala Thr Glu Asp Asp Tyr Tyr Asp Gly Ala
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Met Gln Thr Gly Ala Thr Glu Asp Asp Tyr Tyr Asp Gly Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Gln Thr Gly Ala Thr Glu Asp Asp Tyr Tyr Asp Gly Ala Trp
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Gln Thr Gly Ala Thr Glu Asp Asp Tyr Tyr Asp Gly Ala Trp Cys
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Met Gln Thr Gly Ala Thr Glu Asp Asp Tyr Tyr Asp Gly Ala Trp
1               5                   10                  15
```

```
<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Met Gln Thr Gly Ala Thr Glu Asp Asp Tyr Tyr Asp Gly Ala Trp
1               5                   10                  15

Cys

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Ala Arg Thr Gln Trp
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Ala Arg Thr Gln Trp Ile
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Asp Ala Arg Thr Gln
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Asp Asp Ala Arg Thr Gln
1               5

<210> SEQ ID NO 36
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 36

Asp Asp Ala Arg Thr Gln Trp
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Asp Ala Arg Thr Gln Trp Ile
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Asp Asp Ala Arg Thr Gln Trp
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Asp Asp Ala Arg Thr Gln Trp Ile
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Asp Ser Ser Ile His Asp Asp Phe
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Asp Ser Ser Ile His Asp Asp Phe Val
1               5                   10
```

```
<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Arg Asp Ser Ser Ile His Asp Asp
1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gly Arg Asp Ser Ser Ile His Asp Asp
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Arg Asp Ser Ser Ile His Asp Asp Phe
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Arg Asp Ser Ser Ile His Asp Asp Phe Val
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gly Arg Asp Ser Ser Ile His Asp Asp Phe
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Gln Gly Arg Asp Ser Ser Ile His Asp Phe Val
1               5                   10

<210> SEQ ID NO 48
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Glu Leu Val Pro Arg Gly Ser Gly Asp Pro Ile Glu Gly Arg Gly
1               5                   10                  15

Gly Gly Gly Gly Asp Pro Lys Ser Cys Asp Lys Pro His Thr Cys Pro
                20                  25                  30

Leu Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Ala Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Lys Lys Pro Lys Glu Lys Pro Pro Lys Ala
1               5                   10
```

```
<210> SEQ ID NO 50
<211> LENGTH: 1170
<212> TYPE: PRT
<213> ORGANISM: Macaca fascicularis

<400> SEQUENCE: 50

Met Ala Ala Val Arg Gly Ala Pro Leu Leu Gly Cys Leu Leu Ala Leu
1               5                   10                  15

Leu Ala Leu Cys Pro Gly Gly Arg Pro Gln Thr Val Leu Thr Asp Asp
                20                  25                  30

Glu Ile Glu Glu Phe Leu Glu Gly Phe Leu Ser Glu Leu Gly Pro Glu
            35                  40                  45

Pro Arg Glu Asp Asp Met Glu Ala Pro Pro Pro Glu Pro Thr Pro
    50                  55                  60

Arg Val Arg Lys Ala Gln Ala Gly Gly Lys Pro Gly Ala Arg Pro Gly
65                  70                  75                  80

Ala Ala Ala Glu Val Pro Pro Glu Lys Thr Lys Asp Lys Gly Lys Lys
                85                  90                  95

Gly Lys Lys Asp Lys Gly Pro Lys Val Pro Lys Glu Ser Leu Glu Gly
                100                 105                 110

Ser Pro Lys Pro Pro Lys Lys Gly Lys Glu Lys Pro Pro Lys Ala Thr
            115                 120                 125

Lys Lys Pro Lys Glu Lys Pro Pro Lys Ala Thr Lys Lys Pro Lys Glu
            130                 135                 140

Lys Pro Pro Lys Ala Thr Lys Lys Pro Lys Glu Lys Pro Pro Lys Ala
145                 150                 155                 160

Thr Lys Lys Pro Pro Ser Gly Lys Arg Pro Pro Thr Leu Ala Pro Ser
                165                 170                 175

Glu Thr Leu Glu Trp Pro Leu Pro Pro Pro Ser Pro Gly Pro Glu
            180                 185                 190

Glu Leu Pro Gln Glu Gly Gly Gly Pro Leu Pro Asn Asn Trp Gln Asn
            195                 200                 205

Pro Gly Glu Glu Thr Arg Val Glu Ala Arg Glu His Gln Pro Glu Pro
    210                 215                 220

Glu Glu Glu Thr Glu Leu Pro Thr Leu Asp Tyr Asn Asp Gln Ile Glu
225                 230                 235                 240

Arg Glu Asp Tyr Glu Asp Phe Glu Tyr Ile Arg Arg Gln Lys Gln Pro
                245                 250                 255

Arg Pro Pro Pro Ser Arg Arg Arg Pro Glu Arg Val Trp Pro Glu
                260                 265                 270

Pro Pro Glu Glu Lys Ala Pro Ala Pro Ala Pro Glu Glu Arg
            275                 280                 285

Ile Glu Pro Pro Val Lys Pro Leu Leu Pro Leu Pro Pro Asp Tyr
                290                 295                 300

Gly Asp Gly Tyr Val Ile Pro Asn Tyr Asp Asp Met Asp Tyr Tyr Phe
305                 310                 315                 320

Gly Pro Pro Pro Pro Gln Lys Pro Asp Ala Glu Arg Gln Thr Asp Glu
                325                 330                 335

Glu Lys Glu Glu Leu Lys Lys Pro Lys Lys Glu Asp Gly Arg Pro Lys
                340                 345                 350

Glu Glu Thr Asp Lys Trp Ala Val Glu Lys Gly Lys Asp His Lys Glu
            355                 360                 365

Pro Arg Lys Gly Glu Glu Val Glu Glu Glu Trp Thr Pro Thr Glu Lys
            370                 375                 380
```

```
Val Lys Cys Pro Pro Ile Gly Met Glu Ser His Arg Ile Glu Asp Asn
385                 390                 395                 400

Gln Ile Arg Ala Ser Ser Met Leu Arg His Gly Leu Gly Ala Gln Arg
            405                 410                 415

Gly Arg Leu Asn Met Gln Ala Gly Ala Thr Glu Asp Asp Tyr Tyr Asp
        420                 425                 430

Gly Ala Trp Cys Ala Glu Asp Ala Arg Thr Gln Trp Ile Glu Val
            435                 440                 445

Asp Thr Arg Arg Thr Thr Arg Phe Thr Gly Val Ile Thr Gln Gly Arg
    450                 455                 460

Asp Ser Ser Ile His Asp Asp Phe Val Thr Thr Phe Phe Val Gly Phe
465                 470                 475                 480

Ser Asn Asp Ser Gln Thr Trp Val Met Tyr Thr Asn Gly Tyr Glu Glu
                485                 490                 495

Met Thr Phe His Gly Asn Val Asp Lys Asp Thr Pro Val Leu Ser Glu
                500                 505                 510

Leu Pro Glu Pro Val Val Ala Arg Phe Ile Arg Ile Tyr Pro Leu Thr
        515                 520                 525

Trp Asn Gly Ser Leu Cys Met Arg Leu Glu Val Leu Gly Cys Pro Val
    530                 535                 540

Ala Pro Val Tyr Ser Tyr Tyr Ala Gln Asn Glu Val Val Ala Thr Asp
545                 550                 555                 560

Asp Leu Asp Phe Arg His His Ser Tyr Lys Asp Met Arg Gln Leu Met
                565                 570                 575

Lys Val Val Asn Glu Glu Cys Pro Thr Ile Thr Arg Thr Tyr Ser Leu
                580                 585                 590

Gly Lys Ser Ser Arg Gly Leu Lys Ile Tyr Ala Met Glu Ile Ser Asp
            595                 600                 605

Asn Pro Gly Glu His Glu Leu Gly Glu Pro Glu Phe Arg Tyr Thr Ala
            610                 615                 620

Gly Ile His Gly Asn Glu Val Leu Gly Arg Glu Leu Leu Leu Leu Leu
625                 630                 635                 640

Met Gln Tyr Leu Cys Arg Glu Tyr Arg Asp Gly Asn Pro Arg Val Arg
                645                 650                 655

Ser Leu Val Gln Asp Thr Arg Ile His Leu Val Pro Ser Leu Asn Pro
                660                 665                 670

Asp Gly Tyr Glu Val Ala Ala Gln Met Gly Ser Glu Phe Gly Asn Trp
            675                 680                 685

Ala Leu Gly Leu Trp Thr Glu Glu Gly Phe Asp Ile Phe Glu Asp Phe
            690                 695                 700

Pro Asp Leu Asn Ser Val Leu Trp Gly Ala Glu Glu Arg Lys Trp Val
705                 710                 715                 720

Pro Tyr Arg Val Pro Asn Asn Asn Leu Pro Ile Pro Glu Arg Tyr Leu
                725                 730                 735

Ser Pro Asp Ala Thr Val Ser Thr Glu Val Arg Ala Ile Ile Ala Trp
            740                 745                 750

Met Glu Lys Asn Pro Phe Val Leu Gly Ala Asn Leu Asn Gly Gly Glu
            755                 760                 765

Arg Leu Val Ser Tyr Pro Tyr Asp Met Thr Arg Thr Pro Thr Gln Glu
        770                 775                 780

Gln Leu Leu Ala Ala Ala Met Ala Ala Ala Arg Gly Glu Asp Glu Asp
785                 790                 795                 800
```

```
Glu Val Ser Glu Ala Gln Glu Thr Pro Asp His Ala Ile Phe Arg Trp
            805                 810                 815

Leu Ala Ile Ser Phe Ala Ser Ala His Leu Thr Leu Thr Glu Pro Tyr
            820                 825                 830

Arg Gly Gly Cys Gln Ala Gln Asp Tyr Thr Gly Gly Met Gly Ile Val
            835                 840                 845

Asn Gly Ala Lys Trp Asn Pro Arg Ser Gly Thr Ile Asn Asp Phe Ser
            850                 855                 860

Tyr Leu His Thr Asn Cys Leu Glu Leu Ser Phe Tyr Leu Gly Cys Asp
865                 870                 875                 880

Lys Phe Pro His Glu Ser Glu Leu Pro Arg Glu Trp Glu Asn Asn Lys
                885                 890                 895

Glu Ala Leu Leu Thr Phe Met Glu Gln Val His Arg Gly Ile Lys Gly
            900                 905                 910

Val Val Thr Asp Glu Gln Gly Ile Pro Ile Ala Asn Ala Thr Ile Ser
            915                 920                 925

Val Ser Gly Ile Asn His Gly Val Lys Thr Ala Ser Gly Gly Asp Tyr
            930                 935                 940

Trp Arg Ile Leu Asn Pro Gly Glu Tyr Arg Val Thr Ala His Ala Glu
945                 950                 955                 960

Gly Tyr Thr Pro Ser Ala Lys Thr Cys Asn Val Asp Tyr Asp Ile Gly
                965                 970                 975

Ala Thr Gln Cys Asn Phe Ile Leu Ala Arg Ser Asn Trp Lys Arg Ile
            980                 985                 990

Arg Glu Ile Met Ala Met Asn Gly Asn Arg Pro Ile Pro His Ile Asp
            995                 1000                1005

Pro Ser Arg Pro Met Thr Pro Gln Gln Arg Arg Leu Gln Gln Arg
        1010                1015                1020

Arg Leu Gln His Arg Leu Arg Leu Arg Ala Gln Met Arg Leu Arg
        1025                1030                1035

Arg Leu Asn Ala Thr Thr Thr Leu Gly Pro His Thr Val Pro Ser
        1040                1045                1050

Thr Leu Pro Pro Ala Pro Ala Thr Thr Leu Ser Thr Thr Ile Glu
        1055                1060                1065

Pro Trp Gly Leu Val Pro Pro Thr Thr Ala Gly Trp Glu Glu Ser
        1070                1075                1080

Glu Thr Glu Thr Tyr Thr Glu Val Val Thr Glu Phe Gly Thr Glu
        1085                1090                1095

Val Glu Pro Glu Phe Gly Thr Lys Val Glu Pro Glu Phe Glu Thr
        1100                1105                1110

Gln Leu Glu Thr Glu Phe Glu Thr Gln Leu Glu Pro Glu Phe Glu
        1115                1120                1125

Thr Gln Leu Glu Pro Glu Phe Glu Glu Glu Glu Glu Glu Glu Glu
        1130                1135                1140

Glu Glu Glu Glu Glu Ile Ala Thr Gly Gln Ala Phe Pro Phe Thr
        1145                1150                1155

Thr Val Glu Thr Tyr Thr Val Asn Phe Gly Asp Phe
        1160                1165                1170

<210> SEQ ID NO 51
<211> LENGTH: 1128
<212> TYPE: PRT
<213> ORGANISM: Rattus norvegicus
```

<400> SEQUENCE: 51

```
Met Ala Ala Val Arg Thr Ala Ser Leu Leu Cys Gly Leu Leu Ala Leu
1               5                   10                  15

Leu Ala Leu Cys Pro Glu Gly Ser Pro Gln Thr Val Leu Thr Asp Asp
            20                  25                  30

Glu Ile Gln Glu Phe Leu Glu Gly Phe Leu Ser Glu Phe Glu Thr Gln
        35                  40                  45

Ser Pro Pro Arg Glu Asp Asp Val Glu Ala Gln Leu Pro Glu Pro
    50                  55                  60

Thr Gln Arg Ala Arg Lys Ser Lys Ala Gly Gly Lys Pro Arg Ala Asp
65                  70                  75                  80

Ala Glu Ala Pro Pro Glu Lys Asn Lys Asp Lys Glu Lys Lys Gly Lys
                85                  90                  95

Lys Asp Lys Gly Pro Lys Ala Ala Lys His Leu Glu Gly Ser Thr Arg
            100                 105                 110

Pro Thr Lys Lys Pro Lys Glu Lys Pro Pro Lys Ala Thr Lys Lys Pro
        115                 120                 125

Lys Glu Lys Pro Pro Lys Ala Thr Lys Lys Pro Lys Glu Lys Pro Pro
130                 135                 140

Lys Ala Thr Lys Lys Pro Lys Glu Lys Pro Pro Lys Ala Thr Lys Arg
145                 150                 155                 160

Pro Ser Ala Gly Lys Arg Phe Ser Thr Val Ala Pro Leu Glu Thr Pro
                165                 170                 175

Glu Arg Ser Leu Thr Ser Pro Ser Asn Pro Gly Thr Arg Glu Leu Pro
            180                 185                 190

Glu Glu Arg Gly Arg Thr Ser Leu Asn Thr Trp Gln Gly Gln Gly Glu
        195                 200                 205

Glu Thr Gln Val Glu Ala Arg Gln His Arg Pro Glu Pro Glu Glu Glu
        210                 215                 220

Thr Glu Met Pro Thr Leu Asp Tyr Asn Asp Gln Ile Glu Arg Glu Asp
225                 230                 235                 240

Tyr Glu Asp Phe Glu Tyr Ile Arg Arg Gln Lys Gln Pro Arg Pro Thr
                245                 250                 255

Pro Ser Arg Lys Arg Ile Trp Pro Glu Pro Glu Glu Lys Thr Gln
            260                 265                 270

Glu Pro Glu Glu Arg Lys Glu Val Asp Pro Pro Leu Lys Pro Leu Leu
        275                 280                 285

Pro Pro Asp Tyr Gly Asp Gly Tyr Leu Ile Pro Asn Tyr Asp Asp Leu
290                 295                 300

Asp Tyr Tyr Phe Pro His Pro Pro Gln Lys Pro Asp Val Gly Gln
305                 310                 315                 320

Glu Val Asp Glu Glu Lys Glu Glu Leu Lys Lys Pro Lys Lys Glu Gly
                325                 330                 335

Ser Ser Pro Lys Glu Asp Thr Glu Asp Lys Trp Ala Ala Glu Lys Asn
            340                 345                 350

Lys Asp His Lys Ala Gly Pro Arg Lys Gly Glu Glu Leu Glu Glu Glu
        355                 360                 365

Trp Gly Pro Val Glu Lys Ile Lys Cys Pro Pro Ile Gly Met Glu Ser
        370                 375                 380

His Arg Ile Glu Asp Asn Gln Ile Arg Ala Ser Ser Met Leu Arg His
385                 390                 395                 400
```

```
Gly Leu Gly Ala Gln Arg Gly Arg Leu Asn Met Gln Ala Gly Ala Asn
                405                 410                 415

Glu Asp Asp Tyr Tyr Asp Gly Ala Trp Cys Ala Glu Asp Glu Ser Gln
            420                 425                 430

Thr Gln Trp Ile Glu Val Asp Thr Arg Thr Thr Arg Phe Thr Gly
        435                 440                 445

Val Ile Thr Gln Gly Arg Asp Ser Ser Ile His Asp Asp Phe Val Thr
    450                 455                 460

Thr Phe Phe Val Gly Phe Ser Asn Asp Ser Gln Thr Trp Val Met Tyr
465                 470                 475                 480

Thr Asn Gly Tyr Glu Glu Met Thr Phe His Gly Asn Val Asp Lys Asp
                485                 490                 495

Thr Pro Val Leu Ser Glu Leu Pro Glu Pro Val Val Ala Arg Phe Ile
            500                 505                 510

Arg Ile Tyr Pro Leu Thr Trp Asn Gly Ser Leu Cys Met Arg Leu Glu
        515                 520                 525

Val Leu Gly Cys Pro Val Thr Pro Val Tyr Ser Tyr Tyr Ala Gln Asn
    530                 535                 540

Glu Val Val Thr Thr Asp Ser Leu Asp Phe Arg His His Ser Tyr Lys
545                 550                 555                 560

Asp Met Arg Gln Leu Met Lys Val Val Asn Glu Glu Cys Pro Thr Ile
                565                 570                 575

Thr Arg Thr Tyr Ser Leu Gly Lys Ser Ser Arg Gly Leu Lys Ile Tyr
            580                 585                 590

Ala Met Glu Ile Ser Asp Asn Pro Gly Glu His Glu Leu Gly Glu Pro
        595                 600                 605

Glu Phe Arg Tyr Thr Ala Gly Met His Gly Asn Glu Val Leu Gly Arg
    610                 615                 620

Glu Leu Leu Leu Leu Leu Met Gln Tyr Leu Cys His Glu Tyr Arg Asp
625                 630                 635                 640

Gly Asn Pro Arg Val Arg Asn Leu Val Gln Asp Thr Arg Ile His Leu
                645                 650                 655

Val Pro Ser Leu Asn Pro Asp Gly Tyr Glu Val Ala Ala Gln Met Gly
            660                 665                 670

Ser Glu Phe Gly Asn Trp Ala Leu Gly Leu Trp Thr Glu Glu Gly Phe
        675                 680                 685

Asp Ile Phe Glu Asp Phe Pro Asp Leu Asn Ser Val Leu Trp Ala Ala
    690                 695                 700

Glu Glu Lys Lys Trp Val Pro Tyr Arg Val Pro Asn Asn Asn Leu Pro
705                 710                 715                 720

Ile Pro Glu Arg Tyr Leu Ser Pro Asp Ala Thr Val Ser Thr Glu Val
                725                 730                 735

Arg Ala Ile Ile Ser Trp Met Glu Lys Asn Pro Phe Val Leu Gly Ala
            740                 745                 750

Asn Leu Asn Gly Gly Glu Arg Leu Val Ser Tyr Pro Tyr Asp Met Ala
        755                 760                 765

Arg Thr Pro Ser Gln Glu Gln Leu Leu Ala Ala Ala Leu Ala Ala Ala
    770                 775                 780

Arg Gly Glu Asp Glu Asp Glu Val Ser Glu Ala Gln Glu Thr Pro Asp
785                 790                 795                 800

His Ala Ile Phe Arg Trp Leu Ala Ile Ser Phe Ala Ser Ala His Leu
                805                 810                 815
```

-continued

```
Thr Met Thr Glu Pro Tyr Arg Gly Gly Cys Gln Ala Gln Asp Tyr Thr
                820                 825                 830

Ser Gly Met Gly Ile Val Asn Gly Ala Lys Trp Asn Pro Arg Ser Gly
            835                 840                 845

Thr Phe Asn Asp Phe Ser Tyr Leu His Thr Asn Cys Leu Glu Leu Ser
        850                 855                 860

Ile Tyr Leu Gly Cys Asp Lys Phe Pro His Glu Ser Glu Leu Pro Arg
865                 870                 875                 880

Glu Trp Glu Asn Asn Lys Glu Ala Leu Leu Thr Phe Met Glu Gln Val
                885                 890                 895

His Arg Gly Ile Lys Gly Val Val Thr Asp Glu Gln Gly Ile Pro Ile
            900                 905                 910

Ala Asn Ala Thr Ile Ser Val Ser Gly Ile Asn His Gly Val Lys Thr
        915                 920                 925

Ala Ser Gly Gly Asp Tyr Trp Arg Ile Leu Asn Pro Gly Glu Tyr Arg
    930                 935                 940

Val Thr Ala His Ala Glu Gly Tyr Thr Ser Ala Lys Ile Cys Asn
945                 950                 955                 960

Val Asp Tyr Asp Ile Gly Ala Thr Gln Cys Asn Phe Ile Leu Ala Arg
                965                 970                 975

Ser Asn Trp Lys Arg Ile Arg Glu Ile Leu Ala Met Asn Gly Asn Arg
            980                 985                 990

Pro Ile Leu Arg Val Asp Pro Ser Arg Pro Met Thr Pro Gln Gln Arg
        995                 1000                1005

Arg Leu Gln Gln Arg Arg Leu Arg Tyr Arg Leu Arg Met Arg Glu
    1010                1015                1020

Gln Met Arg Leu Arg Arg Leu Asn Ser Thr Thr Gly Pro Ala Thr
    1025                1030                1035

Ser Pro Thr Pro Ala Leu Thr Leu Pro Pro Ser Pro Thr Pro Gly
    1040                1045                1050

Ser Thr Ser Arg Leu Trp Glu Ile Leu Pro Thr Thr Ala Ala Gly
    1055                1060                1065

Trp Glu Glu Ser Glu Thr Glu Thr Tyr Thr Glu Val Val Thr Glu
    1070                1075                1080

Phe Glu Thr Glu Tyr Gly Pro Asp Leu Glu Val Glu Glu Leu Glu
    1085                1090                1095

Glu Glu Glu Glu Glu Glu Glu Met Asp Thr Gly Leu Thr Phe
    1100                1105                1110

Pro Val Thr Thr Val Glu Thr Tyr Thr Val Asn Phe Gly Asp Phe
    1115                1120                1125

<210> SEQ ID NO 52
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Cys Arg Tyr Ala Leu Gly Met Gln Asp Arg Thr Ile Pro Asp Ser Asp
1               5                   10                  15

Ile Ser Ala Ser Ser Ser Trp Ser Asp Ser Thr Ala Ala Arg His Ser
            20                  25                  30

Arg Leu Glu Ser Ser Asp Gly Asp Gly Ala Trp Cys Pro Ala Gly Ser
        35                  40                  45
```

Val Phe Pro Lys Glu Glu Tyr Leu Gln Val Asp Leu Gln Arg Leu
    50                  55                  60

His Leu Val Ala Leu Val Gly Thr Gln Gly Arg His Ala Gly Gly Leu
 65                  70                  75                  80

Gly Lys Glu Phe Ser Arg Ser Tyr Arg Leu Arg Tyr Ser Arg Asp Gly
                 85                  90                  95

Arg Arg Trp Met
            100

<210> SEQ ID NO 53
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Cys Arg Tyr Pro Leu Gly Met Ser Gly Gly Gln Ile Pro Asp Glu Asp
 1               5                  10                  15

Ile Thr Ala Ser Ser Gln Trp Ser Glu Ser Thr Ala Ala Lys Tyr Gly
                20                  25                  30

Arg Leu Asp Ser Glu Glu Gly Asp Gly Ala Trp Cys Pro Glu Ile Pro
             35                  40                  45

Val Glu Pro Asp Asp Leu Lys Glu Phe Leu Gln Ile Asp Leu His Thr
 50                  55                  60

Leu His Phe Ile Thr Leu Val Gly Thr Gln Gly Arg His Ala Gly Gly
 65                  70                  75                  80

His Gly Ile Glu Phe Ala Pro Met Tyr Lys Ile Asn Tyr Ser Arg Asp
                 85                  90                  95

Gly Thr Arg Trp Ile
            100

<210> SEQ ID NO 54
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Cys Pro Pro Ile Gly Met Glu Ser His Arg Ile Glu Asp Asn Gln Ile
 1               5                  10                  15

Arg Ala Ser Ser Met Leu Arg His Gly Leu Gly Ala Gln Arg Gly Arg
                20                  25                  30

Leu Asn Met Gln Thr Gly Ala Thr Glu Asp Asp Tyr Tyr Asp Gly Ala
             35                  40                  45

Trp Cys Ala Glu Asp Asp Ala Arg Thr Gln Trp Ile Glu Val Asp Thr
 50                  55                  60

Arg Arg Thr Thr Arg Phe Thr Gly Val Ile Thr Gln Gly Arg Asp Ser
 65                  70                  75                  80

Ser Ile His Asp Asp Phe Val Thr Thr Phe Phe Val Gly Phe Ser Asn
                 85                  90                  95

Asp Ser Gln Thr Trp Val
            100

<210> SEQ ID NO 55

```
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Cys Ser Thr Pro Leu Gly Met Glu Asn Gly Lys Ile Glu Asn Lys Gln
1               5                   10                  15

Ile Thr Ala Ser Ser Phe Lys Lys Ser Trp Trp Gly Asp Tyr Trp Glu
            20                  25                  30

Pro Phe Arg Ala Arg Leu Asn Ala Gln Gly Arg Val Asn Ala Trp Gln
        35                  40                  45

Ala Lys Ala Asn Asn Asn Lys Gln Trp Leu Glu Ile Asp Leu Leu Lys
    50                  55                  60

Ile Lys Lys Ile Thr Ala Ile Ile Thr Gln Gly Cys Lys Ser Leu Ser
65                  70                  75                  80

Ser Glu Met Tyr Val Lys Ser Tyr Thr Ile His Tyr Ser Glu Gln Gly
                85                  90                  95

Val Glu Trp Lys
            100

<210> SEQ ID NO 56
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Thr or Ser

<400> SEQUENCE: 56

Lys Glu Lys Pro Pro Lys Ala Thr Lys Lys Pro Lys Glu Lys Pro Pro
1               5                   10                  15

Lys Ala Thr Lys Lys Pro Lys Glu Lys Pro Pro Lys Ala Thr Lys Lys
            20                  25                  30

Pro Lys Glu Lys Pro Pro Lys Ala Xaa Lys Lys
        35                  40

<210> SEQ ID NO 57
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
```

```
<221> NAME/KEY: MOD_RES
<222> LOCATION: (43)..(43)
<223> OTHER INFORMATION: Any amino acid

<400> SEQUENCE: 57

Lys Glu Lys Pro Pro Lys Ala Xaa Lys Lys Pro Xaa Glu Lys Pro Pro
1               5                   10                  15

Lys Ala Thr Lys Lys Pro Lys Glu Lys Pro Pro Lys Ala Thr Lys Lys
            20                  25                  30

Pro Lys Xaa Lys Pro Pro Lys Ala Xaa Lys Xaa
            35                  40

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ugguuuacau gucgacuaa                                                19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ugguuuacau guuguguga                                                19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ugguuuacau guuuuccua                                                19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ugguuuacau guuuucuga                                                19

<210> SEQ ID NO 62
<211> LENGTH: 1128
<212> TYPE: PRT
<213> ORGANISM: Mus musculus

<400> SEQUENCE: 62

Met Ala Pro Val Arg Thr Ala Ser Leu Leu Cys Gly Leu Leu Ala Leu
1               5                   10                  15
```

```
Leu Thr Leu Cys Pro Glu Gly Asn Pro Gln Thr Val Leu Thr Asp Asp
            20                  25                  30

Glu Ile Glu Glu Phe Leu Glu Gly Phe Leu Ser Glu Leu Glu Thr Gln
            35                  40                  45

Ser Pro Pro Arg Glu Asp Val Glu Val Gln Pro Leu Pro Glu Pro
 50                  55                  60

Thr Gln Arg Pro Arg Lys Ser Lys Ala Gly Lys Gln Arg Ala Asp
 65              70                  75                  80

Val Glu Val Pro Pro Glu Lys Asn Lys Asp Lys Glu Lys Lys Gly Lys
                85                  90                  95

Lys Asp Lys Gly Pro Lys Ala Thr Lys Pro Leu Glu Gly Ser Thr Arg
            100                 105                 110

Pro Thr Lys Lys Pro Lys Glu Lys Pro Pro Lys Ala Thr Lys Lys Pro
            115                 120                 125

Lys Glu Lys Pro Pro Lys Ala Thr Lys Lys Pro Lys Glu Lys Pro Pro
            130                 135                 140

Lys Ala Thr Lys Lys Pro Lys Glu Lys Pro Pro Lys Ala Thr Lys Arg
145                 150                 155                 160

Pro Ser Ala Gly Lys Lys Phe Ser Thr Val Ala Pro Leu Glu Thr Leu
                165                 170                 175

Asp Arg Leu Leu Pro Ser Pro Ser Asn Pro Ser Ala Gln Glu Leu Pro
            180                 185                 190

Gln Lys Arg Asp Thr Pro Phe Pro Asn Ala Trp Gln Gly Gln Gly Glu
            195                 200                 205

Glu Thr Gln Val Glu Ala Lys Gln Pro Arg Pro Glu Pro Glu Glu Glu
            210                 215                 220

Thr Glu Met Pro Thr Leu Asp Tyr Asn Asp Gln Ile Glu Lys Glu Asp
225                 230                 235                 240

Tyr Glu Asp Phe Glu Tyr Ile Arg Arg Gln Lys Gln Pro Arg Pro Thr
                245                 250                 255

Pro Ser Arg Arg Arg Leu Trp Pro Glu Arg Pro Glu Glu Lys Thr Glu
            260                 265                 270

Glu Pro Glu Glu Arg Lys Glu Val Glu Pro Pro Leu Lys Pro Leu Leu
            275                 280                 285

Pro Pro Asp Tyr Gly Asp Ser Tyr Val Ile Pro Asn Tyr Asp Asp Leu
            290                 295                 300

Asp Tyr Tyr Phe Pro His Pro Pro Gln Lys Pro Asp Val Gly Gln
305                 310                 315                 320

Glu Val Asp Glu Glu Lys Glu Met Lys Lys Pro Lys Lys Glu Gly
                325                 330                 335

Ser Ser Pro Lys Glu Asp Thr Glu Asp Lys Trp Thr Val Glu Lys Asn
            340                 345                 350

Lys Asp His Lys Gly Pro Arg Lys Gly Glu Glu Leu Glu Glu Glu Trp
            355                 360                 365

Ala Pro Val Glu Lys Ile Lys Cys Pro Pro Ile Gly Met Glu Ser His
            370                 375                 380

Arg Ile Glu Asp Asn Gln Ile Arg Ala Ser Ser Met Leu Arg His Gly
385                 390                 395                 400

Leu Gly Ala Gln Arg Gly Arg Leu Asn Met Gln Ala Gly Ala Asn Glu
            405                 410                 415

Asp Asp Tyr Tyr Asp Gly Ala Trp Cys Ala Glu Asp Glu Ser Gln Thr
            420                 425                 430
```

-continued

```
Gln Trp Ile Glu Val Asp Thr Arg Thr Arg Phe Thr Gly Val
            435                 440                 445

Ile Thr Gln Gly Arg Asp Ser Ser Ile His Asp Asp Phe Val Thr Thr
450                 455                 460

Phe Phe Val Gly Phe Ser Asn Asp Ser Gln Thr Trp Val Met Tyr Thr
465                 470                 475                 480

Asn Gly Tyr Glu Glu Met Thr Phe Tyr Gly Asn Val Asp Lys Asp Thr
                485                 490                 495

Pro Val Leu Ser Glu Leu Pro Glu Pro Val Val Ala Arg Phe Ile Arg
                500                 505                 510

Ile Tyr Pro Leu Thr Trp Asn Gly Ser Leu Cys Met Arg Leu Glu Val
            515                 520                 525

Leu Gly Cys Pro Val Thr Pro Val Tyr Ser Tyr Tyr Ala Gln Asn Glu
        530                 535                 540

Val Val Thr Thr Asp Ser Leu Asp Phe Arg His His Ser Tyr Lys Asp
545                 550                 555                 560

Met Arg Gln Leu Met Lys Ala Val Asn Glu Glu Cys Pro Thr Ile Thr
                565                 570                 575

Arg Thr Tyr Ser Leu Gly Lys Ser Ser Arg Gly Leu Lys Ile Tyr Ala
            580                 585                 590

Met Glu Ile Ser Asp Asn Pro Gly Asp His Glu Leu Gly Glu Pro Glu
        595                 600                 605

Phe Arg Tyr Thr Ala Gly Ile His Gly Asn Glu Val Leu Gly Arg Glu
    610                 615                 620

Leu Leu Leu Leu Leu Met Gln Tyr Leu Cys Gln Glu Tyr Arg Asp Gly
625                 630                 635                 640

Asn Pro Arg Val Arg Asn Leu Val Gln Asp Thr Arg Ile His Leu Val
                645                 650                 655

Pro Ser Leu Asn Pro Asp Gly Tyr Glu Val Ala Ala Gln Met Gly Ser
            660                 665                 670

Glu Phe Gly Asn Trp Ala Leu Gly Leu Trp Thr Glu Glu Gly Phe Asp
        675                 680                 685

Ile Phe Glu Asp Phe Pro Asp Leu Asn Ser Val Leu Trp Ala Ala Glu
    690                 695                 700

Glu Lys Lys Trp Val Pro Tyr Arg Val Pro Asn Asn Asn Leu Pro Ile
705                 710                 715                 720

Pro Glu Arg Tyr Leu Ser Pro Asp Ala Thr Val Ser Thr Glu Val Arg
                725                 730                 735

Ala Ile Ile Ser Trp Met Glu Lys Asn Pro Phe Val Leu Gly Ala Asn
            740                 745                 750

Leu Asn Gly Gly Glu Arg Leu Val Ser Tyr Pro Tyr Asp Met Ala Arg
        755                 760                 765

Thr Pro Ser Gln Glu Gln Leu Leu Ala Glu Ala Leu Ala Ala Ala Arg
    770                 775                 780

Gly Glu Asp Asp Asp Gly Val Ser Glu Ala Gln Glu Thr Pro Asp His
785                 790                 795                 800

Ala Ile Phe Arg Trp Leu Ala Ile Ser Phe Ala Ser Ala His Leu Thr
                805                 810                 815

Met Thr Glu Pro Tyr Arg Gly Gly Cys Gln Ala Gln Asp Tyr Thr Ser
            820                 825                 830

Gly Met Gly Ile Val Asn Gly Ala Lys Trp Asn Pro Arg Ser Gly Thr
        835                 840                 845
```

-continued

```
Phe Asn Asp Phe Ser Tyr Leu His Thr Asn Cys Leu Glu Leu Ser Val
    850             855             860
Tyr Leu Gly Cys Asp Lys Phe Pro His Glu Ser Glu Leu Pro Arg Glu
865             870             875             880
Trp Glu Asn Asn Lys Glu Ala Leu Leu Thr Phe Met Glu Gln Val His
            885             890             895
Arg Gly Ile Lys Gly Val Val Thr Asp Glu Gln Gly Ile Pro Ile Ala
            900             905             910
Asn Ala Thr Ile Ser Val Ser Gly Ile Asn His Gly Val Lys Thr Ala
            915             920             925
Ser Gly Gly Asp Tyr Trp Arg Ile Leu Asn Pro Gly Leu Tyr Arg Val
    930             935             940
Thr Ala His Ala Glu Gly Tyr Thr Ser Ser Ala Lys Ile Cys Asn Val
945             950             955             960
Asp Tyr Asp Ile Gly Ala Thr Gln Cys Asn Phe Ile Leu Ala Arg Ser
            965             970             975
Asn Trp Lys Arg Ile Arg Glu Ile Leu Ala Met Asn Gly Asn Arg Pro
            980             985             990
Ile Leu Arg Val Asp Pro Ser Arg Pro Met Thr Pro Gln Gln Arg Arg
            995             1000            1005
Met Gln Gln Arg Arg Leu Gln Tyr Arg Leu Arg Met Arg Glu Gln
    1010            1015            1020
Met Arg Leu Arg Arg Leu Asn Ser Thr Ala Gly Pro Ala Thr Ser
    1025            1030            1035
Pro Thr Pro Ala Leu Met Pro Pro Pro Ser Pro Thr Pro Ala Ile
    1040            1045            1050
Thr Leu Arg Pro Trp Glu Val Leu Pro Thr Thr Thr Ala Gly Trp
    1055            1060            1065
Glu Glu Ser Glu Thr Glu Thr Tyr Thr Glu Val Val Thr Glu Phe
    1070            1075            1080
Glu Thr Glu Tyr Gly Thr Asp Leu Glu Val Glu Glu Ile Glu Glu
    1085            1090            1095
Glu Glu Glu Glu Glu Glu Glu Met Asp Thr Gly Leu Thr Phe
    1100            1105            1110
Pro Leu Thr Thr Val Glu Thr Tyr Thr Val Asn Phe Gly Asp Phe
    1115            1120            1125
```